(12) United States Patent
Hennequin et al.

(10) Patent No.: US 7,049,438 B2
(45) Date of Patent: May 23, 2006

(54) QUINAZOLINE DERIVATIVES FOR TREATMENT OF TUMOURS

(75) Inventors: Laurent François André Hennequin, Macclesfield (GB); Patrick Ple, Reims Cedex (FR)

(73) Assignee: AstraZeneca AB, Sodertalje (SE)

( * ) Notice: Subject to any disclaimer, the term of this patent is extended or adjusted under 35 U.S.C. 154(b) by 418 days.

(21) Appl. No.: 10/275,382

(22) PCT Filed: Jun. 1, 2001

(86) PCT No.: PCT/GB01/02424

§ 371 (c)(1),
(2), (4) Date: Nov. 5, 2002

(87) PCT Pub. No.: WO01/94341

PCT Pub. Date: Dec. 13, 2001

(65) Prior Publication Data

US 2004/0214841 A1 Oct. 28, 2004

(30) Foreign Application Priority Data

Jun. 6, 2000 (EP) .................................. 00401581
Feb. 7, 2001 (EP) .................................. 01400297
Mar. 5, 2001 (EP) .................................. 01400565

(51) Int. Cl.
*C07D 239/72* (2006.01)
*A01N 43/54* (2006.01)

(52) U.S. Cl. ...................... 544/283; 544/224; 544/285; 544/286; 544/287; 514/247; 514/258; 514/266.1; 514/266.3

(58) Field of Classification Search ................. 544/224, 544/283, 285, 286, 287; 514/247, 258, 266.1, 514/266.3
See application file for complete search history.

(56) References Cited

U.S. PATENT DOCUMENTS

| 5,411,963 | A | | 5/1995 | Dreikorn et al. | |
|---|---|---|---|---|---|
| 5,576,322 | A | | 11/1996 | Takase et al. | |
| 5,955,464 | A | | 9/1999 | Barker | |
| 5,962,458 | A | * | 10/1999 | Lohmann et al. | 514/266.21 |
| 6,046,206 | A | | 4/2000 | Pamukcu et al. | |
| 6,080,747 | A | | 6/2000 | Uckun et al. | |

FOREIGN PATENT DOCUMENTS

| EP | 0 326 330 B1 | 8/1989 |
|---|---|---|
| EP | 0 520 722 A1 | 12/1992 |
| EP | 0 566 226 A | 10/1993 |
| EP | 0 602 851 A1 | 6/1994 |
| EP | 0 787 722 A1 | 8/1997 |
| EP | 0 837 063 A1 | 4/1998 |
| GB | 2 033 894 A | 5/1980 |
| GB | 2 295 387 A | 5/1996 |
| WO | 92/20642 | 11/1992 |
| WO | 95/15758 | 6/1995 |
| WO | 95/23141 | 8/1995 |
| WO | 95/24190 | 9/1995 |
| WO | 96/09294 | 3/1996 |
| WO | 96/15118 | 5/1996 |
| WO | 96/30347 | 10/1996 |
| WO | 96/39145 | 12/1996 |
| WO | 97/03069 | 1/1997 |
| WO | 97/30034 | 8/1997 |
| WO | 97/30035 | 8/1997 |
| WO | 97/30044 | 8/1997 |
| WO | 98/13354 A | 4/1998 |
| WO | 98/02434 | 11/1998 |
| WO | 98/50370 | 11/1998 |
| WO | 99/09016 | 2/1999 |
| WO | 99/55683 A | 11/1999 |
| WO | 99/61428 A | 12/1999 |
| WO | 00/00202 | 1/2000 |
| WO | 00/10981 | 3/2000 |
| WO | 00/20402 | 4/2000 |
| WO | 00/21955 | 4/2000 |
| WO | 00/31048 A | 6/2000 |
| WO | 00/47212 | 8/2000 |
| WO | 00/51991 | 9/2000 |
| WO | 00/55141 | 9/2000 |

(Continued)

OTHER PUBLICATIONS

Bridges, Alexander J. et al., "Tyrosine kinase inhibitors . . . ", Journal of Medicinal Chemistry (1996), 39 (1), 267-76.*

(Continued)

*Primary Examiner*—James O. Wilson
*Assistant Examiner*—Paul V. Ward
(74) *Attorney, Agent, or Firm*—Morgan Lewis & Bockius LLP

(57) ABSTRACT

The invention concerns quinazoline derivatives of Formula (I) wherein each of $Q^1$, Z, m, $R^1$, $R^2$, $R^3$ and $Q^2$ have any of the meanings defined in the description; processes for their preparation, pharmaceutical compositions containing them and their use in the manufacture of a medicament for use as an anti-invasive agent in the containment and/or treatment of solid tumour disease (I)

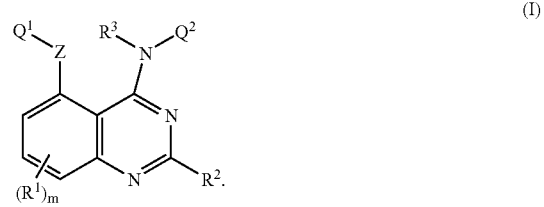

46 Claims, No Drawings

FOREIGN PATENT DOCUMENTS

| | | |
|---|---|---|
| WO | 01/21594 | 3/2001 |
| WO | 01/21595 | 3/2001 |
| WO | 01/21596 | 3/2001 |
| WO | 01/77085 | 10/2001 |
| WO | 02/16352 | 2/2002 |

OTHER PUBLICATIONS

Rewcastle, Gordon W. et al., "Tyrosine kinase inhibitors . . . ", Journal of Medicinal Chemistry (1995), 38 (18), 3482-7.*

* cited by examiner

QUINAZOLINE DERIVATIVES FOR TREATMENT OF TUMOURS

The invention concerns certain novel quinazoline derivatives, or pharmaceutically-acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al., *Ann. Reports in Med. Chem.*, 1989, Chpt. 13). The first group of tyrosine kinases to be identified arose from such viral oncogenes, for example $pp60^{v-Src}$ tyrosine kinase (otherwise known as v-Src), and the corresponding tyrosine kinases in normal cells, for example $pp60^{Src}$ tyrosine kinase (otherwise known as c-Src).

Receptor tyrosine kinases are important in the transmission of biochemical signals which initiate cell replication. They are large enzymes which span the cell membrane and possess an extracellular binding domain for growth factors such as epidermal growth factor 30 (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43–73) based on families of growth factors which bind to different receptor tyrosine kinases. The classification includes Class I receptor tyrosine kinases comprising the EGF family of receptor tyrosine kinases such as the EGF, TGFα, Neu and erbB receptors, Class II receptor tyrosine kinases comprising the insulin family of receptor tyrosine kinases such as the insulin and IGFI receptors and insulin-related receptor (IRR) and Class III receptor tyrosine kinases comprising the platelet-derived growth factor (PDGF) family of receptor tyrosine kinases such as the PDGFα, PDGFβ and colony-stimulating factor 1 (CSF1) receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth (Ullrich et al., *Cell*, 1990, 61, 203–212, Bolen et al., *FASEB J.*, 1992, 6, 3403–3409, Brickell et al., *Critical Reviews in Oncogenesis*, 1992, 3, 401–406, Bohlen et al., *Oncogene*, 1993, 8, 2025–2031, Courtneidge et al., *Semin. Cancer Biol.*, 1994, 5, 239–246, Lauffenburger et al., *Cell*, 1996, 84, 359–369, Hanks et al., *BioEssays*, 1996, 19, 137–145, Parsons et al., *Current Opinion in Cell Biology*, 1997, 9 187–192, Brown et al., *Biochimica et Biophysica Acta*, 1996, 1287, 121–149 and Schlaepfer et al., *Progress in Biophysics and Molecular Biology*, 1999, 71, 435–478). Various classes of non-receptor tyrosine kinases are known including the Src family such as the Src, Lyn, Fyn and Yes tyrosine kinases, the Abl family such as Abl and Arg and the Jak family such as Jak 1 and Tyk 2.

It is known that the Src family of non-receptor tyrosine kinases are highly regulated in normal cells and in the absence of extracellular stimuli are maintained in an inactive conformation. However, some Src family members, for example c-Src tyrosine kinase, is frequently significantly activated (when compared to normal cell levels) in common human cancers such as gastrointestinal cancer, for example colon, rectal and stomach cancer (Cartwright et al., *Proc. Natl. Acad. Sci. USA*, 1990, 87, 558–562 and Mao et al., *Oncogene*, 1997, 15, 3083–3090), and breast cancer (Muthuswanmy et al., *Oncogene*, 1995, 11, 1801–1810).The Src family of non-receptor tyrosine kinases has also been located in other common human cancers such as non-small cell lung cancers (NSCLCs) including adenocarcinomas and squamous cell cancer of the lung (Mazurenko et al., *European Journal of Cancer*, 1992, 28, 372–7), bladder cancer (Fanning et al., *Cancer Research*, 1992, 52, 1457–62), oesophageal cancer (Jankowski et al., *Gut*, 1992, 33, 1033–8), cancer of the prostate, ovarian cancer (Wiener et al., *Clin. Cancer Research*, 1999, 5 2164–70) and pancreatic cancer (Lutz et al., *Biochem. and Biophys. Res. Comm.*, 1998, 243, 503–8). As further human tumour tissues are tested for the Src family of non-receptor tyrosine kinases it is expected that its widespread prevalance will be established.

It is further known that the predominant role of c-Src non-receptor tyrosine kinase is to regulate the assembly of focal adhesion complexes through interaction with a number of cytoplasmic proteins including, for example, focal adhesion kinase and paxillin. In addition c-Src is coupled to signalling pathways that regulate the actin cytoskeleton which facilitates cell motility. Likewise, important roles are played by the c-Src, c-Yes and c-Fyn non-receptor tyrosine kinases in integrin mediated signalling and in disrupting cadherin-dependent cell-cell junctions (Owens et al., *Molecular Biology of the Cell*, 2000, 11, 51–64 and Klinghoffer et al., *EMBO Journal*, 1999, 18, 2459–2471). Cellular motility is necessarily required for a localised tumour to progress through the stages of dissemination into the blood stream, invasion of other tissues and initiation of metastatic tumour growth. For example, colon tumour progression from localised to disseminated, invasive metastatic disease has been correlated with c-Src non-receptor tyrosine kinase activity (Brunton et al., *Oncogene*, 1997, 14) 283–293, Fincham et al., *EMBO J*, 1998, 17, 81–92 and Verbeek et al., *Exp. Cell Research*, 1999, 248, 531–537).

Accordingly it has been recognised that an inhibitor of such non-receptor tyrosine kinases should be of value as a selective inhibitor of the motility of tumour cells and as a selective inhibitor of the dissemination and invasiveness of mammalian cancer cells leading to inhibition of metastatic tumour growth. In particular an inhibitor of such non-receptor tyrosine kinases should be of value as an anti-invasive agent for use in the containment and/or treatment of solid tumour disease.

We have now found that surprisingly certain quinazoline derivatives possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the non-receptor tyrosine-specific protein kinases that are involved in the signal transduction steps which lead to the invasiveness and migratory ability of metastasising tumour cells. In particular, it is believed that the compounds of the present invention provide an anti-tumour effect by way of inhibition of the Src family of non-receptor tyrosine kinases, for example by inhibition of one or more of c-Src, c-Yes and c-Fyn.

It is also known that c-Src non-receptor tyrosine kinase enzyme is involved in the control of osteoclast-driven bone resorption (Soriano et al., *Cell*, 1991, 64, 693–702; Boyce et al., *J. Clin. Invest.*, 1992, 90, 1622–1627; Yoneda et al., *J. Clin. Invest.*, 1993, 91, 2791–2795 and Missbach et al., *Bone*, 1999, 24, 437–49). An inhibitor of c-Src non-receptor tyrosine kinase is therefore of value in the prevention and treatment of bone diseases such as osteoporosis, Paget's disease, metastatic disease in bone and tumour-induced hypercalcaemia.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, hypersensitivity reactions of the skin, blood vessel diseases (for example atherosclerosis and restenosis), allergic asthma, insulin-dependent diabetes, diabetic retinopathy and diabetic nephropathy.

Generally the compounds of the present invention possess potent inhibitory activity against the Src family of non-receptor tyrosine kinases, for example by inhibition of c-Src and/or c-Yes, whilst possessing less potent inhibitory activity against other tyrosine kinase enzymes such as the receptor tyrosine kinases, for example EGF receptor tyrosine kinase and/or VEGF receptor tyrosine kinase. Furthermore, certain compounds of the present invention, possess substantially better potency against the Src family of non-receptor tyrosine kinases, for example c-Src and/or c-Yes, than against EGF receptor tyrosine kinase or VEGF receptor tyrosine kinase. Such compounds possess sufficient potency against the Src family of non-receptor tyrosine kinases, for example c-Src and/or c-Yes, that they may be used in an amount sufficient to inhibit, for example, c-Src and/or c-Yes whilst demonstrating little activity against EGF receptor tyrosine kinase or VEGF receptor tyrosine kinase.

According to one aspect of the invention there is provided a quinazoline derivative of the Formula I

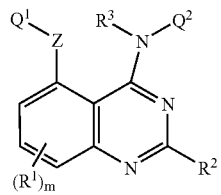

I wherein m is 0, 1, 2 or 3;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^3$-$X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4$-$X^2$— wherein $X^2$ is a direct bond or is selected from CO and $N(R^6)CO$, wherein $R^6$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^3$-$Q^5$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q_5$ is aryl, aryl-(1–6C)alkyl, (3–7C)cycloalkyl, (3–7C)cycloalkyl- (1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$-X^4-R^8$$

wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

$$-X^5-Q^6$$

wherein $X^5$ is a direct bond or is selected from O, CO and $N(R^{10})$, wherein $R^{10}$ is hydrogen or (1–6C)alkyl, and $Q^6$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo or thioxo substituents;

$R^2$ is hydrogen or (1–6C)alkyl;

$R^3$ is hydrogen or (1–6C)alkyl;

Z is a direct bond or is selected from O, S, SO, $SO_2$, $N(R^{11})$, CO, $CH(OR^{11})$, $CON(R^{11})$, $N(R^{11})CO$, $SO_2N(R^{11})$, $N(R^{11})SO_2$, $OC(R^{11})_2$, $SC(R^{11})_2$ and $N(R^{11})C(R^{11})_2$, wherein $R^{11}$ is hydrogen or (1–6C)alkyl;

$Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or, when Z is a direct bond or O, $Q^1$ may be (1–6C)alkyl, (2–8C)alkenyl, (2–8C)alkynyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (1–6C)alkylthio-(1–6C)alkyl, (1–6C)alkylsulphinyl-(1–6C)alkyl or (1–6C)alkylsulphonyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R_{12})SO_2$, CH=CH and C≡C wherein $R^{12}$ is hydrogen or (1–6C)alkyl, and wherein any $CH_2$=CH— or HC≡C— group within the $Q^1$-Z- group optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$$Q^7-X^6-$$

wherein $X^6$ is a direct bond or is selected from CO and $N(R^{13})CO$, wherein $R^{13}$ is hydrogen or (1–6C)alkyl, and $Q^7$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$-X^7-Q^8$$

wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$-X^8-R^{15}$$

wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

$$-X^9-Q^9$$

wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents; and $Q^2$ is an aryl group of formula Ia

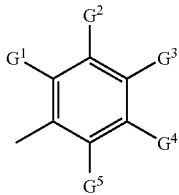

wherein $G^1$ is selected from halogeno, trifluoromethyl, cyano, nitro, hydroxy, amino, carboxy, carbamoyl, (1–6C) alkyl, (2–8C)alkenyl, (2–8C)alkynyl, (1–6C)alkoxy, (2–6C) alkenyloxy, (2–6C)alkynyloxy, (1–6C)alkylthio, (1–6C) alkylsulphinyl, (1–6C)alkylsulphonyl, (1–6C)alkylamino, di-[(1–6C)alkyl]amino, (1–6C)alkoxycarbonyl, N-(1–6C) alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C) alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$-X^{10}-R^{18}$$

wherein $X^{10}$ is a direct bond or is selected from O and $N(R^{19})$, wherein $R^{19}$ is hydrogen or (1–6C)alkyl, and $R^{18}$ is halogeno-(1–6C)alkyl, hydroxy-(1–6C)alkyl, (1–6C) alkoxy-(1–6C)alkyl, cyano-(1–6C)alkyl, amino-(1–6C) alkyl, (1–6C)alkylamino-(1–6C)alkyl or di-[(1–6C)alkyl] amino-(1–6C)alkyl, or from a group of the formula:

$$-X^{11}-Q^{10}$$

wherein $X^{11}$ is a direct bond or is selected from O, S, SO, $SO_2$, $N(R^{20})$, CO, $CH(OR^{20})$, $CON(R^{20})$, $N(R^{20})CO$, $SO_2N(R^{20})$, $N(R^{20})SO_2$, $C(R^{20})_2O$, $C(R^{20})_2S$ and $N(R^{20})C(R^{20})_2$, wherein $R^{20}$ is hydrogen or (1–6C)alkyl, and $Q^{10}$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and any heterocyclyl group within $Q^{10}$ optionally bears 1 or 2 oxo or thioxo substituents, and each of $G^2$, $G^3$, $G^4$ and $G^5$, which may be the same or different, is selected from hydrogen, halogeno, trifluoromethyl, cyano, nitro, hydroxy, amino, (1–6C)alkyl, (2–8C)alkenyl, (2–8C)alkynyl, (1–6C)alkoxy, (1–6C)alkylamino and di-[(1–6C)alkyl]amino, or $G^1$ and $G^2$ together form a group of formula: —CH=CH—CH=CH—, —N=CH—CH=CH—, —CH=N—CH=CH—, —CH=CH—N=CH—, —CH=CH—CH=N—, —N=CH—N=CH—, —CH=N—CH=N—, —N=CH—CH=N—, —N=N—CH=CH—, —CH=CH—N=N—, —CH=CH—O—, —O—CH=CH—, —CH=CH—S—, —S—CH=CH—, —CH₂—CH₂—O—, —O—CH₂—CH₂—, —CH₂—CH₂—S—, —S—CH₂—CH₂—, —O—CH₂—O—, —O—CH₂—CH₂—O—, —S—CH₂—S—, —S—CH₂—CH₂—S—, —CH=CH—NH—, —NH—CH=CH—, —CH₂—CH₂—NH—, —NH—CH₂—CH₂—, —N=CH—NH—, —NH—CH=N—, —NH—CH₂— NH—, —O—CH=N—, —N=CH—O—, —S—CH=N—, —N=CH—S—, —O—CH₂—NH—, —NH—CH₂—O—, —S—CH₂—NH—, —NH—CH₂—S—, —O—N=CH—, —CH=N—O—, —S—N=CH—, —CH=N—S—, —O—NH—CH₂—, —CH₂—NH—O—, —S—NH—CH₂—, —CH₂—NH—S—, —NH—N=CH—, —CH=N—NH—, —NH—NH—CH₂—, —CH₂—NH—NH—, —N=N—NH— or —NH—N=N—, or $G^1$ has any of the meanings defined hereinbefore and $G^2$ and $G^3$ together or $G^3$ and $G^4$ together form a group of formula: —CH=CH—CH=CH—, —N=CH—CH=CH—, —CH=N—CH=CH—, —CH=CH—N=CH—, —CH=CH—CH=N—, —N=CH—N=CH—, —CH=N—CH=N—, —N=CH—CH=N—, —N=N—CH=CH—, —CH=CH—N=N—, —CH=CH—O—, —O—CH=CH—, —CH=CH—S—, —S—CH=CH—, —CH₂—CH₂—O—, —O—CH₂—CH₂—, —CH₂—CH₂—S—, —S—CH₂—CH₂—, —O—CH₂—O—, —O—CH₂—CH₂—O—, —S—CH₂—S—, —S—CH₂—CH₂—S—, —CH=CH—NH—, —NH—CH=CH—, —CH₂—CH₂—NH—, —NH—CH₂—CH₂—, —N=CH—NH—, —NH—CH=N—, —NH—CH₂—NH—, —O—CH=N—, —N=CH—O—, —S—CH=N—, —N=CH—S—, —O—CH₂—NH—, —NH—CH₂—O—, —S—CH₂—NH—, —NH—CH₂—S—, —O—N=CH—, —CH=N—O—, —S—N=CH—, —CH=N—S—, —O—NH—CH₂—, —CH₂—NH—O—, —S—NH—CH₂—, —CH₂—NH—S—, —NH—N=CH—, —CH=N—NH—, —NH—NH—CH₂—, —CH₂—NH—NH—, —N=N—NH— or —NH—N=N—, and the 9- or 10-membered bicyclic heteroaryl or heterocyclic ring formed when $G^1$ and $G^2$ together, $G^2$ and $G^3$ together or $G^3$ and $G^4$ together are linked optionally bears on the heteroaryl or heterocyclic portion of the bicyclic ring 1, 2 or 3 substituents, which may be the same or different, selected from halogeno, trifluoromethyl, cyano, nitro, hydroxy, amino, (1–6C)alkyl, (2–8C)alkenyl, (2–8C)alkynyl, (1–6C)alkoxy, (1–6C)alkylamino and di-[(1–6C)alkyl] amino, and any bicyclic heterocyclic ring so formed optionally bears 1 or 2 oxo or thioxo groups;

or a pharmaceutically-acceptable salt thereof.

According to a further aspect of the invention there is provided a quinazoline derivative of the Formula I wherein each of m, $R^1$, $R^2$, $R^3$ and $Q^2$ has any of the meanings defined hereinbefore and Z is a direct bond or is selected from O, S, SO, $SO_2$, $N(R^{11})$, CO, $CH(OR^{11})$, $CON(R^{11})$, $N(R^{11})CO$, $SO_2N(R^{11})$, $N(R^{11})SO_2$, $OC(R^{11})_2$, $SC(R^{11})_2$ and $N(R^{11})C(R^{11})_2$, wherein $R^{11}$ is hydrogen or (1–6C)alkyl; and $Q_1$ is aryl, aryl-(1–6C)alkyl, (3–7C)cycloalkyl, (3–7C) cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, S, SO, $SO_2N(R^{12})$, CO, $CH(OR^{12})$, $CON(R^{12})$ $N(R^{12})CO$, $SO_2N(R^{12})$, $N(R^{12})SO_2$, CH=CH and C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from-halogeno, (1–6C)alkyl and (1–6C)alkoxy, and wherein any heterocyclyl group within the $Q^1$-Z- group optionally bears 1 or 2 oxo or thioxo substituents.

According to a further aspect of the invention there is provided a quinazoline derivative of the Formula I wherein each of m, $R^1$, $R^2$, $R^3$ and $Q^2$ has any of the meanings defined hereinbefore and Z is selected from O, S, SO, $SO_2$, $N(R^{11})$, CO, $CH(OR^{11})$, $CON(R^{11})$, $N(R^{11})CO$, $SO_2N(R^{11})$, $N(R^{11})SO_2$, $OC(R^{11})_2$, $SC(R_{11})_2$ and $N(R^{11})C(R^{11})_2$, wherein $R^{11}$ is hydrogen or (1–6C)alkyl; and $Q^1$ is (3–7C)cycloalkyl, (3–7C)cycloalkyl-(1–6C)alkyl, (3–7C)cycloalkenyl, (3–7C)cycloalkenyl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, CH=CH and C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

According to a further aspect of the invention there is provided a quinazoline derivative of the Formula I

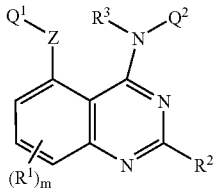

wherein m is 0, 1, 2 or 3;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C) alkoxy, (2–6C)alkenyloxy, (2–6C)alkynyloxy, (1–6C)alkylthio, (1–6C)alkylsulphinyl, (1–6C)alkylsulphonyl, (1–6C) alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)-4alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C) alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^3$-$X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C) alkylenedioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4$-$X^2$— wherein $X^2$ is a direct bond or is selected from CO and $N(R^6)CO$, wherein $R^6$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl] amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C) alkyl]sulphamoyl, (1–6C)alkanesulphonylamino and N-(1–6C)alkyl-(1–6C)alkanesulphonylamino, or from a group of the formula:

—$X^3$-$Q^5$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^5$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C) alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl] sulphamoyl, (1–6C)alkanesulphonylamino and N-(1–6C) alkyl-(1–6C)alkanesulphonylamino, or from a group of the formula:

—$X^4$—$R^8$ wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C)alkyl, (1–6C)alkoxy-(1–6C) alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—$X^5$-$Q^6$ wherein $X^5$ is a direct bond or is selected from O and $N(R^{10})$, wherein $R^{10}$ is hydrogen or (1–6C)alkyl, and $Q^6$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo or thioxo substituents;

$R^2$ is hydrogen or (1–6C)alkyl;

$R^3$ is hydrogen or (1–6C)alkyl;

Z is a direct bond or is selected from O, S, SO, $SO_2$, $N(R^{11})$, CO, $CH(OR^{11})$, $CON(R^{11})$, $N(R^{11})CO$, $SO_2N(R^{11})$, $N(R^{11})SO_2$, $OC(R^{11})_2$, $SC(R^{11})_2$ and $N(R^{11})C(R^{11})_2$, wherein $R^{11}$ is hydrogen or (1–6C)alkyl;

$Q^1$ is aryl, aryl-(1–6C)alkyl, (3–7C)cycloalkyl, (3–7C) cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or, when Z is a direct bond or O, $Q^1$ may be (1–6C)alkyl, (2–8C)alkenyl, (2–8C)alkynyl, halogeno-(1–6C)alkyl, hydroxy-(1–6C) alkyl, (1–6C)alkoxy-(1–6C)alkyl, cyano-(1–6C)alkyl, amino-(1–6C)alkyl, (1–6C)alkylamino-(1–6C)alkyl, di-

[(1–6C)alkyl]amino-(1–6C)alkyl, (1–6C)alkylthio-(1–6C)alkyl, (1–6C)alkylsulphinyl-(1–6C)alkyl or (1–6C)alkylsulphonyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, $CH=CH$ and $C\equiv C$ wherein $R^{12}$ is hydrogen or (1–6C)alkyl, and wherein any $CH_2=CH-$ or $HC\equiv C-$ group within the $Q^1$-Z- group optionally bears at the terminal $CH_2=$ or $HC\equiv$ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^7$-$X^6$— wherein $X^6$ is a direct bond or is selected from CO and $N(R^{13})CO$, wherein $R^{13}$ is hydrogen or (1–6C)alkyl, and $Q^7$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents; and $Q^2$ is an aryl group of formula Ia

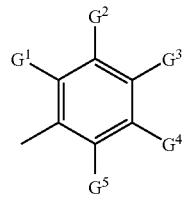

Ia wherein $G^1$ is selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^{10}$—$R^{18}$ wherein $X^{10}$ is a direct bond or is selected from O and $N(R^{19})$, wherein $R^{19}$ is hydrogen or (1–6C)alkyl, and $R^{18}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^{11}$-$Q^{10}$ wherein $X^{11}$ is a direct bond or is selected from O, S, SO, $SO_2$, $N(R^{20})$, CO, $CH(OR^{20})$, $CON(R^{20})$, $N(R^{20})CO$, $SO_2N(R^{20})$, $N(R^{20})SO_2$, $C(R^{20})_2O$, $C(R^{20})_2S$ and $N(R^2)C(R^{20})_2$, wherein $R^{20}$ is hydrogen or (1–6C)alkyl, and $Q^{10}$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and any heterocyclyl group within $Q^{10}$ optionally bears 1 or 2 oxo or thioxo substituents, and each of $G^2$, $G^3$, $G^4$ and $G^5$, which may be the same or different, is selected from hydrogen, halogeno, trifluoromethyl, cyano, nitro, hydroxy, amino, (1–6C)alkyl, (2–8C)alkenyl, (2–8C)alkynyl, (1–6C)alkoxy, (1–6C)alkylamino and di-[(1–6C)alkyl]amino, or G$^1$ and G$^2$ together form a group of formula: —CH=CH—CH=CH—, —N=CH—CH=CH—, —CH=N—CH=CH—, —CH=CH—N=CH—, —CH=CH—CH=N—, —N=CH—N=CH—, —CH=N—CH=N—, —N=CH—CH=N—, —N=N—CH=CH—, —CH=CH—N=N—, —CH=CH—O—, —O—CH=CH—, —CH=CH—S—, —S—CH=CH—, —CH$_2$—CH$_2$—O—, —O—CH$_2$—CH$_2$—, —CH$_2$—CH$_2$—S—, —S—CH$_2$—CH$_2$—, —O—CH$_2$—O—, —O—CH$_2$—CH$_2$—O—, —S—CH$_2$—S—, —S—CH$_2$—CH$_2$—S—, —CH=CH—NH—, —NH—CH=CH—, —CH$_2$—CH$_2$—NH—, —NH—CH$_2$—CH$_2$—, —N=CH—NH—, —NH—CH=N—, —NH—CH$_2$—NH—, —O—CH=N—, —N=CH—O—, —S—CH=N—, —N=CH—S—, —O—CH$_2$—NH—, —NH—CH$_2$—O—, —S—CH$_2$—NH—, —NH—CH$_2$—S—, —O—N=CH—, —CH=N—O—, —S—N=CH—, —CH=N—S—, —O—NH—CH$_2$—, —CH$_2$—NH—O—, —S—NH—CH$_2$—, —CH$_2$—NH—S—, —NH—N=CH—, —CH=N—NH—, —NH—NH—CH$_2$—, —CH$_2$—NH—NH—, —N=N—NH— or —NH—N=N—, or G$^1$ has any of the meanings defined hereinbefore and G$^2$ and G$^3$ together or G$^3$ and G$^4$ together form a group of formula: —CH=CH—CH=CH—, —N=CH—CH=CH—, —CH=N—CH=CH—, —CH=CH—N=CH—, —CH=CH—CH=N—, —N=CH—N=CH—, —CH=N—CH=N—, —N=CH—CH=N—, —N=N—CH=CH—, —CH=CH—N=N—, —CH=CH—O—, —O—CH=CH—, —CH=CH—S—, —S—CH=CH—, —CH$_2$—CH$_2$—O—, —O—CH$_2$—CH$_2$—, —CH$_2$—CH$_2$—S—, —S—CH$_2$—CH$_2$—, —O—CH$_2$—O—, —O—CH$_2$—CH$_2$—O—, —S—CH$_2$—S—, —S—CH$_2$—CH$_2$—S—, —CH=CH—NH—, —NH—CH=CH—, —CH$_2$—CH$_2$—NH—, —NH—CH$_2$—CH$_2$—, —N=CH—NH—, —NH—CH=N—, —NH—CH$_2$—NH—, —O—CH=N—, —N=CH—O—, —S—CH=N—, —N=CH—S—, —O—CH$_2$—NH—, —NH—CH$_2$—O—, —S—CH$_2$—NH—, —NH—CH$_2$—S—, —O—N=CH—, —CH=N—O—, —S—N=CH—, —CH=N—S—, —O—NH—CH$_2$—, —CH$_2$—NH—O—, —S—NH—CH$_2$—, —CH$_2$—NH—S—, —NH—N=CH—, —CH=N—NH—, —NH—NH—CH$_2$—, —CH$_2$—NH—NH—, —N=N—NH— or —NH—N=N—, and the 9- or 10-membered bicyclic heteroaryl or heterocyclic ring formed when G$^1$ and G$^2$ together, G$^2$ and G$^3$ together or G$^3$ and G$^4$ together are linked optionally bears on the heteroaryl or heterocyclic portion of the bicyclic ring 1, 2 or 3 substituents, which may be the same or different, selected from halogeno, trifluoromethyl, cyano, nitro, hydroxy, amino, (1–6C)alkyl, (2–8C)alkenyl, (2–8C)alkynyl, (1–6C)alkoxy, (1–6C)alkylamino and di-[(1–6C)alkyl]amino, and any bicyclic heterocyclic ring so formed optionally bears 1 or 2 oxo or thioxo groups;

or a pharmaceutically-acceptable salt thereof.

According to a further aspect of the invention there is provided a quinazoline derivative of the Formula I wherein each of m, R$^1$, R$^2$, R$^3$ and Q$^2$ has any of the meanings defined hereinbefore and Z is a direct bond or is selected from O, S, SO, SO$_2$, N(R$^{11}$), CO, CH(OR$^{11}$), CON(R$^{11}$), N(R$^{11}$)CO, SO$_2$N(R$^{11}$), N(R$^{11}$)SO$_2$, OC(R$^{11}$)$_2$, SC(R$^{11}$)$_2$ and N(R$^{11}$)C(R$^{11}$)$_2$, wherein R$^{11}$ is hydrogen or (1–6C)alkyl; and Q$^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the Q$^1$-Z- group are optionally separated by the insertion into the chain of a group selected from O, S, SO, SO$_2$, N(R$^{12}$), CO, CH(OR$^{12}$), CON(R$^{12}$), N(R$^{12}$)CO, SO$_2$N(R$^{12}$), N(R$^{12}$)SO$_2$, CH=CH and C≡C wherein R$^{12}$ is hydrogen or (1–6C)alkyl, and wherein any CH$_2$ or CH$_3$ group within the Q$^1$-Z- group optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

X$^7$-Q$^8$ wherein X$^7$ is a direct bond or is selected from O, S, SO, SO$_2$, N(R$^{14}$), CO, CH(OR$^{14}$), CON(R$^{14}$), N(R$^{14}$)CO, SO$_2$N(R$^{14}$), N(R$^{14}$)SO$_2$, C(R$^{14}$)$_2$O, C(R$^{14}$)$_2$S and N(R$^{14}$)C(R$^{14}$)$_2$, wherein R$^{14}$ is hydrogen or (1–6C)alkyl, and Q$^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the Q$^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^8$—R$^{15}$ wherein X$^8$ is a direct bond or is selected from O and N(R$^{16}$), wherein R$^{16}$ is hydrogen or (1–6C)alkyl, and R$^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X$^9$-Q$^9$ wherein X$^9$ is a direct bond or is selected from O and N(R$^{17}$), wherein R$^{17}$ is hydrogen or (1–6C)alkyl, and Q$^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q$^1$-Z- group optionally bears 1 or 2 oxo or thioxo substituents.

According to a further aspect of the invention there is provided a quinazoline derivative of the Formula I wherein each of m, $R^1$, $R^2$, $R^3$ and $Q^2$ has any of the meanings defined hereinbefore and Z is selected from O, S, SO, $SO_2$, $N(R^{11})$, CO, $CH(OR^{11})$, $CON(R^{11})$, $N(R^{11})CO$, $SO_2N(R^{11})$, $N(R^{11})SO_2$, $OC(R^{11})_2$, $SC(R_{11})_2$ and $N(R^{11})C(R^{11})_2$, wherein $R^{11}$ is hydrogen or (1–6C)alkyl; and $Q^1$ is (3–7C)cycloalkyl, (3–7C)cycloalkyl-(1–6C)alkyl, (3–7C)cycloalkenyl, (3–7C)cycloalkenyl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, CH=CH and C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z-group optionally bears 1 or 2 oxo or thioxo substituents.

In this specification the generic term "alkyl" includes both straight-chain and branched-chain alkyl groups such as propyl, isopropyl and tert-butyl However references to individual alkyl groups such as "propyl" are specific for the straight-chain version only; and references to individual branched-chain alkyl groups such as "isopropyl" are specific for the branched-chain version only. An analogous convention applies to other generic terms, for example (1–6C)alkoxy includes methoxy and ethoxy, (1–6C)alkylamino includes methylamino and ethylamino, and di-[(1–6Calkyl]amino includes dimethylamino and diethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$, $Q^3$ to $Q^{10}$) when it is aryl or for the aryl group within a 'Q' group is, for example, phenyl or naphthyl, preferably phenyl.

A suitable value for any one of the 'Q' groups ($Q^1$, $Q^3$ to $Q^{10}$) when it is (3–7C)cycloalkyl or for the (3–7C)cycloalkyl group within a 'Q' group is, for example, cyclopropyl, cyclobutyl, cyclopentyl, cyclohexyl, cycloheptyl or bicyclo[2.2.1]heptyl and a suitable value for any one of the 'Q' groups ($Q^1$, $Q^3$ to $Q^8$) when it is (3–7C)cycloalkenyl or for the (3–7C)cycloalkenyl group within a 'Q' group is, for example, cyclobutenyl, cyclopentenyl, cyclohexenyl or cycloheptenyl.

A suitable value for any one of the 'Q' groups ($Q^1$, $Q^3$ to $Q^{10}$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$, $Q^3$ to $Q^{10}$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, pyrrolinyl, pyrrolidinyl, morpholinyl, tetrahydro, 1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyriridinyl, preferably tetrahydrofuranyl, tetrahydropyranyl, pyrrolidinyl, morpholinyl, 1,1-dioxotetrahydro-4H-1,4-thiazinyl, piperidinyl or piperazinyl, more preferably tetrahydrofuran-3-yl, tetrahydropyran-4-yl, pyrrolidin-3-yl, morpholino, 1,1-dioxotetrahydro-4H-1,4-thiazin-4-yl, piperidino, piperidin-4-yl or piperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1–6C)alkyl is, for example, heteroarylmethyl, 2-heteroarylethyl and 3-heteroarylpropyl. The invention comprises corresponding suitable values for 'Q' groups when, for example, rather than a heteroaryl-(1–6C)alkyl group, an aryl-(1–6C)alkyl, (3–7C)cycloalkyl-(1–6C)alkyl, (3–7C)cycloalkenyl-(1–6C)alkyl or heterocyclyl-(1–6C)alkyl group is present.

Suitable values for any of the 'R' groups ($R^1$ to $R^{20}$), or for various groups within an $R^1$ substituent, or for $G^1$ or for various groups within $G^1$, or for any of the 'G' groups ($G^2$ to $G^5$) within $Q^2$, or for various groups within $Q^2$, or for $Q^1$ or for various groups within $Q^1$, or for various groups within the $Q^1$-Z- group include:

| | |
|---|---|
| for halogeno | fluoro, chloro, bromo and iodo; |
| for (1-6C)alkyl: | methyl, ethyl, propyl, isopropyl and tert-butyl; |
| for (2-8C)alkenyl: | vinyl, isopropenyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl and propionyl; |
| for (2-6C)alkanoyloxy: | acetoxy and propionyloxy; |
| for (2-6C)alkanoylamino: | acetamido and propionamido; |
| for N-(1-6C)alkyl-(2-6C)alkanoylamino: | N-methylacetamido and N-methylpropionamido; |
| for N-(1-6C)alkylsulphamoyl: | N-methylsulphamoyl and N-ethylsulphamoyl; |
| for N,N-di-[(1-6C)alkyl]sulphamoyl: | N,N-dimethylsulphamoyl; |
| for (1-6C)alkanesulphonylamino: | methanesulphonylamino and ethanesulphonylamino; |
| for N-(1-6C)alkyl-(1-6C)alkanesulphonylamino: | N-methylmethanesulphonylamino and N-methylethanesulphonylamino; |
| for (3-6C)alkenoylamino: | acrylamido, methacrylamido and crotonamido; |
| for N-(1-6C)alkyl-(3-6C)alkenoylamino: | N-methylacrylamido and N-methylcrotonamido; |
| for (3-6C)alkynoylamino: | propiolamido; |
| for N-(1-6C)alkyl-(3-6C)alkynoylamino: | N-methylpropiolamido; |
| for amino-(1-6C)alkyl: | aminomethyl, 2-aminoethyl, 1-aminoethyl and 3-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl; |
| for halogeno-(1-6C)alkyl: | chloromethyl, 2-chloroethyl, 1-chloroethyl and 3-chloropropyl; |
| for hydroxy-(1-6C)alkyl: | hydroxymethyl, 2-hydroxyethyl, 1-hydroxyethyl and 3-hydroxypropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for cyano-(1-6C)alkyl: | cyanomethyl, 2-cyanoethyl, 1-cyanoethyl and 3-cyanopropyl; |
| for (1-6C)alkylthio-(1-6C)alky: | methylthiomethyl, ethylthiomethyl, 2-methylthioethyl, 1-methylthioethyl and 3-methylthiopropyl; |
| for (1-6C)alkylsulphinyl-(1-6C)alky: | methylsulphinylmethyl, ethylsulphinylmethyl, 2-methylsulphinylethyl, 1-methylsulphinylethyl and 3-methylsulphinylpropyl; |
| for (1-6C)alkylsulphonyl-(1-6C)alky: | methylsulphonylmethyl, ethylsulphonylmethyl, 2-methylsulphonylethyl, 1-methylsulphonylethyl and 3-methylsulphonylpropyl; |

-continued

| for (2-6C)alkanoylamino-(1-6C)alkyl: | acetamidomethyl, propionamidomethyl and 2-acetamidoethyl; and |
| --- | --- |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl. |

A suitable value for $(R^1)_m$ when it is a (1–3C)alkylenedioxy group is, for example, methylenedioxy or ethylenedioxy and the oxygen atoms thereof occupy adjacent ring positions.

When, as defined hereinbefore, an $R^1$ group forms a group of the formula $Q^3$-$X^1$— and, for example, $X^1$ is a $OC(R^4)_2$ linking group, it is the carbon atom, not the oxygen atom, of the $OC(R^4)_2$ linking group which is attached to the quinazoline ring and the oxygen atom is attached to the $Q^3$ group. Similarly, when, for example a $CH_3$ group within a $R^1$ substituent bears a group of the formula —$X^3$-$Q^5$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^5$ group. A similar convention applies to the attachment of the groups of the formulae $Q^4$-$X^2$— and —$X^7$-$Q^7$.

As defined hereinbefore, adjacent carbon atoms in any (2–6C)alkylene chain within a $R^1$ substituent may be optionally separated by the insertion into the chain of a group such as O, $CON(R^5)$ or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any $CH_2$=CH— or HC≡C— group within a $R^1$ substituent optionally bears at the terminal $CH_2$= or HC≡ position a substituent such as a group of the formula $Q^4$-$X^2$— wherein $X^2$ is, for example, NHCO and $Q^4$ is a heterocyclyl-(1–6C)alkyl group, suitable $R^1$ substituents so formed include, for example, N-[heterocyclyl-(1–6C)alkyl]carbamoylvinyl groups such as N-(2-pyrrolidin-1-ylethyl)carbamoylvinyl or N-[heterocyclyl-(1–6C)alkyl]carbamoylethynyl groups such as N-(2-pyrrolidin-1-ylethyl)carbamoylethynyl.

When, as defined hereinbefore, any $CH_2$ or $CH_3$ group within a $R^1$ substituent optionally bears on each said $CH_2$ or $CH_3$ group one or more halogeno or (1–6C)alkyl substituents, there are suitably 1 or 2 halogeno or (1–6C)alkyl substituents present on each said $CH_2$ group and there are suitably 1, 2 or 3 such substituents present on each said $CH_3$ group.

When, as defined hereinbefore, any $CH_2$ or $CH_3$ group within a $R^1$ substituent optionally bears on each said $CH_2$ or $CH_3$ group a substituent as defined hereinbefore, suitable $R^1$ substituents so formed include, for example, hydroxy-substituted heterocyclyl-(1–6C)alkoxy groups such as 2-hydroxy-3-piperidinopropoxy and 2-hydroxy-3-morpholinopropoxy, hydroxy-substituted amino-(2–6C)alkoxy groups such as 3-amino-2-hydroxypropoxy, hydroxy-substituted (1–6C)alkylamino-(2–6C)alkoxy groups such as 2-hydroxy-3-methylaminopropoxy, hydroxy-substituted di-[(1–6C)alkyl]amino-(2–6C)alkoxy groups such as 3-dimethylamino-2-hydroxypropoxy, hydroxy-substituted heterocyclyl-(1–6C)alkylamino groups such as 2-hydroxy-3-piperidinopropylamino and 2-hydroxy-3-morpholinopropylamino, hydroxy-substituted amino-(2–6C)alkylamino groups such as 3-amino-2-hydroxypropylamino, hydroxy-substituted (1–6C)alkylamino-(2–6C)alkylamino groups such as 2-hydroxy-3-methylaminopropylanmino, hydroxy-substituted di-[(1–6C)alkyl]amino-(2–6C)alkylamino groups such as 3-dimethylamino-2-hydroxypropylamino, hydroxy-substituted (1–6C)alkoxy groups such as 2-hydroxyethoxy, (1–6C)alkoxy-substituted (1–6C)alkoxy groups such as 2-methoxyethoxy and 3-ethoxypropoxy, (1–6C)alkylsulphonyl-substituted (1–6C)alkoxy groups such as 2-methylsulphonylethoxy and heterocyclyl-substituted (1–6C)alkylamino-(1–6C)alkyl groups such as 2-morpholinoethylaminomethyl, 2-piperazin-1-ylethylaminomethyl and 3-morpholinopropylaminomethyl.

Similar considerations apply to the attachments and substitutions within the —Z-$Q^1$ group.

When, as defined hereinbefore, $G^1$ and $G^2$ together form, for example, a group of formula —O—CH=CH—, it is the oxygen atom, not the carbon atom, which is attached to the ortho-position of the phenyl ring of formula Ia and the carbon atom is attached to the adjacent meta-position of the phenyl ring of formula Ia. Similarly, when, for example, $G^2$ and $G^3$ together form, for example, a group of formula —CH=CH—CH=N—, it is the carbon atom, not the nitrogen atom, which is attached to the $G^2$ meta-position of the phenyl ring of formula Ia and the nitrogen atom is attached to the adjacent $G^3$ para-position of the phenyl ring of formula Ia. A similar convention applies to the attachment of the groups when, for example, $G^3$ and $G^4$ are joined.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinazoline derivatives of the Formula I, or pharmaceutically-acceptable salts thereof, wherein, unless otherwise stated, each of m, $R^1$, $R^2$, $R^3$, Z, $Q^1$ and $Q^2$ has any of the meanings defined hereinbefore or in paragraphs (a) to (ee) hereinafter:

(a) m is 1 or 2, and each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino, or from a group of the formula:

$Q^3$-$X^1$— wherein $X^1$ is a direct bond or is selected from O, N($R^4$), CON($R^4$), N($R^4$)CO and OC($R^4$)$_2$ wherein $R^4$ is hydrogen or (1–6C)alkyl, and $Q^3$ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, N($R^5$), CON($R^5$), N($R^5$)CO, CH=CH and C≡C wherein $R^5$ is hydrogen or (1–6C)alkyl, and wherein any CH$_2$=CH— or HC≡C— group within a $R^1$ substituent optionally bears at the terminal CH$_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4$-$X^2$— wherein $X^2$ is a direct bond or is CO or N($R^6$)CO, wherein $R^6$ is hydrogen or (1–6C)alkyl, and $Q^4$ is heteroaryl, heteroaryl-(1–6C)alkyl, heterocyclyl or heterocyclyl-(1–6C)alkyl, and wherein any CH$_2$ or CH$_3$ group within a $R^1$ substituent optionally bears on each said CH$_2$ or CH$_3$ group a substituent selected from hydroxy, amino, (1–6C)alkoxy, (1–6C)alkylsulphonyl, (1–6C)alkylamino and di-[(1–6C)alkyl]amino, or from a group of the formula:

—$X^3$-$Q^5$ wherein $X^3$ is a direct bond or is selected from O, N($R^7$), CON($R^7$), N($R^7$)CO and C($R^7$)$_2$O, wherein $R^7$ is hydrogen or (1–6C)alkyl, and $Q^5$ is heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—$X^4$—$R^8$ wherein $X^4$ is a direct bond or is selected from O and N($R^9$), wherein $R^9$ is hydrogen or (1–6C)alkyl, and $R^8$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and from a group of the formula:

—$X^5$-$Q^6$ wherein $X^5$ is a direct bond or is selected from O and N($R^{10}$), wherein $R^{10}$ is hydrogen or (1–6C)alkyl, and $Q^6$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo substituents;

(b) m is 1 or 2, and each $R^1$ group, which may be the same or different, is selected from fluoro, chloro, trifluoromethyl, hydroxy, amino, carbamoyl, methyl, ethyl, propyl, vinyl, ethynyl, methoxy, ethoxy, propoxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

$Q^3$-$X^1$— wherein $X^1$ is a direct bond or is selected from O, NH, CONH, NHCO and OCH$_2$ and $Q^3$ is phenyl, benzyl, cyclopropylmethyl, 2-thienyl, 1-imidazolyl, 1,2,3-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-, 3- or 4-pyridylmethyl, 2-(2-, 3- or 4-pyridyl)ethyl, 3-(2-, 3- or 4-pyridyl)propyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within a $R^1$ substituent are optionally separated by the insertion into the chain of a group selected from O, NH, CONH, NHCO, CH=CH and C≡C, and wherein any CH$_2$=CH— or HC≡C— group within a $R^1$ substituent optionally bears at the terminal CH$_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$Q^4$-$X^2$— wherein $X^2$ is a direct bond or is CO, NHCO or N(Me)CO and $Q^4$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any CH$_2$ or CH$_3$ group within a $R^1$ substituent optionally bears on each said CH$_2$ or CH$_3$ group a substituent selected from hydroxy, amino, methoxy, methylsulphonyl, methylamino and dimethylamino, or from a group of the formula:

—$X^3$-$Q^5$ wherein $X^3$ is a direct bond or is selected from O, NH, CONH, NHCO and CH$_2$O and $Q^5$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl and methoxy, or optionally bears 1 substituent selected from a group of the formula:

—$X^4$—$R^8$ wherein $X^4$ is a direct bond or is selected from O and NH and $R^8$ is 2-hydroxyethyl, 3-hydroxypropyl, 2-methoxyethyl, 3-methoxypropyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—$X^5$-$Q^6$ wherein $X^5$ is a direct bond or is selected from O and NH and $Q^6$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(c) m is 1 or 2 and the $R^1$ groups, which may be the same or different, are located at the 6- and/or 7-positions and are selected from hydroxy, amino, methyl, ethyl, propyl, vinyl, ethynyl, methoxy, ethoxy, propoxy, methylamino, ethylamino, dimethylamino, diethylamino, acetamido, propionamido, benzyloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2–6C)alkylene chain within a $R^1$ substituent are optionally separated by the insertion into the chain of a group selected from O, NH, CH=CH and C≡C, and when $R^1$ is a vinyl or ethynyl group, the $R^1$ substituent optionally bears at the terminal $CH_2$= or HC≡ position a substituent selected from N-(2-dimethylaminoethyl)carbamoyl, N-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$Q^4$-$X^2$— wherein $X^2$ is a direct bond or is NHCO or N(Me)CO and $Q^4$ is imidazolylmethyl, 2-imidazolylethyl, 3-imidazolylpropyl, pyridylmethyl, 2-pyridylethyl, 3-pyridylpropyl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl and methoxy, and a piperidin-3-ylmethyl or piperidin-4-ylmethyl group within a $R^1$ substituent is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(d) m is 1 and the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy or 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a susbtituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

(e) m is 0;

(f) $R^2$ is hydrogen;

(g) $R^3$ is hydrogen;

(h) Z is a direct bond or is selected from O, S, SO, $SO_2$, $N(R^{11})$ and CO;

(i) Z is selected from $CON(R^{11})$, $N(R^{11})CO$, $SO_2N(R^{11})$, $N(R^{11})SO_2$, $OC(R^{11})_2$, $SC(R^{11})_2$ and $N(R^{11})C(R^{11})_2$, wherein $R^{11}$ is hydrogen or (1–6C)alkyl;

(j) the $Q^1$-Z- group is selected from (1–6C)alkyl, (2–8C)alkenyl, (2–8C)alkynyl, (1–6C)alkoxy, (2–8C)alkenyloxy, (2–8C)alkynyloxy, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, halogeno-(1–6C)alkoxy, hydroxy-(1–6C)alkoxy, (1–6C)alkoxy-(1–6C)alkoxy, cyano-(1–6C)alkoxy, amino-(1–6C)alkoxy, (1–6C)alkylamino-(1–6C)alkoxy and di-[(1–6C)alkyl]amino-(1–6C)alkoxy, or Z is a direct bond or is selected from O, S, SO, $SO_2$, $N(R^{11})$ and CO wherein $R^{11}$ is hydrogen or (1–6C)alkyl, and $Q^1$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, $N(R^{12})$, $CON(R^{12})$, $N(R^{12})CO$, CH=CH and C≡C wherein $R^{12}$ is hydrogen or (1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and a group of the formula:

—$X^9$-$Q^9$ wherein $X^9$ is a direct bond or is selected from O and $N(R^{17})$, wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any aryl, heteroaryl or heterocyclyl group within the $Q^1$-Z- group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—$X^8$—$R^{15}$ wherein $X^4$ is a direct bond or is selected from O and $N(R^{16})$, wherein $R^{16}$ is hydrogen or (1–6C)alkyl, and $R^{15}$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and a group of the formula:

—$X^9$-$Q^9$ wherein $X^9$ is a direct bond or is selected from O and $N(R^{17})$, wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo substituents;

(k) the $Q^1$-Z- group is selected from methoxy, ethoxy, propoxy, isopropoxy, 2-hydroxyethoxy, 3-hydroxypropoxy, 2-methoxyethoxy, 3-methoxypropoxy, 2-aminoethoxy, 3-aminopropoxy, 2-methylaminoethoxy, 3-methylaminopropoxy, 2-ethylaminoethoxy, 3-ethylaminopropoxy, 2-dimethylaminoethoxy, 3-dimethylaminopropoxy, cyclopropyloxy, cyclobutyloxy, cyclopentyloxy, cyclohexyloxy, cycloheptyloxy, cyclopropylmethoxy, cyclobutylmethoxy, cyclopentylmethoxy, cyclohexylmethoxy and cycloheptylmethoxy, or Z is a direct bond or is selected from O, S, SO, $SO_2$ and NH and $Q^1$ is phenyl, benzyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazol-1-yl)ethyl, 2-(1,2,4-triazol-1-yl)ethyl, 3-(1,2,3-triazol-1-yl)propyl, 3-(1,2,4-triazol-1-yl)propyl, 2-, 3- or 4-pyridylmethyl, 2-(2-, 3- or 4-pyridyl)ethyl, 3-(2-, 3- or 4-pyridyl)propyl, oxetan-3-yl, tetrahydrofuran-3-yl, 3- or 4-tetrahydropyranyl, 3- or 4-oxepanyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-1-ylpropyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within the $Q^1$-Z- group are optionally separated by the insertion into the chain of a group selected from O, NH, CONH, NHCO, CH=CH and C≡C, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, or from a group of the formula:

—$X^7$-$Q^8$ wherein $X^7$ is a direct bond or is selected from O, NH, CONH, NHCO and $CH_2O$ and $Q^8$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within the $Q^1$-Z- group optionally bears 1, 2 or 3 substituents, which may be the same or different, selected from fluoro, chloro, trifluoromethyl, hydroxy, amino, carbamoyl, methyl, ethyl and methoxy, or optionally bears 1 substituent selected from a group of the formula:

—$X^8$—$R^{15}$ wherein $X^8$ is a direct bond or is selected from O and NH and $R^{15}$ is 2-hydroxyethyl, 3-hydroxypropyl, 2-methoxyethyl, 3-methoxypropyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—$X^9$-$Q^9$ wherein $X^9$ is a direct bond or is selected from O and NH and $Q^9$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within the $Q^1$-Z- group optionally bears 1 or 2 oxo substituents;
(l) the $Q^1$-Z- group is selected from methoxy, ethoxy, propoxy, isopropoxy, 2-hydroxyethoxy, 3-hydroxypropoxy, 2-methoxyethoxy, 3-methoxypropoxy, cyclobutyloxy, cyclopentyloxy, cyclohexyloxy, cycloheptyloxy, phenoxy, phenylthio, anilino, benzyloxy, cyclopropylmethoxy, tetrahydrofuran-3-yloxy, 3- or 4-tetrahydropyranyloxy, 2-imidazol-1-ylethoxy, 3-imidazol-1-ylpropoxy, 2-(1,2,3-triazol-1-yl)ethoxy, 2-(1,2,4-triazol-1-yl)ethoxy, 3-(1,2,3-triazol-1-yl)propoxy, 3-(1,2,4-triazol-1-yl)propoxy, pyrrolidin-1-yl, morpholino, piperidino, piperazin-1-yl, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, homopiperidin-3-yloxy, homopiperidin-4-yloxy, homopiperidin-3-ylmethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, homopiperidin-3-ylamino, homopiperidin-4-ylamino, homopiperidin-3-ylmethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2–6C)alkylene chain within the $Q^1$-Z- group are optionally separated by the insertion into the chain of a group selected from O, NH, CH=CH and C≡C, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z group optionally bears 1 or 2 substituents, which may be the same or different, selected from fluoro, chloro, trifluoromethyl, hydroxy, amino, carbamoyl, methyl, ethyl and methoxy, and a piperidin-3-ylmethyl or piperidin-4-ylmethyl group within the $Q^1$-Z- group is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within the $Q^1$-Z- group optionally bears 1 or 2 oxo substituents;
(m) the $Q^1$-Z- group is selected from propoxy, isopropoxy, 2-hydroxyethoxy, 3-hydroxypropoxy, 2-methoxyethoxy, 3-methoxypropoxy, cyclopentyloxy, cyclohexyloxy, phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

(n) Z is a direct bond or is selected from O, S, SO, $SO_2$, $N(R^{11})$ and CO wherein $R^{11}$ is hydrogen or (1–6C)alkyl, and $Q^1$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, $N(R^{12})$, $CON(R^{12})$, $N(R^{12})CO$, $CH=CH$ and $C\equiv C$ wherein $R^{12}$ is hydrogen or (1–6C)alkyl, and wherein any $CH_2=CH-$ or $HC\equiv C-$ group within the $Q^1$-Z- group optionally bears at the terminal $CH_2=$ or $HC\equiv$ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$$Q^7\text{-}X^6-$$

wherein $X^6$ is a direct bond or is CO or $N(R^{13})CO$, wherein $R^{13}$ is hydrogen or (1–6C)alkyl, and $Q^7$ is heteroaryl, heteroaryl-(1–6C)alkyl, heterocyclyl or heterocyclyl-(1–6C)alkyl, and wherein any $CH_2$ or $CH_3$ group within the $Q^1$-Z- group optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

$$-X^7\text{-}Q^8$$

wherein $X^7$ is a direct bond or is selected from O, $N(R^{14})$, $CON(R^{14})$, $N(R^{14})CO$ and $C(R^{14})_2O$, wherein $R^{14}$ is hydrogen or (1–6C)alkyl, and $Q^8$ is heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

$$-X^8-R^{15}$$

wherein $X^4$ is a direct bond or is selected from O and $N(R^{16})$, wherein $R^{16}$ is hydrogen or (1–6C)alkyl, and $R^{15}$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and a group of the formula:

$$-X^9\text{-}Q^9$$

wherein $X^9$ is a direct bond or is selected from O and $N(R^{17})$, wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo substituents;

(o) Z is a direct bond or is selected from O, S, SO, $SO_2$ and NH and $Q^1$ is phenyl, benzyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazol-1-yl)ethyl, 2-(1,2,4-triazol-1-yl)ethyl, 3-(1,2,3-triazol-1-yl)propyl, 3-(1,2,4-triazol-1-yl)propyl, 2-, 3- or 4-pyridylmethyl, 2-(2-, 3- or 4-pyridyl)ethyl, 3-(2-, 3- or 4-pyridyl)propyl, oxetan-3-yl, tetrahydrofuran-3-yl, 3- or 4-tetrahydropyranyl, 3- or 4-oxepanyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-1-ylpropyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within the $Q^1$-Z- group are optionally separated by the insertion into the chain of a group selected from O, NH, CONH, NHCO, $CH=CH$ and $C\equiv C$, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, or from a group of the formula:

$$-X^7\text{-}Q^8$$

wherein $X^7$ is a direct bond or is selected from O, NH, CONH, NHCO and $CH_2O$ and $Q^8$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within the $Q^1$-Z- group optionally bears 1, 2 or 3 substituents, which may be the same or different, selected from fluoro, chloro, trifluoromethyl, hydroxy, amino, carbamoyl, methyl, ethyl and methoxy, or optionally bears 1 substituent selected from a group of the formula:

$$-X^8-R^{15}$$

wherein $X^8$ is a direct bond or is selected from O and NH and $R^{15}$ is 2-hydroxyethyl, 3-hydroxypropyl, 2-methoxyethyl, 3-methoxypropyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—X⁹-Q⁹ wherein $X^9$ is a direct bond or is selected from O and NH and $Q^9$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within the $Q^1$-Z-group optionally bears 1 or 2 oxo substituents;

(p) the $Q^1$-Z- group is selected from phenoxy, phenylthio, anilino, benzyloxy, cyclopropylmethoxy, tetrahydrofuran-3-yloxy, 3- or 4-tetrahydropyranyloxy, 2-imidazol-1-ylethoxy, 3-imidazol-1-ylpropoxy, 2-(1,2,3-triazol-1-yl)ethoxy, 2-(1,2,4-triazol-1-yl)ethoxy, 3-(1,2,3-triazol-1-yl)propoxy, 3-(1,2,4-triazol-1-yl)propoxy, pyrrolidin-1-yl, morpholino, piperidino, piperazin-1-yl, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, homopiperidin-3-yloxy, homopiperidin-4-yloxy, homopiperidin-3-ylmethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, homopiperidin-3-ylamino, homopiperidin-4-ylamino, homopiperidin-3-ylmethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2–6C)alkylene chain within the $Q^1$-Z- group are optionally separated by the insertion into the chain of a group selected from O, NH, CH=CH and C≡C, and wherein any $CH_2$ or $CH_3$ group within the $Q^1$-Z-group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, carbamoyl, methyl, ethyl and methoxy, and a piperidin-3-ylmethyl or piperidin-4-ylmethyl group within the $Q^1$-Z- group is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within the $Q^1$-Z group optionally bears 1 or 2 oxo substituents;

(q) the $Q^1$-Z- group is selected from phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z-group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z-group optionally bears 1 or 2 oxo substituents;

(r) Z is selected from O, S, SO, $SO_2$, $N(R^{11})$ and CO wherein $R^{11}$ is hydrogen or (1–6C)alkyl, and $Q^1$ is (3–7C)cycloalkyl, (3–7C)cycloalkyl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, $N(R^{12})$, $CON(R^{12})$, $N(R^{12})CO$, CH=CH and C≡C wherein $R^{12}$ is hydrogen or (1–6C)alkyl, and wherein any $CH_2$ or $CH_3$ group within the $Q^1$-Z-group optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

—X⁷-Q⁸ wherein $X^7$ is a direct bond or is selected from O, $N(R^{14})$, $CON(R^{14})$, $N(R^{14})CO$ and $C(R^{14})_2O$, wherein $R^{14}$ is hydrogen or (1–6C)alkyl, and $Q^8$ is heteroaryl, heteroaryl-(1–6C)alkyl, heterocyclyl or heterocyclyl-(1–6C)alkyl, and wherein any heterocyclyl group within the $Q^1$-Z-group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—X⁸—R¹⁵ wherein $X^4$ is a direct bond or is selected from O and $N(R^{16})$, wherein $R^{16}$ is hydrogen or (1–6C)alkyl, and $R^{15}$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and a group of the formula:

—$X^9$-$Q^9$ wherein $X^9$ is a direct bond or is selected from O and $N(R^{17})$, wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo substituents;

(s) Z is selected from O, S, SO, $SO_2$ and NH and $Q^1$ is oxetan-3-yl, tetrahydrofuran-3-yl, 3- or 4-tetrahydropyranyl, 3- or 4-oxepanyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-1-ylpropyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within the $Q^1$-Z- group are optionally separated by the insertion into the chain of a group selected from O, NH, CONH, NHCO, CH═CH and C≡C, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, or from a group of the formula:

—$X^7$-$Q^8$ wherein $X^7$ is a direct bond or is selected from O, NH, CONH, NHCO and $CH_2O$ and $Q^8$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any heterocyclyl group within the $Q^1$-Z- group optionally bears 1, 2 or 3 substituents, which may be the same or different, selected from fluoro, chloro, trifluoromethyl, hydroxy, amino, carbamoyl, methyl, ethyl and methoxy, or optionally bears 1 substituent selected from a group of the formula:

—$X^8$—$R^{15}$ wherein X8 is a direct bond or is selected from O and NH and $R^{15}$ is 2-hydroxyethyl, 3-hydroxypropyl, 2-methoxyethyl, 3-methoxypropyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—$X^9$-$Q^9$ wherein $X^9$ is a direct bond or is selected from O and NH and $Q^9$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within the $Q^1$-Z- group optionally bears 1 or 2 oxo substituents;

(t) the $Q^1$-Z- group is selected from cyclopropylmethoxy, tetrahydrofuran-3-yloxy, 3- or 4-tetrahydropyranyloxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, homopiperidin-3-yloxy, homopiperidin-4-yloxy, homopiperidin-3-ylmethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, homopiperidin-3-ylamino, homopiperidin-4-ylamino, homopiperidin-3-ylmethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2–6C)alkylene chain within the $Q^1$-Z- group are optionally separated by the insertion into the chain of a group selected from O, NH, CH═CH and C≡C, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any heterocyclyl group within the $Q^1$-Z- group optionally bears 1 or 2 substituents, which may be the same or different, selected from fluoro, chloro, trifluoromethyl, hydroxy, amino, carbamoyl, methyl, ethyl and methoxy, and a piperidin-3-ylmethyl or piperidin-4-ylmethyl group within the $Q^1$-Z group is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within the $Q^1$-Z-group optionally bears 1 or 2 oxo substituents;

(u) the $Q^1$-Z- group is selected from tetrahydrofuran-3-yloxy, tetrahydropyran-3-yloxy, tetrahydropyran-4-yloxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z-group optionally bears on each said $CH_2$ or $CH_3$ group a substituent selected from hydroxy, amino, methoxy, methylsulphonyl, methylamino and dimethylamino, and wherein any heterocyclyl group within the $Q^1$-Z-group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z-group optionally bears 1 or 2 oxo substituents;

(v) $Q^2$ is an aryl group of formula Ia

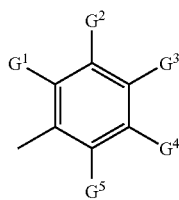

Ia wherein $G^1$ is selected from halogeno, trifluoromethyl, cyano, hydroxy, (1–6C)alkyl, (2–8C)alkenyl, (2–8C)alkynyl and (1–6C)alkoxy, and each of $G^2$, $G^3$, $G^4$ and $G^5$, which may be the same or different, is selected from hydrogen, halogeno, trifluoromethyl, cyano, hydroxy, (1–6C)alkyl, (2–8C)alkenyl, (2–8C)alkynyl and (1–6C)alkoxy;

(w) $Q^2$ is an aryl group of formula Ia wherein $G^1$ and $G^2$ together form a group of formula: —CH=CH—CH=CH—, —N=CH—CH=CH—, —CH=N—CH=CH—, —CH=CH—N=CH—, —CH=CH—CH=N—, —CH=CH—O—, —O—CH=CH—, —CH=CH—S—, —S—CH=CH—, —O—CH$_2$—O— or —O—CH$_2$—CH$_2$—O—, and the 9- or 10-membered bicyclic heteroaryl or heterocyclic ring formed when $G^1$ and $G^2$ together are linked optionally bears on the heteroaryl or heterocyclic portion of the bicyclic ring 1, 2 or 3 substituents, which may be the same or different, selected from halogeno, trifluoromethyl, cyano, hydroxy, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of $G^3$, $G^4$ and $G^5$ which may be the same or different, is selected from hydrogen, halogeno, trifluoromethyl, cyano, hydroxy, (1–6C)alkyl, (2–8C)alkenyl, (2–8C)alkynyl and (1–6C)alkoxy;

(x) $Q^2$ is an aryl group of formula Ia wherein $G^1$ is selected from halogeno, trifluoromethyl, cyano, hydroxy, (1–6C)alkyl, (2–8C)alkenyl, (2–8C)alkynyl and (1–6C)alkoxy, and $G^2$ and $G^3$ together or $G^3$ and $G^4$ together form a group of formula: —CH=CH—CH=CH—, —N=CH—CH=CH—, —CH=N—CH=CH—, —CH=CH—N=CH—, —CH=CH—CH—N—, —CH=CH—O—, —O—CH=CH—, —CH=CH—S—, —S—CH=CH—, —O—CH$_2$—O— or —O—CH$_2$—CH$_2$—O—, and the 9- or 10-membered bicyclic heteroaryl or heterocyclic ring formed when $G^2$ and $G^3$ together or $G^3$ and $G^4$ together are linked optionally bears on the heteroaryl or heterocyclic portion of the bicyclic ring 1, 2 or 3 substituents, which may be the same or different, selected from halogeno, trifluoromethyl, cyano, hydroxy, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of $G^4$ and $G^5$ or $G^2$ and $G^5$ as appropriate, which may be the same or different, is selected from hydrogen, halogeno, trifluoromethyl, cyano, hydroxy, (1–6C)alkyl, (2–8C)alkenyl, (2–8C)alkynyl and (1–6C)alkoxy;

(y) $Q^2$ is an aryl group of formula Ia wherein $G^1$ is selected from fluoro, chloro, bromo, iodo, trifluoromethyl, cyano, hydroxy, methyl, ethyl, vinyl, allyl, isopropenyl, ethynyl, 1-propynyl, 2-propynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, 1-propynyl, 2-propynyl, methoxy and ethoxy;

(z) $Q^2$ is an aryl group of formula Ia wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy;

(aa) $Q^2$ is an aryl group of formula Ia wherein $G^1$ and $G^2$ together form a group of formula: —CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoromethyl, cyano, hydroxy, methyl, ethyl, methoxy and ethoxy;

(bb) $Q^2$ is an aryl group of formula Ia wherein $G^1$ is selected from fluoro, chloro, bromo, iodo, trifluoromethyl, cyano, methyl, ethyl, methoxy and ethoxy, and $G^2$ and $G^3$ together or $G^3$ and $G^4$ together form a group of formula: —CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^4$ and $G^5$ or $G^2$ and $G^5$ as appropriate, which may be the same or different, is selected from hydrogen, fluoro, chloro, bromo, trifluoromethyl, cyano, hydroxy, methyl, ethyl, methoxy and ethoxy;

(cc) $Q^2$ is an aryl group of formula Ia wherein $G^1$ and $G^2$ together form a group of formula: —O—$CH_2$—O—, and the 9-membered bicyclic heterocyclic ring so formed optionally bears on the heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and the bicyclic heterocyclic ring so formed optionally bears 1 oxo or thioxo groups, each of $G^3$ and $G^4$, which may be the same or different, is selected from hydrogen, fluoro, chloro, bromo, trifluoromethyl, cyano, hydroxy, methyl, ethyl, methoxy and ethoxy, and $G^5$ is selected from hydrogen, fluoro, chloro or bromo;

(dd) m is 1 or 2, and each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino, or from a group of the formula:

$Q^3$-$X^1$— wherein $X^1$ is a direct bond or is selected from O, N($R^4$), CON($R^4$), N($R^4$)CO and OC($R^4$)$_2$ wherein $R^4$ is hydrogen or (1–6C)alkyl, and $Q^3$ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, N($R^5$), CON($R^5$), N($R^5$)CO, CH=CH and C≡C wherein $R^5$ is hydrogen or (1–6C)alkyl, and wherein any $CH_2$=CH— or HC≡C— group within a $R^1$ substituent optionally bears at the terminal $CH_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4$-$X^2$— wherein $X^2$ is a direct bond or is CO or N($R^6$)CO, wherein $R^6$ is hydrogen or (1–6C)alkyl, and $Q^4$ is heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

—$X^3$-$Q^5$ wherein $X^3$ is a direct bond or is selected from O, N($R^7$), CON($R^7$), N($R^7$)CO and C($R^7$)$_2$O, wherein $R^7$ is hydrogen or (1–6C)alkyl, and $Q^5$ is heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—$X^4$—$R^8$ wherein $X^4$ is a direct bond or is selected from O and N($R^9$), wherein $R^9$ is hydrogen or (1–6C)alkyl, and $R^8$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and from a group of the formula:

—$X^5$-$Q^6$ wherein $X^5$ is a direct bond or is selected from O, CO and N($R^{10}$), wherein $R^{10}$ is hydrogen or (1–6C)alkyl, and $Q^6$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo substituents; and (ee) the $Q^1$-Z- group is selected from (1–6C)alkyl, (2–8C)alkenyl, (2–8C)alkynyl, (1–6C)alkoxy, (2–8C)alkenyloxy, (2–8C)alkynyloxy, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, halogeno-(1–6C)alkoxy, hydroxy-(1–6C)alkoxy, (1–6C)alkoxy-(1–6C)alkoxy, cyano-(1–6C)alkoxy, amino-(1–6C)alkoxy, (1–6C)alkylamino-(1–6C)alkoxy and di-[(1–6C)alkyl]amino-(1-6C)alkoxy, or Z is a direct bond or is selected from O, S, SO, $SO_2$, N($R^{11}$) and CO wherein $R^{11}$ is hydrogen or (1–6C)alkyl, and $Q^1$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, N($R^{12}$), CON($R^{12}$), N($R^{12}$)CO, CH=CH and C≡C wherein $R^{12}$ is hydrogen or (1–6C)alkyl, and wherein any $CH_2$=CH— or HC≡C— group within the $Q^1$-Z- group optionally bears at the terminal $CH_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^7$-$X^6$— wherein $X^6$ is a direct bond or is CO or N($R^{13}$)CO, wherein $R^{13}$ is hydrogen or (1–6C)alkyl, and $Q^7$ is heteroaryl, heteroaryl-(1–6C)alkyl, heterocyclyl or heterocyclyl-(1–6C)alkyl, and wherein any $CH_2$ or $CH_3$ group within the $Q^1$-Z- group optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

—$X^7$-$Q^8$ wherein $X^7$ is a direct bond or is selected from O, N($R^{14}$), CON($R^{14}$), N($R^{14}$)CO and C($R^{14}$)$_2$O, wherein $R^{14}$ is hydrogen or (1–6C)alkyl, and $Q^8$ is heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—$X^8$—$R^{15}$ wherein $X^8$ is a direct bond or is selected from O and N($R^{16}$), wherein $R^{16}$ is hydrogen or (1–6C)alkyl, and $R^{15}$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and a group of the formula:

—$X^9$-$Q^9$ wherein $X^9$ a direct bond or is selected from O, CO and N($R^{17}$), wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo substituents.

As stated hereinbefore, certain compounds of the present invention, possess substantially better potency against the Src family of non-receptor tyrosine kinases, for example c-Src and/or c-Yes, than against EGF receptor tyrosine kinase or VEGF receptor tyrosine kinase. Particular groups of novel compounds of the invention that possess such selectivity include, for example, quinazoline derivatives of the Formula I, or pharmaceutically-acceptable salts thereof, wherein each of m, $R^1$, $R^2$, $R^3$, Z and $Q^1$ has any of the meanings defined hereinbefore and:

(a) $Q^2$ is an aryl group of formula Ia

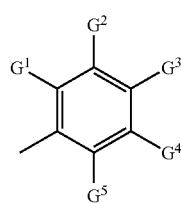

Ia wherein $G^1$ is halogeno or trifluoromethyl,
each of $G^2$ and $G^5$ is hydrogen,
$G^3$ is selected from hydrogen, halogeno, trifluoromethyl, cyano, hydroxy, (1–6C)alkyl, (2–8C)alkenyl, (2–8C)alkynyl and (1–6C)alkoxy,
and $G^4$ is halogeno or (1–6C)alkoxy;

(b) $Q^2$ is an aryl group of formula Ia wherein $G^1$ is fluoro, chloro, bromo, iodo or trifluoromethyl,
each of $G^2$ and $G^5$ is hydrogen,
$G^3$ is selected from hydrogen, fluoro, chloro, bromo, trifluoromethyl, cyano, hydroxy, methyl, ethyl, vinyl, allyl, isopropenyl, ethynyl, methoxy and ethoxy, and $G^4$ is fluoro, chloro, bromo, methoxy or ethoxy;

(c) $Q^2$ is an aryl group of formula Ia wherein $G^1$ and $G^2$ together form a group of formula: —O—$CH_2$—O—,
each of $G^3$ and $G^4$, which may be the same or different, is selected from hydrogen, halogeno, trifluoromethyl, cyano, hydroxy, (1–6C)alkyl and (1–6C)alkoxy, and $G^5$ is halogeno; or (d) $Q^2$ is an aryl group of formula Ia wherein $G^1$ and $G^2$ together form a group of formula: —O—$CH_2$—O—,
each of $G^3$ and $G^4$, which may be the same or different, is selected from hydrogen, fluoro, chloro, bromo, trifluoromethyl, cyano, hydroxy, methyl, ethyl, methoxy and ethoxy,
and $G^5$ is selected from fluoro, chloro or bromo.

A preferred compound of the invention is a quinazoline derivative of the Formula I wherein:
m is 0 or m is 1 and the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

the $Q^1$-Z- group is selected from propoxy, isopropoxy, 2-hydroxyethoxy, 3-hydroxypropoxy, 2-methoxyethoxy, 3-methoxypropoxy, cyclopentyloxy, cyclohexyloxy, phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl- group within the $Q^1$-Z- group optionally bears 1 or 2 oxo substituents;

each of $R^2$ and $R^3$ is hydrogen; and $Q^2$ is an aryl group of formula Ia

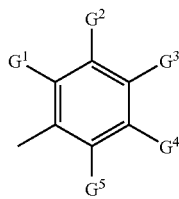

Ia wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, or $G^1$ and $G^2$ together form a group of formula: —CH═CH—CH═CH—, —O—CH═CH— or —O—$CH_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoromethyl, cyano, hydroxy, methyl, ethyl, methoxy and ethoxy; or a pharmaceutically-acceptable acid-addition salt thereof.

A further preferred compound of the invention is a quinazoline derivative of the Formula I wherein:

m is 1 and the $R^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

and wherein any $CH_2$ group within a $R^1$ substituent that is attached to two carbon atoms optionally bears a hydroxy group on said $CH_2$ group;

the $Q^1$-Z- group is selected from propoxy, isopropoxy, 2-hydroxyethoxy, 3-hydroxypropoxy, 2-methoxyethoxy, 3-methoxypropoxy, cyclopentyloxy, cyclohexyloxy, tetrahydrofuran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy and 3-(4-methylpiperazin-1-yl)propoxy, and wherein any $CH_2$ group within the $Q^1$-Z- group that is attached to two carbon atoms optionally bears a hydroxy group on said $CH_2$ group;

and wherein any heterocyclyl group within the $Q^1$-Z- group optionally bears 1 or 2 oxo substituents;

each of $R^2$ and $R^3$ is hydrogen; and $Q^2$ is an aryl group of formula Ia

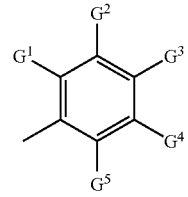

Ia wherein $G^1$ is selected from fluoro, chloro, bromo, iodo, trifluoromethyl, cyano, methyl, ethyl, vinyl, isopropenyl and ethynyl, each of $G^3$ and $G^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and each of $G^2$ and $G^5$ is hydrogen, or $G^1$ and $G^2$ together form a group of formula: —CH═CH—CH═CH—, —O—CH═CH— or —O—$CH_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of $G^3$, $G^4$ and $G^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound of the invention is a quinazoline derivative of the Formula I wherein:

m is 1 and the $R^1$ group is located at the 7-position and is selected from hydroxy, methoxy, benzyloxy, 3-morpholinopropoxy, 2-hydroxy-3-morpholinopropoxy, 3-(4-methylpiperazin-1-yl)propoxy, 2-hydroxy-3-(4-methylpiperazin-1-yl)propoxy, 2-methoxyethoxy and 2-(2-methoxyethoxy)ethoxy;

the $Q^1$-Z- group is selected from isopropoxy, 2-methoxyethoxy, cyclohexyloxy, tetrahydrofuran-3-yloxy, tetrahydropyran-4-yloxy, 2-imidazol-1-ylethoxy, 2-(1,2,4-triazol-1-yl)ethoxy, 3-pyrrolidin-1-ylpropoxy, N-methylpyrrolidin-3- yloxy, 3-morpholinopropoxy, 3-(1,1-dioxotetrahydro-4H-1, 4-thiazin-4-yl)propoxy, 2-piperidinoethoxy, N-methylpiperidin-4-yloxy, piperidin-4-ylmethoxy, N-methylpiperidin-4-ylmethoxy and 3-(4-methylpiperazin-1-yl)propoxy, each of $R^2$ and $R^3$ is hydrogen; and $Q^2$ is an aryl group of formula Ia

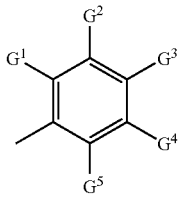

wherein $G^1$ is selected from fluoro, chloro, bromo and iodo, each of $G^3$ and $G^4$, which may be the same or different, is selected from hydrogen, chloro and methoxy, and each of $G^2$ and $G^5$ is hydrogen, or $G^1$ and $G^2$ together form a group of formula: —CH═CH—CH═C(Cl)—, —O—CH═C(Cl)— or —O—CH$_2$—O—, and each of $G^3$, $G^4$ and $G^5$ is hydrogen;

or a pharmaceutically-acceptable acid-addition salt thereof

A further preferred compound of the invention is a quinazoline derivative of the Formula I wherein:

m is 0 or m is 1 and the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, CH═CH and C≡C, and wherein any CH$_2$ or CH$_3$ group within a $R^1$ substituent optionally bears on each said CH$_2$ or CH$_3$ group a substituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

the $Q^1$-Z- group is selected from phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any CH$_2$ or CH$_3$ group within the $Q^1$-Z-group optionally bears on each said CH$_2$ or CH$_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z-group optionally bears 1 or 2 oxo substituents;

each of $R^2$ and $R^3$ is hydrogen; and $Q^2$ is an aryl group of formula Ia

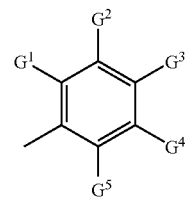

wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, or $G^1$ and $G^2$ together form a group of formula: —CH═CH—CH═CH—, —O—CH═CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoromethyl, cyano, hydroxy, methyl, ethyl, methoxy and ethoxy;

or a pharmaceutically-acceptable acid-addition salt thereof.

A further preferred compound of the invention is a quinazoline derivative of the Formula I wherein:

m is 1 and the $R^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

and wherein any $CH_2$ group within a $R^1$ substituent that is attached to two carbon atoms optionally bears a hydroxy group on said $CH_2$ group;

the $Q^1$-Z- group is selected from tetrahydrofuran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy and 3-(4-methylpiperazin-1-yl)propoxy, and wherein any $CH_2$ group within the $Q^1$-Z- group that is attached to two carbon atoms optionally bears a hydroxy group on said $CH_2$ group;

and wherein any heterocyclyl group within the $Q^1$-Z- group optionally bears 1 or 2 oxo substituents;

each of $R^2$ and $R^3$ is hydrogen; and $Q^2$ is an aryl group of formula Ia

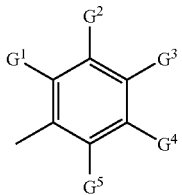

Ia wherein $G^1$ is selected from fluoro, chloro, bromo, iodo, trifluoromethyl, cyano, methyl, ethyl, vinyl, isopropenyl and ethynyl, each of $G^3$ and $G^4$, which may be the same or different, is selected from hydrogen, fluoro, chloro, bromo, trifluoromethyl, cyano, hydroxy, methyl, vinyl, ethyl, vinyl, allyl, isopropenyl, ethynyl, methoxy and ethoxy, and each of $G^2$ and $G^5$ is hydrogen, or $G^1$ and $G^2$ together form a group of formula: —CH=CH—CH=CH—, —O—CH=CH— or —O—$CH_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of $G^3$, $G^4$ and $G^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound of the invention is a quinazoline derivative of the Formula I wherein:

m is 1 and the $R^1$ group is located at the 7-position and is selected from hydroxy, methoxy, benzyloxy, 3-morpholinopropoxy, 2-hydroxy-3-morpholinopropoxy, 3-(4-methylpiperazin-1-yl)propoxy, 2-hydroxy-3-(4-methylpiperazin-1-yl) propoxy, 2-methoxyethoxy and 2-(2-methoxyethoxy) ethoxy;

the $Q^1$-Z- group is selected from tetrahydrofuran-3-yloxy, tetrahydropyran-4-yloxy, 2-imidazol-1-ylethoxy, 2-(1,2,4-triazol-1-yl)ethoxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, N-methylpiperidin-4-yloxy, piperidin-4-ylmethoxy, N-methylpiperidin-4-ylmethoxy and 3-(4-methylpiperazin-1-yl) propoxy, each of $R^2$ and $R^3$ is hydrogen; and $Q^2$ is an aryl group of formula Ia

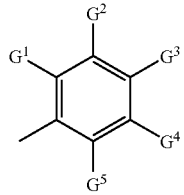

Ia wherein $G^1$ is selected from fluoro, chloro, bromo and iodo, each of $G^3$ and $G^4$, which may be the same or different, is selected from hydrogen, chloro and methoxy, and each of $G^2$ and $G^5$ is hydrogen, or $G^1$ and $G^2$ together form a group of formula: —CH=CH—CH=C(Cl)—, —O—CH=C(Cl)— or —O—$CH_2$—O—, and each of $G^3$, $G^4$ and $G^5$ is hydrogen;

or a pharmaceutically-acceptable acid-addition salt thereof.

A further preferred compound of the invention is a quinazoline derivative of the Formula I wherein:

m is 0 or m is 1 and the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

the $Q^1$-Z- group is selected from tetrahydrofuran-3-yloxy, tetrahydropyran-3-yloxy, tetrahydropyran-4-yloxy, 2-pyrrolidin-1-ylethoxy, 3-pyrrolidin-1-ylpropoxy, pyrrolidin-3- yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

each of $R^2$ and $R^3$ is hydrogen; and $Q^2$ is an aryl group of formula Ia

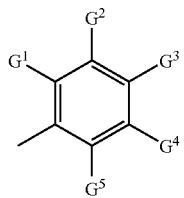

wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, or $G^1$ and $G^2$ together form a group of formula: —CH=CH—CH=CH—, —O—CH=CH— or —O—$CH_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoronmethyl, cyano, hydroxy, methyl, ethyl, methoxy and ethoxy;

or a pharmaceutically-acceptable acid-addition salt thereof.

A further preferred compound of the invention is a quinazoline derivative of the Formula I wherein:

m is 1 and the $R^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

and wherein any $CH_2$ group within a $R^1$ substituent that is attached to two carbon atoms optionally bears a hydroxy group on said $CH_2$ group;

the $Q^1$-Z- group is selected from tetrahydrofuran-3-yloxy, tetrahydropyran-4-yloxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy and 3-(4-methylpiperazin-1-yl)propoxy, and wherein any $CH_2$ group within the $Q^1$-Z- group that is attached to two carbon atoms optionally bears a hydroxy group on said $CH_2$ group;

and wherein any heterocyclyl group within the $Q^1$-Z- group optionally bears 1 or 2 oxo substituents;

each of $R^2$ and $R^3$ is hydrogen; and $Q^2$ is an aryl group of formula Ia

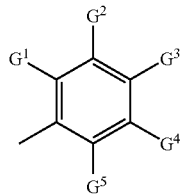

wherein $G^1$ is selected from fluoro, chloro, bromo, iodo, trifluoronmethyl, cyano, methyl, ethyl, vinyl, isopropenyl and ethynyl, each of $G^3$ and $G^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and each of $G^2$ and $G^5$ is hydrogen, or $G^1$ and $G^2$ together form a group of formula: —CH=CH—CH=CH—, —O—CH=CH— or —O—$CH_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of $G^3$, $G^4$ and $G^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound of the invention is a quinazoline derivative of the Formula I wherein:

m is 1 and the $R^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1-,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 2-[(2S)-2-(N-methyl-carbamoyl)pyrrolidin-1-yl]ethoxy, 2-[(2S)-2-(N,N-dimethylcarbamoyl)pyrrolidin-1-yl]ethoxy, 2-hydroxyethoxy, 3-hydroxypropoxy, 2-methoxyethoxy, 3-methoxypropoxy, 2-methylsulphonylethoxy, 3-methylsulphonylpropoxy, 2-(2-methoxyethoxy)ethoxy, 2-(4-pyridyloxy)ethoxy, 2-pyridylmethoxy, 3-pyridylmethoxy and 4-pyridylmethoxy;

and wherein any CH$_2$ group within a R$^1$ substituent that is attached to two carbon atoms optionally bears a hydroxy group on said CH$_2$ group;

the Q$^1$-Z- group is selected from tetrahydrofuran-3-yloxy, tetrahydropyran-4-yloxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 3-piperidinyloxy, N-methylpiperidin-3-yloxy, 4-piperidinyloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy, 3-(4-methylpiperazin-1-yl)propoxy, cyclobutyloxy, cyclopentyloxy and cyclohexyloxy, and wherein any CH$_2$ group within the Q$^1$-Z- group that is attached to two carbon atoms optionally bears a hydroxy group on said CH$_2$ group;

and wherein any heterocyclyl group within the Q$^1$-Z- group optionally bears 1 or 2 oxo substituents;

each of R$^2$ and R$^3$ is hydrogen; and

Q$^2$ is an aryl group of formula Ia

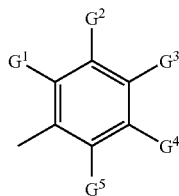

Ia wherein G$^1$ is selected from fluoro, chloro, bromo, iodo, trifluoromethyl, cyano, methyl, ethyl, vinyl, isopropenyl, ethynyl, methoxy and pyrrolidin-1yl, G$^2$ is hydrogen, each of G$^3$ and G$^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and G$^5$ is hydrogen or methoxy, or G$^1$ and G$^2$ together form a group of formula: —CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of G$^3$, G$^4$ and G$^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound of the invention is a quinazoline derivative of the Formula I wherein:

m is 1 and the R$^1$ group is located at the 7-position and is selected from hydroxy, methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperidin-4-ylethoxy, 2-(N-methylpiperidin-4-yl)ethoxy, 2-homopiperidin-1-ylethoxy, 3-homopiperidin-1-ylpropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 2-tetrahydropyran-4-ylethoxy, 2-hydroxyethoxy, 3-hydroxypropoxy, 2-methoxyethoxy, 3-methoxypropoxy, 2-methylsulphonylethoxy, 3-methylsulphonylpropoxy, 2-(2-methoxyethoxy)ethoxy, piperidin-4-ylmethoxy, N-methylpiperidin-4-ylmethoxy, 2-(4-pyridyloxy)ethoxy, 2-pyridylmethoxy, 3-pyridylmethoxy, 4-pyridylmethoxy and 3-cyanopyrid-4-ylmethoxy;

and wherein any CH$_2$ group within a R$^1$ substituent that is attached to two carbon atoms optionally bears a hydroxy group on said CH$_2$ group;

the Q$^1$-Z- group is selected from tetrahydrofuran-3-yloxy, tetrahydropyran-4-yloxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 3-piperidinyloxy, N-methylpiperidin-3-yloxy, 4-piperidinyloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy, 3-(4-methylpiperazin-1-yl)propoxy, cyclobutyloxy, cyclopentyloxy and cyclohexyloxy, and wherein any CH$_2$ group within the Q$^1$-Z- group that is attached to two carbon atoms optionally bears a hydroxy group on said CH$_2$ group;

and wherein any heterocyclyl group within the Q$^1$-Z- group optionally bears 1 or 2 oxo substituents;

each of R$^2$ and R$^3$ is hydrogen; and

Q$^2$ is an aryl group of formula Ia

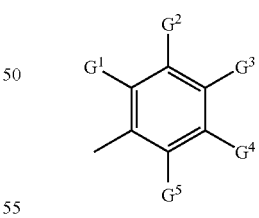

Ia wherein G$^1$ is selected from fluoro, chloro, bromo, iodo, trifluoromethyl, cyano, methyl, ethyl, vinyl, isopropenyl, ethynyl, methoxy and pyrrolidin-1yl, G$^2$ is hydrogen, each of G$^3$ and G$^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and G$^5$ is hydrogen or methoxy, or G$^1$ and G$^2$ together form a group of formula: —CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of G$^3$, G$^4$ and G$^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound of the invention is a quinazoline derivative of the Formula I wherein:

m is 1 and the R$^1$ group is located at the 7-position and is selected from hydroxy, methoxy, benzyloxy, 3-morpholinopropoxy, 2-hydroxy-3-morpholinopropoxy, 3-(4-methylpiperazin-1-yl)propoxy, 2-hydroxy-3-(4-methylpiperazin-1-yl)propoxy, 2-methoxyethoxy and 2-(2-methoxyethoxy)ethoxy;

the Q$^1$-Z- group is selected from tetrahydrofuran-3-yloxy, tetrahydropyran-4-yloxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, N-methylpiperidin-4-yloxy, piperidin-4-ylmethoxy, N-methylpiperidin-4-ylmethoxy and 3-(4-methylpiperazin-1-yl)propoxy, each of R$^2$ and R$^3$ is hydrogen; and Q$^2$ is an aryl group of formula Ia

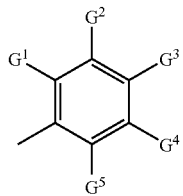

wherein G$^1$ is selected from fluoro, chloro, bromo and iodo, each of G$^3$ and G$^4$, which may be the same or different, is selected from hydrogen, chloro and methoxy, and each of G$^2$ and G$^5$ is hydrogen, or G$^1$ and G$^2$ together form a group of formula: —CH═CH—CH═C(Cl)—, —O—CH═C(Cl)— or —O—CH$_2$—O—, and each of G$^3$, G$^4$ and G$^5$ is hydrogen;

or a pharmaceutically-acceptable acid-addition salt thereof.

A further preferred compound of the invention is a quinazoline derivative of the Formula I wherein:

m is 1 and the R$^1$ group is located at the 7-position and is selected from methoxy, benzyloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-(4-methylpiperazin-1-yl)ethoxy, 3-(4-methylpiperazin-1-yl)propoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, 2-(4-pyridyloxy)ethoxy, 2-pyridylmethoxy, 3-pyridylmethoxy and 4-pyridylmethoxy;

the Q$^1$-Z- group is selected from tetrahydropyran-4-yloxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, 4-piperidinyloxy, N-methylpiperidin-4-yloxy, piperidin-4-ylmethoxy, N-methylpiperidin-4-ylmethoxy, 3-(4-methylpiperazin-1-yl)propoxy, cyclopentyloxy and cyclohexyloxy;

each of R$^2$ and R$^3$ is hydrogen; and

Q$^2$ is an aryl group of formula Ia

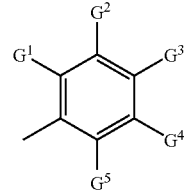

wherein G$^1$ is selected from chloro, bromo, trifluoronmethyl, methyl, methoxy and pyrrolidin-1-yl, G$^2$ is hydrogen, G$^3$ is selected from hydrogen and chloro, G$^4$ is methoxy, and G$^5$ is hydrogen, or G$^1$ and G$^2$ together form a group of formula: —CH═CH—CH═C(Cl)—, —O—CH═C(Cl)— or —O—CH$_2$—O—, each of G$^3$ and G$^4$ is hydrogen, and G$^5$ is hydrogen or chloro;

or a pharmaceutically-acceptable acid-addition salt thereof.

A further preferred compound of the invention is a quinazoline derivative of the Formula I wherein:

m is 1 and the R$^1$ group is located at the 7-position and is selected from methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-piperidinoethoxy, 3-piperidinopropoxy, 2-piperidin-4-ylethoxy, 2-(N-methylpiperidin-4-yl)ethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-homopiperidin-1-ylethoxy, 3-homopiperidin-1-ylpropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, piperidin-4-ylmethoxy, N-methylpiperidin-4-ylmethoxy, 2-(4-pyridyloxy)ethoxy, 2-pyridylmethoxy, 3-pyridylmethoxy, 4-pyridylmethoxy and 2-cyanopyrid-4-ylmethoxy, and wherein any CH$_2$ group within a R$^1$ substituent that is attached to two carbon atoms optionally bears a hydroxy group on said CH$_2$ group;

the Q$^1$-Z- group is selected from tetrahydropyran-4-yloxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, 4-piperidinyloxy, N-methylpiperidin-4-yloxy, piperidin-4-ylmethoxy, N-methylpiperidin-4-ylmethoxy, 3-(4-methylpiperazin-1-yl)propoxy, cyclopentyloxy and cyclohexyloxy;

each of R$^2$ and R$^3$ is hydrogen; and

Q$^2$ is an aryl group of formula Ia

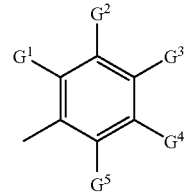

wherein G¹ is selected from chloro, bromo, trifluoromethyl, methyl, methoxy and pyrrolidin-1-yl, G² is hydrogen, G³ is selected from hydrogen and chloro, G⁴ is methoxy, and G⁵ is hydrogen, or G¹ and G² together form a group of formula: —O—CH=CH—, —O—CH=C(Cl)— or —O—CH₂—O—, each of G³ and G⁴ is hydrogen, and G⁵ is hydrogen or chloro;

or a pharmaceutically-acceptable acid-addition salt thereof.

A further preferred compound of the invention is a quinazoline derivative of the Formula I wherein:

m is 1 and the R¹ group is located at the 7-position and is selected from methoxy, benzyloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-(4-methylpiperazin-1-yl)ethoxy, 3-(4-methylpiperazin-1-yl)propoxy, 2-[(2S)-2-(N-methylcarbamoyl)pyrrolidin-(1-yl)]ethoxy, 2-[(2S)-2-(N,N-dimethylcarbamoyl)pyrrolidin-1-yl]ethoxy, 3-methylsulphonylpropoxy, 2-(4-pyridyloxy)ethoxy, 2-pyridylmethoxy, 3-pyridylmethoxy and 4-pyridylmethoxy;

the Q¹-Z- group is selected from tetrahydropyran-4-yloxy, 4-piperidinyloxy, N-methylpiperidin-4-yloxy, cyclopentyloxy and cyclohexyloxy;

each of R² and R³ is hydrogen; and

Q² is an aryl group of formula Ia

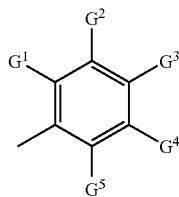

wherein G¹ and G² together form a group of formula: —O—CH₂—O—, each of G³ and G⁴ is hydrogen, and G⁵ is chloro;

or a pharmaceutically-acceptable acid-addition salt thereof.

A further preferred compound of the invention is a quinazoline derivative of the Formula I wherein:

m is 1 and the R¹ group is located at the 7-position and is selected from methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-piperidinoethoxy, 3-piperidinopropoxy, 3-(4-hydroxypiperidin-1-yl)propoxy, 2-piperidin-4-ylethoxy, 2-(N-methylpiperidin-4-yl)ethoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, piperidin-4-ylmethoxy, N-methylpiperidin-4-ylmethoxy, 2-(4-pyridyloxy)ethoxy, 2-pyridylmethoxy, 3-pyridylmethoxy and 4-pyridylmethoxy;

the Q¹-Z- group is selected from tetrahydropyran-4-yloxy, 4-piperidinyloxy, N-methylpiperidin-4-yloxy, piperidin-4-ylmethoxy, N-methylpiperidin-4-ylmethoxy, cyclopentyloxy and cyclohexyloxy;

each of R² and R³ is hydrogen; and

Q² is an aryl group of formula Ia

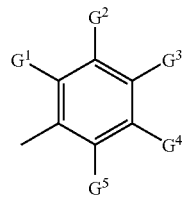

wherein G¹ and G² together form a group of formula: —O—CH₂—O—, each of G³ and G⁴ is hydrogen, and G⁵ is chloro;

or a pharmaceutically-acceptable acid-addition salt thereof.

A particular preferred compound of the invention is, for example, a quinazoline derivative of the Formula I selected from:

4-(2-chloro-5-methoxyanilino)-5,7-di-(3-morpholinopropoxy)quinazoline, 4-(2-bromo-5-methoxyanilino)-7-methoxy-5-(N-methylpiperidin-4-yloxy)quinazoline, 4-(2-chloro-5-methoxyanilino)-7-methoxy-5-(N-methylpiperidin-4-yloxy)quinazoline, 4-(2-chloro-5-methoxyanilino)-7-[3-(4-methylpiperazin-1-yl)propoxy]-5-tetrahydropyran-4-yloxyquinazoline, 4-(2-chloro-5-methoxyanilino)-7-(3-morpholinopropoxy)-5-tetrahydropyran-4-yloxyquinazoline, 4-(2-chloro-5-methoxyanilino)-7-[2-hydroxy-3-(4-methylpiperazin-1-yl)propoxy]-5-tetrahydropyran-4-yloxyquinazoline, 4-(2-chloro-5-methoxyanilino)-7-(2-hydroxy-3-morpholinopropoxy)-5-tetrahydropyran-4-yloxyquinazoline, 4-(2-chloro-5-methoxyanilino)-7-[3-(4-methylpiperazin-1-yl)propoxy]-5-tetrahydrofuran-3-yloxyquinazoline, 4-(2-chloro-5-methoxyanilino)-7-(3-morpholinopropoxy)-5-tetrahydrofuran-3-yloxyquinazoline, 4-(5-chloronaphth-1-ylamino)-7-methoxy-5-(N-methylpiperidin-4-yloxy)quinazoline and 4-(3-chlorobenzofuran-7-ylamino)-7-methoxy-5-(N-methylpiperidin-4-yloxy)quinazoline, or a pharmaceutically-acceptable acid-addition salt thereof.

A further particular preferred compound of the invention is, for example, a quinazoline derivative of the Formula I selected from:

4-(2-chloro-5-methoxyanilino)-5-isopropoxy-7-(3-morpholinopropoxy)quinazoline and 4-(2-chloro-5-methoxyanilino)-5-isopropoxy-7-[3-(4-methylpiperazin-1-yl)propoxy]quinazoline, or a pharmaceutically-acceptable acid-addition salt thereof.

A particular preferred compound of the invention is, for example, a quinazoline derivative of the Formula I selected from:

7-benzyloxy-4-(2-bromo-5-methoxyanilino)-5-piperidin-4-yloxyquinazoline, 4-(2-bromo-5-methoxyanilino)-7-(3-methylsulphonylpropoxy)-5-piperidin-4-yloxyquinazoline, 4-(2-bromo-5-methoxyanilino)-7-methoxy-5-piperidin-4-ylmethoxyquinazoline, 4-(2,4-dichloro-5-methoxyanilino)-7-methoxy-5-(N-methylpiperidin-4-yloxy)quinazoline, 4-(2,5-dimethoxyanilino)-7-methoxy-5-(N-methylpiperidin-4-yloxy)quinazoline, 4-(2,4-dichloro-5-methoxyanilino)-7-(2-pyrrolidin-1-ylethoxy)-5-tetrahydropyran-4-yloxyquinazoline,
4-(2,4-dichloro-5-methoxyanilino)-7-(2-piperidinoethoxy)-5-tetrahydropyran-4-yloxyquinazoline,
4-(2,4-dichloro-5-methoxyanilino)-7-(2-morpholinoethoxy)-5-tetrahydopyran-4-yloxyquinazoline,
4-(2,4-dichloro-5-methoxyanilino)-7-[2-(4-methylpiperazin-1-yl)ethoxy]-5-tetrahydropyran-4-yloxyquinazoline,
4-(2-bromo-5-methoxyanilino)-7-(2-pyrrolidin-1-ylethoxy)-5-tetrahydropyran-4-yloxyquinazoline,
4-(2-bromo-5-methoxyanilino)-7-(2-piperidinoethoxy)-5-tetrahydropyran-4-yloxyquinazoline,
4-(2-bromo-5-methoxyanilino)-7-[2-(4-methylpiperazin-1-yl)ethoxy]-5-tetrahydropyran-4-yloxyquinazoline,
4-(2-bromo-5-methoxyanilino)-7-(4-pyridyloxyethoxy)-5-tetrahydropyran-4-yloxyquinazoline,
4-(2-bromo-5-methoxyanilino)-7-{2-[(2S)-2-(N,N-dimethylcarbamoyl)pyrrolidin-1-yl]ethoxy}-5-tetrahydropyran-4-yloxyquinazoline,
4-(2-bromo-5-methoxyanilino)-7-{2-[(2S)-2-(N-methylcarbamoyl)pyrrolidin-1-yl]ethoxy}-5-tetrahydropyran-4-yloxyquinazoline,
4-(2-bromo-5-methoxyanilino)-7-(4-pylidylmethoxy)-5-tetrahydropyran-4-yloxyquinazoline,
4-(5-methoxy-2-pyrrolidin-1-ylanilino)-7-[3-(4-methylpiperazin-1-yl)propoxy]-5-tetrahydropyran-4-yloxyquinazoline, and
4-(2-bromo-5-methoxyanilino)-5-cyclopentyloxy-7-(2-pyrrolidin-1-ylethoxy)quinazoline;

or a pharmaceutically-acceptable acid-addition salt thereof.

A further particular preferred compound of the invention is, for example, a quinazoline derivative of the Formula I selected from:
4-(6-chloro-2,3-methylenedioxyanilino)-5-cyclopentyloxy-7-(2-pyrrolidin-1-ylethoxy)quinazoline,
4-(6-chloro-2,3-methylenedioxyanilno)-5-piperidin-4-yloxyquinazoline,
4-(6-chloro-2,3-methylenedioxyanilino)-7-methoxy-5-piperidin-4-yloxyquinazoline,
4-(6-chloro-2,3-methylenedioxyanilino)-7-methoxy-5-(N-methylpiperidin-4-yloxy)quinazoline,
4-(6-chloro-2,3-methylenedioxyanilino)-7-methoxy-5-piperidin-4-ylmethoxyquinazoline,
4-(6-chloro-2,3-methylenedioxyanilino)-7-(2-pyrrolidin-1-ylethoxy)-5-tetrahydropyran-4-yloxyquinazoline,
4-(6-chloro-2,3-methylenedioxyanilino)-7-(3-pyrrolidin-1-ylpropoxy)-5-tetrahydropyran-4-yloxyquinazoline,
4-(6-chloro-2,3-methylenedioxyanilino)-7-[3-(4-methylpiperazin-1-yl)propoxy]-5-tetrahydropyran-4-yloxyquinazoline,
4-(6-chloro-2,3-methylenedioxyanilino)-7-[2-(4-methylpiperazin-1-yl)ethoxy]-5-tetrahydropyran-4-yloxyquinazoline,
4-(6-chloro-2,3-methylenedioxyanilino)-7-(2-piperidinoethoxy)-5-tetrahydropyran-4-yloxyquinazoline,
4-(6-chloro-2,3-methylenedioxyanilino)-7-[2-(4-pyridyloxy)ethoxy]-5-tetrahydropyran-4-yloxyquinazoline,
4-(6-chloro-2,3-methylenedioxyanilino)-7-piperidin-4-ylmethoxy-5-tetrahydropyran-4-yloxyquinazoline and
4-(6-choro-2,3-methylenedioxyanilno)-7-(N-methylpiperidin-4-ylmethoxy)-5-tetrahydropyran-4-yloxyquinazoline;

or a pharmaceutically-acceptable acid-addition salt thereof.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I are provided as a further feature of the invention and are illustrated by the following representative process variants in which, unless otherwise stated, $Q^1$, Z, m, $R^1$, $R^2$, $R^3$ and $Q^2$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) The reaction, conveniently in the presence of a suitable base, of a quinazoline of the Formula II

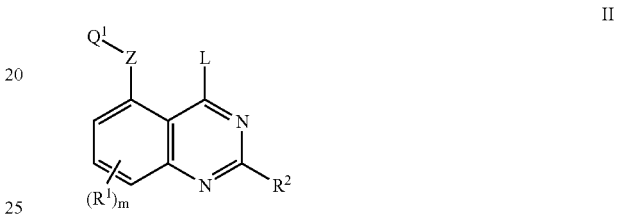

wherein L is a displaceable group and $Q^1$, Z, m, $R^1$ and $R^2$ have any of the meanings defined hereinbefore except that any functional group is protected if necessary, with an aniline of the Formula $Q^2NHR^3$ wherein $Q^2$ and $R^3$ have any of the meanings defined hereinbefore except that any functional group is protected if necessary, whereafter any protecting group that is present is removed by conventional means.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylfolmamide, N,N-dimethylacetamide, N-methylpyrrolidin-2-one or dimethylsulphoxide. The reaction is conveniently carried out at a temperature in the range, for example, 10 to 250° C., preferably in the range 40 to 80° C.

Typically, the quinazoline of the Formula II may be reacted with an aniline of the formula $Q^2NHR^3$ in the presence of a protic solvent such as isopropanol, conveniently in the presence of an acid, for example hydrogen chloride gas in diethyl ether, or hydrochloric acid, and at a temperature in the range, for example, 0 to 150° C., preferably at or near the reflux temperature of the reaction solvent.

The quinazoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2–6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, 2$^{nd}$ Edition, by T. Green et al., also published by John Wiley & Son, for general guidance on protecting groups.

Quinazoline starting materials of the Formula II may be obtained by conventional procedures. For example, a 3,4-dihydroquinazolin-4-one of Formula III

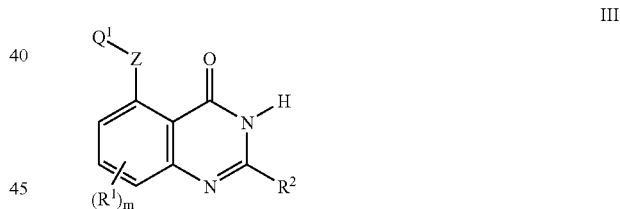

III wherein m, $R^1$, $Q^1$, Z and $R^2$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means.

The 4-chloroquinazoline so obtained may be converted, if required, into a 4-pentafluorophenoxyquinazoline by reaction with pentafluorophenol in the presence of a suitable base such as potassium carbonate and in the presence of a suitable solvent such as N,N-dimethylformamide.

(b) For the production of those compounds of the Formula I wherein Z is an oxygen atom, the coupling, conveniently in the presence of a suitable dehydrating agent, of an alcohol of the Formula $Q^1$-OH wherein Q¹ has any of the meanings defined hereinbefore except that any functional group is protected if necessary with a quinazoline of the Formula IV

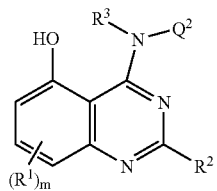

IV wherein m, R¹, R², R³ and Q² have any of the meanings defined hereinbefore except that any functional group is protected if necessary, whereafter any protecting group that is present is removed by conventional means.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

The quinazoline of the Formula IV may be obtained by conventional procedures. For example, a quinazoline of the Formula V

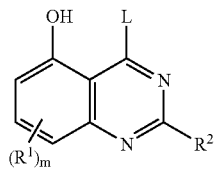

V wherein L is a displaceable group as defined hereinbefore and m, R¹ and R² have any of the meanings defined hereinbefore except that any functional group is protected if necessary, may be reacted with an aniline of the Formula

Q²NHR³ wherein Q² and R³ have any of the meanings defined hereinbefore except that any functional group is protected if necessary, whereafter any protecting group that is present is removed by conventional means.

(c) For the production of those compounds of the Formula I wherein m is 1 and R¹ is a group of the formula

Q³-X¹— wherein Q³ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)alkyl group and X¹ is an oxygen atom, the coupling, conveniently in the presence of a suitable dehydrating agent as defined hereinbefore, of a quinazoline of the Formula VI

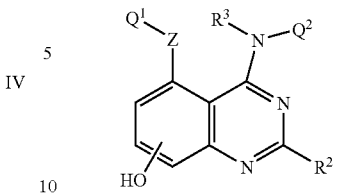

VI wherein Q¹, Z, R², R³ and Q² have any of the meanings defined hereinbefore except that any functional group is protected if necessary, with an appropriate alcohol wherein any functional group is protected if necessary, whereafter any protecting group that is present is removed by conventional means.

The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

(d) For the production of those compounds of the Formula I wherein R¹ is a hydroxy group, the cleavage of a quinazoline derivative of the Formula I wherein R¹ is a (1–6C) alkoxy or arylmethoxy group.

The cleavage reaction may conveniently be carried out by any of the many procedures known for such a transformation. The cleavage reaction of a compound of the Formula I wherein R¹ is a (1–6C)alkoxy group may be carried out, for example, by treatment of the quinazoline derivative with an alkali metal (1–6C)alkylsulphide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide. The cleavage reaction of a compound of the Formula I wherein R¹ is a arylmethoxy group may be carried out, for example, by hydrogenation of the quinazoline derivative in the presence of a suitable metallic catalyst such as palladium or by reaction with an organic or inorganic acid, for example trifluoroacetic acid. Such reactions are preferably carried out in the presence of a suitable inert solvent or diluent as defined hereinbefore and at a temperature in the range, for example, 10 to 150° C., preferably at or near ambient temperature.

(e) For the production of those compounds of the Formula I wherein Q¹, R¹ or Q² contains a primary or secondary amino group, the cleavage of the corresponding compound of Formula I wherein Q¹, R¹ or Q² contains a protected primary or secondary amino group.

Suitable protecting groups for an amino group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis, for example in the presence of trifluoroacetic acid.

(f) For the production of those compounds of the Formula I wherein Q¹, R¹ or Q² contains a (1–6C)alkoxy or substituted (1–6C)alkoxy group or a (1–6C)alkylamino or substituted (1–6C)alkylamino group, the alkylation, conveniently in the presence of a suitable base as defined hereinbefore, of a quinazoline derivative of the formula I wherein $Q^1$, $R^1$ or $Q^2$ contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature.

Conveniently for the production of those compounds of the Formula I wherein $Q^1$, $R^1$ or $Q^2$ contains a (1–6C) alkylamino or substituted (1–6C)alkylamino group, a reductive amination reaction may be employed. For example, for the production of those compounds of the Formula I wherein $Q^1$, $R^1$ or $Q^2$ contains a N-methyl group, the corresponding compound containing a N—H group may be reacted with formaldehyde in the presence of a suitable reducing agent. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxybdrohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

(g) For the production of those compounds of the Formula I wherein $Q^1$, $R^1$ or $Q^2$ contains an amino-hydroxy-disubstituted (1–6C)alkoxy group (such as 2-hydroxy-3-piperidinopropoxy, 2-hydroxy-3-methylaminopropoxy, 3-dimethylamino-2-hydroxypropoxy or 3-[N-(3-dimethylaminopropyl)-N-methylamino]-2-hydroxypropoxy), the reaction of a compound of the Formula I wherein $Q^1$, $R^1$ or $Q^2$ contains an epoxy-substituted (1–6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(h) The reaction, conveniently in the presence of a suitable base as defined hereinbefore, of a quinazoline of the Formula VII

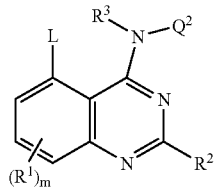

wherein L is a displaceable group as defined hereinbefore and m, $R^1$, $R^2$, $R^3$ and $Q^1$ have any of the meanings defined hereinbefore except that any functional group is protected if necessary, with a compound of the Formula $Q^1ZH$ wherein $Q^1$ and Z have any of the meanings defined hereinbefore except that any functional group is protected if necessary, whereafter any protecting group that is present is removed by conventional means.

The reaction is conveniently carried out in the presence of a suitable inert diluent or carrier as defined hereinbefore and at a temperature in the range 10 to 150° C., preferably at or near 50° C.

(i) For the production of those compounds of the Formula I wherein $Q^1$, $R^1$ or $Q^2$ contains an amino-substituted (1–6C) alkoxy group (such as 3-piperidinopropoxy, 3-methylaminopropoxy or 3-dimethylaminopropoxy), the reaction of a compound of the Formula I wherein $Q^1$, $R^1$ or $Q^2$ contains a halogeno-substituted (1–6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

When a pharmaceutically-acceptable salt of a quinazoline derivative of the Formula I is required, for example an acid-addition salt, it may be obtained by, for example, reaction of said quinazoline derivative with a suitable acid using a conventional procedure.

Biological Assays

The following assays can be used to measure the effects of the compounds of the present invention as c-Src tyrosine kinase inhibitors, as inhibitors in vitro of the proliferation of c-Src transfected fibroblast cells, as inhibitors in vitro of the migration of A549 human lung tumour cells and as inhibitors in vivo of the growth in nude mice of xenografts of A549 tissue.

(a) In Vitro Enzyme Assay

The ability of test compounds to inhibit the phosphorylation of a tyrosine containing polypeptide substrate by the enzyme c-7Src kinase was assessed using a conventional Elisa assay.

A substrate solution [100 µl of a 20 µg/ml solution of the polyamino acid Poly(Glu, Tyr) 4:1 (Sigma Catalogue No. P0275) in phosphate buffered saline (PBS) containing 0.2 mg/ml of sodium azide] was added to each well of a number of Nunc 96-well immunoplates (Catalogue No. 439454) and the plates were sealed and stored at 4° C. for 16 hours. The excess of substrate solution was discarded, and aliquots of Bovine Serum Albumin (BSA; 150 µl of a 5% solution in PBS) were transferred into each substrate-coated assay well and incubated for 1 hour at ambient temperature to block non specific binding. The assay plate wells were washed in turn with PBS containing 0.05% v/v Tween 20 (PBST) and with Hepes pH7.4 buffer (50 mM, 300 µl/well) before being blotted dry.

Each test compound was dissolved in dimethyl sulphoxide and diluted with distilled water to give a series of dilutions (from 100 µM to 0.001 µM). Portions (25 µl) of each dilution of test compound were transferred to wells in the washed assay plates. "Total" control wells contained diluted DMSO instead of compound. Aliquots (25 µl) of an aqueous magnesium chloride solution (80 mM) containing adenosine-5'-triphosphate (ATP; 40 µM) was added to all test wells except the "blank" control wells which contained magnesium chloride without ATP.

Active human c-Src kinase (recombinant enzyme expressed in Sf9 insect cells; obtained from Upstate Biotechnology Inc. product 14-117) was diluted immediately prior to use by a factor of 1:10,000 with an enzyme diluent which comprised 100 mM Hepes pH7.4 buffer, 0.2 mM sodium orthovanadate, 2 mM dithiothreitol and 0.02% BSA. To start the reactions, aliquots (50 µl) of freshly diluted enzyme were added to each well and the plates were incubated at ambient temperature for 20 minutes. The supernatant liquid in each well was discarded and the wells were washed twice with PBST. Mouse IgG anti-phosphotyrosine antibody (Upstate Biotechnology Inc. product 05-321; 100 µl) was diluted by a factor of 1:6000 with PBST containing 0.5% w/v BSA and added to each well. The plates were incubated for 1 hour at ambient temperature. The supernatant liquid was discarded and each well was washed with PBST (×4). Horse radish peroxidase (HRP)-linked sheep anti-mouse Ig antibody (Amersham Catalogue No. NXA 931; 100 µl) was diluted by a factor of 1:500 with PBST containing 0.5% w/v BSA and added to each well. The plates were incubated for 1 hour at ambient temperature. The supernatant liquid was discarded and the wells were washed with PBST (×4).

A PCSB capsule (Sigma Catalogue No. P4922) was dissolved in distilled water (100 ml) to provide phosphate-citrate pH5 buffer (50 mM) containing 0.03% sodium perborate. An aliquot (50 µl) of this buffer was mixed with a 50 mg tablet of 2,2'-azinobis(3-ethylbenzothiazoline-6-sulphonic acid) (ABTS; Boehringer Catalogue No. 1204 521). Aliquots (100 µl) of the resultant solution were added to each well. The plates were incubated for 20 to 60 minutes at ambient temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro c-Src Transfected NIH 3T3 (c-src 3T3) Fibroblast Proliferation Assay This assay determined the ability of a test compound to inhibit the proliferation of National Institute of Health (NIH) mouse 3T3 fibroblast cells that had been stably-transfected with an activating mutant (Y530F) of human c-Src.

Using a similar procedure to that described by Shalloway et al., Cell, 1987, 49, 65–73, NIH 3T3 cells were transfected with an activating mutant (Y530F) of human c-Src. The resultant c-Src 3T3 cells were typically seeded at $1.5 \times 10^4$ cells per well into 96-well tissue-culture-treated clear assay plates (Costar) each containing an assay medium comprising Dulbecco's modified Eagle's medium (DMEM; Sigma) plus 0.5% foetal calf serum (FCS), 2 mM glutamine, 100 units/ml penicillin and 0.1 mg/ml streptomycin in 0.9% aqueous sodium chloride solution. The plates were incubated overnight at 37° C. in a humidified (7.5% $CO_2$: 95% air) incubator.

Test compounds were solubilised in DMSO to form a 10 mM stock solution. Aliquots of the stock solution were diluted with the DMEM medium described above and added to appropriate wells. Serial dilutions were made to give a range of test concentrations. Control wells to which test compound was not added were included on each plate. The plates were incubated overnight at 37° C. in a humidified (7.5% $CO_2$: 95% air) incubator.

BrdU labelling reagent (Boehringer Mannheim Catalogue No. 647 229) was diluted by a factor of 1:100 in DMEM medium containing 0.5% FCS and aliquots (20 µl) were added to each well to give a final concentration of 10 µM). The plates were incubated at 37° C. for 2 hours. The medium was decanted. A denaturating solution (FixDenat solution, Boehringer Mannheim Catalogue No. 647 229; 50 µl) was added to each well and the plates were placed on a plate shaker at ambient temperature for 45 minutes. The supernatant was decanted and the wells were washed with PBS (200 µl per well). Anti-BrdU-Peroxidase solution (Boehringer Mannheim Catalogue No. 647 229) was diluted by a factor of 1:100 in PBS containing 1% BSA and 0.025% dried skimmed milk (Marvel (registered trade mark), Premier Beverages, Stafford, GB) and an aliquot (100 µl) of the resultant solution was added to each well. The plates were were placed on a plate shaker at ambient temperature for 90 minutes. The wells were washed with PBS (×5) to ensure removal of non bound antibody conjugate. The plates were blotted dry and tetramethylbenzidine substrate solution (Boehringer Mannheim Catalogue No. 647 229; 100 µl) was added to each well. The plates were gently agitated on a plate shaker while the colour developed during a 10 to 20 minute period. The absorbance of the wells was measured at 690 nm. The extent of inhibition of cellular proliferation at a range of concentrations of each test compound was determined and an anti-proliferative $IC_{50}$ value was derived.

(c) In Vitro Microdroplet Migration Assay

This assay determines the ability of a test compound to inhibit the migration of adherent mammalian cell lines, for example the human tumour cell line A549.

RPMI medium(Sigma) containing 10% FCS, 1% L-glutamine and 0.3% agarose (Difco Catalogue No. 0142-01) was warmed to 37° C. in a waterbath. A stock 2% aqueous agar solution was autoclaved and stored at 42° C. An aliquot (1.5 ml) of the agar solution was added to RPMI medium (10 ml) immediately prior to its use. A549 cells (Accession No. ATCC CCL185) were suspended at a concentration of $2 \times 10^7$ cells/ml in the medium and maintained at a temperature of 37° C.

A droplet (2 µl) of the cell/agarose mixture was transferred by pipette into the centre of each well of a number of 96-well, flat bottomed non-tissue-culture-treated microtitre plate (Bibby Sterilin Catalogue No. 642000). The plates were placed briefly on ice to speed the gelling of the agarose-cantaining droplets. Aliquots (90 µl) of medium which had been cooled to 4° C. were transferred into each well, taking care not to disturb the microdroplets. Test compounds were diluted from a 10 mM stock solution in DMSO using RPMI medium as described above. Aliquots (10 µl) of the diluted test compounds were transferred to the wells, again taking care not to disturb the microdroplets. The plates were incubated at 37° C. in a humidified (7.5% $CO_2$: 95% air) incubator for about 48 hours.

Migration was assessed visually and the distance of migration was measured back to the edge of the agar droplet. A migratory inhibitory $IC_{50}$ was derived by plotting the mean migration measurement against test compound concentration.

(d) In Vivo A549 Xenograft Growth Assay

This test measures the ability of compounds to inhibit the growth of the A549 human carcinoma grown as a tumour in athymic nude mice (Alderley Park nu/nu strain). A total of about $5 \times 10^6$ A549 cells in matrigel (Beckton Dickinson Catalogue No. 40234) were injected subcutaneously into the left flank of each test mouse and the resultant tumours were allowed to grow for about 14 days. Tumour size was measured twice weekly using callipers and a theoretical volume was calculated. Animals were selected to provide control and treatment groups of approximately equal average tumour volume. Test compounds were prepared as a ball-milled suspension in 1% polysorbate vehicle and dosed orally once daily for a period of about 28 days. The effect on tumour growth was assessed.

Although the pharmacological properties of the compounds of the Formula I vary with structural change as expected, in general activity possessed by compounds of the Formula I, may be demonstrated at the following concentrations or doses in one or more of the above tests (a), (b), (c) and (d):

| | |
|---|---|
| Test (a):- | IC$_{50}$ in the range, for example, 0.001–10 µM; |
| Test (b):- | IC$_{50}$ in the range, for example, 0.01–20 µM; |
| Test (c):- | activity in the range, for example, 0.01–25 µM; |
| Test (d):- | activity in the range, for example, 1–200 mg/kg/day. |

No physiologically-unacceptable toxicity was observed in Test (d) at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinazoline derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing) or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinazoline derivative of the Formula I, or a pharmaceutically-acceptable salt thereof, as defined hereinbefore for use in a method of treatment of the human or animal body by therapy.

As stated above, it is known that the predominant role of c-Src non-receptor tyrosine kinase is to regulate cell motility which is necessarily required for a localised tumour to progress through the stages of dissemination into the blood stream, invasion of other tissues and initiation of metastatic tumour growth. We have found that the quinazoline derivatives of the present invention possess potent anti-tumour activity which it is believed is obtained by way of inhibition of one or more of the non-receptor tyrosine-specific protein kinases such as c-Src kinase that are involved in the signal transduction steps which lead to the invasiveness and migratory ability of metastasising tumour cells.

Accordingly the quinazoline derivatives of the present invention are of value as anti-tumour agents, in particular as selective inhibitors of the motility, dissemination and invasiveness of mammalian cancer cells leading to inhibition of metastatic tumour growth. Particularly, the quinazoline derivatives of the present invention are of value as anti-invasive agents in the containment and/or treatment of solid tumour disease. Particularly, the compounds of the present invention are expected to be useful in the prevention or treatment of those tumours which are sensitive to inhibition of one or more of the multiple non-receptor tyrosine kinases such as c-Src kinase that are involved in the signal transduction steps which lead to the invasiveness and migratory ability of metastasising tumour cells. Further, the compounds of the present invention are expected to be useful in the prevention or treatment of those tumours which are mediated alone or in part by inhibition of the enzyme c-Src, ie. the compounds may be used to produce a c-Src enzyme inhibitory effect in a warm-blooded animal in need of such treatment. Specifically, the compounds of the present invention are expected to be useful in the prevention or treatment of solid tumour disease.

Thus according to this aspect of the invention there is provided the use of a quinazoline derivative of the Formula I, or a pharmaceutically-acceptable salt thereof, as defined hereinbefore in the manufacture of a medicament for use as an anti-invasive agent in the containment and/or treatment of solid tumour disease.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in the prevention or treatment of solid tumour disease in a warm-blooded animal such as man.

According to a further feature of this aspect of the invention there is provided a method for the prevention or treatment of solid tumour disease in a warm-blooded animal, such as man, in need of such treatment which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in the prevention or treatment of those tumours which are sensitive to inhibition of non-receptor tyrosine kinases such as c-Src kinase that are involved in the signal transduction steps which lead to the invasiveness and migratory ability of metastasising tumour cells.

According to a further feature of this aspect of the invention there is provided a method for the prevention or treatment of those tumours which are sensitive to inhibition of non-receptor tyrosine kinases such as c-Src kinase that are involved in the signal transduction steps which lead to the invasiveness and migratory ability of metastasising tumour cells which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in providing a c-Src kinase inhibitory effect.

According to a further feature of this aspect of the invention there is provided a method for providing a c-Src kinase inhibitory effect which comprises administering to said animal an effective amount of a quinazoline derivative of the Formula I, or a pharmaceutically-acceptable salt thereof, as defined hereinbefore.

The anti-invasive treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:

(i) other anti-invasion agents (for example metalloproteinase inhibitors like marimastat and inhibitors of urokinase plasminogen activator receptor function);
(ii) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylmethyl)-N-(prop-2-ynyl)amino]benzamido}-4-(tetrazol-5-yl)butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);
(iii) cytostatic agents such as antioestrogens (for example tanioxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5α-reductase such as finasteride;
(iv) inhibitors of growth factor function, for example such inhibitors include growth factor antibodies, growth factor receptor antibodies, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholinopropoxy)quinazolin-4-amine (ZD1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family; and
(v) antiangiogenic agents such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin αvβ3 function and angiostatin).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of c-Src. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture;

(viii) the following abbreviations have been used:
DMF N,N-dimethylformamide
DMSO dimethylsulphoxide
THF tetrahydrofuran
DMA N,N-dimethylacetamide

EXAMPLE 1

4-(2-chloro-5-methoxyanilino)-7-methoxy-5-(3-morpholinopropoxy)-quinazoline

Di-tert-butyl azodicarboxylate (0.208 g) was added dropwise to a stirred mixture of 4-(2-chloro-5-methoxyanilino)-5-hydroxy-7-methoxyquinazoline (0.2 g), 4-(3-hydroxypropyl)morpholine (*Bull. Soc. Chim. Fr.*, 1962, 1117; 0.131 g), triphenylphosphine (0.237 g) and methylene chloride (3 ml). The reaction mixture was stirred at ambient temperature for 1 hour. The mixture was evaporated and the residue was purified by column chromatography on silica using a 99:1 mixture of methylene chloride and a saturated methanolic ammonia solution as eluent. The material so obtained was triturated under diethyl ether. The resultant solid was isolated, washed with diethyl ether and dried under vacuum to give the title compound (0.12 g); NMR Spectrum: (DMSOd$_6$ and CF$_3$COOD) 2.35 (m, 2H), 3.1 (t, 2H), 3.3 (t, 2H), 3.5 (d, 2H), 3.68 (t, 2H), 3.8 (s, 3H), 4.0 (d, 2H), 4.02 (s, 3H), 4.6 (t, 2H), 6.93 (s, 1H), 7.05–7.15 (m, 2H), 7.5 (s, 1H), 7.57 (d, 1H), 8.87 (s, 1H); Mass Spectrum: M+H$^+$ 459 and 461; Elemental Analysis: Found C, 60.0; H, 6.0; N, 12.1; C$_{23}$H$_{27}$ClN$_4$O$_4$ requires C, 60.19; H, 5.93; N, 12.2%.

The 4-(2-chloro-5-methoxyanilino)-5-hydroxy-7-methoxyquinazoline used as a starting material was prepared as follows:

A mixture of 3,5-dimethoxyaniline hydrochloride (54.7 g), oxalyl chloride (54 ml) and methanol (500 ml) was stirred and heated to reflux for 1.5 hours. The mixture was cooled to ambient temperature. The precipitate was isolated, washed in turn with methanol and diethyl ether and dried under vacuum to give 4,6-dimethoxy-2,3-dioxoindoline (55 g); NMR Spectrum: (DMSOd$_6$) 3.85 (s, 3H), 3.9 (s, 3H), 6.0 (s, 1H), 6.2 (s, 1H), 10.9 (s, 1H); Mass Spectrum: M+Na$^+$ 230.

Hydrogen peroxide (30% solution in water, 30 ml) was added dropwise to a stirred solution of 4,6-dimethoxy-2,3-dioxoindoline (27 g) in a concentrated aqueous sodium hydroxide solution (33%, 220 ml). The resultant mixture was stirred at ambient temperature for 10 minutes. Ice was added and the basicity of the mixture was reduced to pH9 by the addition of concentrated aqueous hydrochloric acid and the mixture was then acidified to pH3.5 by the addition of glacial acetic acid. The resultant precipitate was isolated, washed with water and dried overnight under vacuum to give 2-amino-4,6-dimethoxybenzoic acid (15.9 g); NMR Spectrum: (DMSOd$_6$) 3.7 (s, 3H), 3.78 (s, 3H), 5.79 (s, 1H), 5.92 (s, 1H).

Using an analogous procedure to that described by Lombardi et al., *Chemistry & Industry*, 1990, 708, diazomethane was generated from a mixture of N-methyl-N-nitroso-4-toluenesulphonamide (31 g), ethanol (200 ml) and a saturated aqueous sodium hydroxide solution (35 ml) and bubbled though a solution of 2-amino-4,6-dimethoxybenzoic acid (15.9 g) in methylene chloride (280 ml) which had been cooled to 0° C. The resultant reaction mixture was evaporated and the residue was purified by column chromatography on silica using methylene chloride as eluent. There was thus obtained methyl 2-amino-4,6-dimethoxybenzoate (16.2 g); NMR Spectrum: (DMSOd$_6$) 3.65 (s, 3H), 3.7 (s, 6H), 5.75 (s, 1H), 5.9 (s, 1H), 6.2 (br s, 2H).

A mixture of methyl 2-amino-4,6-dimethoxybenzoate (16 g), formamidine acetate (24 g) and 2-methoxyethanol (330 ml) was stirred and heated to reflux until all of the starting material had reacted. The mixture was evaporated and the residue was triturated under water (100 ml). The resultant solid was isolated, washed with water and dried under vacuum to give 5,7-dimethoxy-3,4-dihydroquinazolin-4-one (14.5 g); NMR Spectrum: (DMSOd$_6$) 3.82 (s, 3H), 3.86 (s, 3H), 6.5 (s, 1H), 6.7 (s, 1H), 7.9 (s, 1H), 11.7 (br s, 1H).

A mixture of a portion (0.35 g) of the material so obtained, phosphoryl chloride (0.95 ml) and acetonitrile (8 ml) was stirred and heated to reflux for 2 hours. The mixture was cooled to 0°C. and isopropanol (8 ml) and 2-chloro-5-methoxyaniline (0.321 g) were added in turn. The resultant mixture was heated to reflux for 1.5 hours. The mixture was cooled to ambient temperature and the resultant precipitate was filtered, washed with isopropanol and with diethyl ether and dried under vacuum. There was thus obtained 4-(2-chloro-5-methoxyanilino)-5,7-dimethoxyquinazoline hydrochloride (0.365 g); NMR Spectrum: (DMSOd$_6$) 3.8 (s, 3H), 4.0 (s, 3H), 4.2 (s, 3H), 7.0 (m, 3H), 7.6 (d, 1H), 7.62 (s, 1H), 8.8 (s, 1H), 10.9 (s, 1H); Mass Spectrum: M+H$^+$ 346 and 348.

A mixture of 4-(2-chloro-5-methoxyanilino)-5,7-dimethoxyquinazoline hydrochloride (2.5 g), pyridine hydrochloride (0.76 g) and pyridine (50 ml) was stirred and heated to reflux for 9 hours. The mixture was cooled to ambient temperature and evaporated. The residue was suspended in water and the mixture was basified to pH10 by the addition of aqueous sodium bicarbonate solution. The resultant solid precipitate was isolated, washed in turn with water, with methylene chloride and with diethyl ether and dried overnight under vacuum at 50° C. There was thus obtained 4-(2-chloro-5-methoxyanilino)-5-hydroxy-7-methoxyquinazoline (2.1 g); NMR Spectrum: (DMSOd$_6$) 3.8 (s, 3H), 3.85 (s, 3H), 6.3–6.5 (m, 2H), 6.8 (d, 1H), 7.4 (d, 1H), 8.1 (br s, 1H), 8.42 (br s, 1H).

EXAMPLE 2

Using an analogous procedure to that described in Example 1, the appropriate 5-hydroxyquinazoline was reacted with the appropriate alcohol to give the compounds described in Table I.

The 1-(3-hydroxypropyl)-4-methylpiperazine used as a starting material was prepared as follows:

A mixture of 3-bromopropanol (20 ml), N-methylpiperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distil-

TABLE I

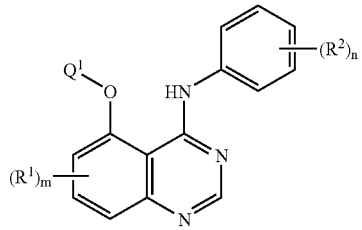

| No. & Note | $(R^1)_m$ | $Q^1$ | $(R^2)_n$ |
|---|---|---|---|
| [1] | 7-methoxy | 3-(4-methylpiperazin-1-yl)propyl | 2-chloro-5-methoxy |
| [2] | 7-methoxy | 2-piperidinomethyl | 2-chloro-5-methoxy |
| [3] | 7-methoxy | 3-pyrrolidin-1-ylpropyl | 2-chloro-5-methoxy |
| [4] | 7-methoxy | 2-(1,2,4-triazol-1-yl)ethyl | 2-chloro-5-methoxy |
| [5] | 7-benzyloxy | 3-morpholinopropyl | 2-chloro-5-methoxy |
| [6] | 7-benzyloxy | 3-pyrrolidin-1-ylpropyl | 2-chloro-5-methoxy |
| [7] | hydrogen | 3-morpholinopropyl | 2-bromo-5-methoxy |
| [8] | hydrogen | 3-(1,1-dioxotetrahydro-4H-1,4-thiazin-4-yl)propyl | 2-bromo-5-methoxy |
| [9] | hydrogen | 2-(4-methylpiperiazin-1-yl)ethyl | 2-bromo-5-methoxy |
| [10] | hydrogen | 3-(4-methylpiperazin-1-yl)propyl | 2-chloro-5-methoxy |
| [11] | hydrogen | 2-imidazol-1-ylethyl | 2-chloro-5-methoxy |
| [12] | 7-methoxy | N-methylpiperidin-4-yl | 2-chloro-5-methoxy |
| [13] | hydrogen | N-methylpiperidin-4-yl | 2-chloro-5-methoxy |
| [14] | hydrogen | N-methylpiperidin-4-yl | 2-bromo-5-methoxy |
| [15] | hydrogen | N-methylpiperidin-4-yl | 2,5-dichloro |
| [16] | hydrogen | N-(tert-butoxycarbonyl)-piperidin-4-ylmethyl | 2-chloro-5-methoxy |
| [17] | hydrogen | N-(tert-butoxycarbonyl)-piperidin-4-ylmethyl | 2-bromo-5-methoxy |
| [18] | 7-methoxy | 2-methoxyethyl | 2-chloro-5-methoxy |
| [19] | 7-methoxy | N-methylpyrrolidin-3-yl | 2-bromo-5-methoxy |
| [20] | 7-benzyloxy | 4-tetrahydropyranyl | 2-chloro-5-methoxy |
| [21] | hydrogen | 4-tetrahydropyranyl | 2-chloro-5-methoxy |
| [22] | 7-benzyloxy | 3-tetrahydrofuranyl | 2-chloro-5-methoxy |
| [23] | 7-(3-morpholinopropoxy) | 3-tetrahydrofuranyl | 2-chloro-5-methoxy |
| [24] | 7-[3-(4-methylpiperiazin-1-yl)propoxy] | 3-tetrahydrofuranyl | 2-chloro-5-methoxy |
| [25] | 7-benzyloxy | isopropyl | 2-chloro-5-methoxy |
| [26] | 7-methoxy | 4-tetrahydropyranyl | 2-bromo-5-methoxy |
| [27] | 7-methoxy | 3-pyrrolidin-1-ylpropyl | 6-chloro-2,3-methylenedioxy |
| [28] | 7-methoxy | 3-(4-methylpiperazin-1-ylpropyl) | 6-chloro-2,3-methylenedioxy |

Notes

[1] The reaction product was triturated under a mixture of isopropanol and diethyl ether and a 6M solution of hydrogen chloride in isopropanol was added. The resultant precipitate was isolated, washed with diethyl ether and dried under vacuum to give the product as the dihydrochloride salt; NMR Spectrum: (DMSOd$_6$) 2.2–2.4 (m, 2H), 2.8 (br s, 3H), 3.2–3.7 (m, 10H), 3.8 (s, 3H), 4.0 (s, 3H), 4.6 (m, 2H), 6.95–7.0 (m, 2H), 7.08 (s, 1H), 7.55 (d, 1H), 7.6 (s, 1H), 8.8 (s, 1H), 10.6 (s, 1H); Mass Spectrum: M+H$^+$ 472 and 474.

lation to give the required starting material as an oil; NMR Spectrum: (CDCl$_3$) 1.72 (m, 2H), 2.3 (s, 3H), 2.2–2.8 (m, 8H), 2.6 (t, 2H), 3.8 (t, 2H), 5.3 (br s, 1H).

[2] The reaction product was dissolved in a mixture of isopropanol and diethyl ether and a 6M solution of hydrogen chloride in isopropanol was added. The resultant precipitate was isolated, washed with diethyl ether and dried under vacuum to give the product as the dihydrochloride salt; NMR Spectrum: (DMSOd$_6$ and CF$_3$COOD) 1.3–1.5 (m, 2H), 1.65–1.9 (m, 4H), 3.02 (t, 2H), 3.6 (d, 2H), 3.7 (br s, 2H), 3.8 (s, 3H), 4.02 (s, 3H), 4.9 (br s, 2H), 7.0 (s, 1H), 7.05 (m, 1H), 7.1 (s, 1H), 7.3 (s, 1H), 7.58 (d, 1H), 8.8 (s, 1H); Mass Spectrum: M+H$^+$ 443 and 445.

[3] The reaction product was dissolved in a mixture of isopropanol and diethyl ether and a 6M solution of hydrogen chloride in isopropanol was added. The resultant precipitate was isolated, washed with diethyl ether and dried under vacuum to give the product as the dihydrochloride salt; NMR Spectrum: (DMSOd$_6$ and CF$_3$COOD) 1.9 (m, 2H), 2.05 (m, 2H), 2.35 (m, 2H), 3.02 (m, 2H), 3.35 (t, 2H), 3.6 (m, 2H), 3.8 (s, 3H), 4.02 (s, 3H), 4.6 (t, 2H), 6.95 (d, 1H), 7.05 (m, 1H), 7.1 (s, 1H), 7.5 (d, 1H), 7.6 (d, 1H), 8.9 (s, 1H); Mass Spectrum: M+H$^+$ 443 and 445.

The N-(3-hydroxypropyl)pyrrolidine used as a starting material was prepared as follows:

A mixture of 3-chloropropanol (66 g), pyrrolidine (50 g), potassium carbonate (145 g) and acetonitrile (1 L) was stirred and heated to reflux for 20 hours. The mixture was cooled to ambient temperature and filtered. The filtrate was evaporated and the residue was purified by distillation to give the required starting material as an oil (62 g); NMR Spectrum: (CDCl$_3$) 1.6–1.8 (m, 6H), 2.55 (br s, 4H), 2.75 (t, 2H), 3.85 (t, 2H), 5.5 (br s, 1H).

[4] The product was precipitated from the reaction mixture by the addition of further methylene chloride. The product was isolated, washed with diethyl ether and dried under vacuum. The product so obtained gave the following data: NMR Spectrum: (DMSOd$_6$ and CF$_3$COOD) 3.82 (s, 3H), 4.0 (s, 3H), 4.8 (m, 2H), 4.85 (m, 2H), 6.9 (s, 1H), 7.05 (s, 1H), 7.1 (m, 1H), 7.3 (d, 1H), 7.58 (d, 1H), 7.65 (s, 1H), 8.67 (s, 1H), 8.79 (s, 1H); Mass Spectrum: M+H$^+$ 427 and 429.

The N$^1$-(2-hydroxyethyl)-1,2,4-triazole used as a starting material was prepared according to the procedure disclosed in *Ann. Pharm. Fr.*, 1977, 35, 503.

[5] The product gave the following data: NMR Spectrum: (DMSOd$_6$) 2.1 (m, 2H), 2.32 (br s, 4H), 2.45 (t, 2H), 3.52 (m, 4H), 3.8 (s, 3H), 4.5 (t, 2H), 5.3 (s, 2H), 6.8 (m, 1H), 6.95 (s, 1H), 6.92 (s, 1H), 7.3–7.6 (m, 6H), 8.35 (s, 1H), 8.55 (s, 1H), 10.12 (s, 1H); Mass Spectrum: M+H$^+$ 535 and 537.

The 7-benzyloxy-4-(2-chloro-5-methoxyanilino)-5-hydroxyquinazoline used as a starting material was prepared as follows:

A mixture of 3,5-dibenzyloxyaniline hydrochloride (*J. Org. Chem.*, 1975, 40, 1556; 10 g) and oxalyl chloride (15 ml) was heated to 170° C. for 3 hours. The mixture was cooled to ambient temperature, methanol (45 ml) was added and the mixture was heated to reflux for 1 hour. The mixture was cooled to ambient temperature and the precipitate was isolated, washed with methanol and dried under vacuum to give 4,6-dibenzyloxy-2,3-dioxoindoline (8.8 g); NMR Spectrum: (DMSOd$_6$) 5.22 (s, 2H), 5.28 (s, 2H), 6.12 (s, 1H), 6.42 (s, 1H), 7.3–7.55 (m, 10H), 10.97 (s, 1H).

Hydrogen peroxide (30% solution in water, 13 ml) was added dropwise to a stirred solution of 4,6-dibenzyloxy-2,3-dioxoindoline (14.3 g) in a concentrated aqueous sodium hydroxide solution (22.3 g in 90 ml of water) which had been heated to 70° C. The resultant mixture was stirred at 70° C. for 30 minutes and then cooled to ambient temperature. Ice was added and the basicity of the mixture was reduced to pH9 by the addition of 2N aqueous hydrochloric acid and the mixture was then acidified to pH3.7 by the addition of glacial acetic acid. The resultant precipitate was purified by column chromatography on silica using a 99:1 mixture of methylene chloride and methanol as eluent. There was thus obtained 2-amino-4,6-dibenzyloxybenzoic acid (8 g); NMR Spectrum: (DMSOd$_6$) 5.05 (s, 2H), 5.15 (s, 2H), 6.01 (s, 1H), 6.05 (s, 1H), 7.3–7.6 (m, 10H).

Using an analogous procedure to that described by Lombardi et al., *Chemistry & Industry*, 1990, 708, diazomethane was generated from a mixture of N-methyl-N-nitroso-4-toluenesulphonamide (11.5 g), ethanol (60 ml) and a saturated aqueous sodium hydroxide solution (30 ml) and bubbled though a solution of 2-amino-4,6-dibenzyloxybenzoic acid (8 g) in methylene chloride (170 ml) which had been cooled to 0° C. The resultant reaction mixture was evaporated and the residue was triturated under diethyl ether. There was thus obtained methyl 2-amino-4,6-dibenzyloxybenzoate (7.7 g); NMR Spectrum: (DMSOd$_6$) 3.74 (s, 3H), 5.07 (s, 2H), 5.11 (s, 2H), 6.0 (s, 1H), 6.04 (s, 1H), 6.25 (br s, 2H), 7.28–7.5 (m, 10H).

A mixture of methyl 2-amino-4,6-dibenzyloxybenzoate (7.7 g), formamidine acetate (7.2 g) and 2-methoxyethanol (100 ml) was stirred and heated to reflux until all of the starting material had reacted. The mixture was evaporated and the residue was triturated under water (60 ml). The resultant solid was isolated, washed with water and dried under vacuum to give 5,7-dibenzyloxy-3,4-dihydroquinazolin-4-one (6.8 g); NMR Spectrum: (DMSOd$_6$) 5.24 (s, 4H), 6.75 (s, 1H), 6.8 (s, 1H), 7.3–7.7 (m, 10H), 7.95 (s, 1H), 11.75 (br s, 1H).

A mixture of a portion (6 g) of the material so obtained, phosphoryl chloride (1.72 ml), diisopropylethylamine (7.3 ml) and 1,2-dichloroethane (60 ml) was stirred and heated to reflux for 2 hours. The mixture was evaporated and a mixture of the residue and isopropanol (80 ml) was cooled to 10° C. and 2-chloro-5-methoxyaniline (3.4 g) and diisopropylethylamine (1.45 ml) were added in turn. The resultant mixture was heated to reflux for 1.5 hours. The mixture was cooled to ambient temperature and the resultant precipitate was isolated, washed with isopropanol and with diethyl ether and dried under vacuum. There was thus obtained 4-(2-chloro-5-methoxyanilino)-5,7-dibenzyloxyquinazoline hydrochloride (6.35 g); NMR Spectrum: (DMSOd$_6$) 3.8 (s, 3H), 5.31 (s, 2H), 5.65 (s, 2H), 6.95 (m, 1H), 7.02 (s, 1H), 7.15 (s, 1H), 7.3–7.5 (m, 9H), 7.6 (d, 2H), 7.7 (s, 1H), 8.8 (s, 1H); Mass Spectrum: M+H$^+$ 498 and 500.

A mixture of 4-(2-chloro-5-methoxyanilino)-5,7-dibenzyloxyquinazoline hydrochloride (4.3 g), pyridine hydrochloride (0.94 g) and pyridine (90 ml) was stirred and heated to reflux for 9 hours. The mixture was cooled to ambient temperature and evaporated. The residue was triturated under water. The resultant solid precipitate was isolated, washed with water and dried overnight under vacuum. The material was then triturated under methanol. The resultant solid was isolated and dried under vacuum. There was thus obtained 7-benzyloxy-4-(2-chloro-5-methoxyanilino)-5-hydroxyquinazoline (3.1 g); NMR Spectrum: (DMSOd$_6$ and CF$_3$COOD) 3.85 (s, 3H), 5.3 (s, 2H), 6.85 (s, 2H), 7.0 (m, 1H), 7.3–7.6 (m, 6H), 7.8 (d, 1H), 8.85 (s, 1H).

[6] The product gave the following data: NMR Spectrum: (CDCl$_3$) 1.75 (br s, 4H), 2.2 (m, 2H), 2.5 (br s, 4H), 2.65 (t, 2H), 3.85 (s, 3H), 4.4 (t, 2H), 5.2 (s, 2H), 6.62 (d, 1H), 6.7 (s, 1H), 6.95 (s, 1H), 7.2–7.5 (m, 6H), 8.4 (s, 1H), 8.6 (s, 1H), 10.1 (s, 1H); Mass Spectrum: M+H$^+$ 519.

[7] The reaction product was triturated under diethyl ether, a 6.3M solution of hydrogen chloride in isopropanol was added and the mixture was stirred at ambient temperature for 1 hour. The resultant precipitate was isolated, washed with diethyl ether and dried under vacuum to give the product as a dihydrochloride salt which gave the following data: NMR Spectrum: (DMSOd$_6$ and CF$_3$COOD) 2.3–2.45 (m, 2H), 3.1 (t, 2H), 3.3 (t, 2H), 3.45 (d, 2H), 3.75

(t, 2H), 3.81 (s, 3H), 4.0 (d, 2H), 4.68 (t, 2H), 7.08 (m, 1H), 7.5–7.7 (m, 4H), 8.1 (m, 1H), 8.95 (s, 1H); Mass Spectrum: M+H$^+$ 473 and 475.

The 4-(2-bromo-5-methoxyanilino)-5-hydroxyquinazoline used as a starting material was prepared as follows:

A mixture of 5-methoxy-3,4-dihydroquinazolin-4-one (International Patent Application WO 96/09294, pages 28 and 29; 2.1 g), phosphoryl chloride (1.23 ml), diisopropylethylamine (5.2 ml) and 1,2-dichloroethane (20 ml) was stirred and heated to 80° C. for 3 hours. The mixture was evaporated. The residue was dissolved in isopropanol (20 ml) and 2-bromo-5-methoxyaniline (*J. Amer. Chem. Soc.*, 1994, 116, 11797; 2.45 g) and a 6M solution of hydrogen chloride in isopropanol (0.33 ml) were added in turn. The resultant mixture was heated to 80° C. for 1.5 hours. The mixture was cooled to ambient temperature and the resultant precipitate was isolated, washed with isopropanol and with diethyl ether and dried under vacuum. There was thus obtained 4-(2-bromo-5-methoxyanilino)-5-methoxyquinazoline hydrochloride (3.8 g); NMR Spectrum: (DMSOd$_6$ and CF$_3$COOD) 3.82 (s, 3H), 4.2 (s, 3H), 7.0 (m, 1H), 7.48 (d, 1H), 7.5 (d, 1H), 7.55 (d, 1H), 7.75 (d, 1H), 8.1 (m, 1H), 7.92 (s, 1H); Mass Spectrum: M+H$^+$ 360 and 362.

A mixture of 4-(2-bromo-5-methoxyanilino)-5-methoxyquinazoline hydrochloride (3.5 g), pyridine hydrochloride (2 g) and pyridine (30 ml) was stirred and heated to reflux for 18 hours. The mixture was cooled to ambient temperature and evaporated. The residue was suspended in water. the mixture was basified to pH11 by the addition of a concentrated ammonium hydroxide solution and stirred for 1 hour. The resultant precipitate was isolated, washed with water and with diethyl ether and dried under vacuum. There was thus obtained 4-(2-bromo-5-methoxyanilino)-5-hydroxyquinazoline (2.15 g); NMR Spectrum: (DMSOd$_6$ and CF$_3$COOD) 3.8 (s, 3H), 6.95 (m, 1H), 7.25 (d, 1H), 7.3 (d, 1H), 7.7 (s, 1 H), 7.75 (d, 1H), 7.9 (m, 1H), 8.9 (s, 1H); Mass Spectrum: M+H$^+$ 346 and 348.

[8] Using a similar work-up to that described in Note [7] above, the product was obtained as a dihydrochloride salt which gave the following data: NMR Spectrum: (DMSOd$_6$ and CF$_3$COOD) 2.4–2.5 (m, 2H), 3.5 (m, 2H), 3.7 (br s, 4H), 3.72–3.9 (br s, 4H), 3.8 (s, 3H), 4.7 (t, 2H), 7.0 (m, 1H), 7.4–7.6 (m, 3H), 7.75 (d, 1H), 8.1 (m, 1H), 9.02 (s, 1H); Mass Spectrum: M+H$^+$ 521 and 523.

The 3-(1,1-dioxotetrahydro-4H-1,4-thiazin-4-yl)propan-1-ol used as a starting material was prepared as follows:

A mixture of 3-aminopropan-1-ol (0.650 ml) and divinyl sulphone (1 g) was heated to 110° C. for 45 minutes. The mixture was allowed to cool to ambient temperature and was purified by column chromatography on silica using a 19:1 mixture of methylene chloride and methanol as eluent. There was thus obtained 3-(1,1-dioxotetrahydro-4H-1,4-thiazin-4-yl)propan-1-ol (0.8 g); NMR Spectrum: (CDCl$_3$) 1.7–1.8 (m, 2H), 2.73 (t, 2H), 3.06 (br s, 8H), 3.25 (s, 3H), 3.78 (t, 2H); Mass Spectrum: M+H$^+$ 194.

[9] Using a similar work-up to that described in Note [7] above, the product was obtained as a dihydrochloride salt which gave the following data: Mass Spectrum: M+H$^+$ 472 and 474.

The 1-(2-hydroxyethyl)-4-methylpiperazine used as a starting material was prepared as follows:

A mixture of 2-bromoethanol (2.36 g), N-methylpiperazine (1.26 g), potassium carbonate (5.0 g) and ethanol (150 ml) was stirred and heated to reflux for 18 hours. The mixture was cooled to ambient temperature and filtered. The filtrate was evaporated and the residue was triturated under a mixture of methylene chloride and acetone. The resultant mixture was filtered and the filtrate was evaporated to give the required starting material as an oil (0.87 g); NMR Spectrum: (CDCl$_3$) 2.18 (s, 3H), 2.3–2.7 (br m, 8H), 2.56 (t, 2H), 3.61 (t, 2H).

[10] Using a similar work-up to that described in Note [7] above, the product was obtained as a dihydrochloride salt which gave the following data: NMR Spectrum: (DMSOd$_6$ and CF$_3$COOD) 2.35–2.45 (m, 2H), 2.9 (s, 3H), 3.2–3.9 (m, 10H), 3.85 (s, 3H), 4.7 (t, 2H), 7.05 (m, 1H), 7.45–7.6 (m, 4H), 8.1 (m, 1H), 8.95 (s, 1H); Mass Spectrum: M+H$^+$ 442 and 444.

[11] Using a similar work-up to that described in Note [7] above, the product was obtained as a dihydrochloride salt which gave the following data: NMR Spectrum: (DMSOd$_6$ and CF$_3$COOD) 3.82 (s, 3H), 4.85 (t, 2H), 5.05 (t, 2H), 7.05 (m, 1H), 7.35 (d, 1H), 7.5–7.65 (m, 3H), 7.7 (s, 1H), 7.8 (s, 1H), 8.1 (m, 1H), 8.95 (s, 1H), 9.15 (s, 1H); Mass Spectrum: M+H$^+$ 396 and 398.

The N-(2-hydroxyethyl)imidazole used as a starting material was prepared according to the procedure disclosed in *J. Med. Chem.*, 1993, 25, 4052.

[12] The 4-hydroxy-1-methylpiperidine was added after the other reaction components had been stirred together at 0° C. for 1 hour. The resultant reaction mixture was stirred at ambient temperature for 3 hours. The reaction mixture was filtered and the filtrate was washed with a 1N aqueous sodium hydroxide solution. The organic solution was evaporated and the residue was purified by column chromatography on silica using a 98:2 mixture of methylene chloride and methanol as eluent. The material so obtained was triturated under a 6M solution of hydrogen chloride in diethyl ether. The resultant solid was isolated, washed with diethyl ether and dried under vacuum to give the product as a dihydrochloride salt which gave the following data: NMR Spectrum: (DMSOd$_6$ and CF$_3$COOD) 2.0–2.15 (m, 2H), 2.15–2.3 (m, 4H), 2.35 (s, 3H), 2.8–2.9 (m, 2H), 3.85 (s, 3H), 3.95 (s, 3H), 4.55 (m, 1H), 6.55 (s, 1 H), 6.65 (m, 1H), 6.85 (s, 1H), 7.3 (d, 1H), 8.15 (d, 1H), 8.55 (s, 1H), 9.85 (br s, 1H); Mass Spectrum: M+H$^+$ 429 and 431.

[13] Using a similar work-up to that described in Note [7] above, the product was obtained as a dihydrochloride salt which gave the following data: NMR Spectrum: (DMSOd$_6$ and CF$_3$COOD) (two conformational isomers were noted in a ratio of about 3:2) 2.2–2.4 (m, 2H), 2.5 (d, 2H), 2.85 (s, 3H), 3.1–3.3 (m, 2H), 3.4–3.5 (m, 0.5H minor conformer), 3.55–3.7 (d, 1H major conformer and 0.5H minor conformer), 2.8 (s, 3H), 5.1–5.2 (m, 1H major conformer), 5.2–5.3 (m, 1H minor conformer), 7.05 (m, 1H major conformer), 7.1 (m, 1H minor conformer), 7.4–7.8 (m, 4H), 8.05–8.15 (m, 1H), 8.95 (s, 1H minor conformer), 9.0 (s, 1H major conformer); Mass Spectrum: M+H$^+$ 399 and 401.

[14] Using a similar work-up to that described in Note [7] above, the product was obtained as a dihydrochloride salt which gave the following data: NMR Spectrum: (DMSOd$_6$ and CF$_3$COOD) (two conformational isomers were noted in a ratio of about 3:2) 2.2–2.4 (m, 2H), 2.4–2.65 (m, 2H), 2.8 (s, 3H major conformer), 2.82 (s, 3H minor conformer), 3.1–3.3 (m, 2H), 3.45 (m, 0.5H minor conformer), 3.5–3.7 (m, 0.5H minor conformer), 3.8 (s, 3H), 5.1–5.2 (m, 1H major conformer), 5.25 (br s, 1H minor conformer), 7.0 (m, 1H major conformer), 7.05 (m, 1H minor conformer), 7.4–7.8 (m, 4H), 8.12 (m, 1H), 8.9 (s, 1H minor conformer), 9.0 (s, 1H); Mass Spectrum: M+H$^+$ 443 and 445.

[15] Using a similar work-up to that described in Note [7] above, the product was obtained as a dihydrochloride salt which gave the following data: NMR Spectrum: (DMSOd$_6$ and CF$_3$COOD) (two conformational isomers were noted in a ratio of about 3:2) 2.15–2.3 (m, 2H), 2.4–2.52 (m, 2H), 2.85 (s, 3H), 3.1–3.3 (m, 2H), 3.4–3.5 (m, 0.5H minor conformer), 3.6–3.7 (m, 1H minor conformer, 0.5H minor conformer), 5.1–5.2 (m, 1H), 5.2–5.3 (m, 1H minor conformer), 7.5–7.6 (m, 2H), 7.6–7.8 (m, 2H), 8.0–8.25 (m, 2H), 9.0 (s, 1H minor conformer), 9.1 (s, 1H major conformer); Mass Spectrum: M+H$^+$ 402 and 404.

The 4-(2,5-dichloroanilino)-5-hydroxyquinazoline used as a starting material was prepared as follows:

A mixture of 5-methoxy-3,4-dihydroquinazolin-4-one (1.8 g), phosphoryl chloride (1.03 ml), diisopropylethylamine (4.4 ml) and 1,2-dichloroethane (20 ml) was stirred and heated to 80° C. for 3 hours. The mixture was evaporated. The residue was dissolved in isopropanol (20 ml) and 2,5-dichloroaniline (1.95 g) and a 6M solution of hydrogen chloride in isopropanol (0.33 ml) were added in turn. The resultant mixture was heated to 80° C. for 1.5 hours. The mixture was cooled to ambient temperature and the resultant precipitate was isolated, washed with isopropanol and with diethyl ether and dried under vacuum. There was thus obtained 4-(2,5-dichloroanilino)-5-methoxyquinazoline hydrochloride (3.2 g); NMR Spectrum: (DMSOd$_6$) 4.19 (s, 3H), 7.45 (d, 1H), 7.5–7.6 (m, 2H), 7.75 (d, 1H), 8.05–8.15 (m, 2H), 8.95 (s, 1H).

A mixture of 4-(2,5-dichloroanilino)-5-methoxyquinazoline hydrochloride (3.2 g), pyridine hydrochloride (2.1 g) and pyridine (30 ml) was stirred and heated to reflux for 18 hours. The mixture was cooled to ambient temperature and evaporated. The residue was suspended in water. the mixture was basified to pH11 by the addition of a concentrated ammonium hydroxide solution and stirred for 1 hour. The resultant precipitate was isolated, washed with water and with diethyl ether and dried under vacuum. There was thus obtained 4-(2,5-dichloroanilino)-5-hydroxyquinazoline (1.3 g); NMR Spectrum: (DMSOd$_6$ and CF$_3$COOD) 7.25 (d, 1H), 7.3 (d, 1H), 7.5 (m, 1H), 7.7 (d, 1H), 7.95 (m, 1H), 8.3 (s, 1H), 9.0 (s, 1H); Mass Spectrum: M+H$^+$ 306 and 308.

[16] The product gave the following data: NMR Spectrum: (CDCl$_3$) 1.2–1.4 (m, 2H), 1.5 (s, 9H), 1.9 (d, 2H), 2.3 (m, 1H), 2.8 (t, 2H), 3.9 (s, 3H), 4.1–4.2 (m, 2H), 4.2 (d, 2H), 6.66 (m, 1H), 6.93 (d, 1H), 7.7 (m, 1H), 8.45 (d, 1H), 8.7 (s, 1H); Mass Spectrum: M+H$^+$ 499 and 501.

The 4-(2-chloro-5-methoxyanilino)-5-hydroxyquinazoline used as a starting material was prepared as follows:

A mixture of 5-methoxy-3,4-dihydroquinazolin-4-one (2.1 g), phosphoryl chloride (1.23 ml), diisopropylethylamine (5.2 ml) and 1,2-dichloroethane (20 ml) was stirred and heated to 80° C. for 3 hours. The mixture was evaporated. The residue was dissolved in isopropanol (20 ml) and 2-chloro-5-methoxyaniline (1.9 g) and a 6M solution of hydrogen chloride in isopropanol (0.33 ml) were added in turn. The resultant mixture was heated to 80° C. for 1.5 hours. The mixture was cooled to ambient temperature and the resultant precipitate was isolated, washed with isopropanol and with diethyl ether and dried under vacuum. There was thus obtained 4-(2-chloro-5-methoxyanilino)-5-methoxyquinazoline hydrochloride (3.4 g); NMR Spectrum: (DMSOd$_6$) 3.8 (s, 3H), 4.17 (s, 3H), 7.02 (m, 1H), 7.43 (d, 1H), 7.6 (m, 3H), 8.07 (m, 1H), 8.9 (s, 1H).

A mixture of the material so obtained, pyridine hydrochloride (1.1 g) and pyridine (30 ml) was stirred and heated to reflux for 18 hours. The mixture was cooled to ambient temperature and evaporated. The residue was suspended in water, the mixture was basified to pH11 by the addition of a concentrated ammonium hydroxide solution and stirred for 1 hour. The resultant precipitate was isolated, washed with water and with diethyl ether and dried under vacuum. There was thus obtained 4-(2-chloro-5-methoxyanilino)-5-hydroxyquinazoline (1.4 g); NMR Spectrum: (DMSOd$_6$ and CF$_3$COOD) 3.83 (s, 3H), 7.01 (m, 1H), 7.25 (d, 1H), 7.3 (d, 1H), 7.6 (d, 1H), 7.82 (d, 1H), 7.92 (m, 1H), 8.95 (s, 1H); Mass Spectrum: M+H$^+$ 302 and 304.

The N-(tert-butoxycarbonyl)piperidin-4-ylmethanol used as a starting material was prepared as follows:

A solution of di-tert-butyl dicarbonate (41.7 g) in ethyl acetate (75 ml) was added dropwise to a stirred solution of ethyl piperidine-4-carboxylate (30 g) in ethyl acetate (150 ml) which had been cooled to 0 to 5° C. in an ice-bath. The resultant mixture was stirred at ambient temperature for 48 hours. The mixture was poured into water (300 ml). The organic layer was separated, washed in turn with water (200 ml), 0.1N aqueous hydrochloric acid solution (200 ml), a saturated aqueous sodium bicarbonate solution (200 ml) and brine (200 ml), dried over magnesium sulphate and evaporated. There was thus obtained ethyl N-(tert-butoxycarbonyl)piperidine-4-carboxylate (48 g); NMR Spectrum: (CDCl$_3$) 1.25 (t, 3H), 1.45 (s, 9H), 1.55–1.7 (m, 2H), 1.8–2.0 (d, 2H), 2.35–2.5 (m, 1H), 2.7–2.95 (t, 2H), 3.9–4.1 (br s, 2H), 4.15 (q, 2H).

A solution of the material so obtained in THF (180 ml) was cooled at 0° C. and lithium aluminium hydride (1M solution in THF; 133 ml) was added dropwise. The mixture was stirred at 0° C. for 2 hours. Water (30 ml) and 2N aqueous sodium hydroxide solution (10 ml) were added in turn and the mixture was stirred for 15 minutes. The resultant mixture was filtered through diatomaceous earth and the solids were washed with ethyl acetate. The filtrate was washed in turn with water and with brine, dried over magnesium sulphate and evaporated. There was thus obtained N-(tert-butoxycarbonyl)piperidin-4-ylmethanol (36.3 g); NMR Spectrum: (CDCl$_3$) 1.05–1.2 (m, 2H), 1.35–1.55 (m, 10H), 1.6–1.8 (m, 2H), 2.6–2.8 (t, 2H), 3.4–3.6 (t, 2H), 4.0–4.2 (br s, 2H).

[17] The product gave the following data: NMR Spectrum: (CDCl$_3$) 1.2–1.35 (m, 2H), 1.5 (s, 9H), 1.9 (d, 2H), 2.35 (m, 1H), 2.75 (t, 2H), 3.85 (s, 3H), 4.05–4.2 (m, 2H), 4.2 (d, 2H), 6.62 (m, 1H), 6.95 (d, 1H), 7.7 (m, 1H), 8.25 (d, 1H), 8.7 (s, 1H); Mass Spectrum: M+H$^+$ 543 and 545.

The 4-(2-bromo-5-methoxyanilino)-5-hydroxyquinazoline used as a starting material was prepared from 5-methoxy-3,4-dihydroquinazolin-4-one using analogous procedures to those described in the portion of Note [16] immediately above except that 2-bromo-5-methoxyaniline was used in place of 2-chloro-5-methoxyaniline.

[18] The product gave the following data: NMR Spectrum: (DMSOd$_6$) 3.25 (s, 3H), 3.79 (s, 3H), 3.83 (m, 2H), 3.98 (s, 3H), 4.58 (m, 2H), 6.95 (s, 1H), 7.0 (m, 1H), 7.07 (s, 1H), 7.55 (m, 2H), 8.8 (s, 1H), 10.64 (s, 1H); Mass Spectrum: M+H$^+$ 390 and 392.

[19] The reaction product was triturated under a mixture of isopropanol and diethyl ether and a 6M solution of hydrogen chloride in isopropanol was added. The resultant precipitate was isolated, washed with diethyl ether and dried under vacuum to give the product as the dihydrochloride salt; NMR Spectrum: (CDCl$_3$) 2.2–2.3 (m, 1H), 2.4 (s, 3H), 2.4–2.5 (m, 1H), 2.5–2.6 (m, 1H), 2.8–2.9 (m, 1H), 2.95–3.1 (m, 2H), 3.85 (s, 3H), 3.95 (s, 3H), 5.05 (m, 1H), 6.42 (s, 1H), 6.65 (m, 1H), 6.88 (s, 1H), 7.5 (d, 1H), 7.9 (d, 1H), 8.55 (s, 1H), 9.7 (s, 1H); Mass Spectrum: M+H$^+$ 459 and 461.

The 4-(2-bromo-5-methoxyanilino)-5-hydroxy-7-methoxyquinazoline used as a starting material was prepared as follows:

Using analogous procedures to those described in the second last paragraph of the portion of Example 1 that is concerned with the preparation of starting materials, 5,7-dimethoxy-3,4-dihydroquinazolin-4-one (3 g) was reacted with phosphoryl chloride (1.5 ml) and the resultant product was reacted with 2-bromo-5-methoxyaniline (3.53 g). There was thus obtained 4-(2-bromo-5-methoxyanilino)-5,7-dimethoxyquinazoline hydrochloride (5 g); NMR Spectrum: (DMSOd$_6$) 3.8 (s, 3H), 4.0 (s, 3H), 4.18 (s, 3H), 6.95 (m, 3H), 7.6 (br s, 1H), 7.7 (d, 1H), 7.8 (s, 1H), 10.85 (s, 1H); Mass Spectrum: M+H$^+$ 391 and 393.

A mixture of the material so obtained, pyridine hydrochloride (1.4 g) and pyridine (100 ml) was stirred and heated to reflux for 6 hours. A second portion (2.8 g) of pyridine hydrochloride was added portionwise and the mixture was heated to reflux for a further 18 hours. The mixture was cooled to ambient temperature and evaporated. The material so obtained was triturated under water. The precipitate was isolated and washed with methylene chloride (100 ml) for 1 hour. The solid was isolated and dried under vacuum. There was thus obtained 4-(2-bromo-5-methoxyanilino)-5-hydroxy-7-methoxyquinazoline (39 g); NMR Spectrum: (DMSOd$_6$ and CF$_3$COOD) 3.75 (s, 3H), 3.9 (s, 3H), 6.75 (s, 2H), 6.92 (m, 1H), 7.58–7.7 (m, 2H), 8.8 (s, 1H).

[20] 4-Hydroxytetrahydropyran was used as the appropriate alcohol. The product gave the following data: NMR Spectrum: (DMSOd$_6$) 1.75–1.9 (m, 2H), 2.15 (d, 2H), 3.5 (t, 2H), 3.8 (s, 3H), 3.9 (m, 2H), 5.05 (m, 1H), 5.3 (s, 2H), 5.8 (m, 1H), 6.95 (d, 1H), 7.05 (d, 1H), 7.3–7.6 (m, 6H), 8.1 (d, 1H), 8.5 (s, 1H), 9.85 (s, 1H); Mass Spectrum: M+H$^+$ 492 and 494.

[21] The reaction product was dissolved in diethyl ether and a 6M solution of hydrogen chloride in diethyl ether (0.1 ml) was added. The resultant precipitate was isolated, washed with diethyl ether and dried under vacuum to give the product as a hydrochloride salt which gave the following data: NMR Spectrum: (DMSOd$_6$ and CF$_3$CO$_2$D) 1.9–2.05 (m, 2H), 2.18 (d, 2H), 3.55 (t, 2H), 3.82 (s, 3H), 3.95 (m, 2H), 5.15 (m, 1H), 7.05 (m, 1H), 7.5 (d, 1H), 7.58 (d, 2H), 7.65 (d, 1H), 8.05 (m, 1H), 8.95 (s, 1H); Mass Spectrum: M+H$^+$ 386 and 388.

[22] The product gave the following data: NMR Spectrum: (DMSOd$_6$ and CF$_3$CO$_2$D) 2.2–2.3 (m, 1H), 2.35–2.5 (m, 1H), 3.8 (s, 3H), 3.8–3.9 (m, 1H), 3.9–4.0 (m, 2H), 4.2 (d, 1H), 5.4 (s, 2H), 5.6 (br s, 1H), 7.01 (d, 1H), 7.05 (s, 1H), 7.18 (s, 1H), 7.42 (d, 1H), 7.45 (m, 2H), 7.52 (s, 1H), 7.55 (d, 2H), 7.6 (d, 1H), 8.9 (s, 1H); Mass Spectrum: M+H$^+$ 477 and 479

[23] The product gave the following data: NMR Spectrum: (DMSOd$_6$) 1.9–2.0 (m, 2H), 2.15–2.25 (m, 1H), 2.3–2.5 (m, 5H), 2.5 (t, 2H), 3.6 (t, 4H), 3.8 (s, 3H), 3.9–4.0 (m, 3H), 4.1 (d, 1H), 4.2 (t, 2H), 5.45 (t, 1H), 6.75–6.8 (m, 2H), 6.85 (s, 1H), 7.45 (d, 1H), 8.1 (s, 1H), 8.5 (s, 1H), 9.72 (s, 1H); Mass Spectrum: M+H$^+$ 515 and 517.

[24] The product gave the following data: NMR Spectrum: (DMSOd$_6$) 1.9–2.0 (m, 2H), 2.14 (s, 3H), 2.15–2.35 (m, 2H), 2.2–2.6 (m, 10H), 3.8 (s, 3H), 3.85–4.0 (m, 3H), 4.12 (d, 1H), 4.2 (t, 2H), 5.45 (t, 1H), 7.75–7.8 (m, 2H), 7.85 (s, 1H), 7.45 (d, 1H), 8.1 (s, 1H), 8.5 (s, 1H), 9.72 (s, 1H); Mass Spectrum: M+H$^+$ 528 and 530.

[25] The product gave the following data: NMR Spectrum: (DMSOd$_6$ and CF$_3$CO$_2$D) 1.5 (d, 6H), 3.82 (s, 3H), 5.2 (m, 1H), 5.4 (s, 2H), 6.98 (s, 1H, 7.0 (m, 1H), 7.18 (s, 1H), 7.4 (d, 1H), 7.45 (m, 2H), 7.5–7.6 (m, 2H), 7.65 (d, 1H), 8.9 (s, 1H); Mass Spectrum: M+H$^+$ 449 and 451.

[26] The reaction product was dissolved in methylene chloride (2 ml) containing methanol (a few drops) and a 6M hydrogen chloride solution in diethyl ether (2 equivalents) was added. Diethyl ether (50 ml) was added and the resultant precipitate was isolated, washed with diethyl ether and dried under vacuum to give the product as a dihydrochloride salt (0.135 g); NMR Spectrum: (DMSOd$_6$ and CF$_3$CO$_2$D) 1.9–2.1. (m, 2H), 2.1–2.2 (m, 2H), 3.55 (m, 2 H), 3.79 (s, 3H), 3.92 (m, 2H), 4.0 (s, 3H), 5.15 (m, 1H), 6.9 (s, 1H), 6.95 (m, 1H), 7.15 (d, 1H), 7.45 (d, 1H), 7.7 (d, 1H), 8.85 (s, 1H); Mass Spectrum: M+H$^+$ 460 and 462.

[27] The reaction product was triturated under a mixture of a 5M solution of hydrogen chloride in isopropanol was added. The resultant precipitate was isolated, washed with diethyl ether and dried under vacuum to give the product as the dihydrochloride salt; NMR Spectrum: (DMSOd$_6$ and CF$_3$CO$_2$D) 1.9 (m, 2H), 2.05 (m, 2H), 2.35 (m, 2H), 3.05 (m, 2H), 3.3 (m, 2H), 3.6 (m, 2H), 4.05 (s, 3H), 4.65 (t, 2H), 6.15 (s, 2H), 6.95 (d, 1H), 7.1 (m, 2H), 7.15 (d, 1H), 8.85 (s, 1H); Mass Spectrum: M+H$^+$ 457 and 459.

The 4-(6-chloro-2,3-methylenedioxyanilino)-5-hydroxy-7-methoxyquinazoline used as a starting, material was prepared as follows:

Phosphoryl chloride (2.7 ml) was added dropwise to a mixture of 5,7-dimethoxy-3,4-dihydroquinazolin-4-one (1 g), diisopropylethylamine (2.27 ml) and 1,2-dichloroethane (20 ml) and the resultant mixture was stirred and heated to 80° C. for 3 hours. The mixture was evaporated. There was thus obtained 4-chloro-5,7-dimethoxyquinazoline which was used without further purification. The material so obtained was suspended in isopropanol (14 ml) and 6-chloro-2,3-methylenedioxyaniline (Example 17, Note [30]; 0.915 g) and a 5N solution of hydrogen chloride in isopropanol (0.97 ml) were added in turn. The reaction mixture was stirred and heated to 90° C. for 1.5 hours. The mixture was cooled to ambient temperature and the precipitate was isolated, washed with isopropanol and with diethyl ether and dried under vacuum. The material so obtained was dissolved in a mixture of methylene chloride and methanol and a saturated methanolic ammonia solution was added. The resultant mixture was filtered and the filtrate was evaporated. There was thus obtained 4-(6-chloro-2,3-methylenedioxyanilino)-5,7-dimethoxyquinazoline (1.36 g); NMR Spectrum: (DMSOd$_6$) 3.95 (s, 3H), 4.1 (s, 3H), 6.1 (s, 2H), 6.85 (d, 1H), 6.9 (d, 1H), 7.05 (d, 1H), 7.1 (d, 1H), 8.65 (s, 1H).

Pyridine (0.54 ml) was dissolved in methylene chloride (5 ml) and a 5N solution of hydrogen chloride in isopropanol (1.34 ml) was added. After a few minutes the mixture was evaporated. Pyridine (24 ml) was added followed by 4-(6-chloro-2,3-methylenedioxyanilino)-5,7-dimethoxyquinazoline (1.2 g) and the reaction mixture was heated to 125° C. for 6 hours. The resultant mixture was evaporated and the residue was triturated under water. The resultant solid was isolated, washed with water and dried under vacuum. The material so obtained was purified by column chromatography on silica using a 7:3 mixture of methylene chloride and acetonitrile as eluent. There was thus obtained 4-(6-chloro-2,3-methylenedioxyanlino)-5-hydroxy-7-methoxyquinazoline (0.72 g); NMR Spectrum: (DMSOd$_6$ and CF$_3$CO$_2$D) 3.9 (s, 3H), 6.15 (s, 2H), 6.75 (m, 2H), 7.05 (d, 1H), 7.1 (d, 1H), 8.75 (s, 1H).

[28] The reaction product was triturated under a mixture of a 5M solution of hydrogen chloride in isopropanol was added. The resultant precipitate was isolated, washed with diethyl ether and dried under vacuum to give the product as the dihydrochloride salt; NMR Spectrum: (DMSOd$_6$ and CF$_3$CO$_2$D) 2.35 (m, 2H), 2.9 (s, 3H), 3.2–4.0 (m, 10H), 4.05 (s, 3H), 4.65 (t, 2H), 6.15 (s, 2H), 6.95 (d, 1H), 7.1 (m, 3H), 8.85 (s, 1H); Mass Spectrum: M+H$^+$ 486 and 488.

EXAMPLE 3

4-(2-bromo-5-methoxyanilino)-7-methoxy-5-(N-methylpiperidin-4-yloxy)quinazoline A mixture of 4-chloro-7-methoxy-5-(N-methylpiperidin-4-yloxy)quinazoline (0.11 g), 2-bromo-5-methoxyaniline hydrochloride (0.099 g) and isopropanol (8 ml) was stirred and heated to 80° C. for 30 minutes. The mixture was evaporated and the residue was triturated under the minimum volume of isopropanol. The resultant solid was isolated, washed with isopropanol and with diethyl ether and dried under vacuum. There was thus obtained the title compound as a dihydrochloride salt (0.06 g). A sample of the material was treated with a saturated methanolic ammonia solution. The mixture was filtered and the filtrate was evaporated to give the title compound in free base form; NMR Spectrum (CDCl$_3$): 2.15–2.25 (m, 6H), 2.35 (s, 3H), 2.9 (m, 2H), 3.84 (s, 3H), 3.93 (s, 3H), 4.6 (br s, 1H), 6.62 (s, 1H), 6.6 (m, 1H), 6.85 (s, 1H), 7.5 (d, 1H), 7.9 (s, 1H), 8.55 (s, 1H), 9.64 (br s, 1H); Mass Spectrum: M+H$^+$ 473 and 475.

The 4-chloro-7-methoxy-5-(N-methylpiperidin-4-yloxy) quinazoline used as a starting material was prepared as follows:

Pyridine (40 ml) was added dropwise to magnesium bromide (3.6 g) which had been cooled to 0°C. 5,7-Dimethoxy-3,4-dihydroquinazolin-4-one (4 g) was added and the mixture was heated to reflux for 15 minutes. The mixture was evaporated and the residue was stirred under a mixture of glacial acetic acid (12 ml) and water (80 ml) for 10 minutes The resultant solid was isolated, washed with water and dried under vacuum at 50° C. There was thus obtained 5-hydroxy-7-methoxy-3,4-dihydroquinazolin-4-one (3.75 g); NMR Spectrum: (DMSOd$_6$) 3.95 (s, 3H), 6.45 (s, 1H), 6.62 (s, 1H), 8.1 (s, 1H).

A portion (1.8 g) of the material so obtained was added to a stirred suspension of sodium hydride (0.79 g of a 60% dispersion in mineral oil which was washed with THF) in DMF (18 ml). The mixture was stirred at ambient temperature for 1 hour. The mixture was cooled to 0° C. and chloromethyl pivalate (1.62 ml) was added dropwise. The mixture was stirred at ambient temperature for 1 hour, poured into a mixture of glacial acetic acid (50 ml) and water (200 ml) and stirred at ambient temperature for 5 minutes. The resultant precipitate was isolated, washed with water and dried overnight under vacuum. The solid was triturated under pentane, isolated and dried under vacuum. There was thus obtained 5-hydroxy-7-methoxy-3-pivaloyloxymethyl-3,4-dihydroquinazolin-4-one (2.5 g); NMR Spectrum: (CDCl$_3$) 1.2 (s, 9H), 3.9 (s, 3H), 5.88 (s, 2H), 6.5 (s, 1H), 6.68 (s, 1H), 8.15 (s, 1H), 11.36 (s, 1H).

A solution of di-tert-butyl azodicarboxylate (1.7 g) in methylene chloride (5 ml) was added to a stirred mixture of 5-hydroxy-7-methoxy-3-pivaloyloxymethyl-3,4-dihydroquinazolin-4-one (1.5 g), triphenylphosphine (1.9 g), 4-hydroxy-1-methylpiperidine (0.675 g) and methylene chloride (20 ml) which had been cooled to 5° C. The mixture was stirred at ambient temperature for 1 hour. The mixture was evaporated and the residue was purified by column chromatography on silica using a 9:10:1 mixture of methylene chloride, ethyl acetate and a saturated methanolic ammonia solution as eluent. The material so obtained was triturated under diethyl ether. The resultant solid was washed with diethyl ether and dried under vacuum to give 7-methoxy-5-(N-methylpiperidin-4-yloxy)-3-pivaloyloxymethyl-3,4-dihydroquinazolin-4-one (1.75 g); NMR Spectrum: (CDCl$_3$): 1.2 (s, 9H), 2.05 (br s, 4H), 2.3 (s, 3H), 2.3–2.42 (m, 2H), 2.7–2.8 (m, 2H), 3.9 (s, 3H), 4.48 (m, 1H), 5.9 (s, 2H), 6.5 (d, 1H), 6.71 (d, 1H), 8.18 (s, 1H).

A mixture of the material so obtained and a saturated methanolic ammonia solution (100 ml) was stirred at ambient temperature for 15 hours. The mixture was evaporated and the residue was triturated under diethyl ether. The resultant precipitate was isolated, washed with diethyl ether and dried under vacuum. There was thus obtained 7-methoxy-5-(N-methylpiperidin-4-yloxy)-3,4-dihydroquinazolin-4-one (0.855 g); NMR Spectrum: (DMSOd$_6$) 1.7 (m, 2H), 1.9 (m, 2H), 2.15 (s, 3H), 1.15–1.25 (m, 2H), 2.55–2.7 (m, 2H), 3.85 (s, 3H), 4.5 (m, 1H), 6.55 (d, 1H), 6.65 (d, 1H), 7.89 (s, 1H), 11.62 (br s, 1H).

A mixture of 7-methoxy-5-(N-methylpiperidin-4-yloxy)-3,4-dihydroquinazolin-4-one (0.65 g), triphenylphosphine (1.18 g), carbon tetrachloride (0.45 ml) and methylene chloride (25 ml) was stirred and heated to reflux for 2 hours. The mixture was evaporated and the residue was purified by column chromatography on silica using a 10:9:1 mixture of ethyl acetate, methylene chloride and a saturated methanolic ammonia solution as eluent. The material so obtained was triturated under pentane and the resultant solid was isolated and dried under vacuum. There was thus obtained 4-chloro-7-methoxy-5-(N-methylpiperidin- 4-yloxy)quinazoline (0.5 g); NMR Spectrum: (CDCl$_3$) 1.95–2.15 (m, 4H), 2.3 (s, 3H), 2.3–2.45 (m, 2H), 2.6–2.8 (m, 2H), 3.92 (s, 3H), 4.55 (br s, 1H), 6.56 (s, 1H), 6.9 (s, 1H), 8.77 (s, 1H).

EXAMPLE 4

Using an analogous procedure to that described in Example 3, the appropriate 4-chloroquinazoline was reacted with the appropriate aniline to give the compound described in Table II.

TABLE II

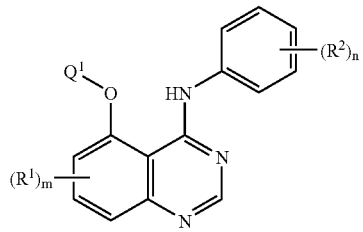

| No. and Note | (R$^1$)$_m$ | Q$^1$ | (R$^2$)$_n$ |
|---|---|---|---|
| [1] | 7-methoxy | N-methylpiperidin-4-yl | 2,4-dichloro-5-methoxy |

TABLE II-continued

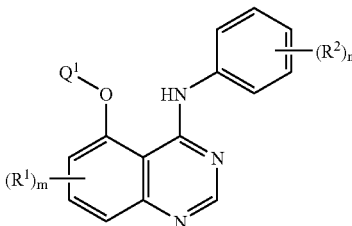

| No. and Note | (R¹)ₘ | Q¹ | (R²)ₙ |
|---|---|---|---|
| [2] | 7-methoxy | N-methylpiperidin-4-yl | 2-fluoro-4-chloro-5-methoxy |
| [3] | 7-(2-pyrrolidin-1-ylethoxy) | 4-tetrahydropyranyl | 2,5-dimethoxy |
| [4] | 7-methoxy | N-methylpiperidin-4-yl | 6-chloro-2,3-methylenedioxy |
| [5] | 7-fluoro | 4-tetrahydropyranyl | 6-chloro-2,3-methylenedioxy |
| [6] | 7-(2-pyrrolidin-1-ylethoxy) | 4-tetrahydropyranyl | 2,3-ethylenedioxy |
| [7] | 7-methoxy | N-methylpiperidin-4-yl | 2,3-ethylenedioxy |
| [8] | 7-methoxy | piperidin-4-yl | 2,3-ethylenedioxy |

Notes

[1] The reaction product was obtained as the dihydrochloride salt from which the free base was isolated using an analogous procedure to that described in Example 3. The free base gave the following data: NMR Spectrum: (CDCl₃) 2.0–2.15 (m, 2H), 2.15–2.3 (m, 4H), 2.32 (s, 3H), 2.85 (m, 2H), 3.92 (s, 3H), 3.95 (s, 3H), 4.55 (m, 1H), 6.56 (d, 1H), 6.86 (d, 1H), 7.42 (s, 1H), 8.31 (s, 1H), 8.56 (s, 1H), 9.87 (s, 1H); Mass Spectrum: M+H⁺ 463 and 465.

[2] The reaction product was obtained as the dihydrochloride salt; NMR Spectrum: (DMSOd₆ and NaOD) 1.9–2.1 (m, 2H), 2.2–2.35 (m, 2H), 2.6 (s, 3H), 2.6 (m, 2H), 3.1–3.2 (m, 2H), 3.92 (s, 3H), 3.95 (s, 3H), 4.95 (m, 1H), 6.92 (s, 1H), 6.95 (s, 1H), 7.6 (d, 1H), 8.6 (s, 1H), 8.7 (br s, 1H); Mass Spectrum: M+H⁺ 447 and 449.

The 4-chloro-2-fluoro-5-methoxyaniline used as starting material was prepared as follows:

A 6N aqueous sodium hydroxide solution (17 ml) was added dropwise to a stirred solution of 4-chloro-2-fluoro-5-methoxycarbonyloxy-1-nitrobenzene (*J. Med. Chem.*, 1999, 42, 5369; 25 g) in methanol (200 ml) which was cooled to 5° C. The reaction mixture was stirred at ambient temperature for 30 minutes. A 12N aqueous hydrochloric acid solution (8.5 ml) was added and the mixture was evaporated. The residue was partitioned between methylene chloride and water. The organic layer was washed with brine, dried over magnesium sulphate and evaporated to give 4-chloro-2-fluoro-5-hydroxy-1-nitrobenzene (18.5 g); NMR Spectrum: (CDCl₃) 5.8 (br s, 1H), 7.35 (d, 1H), 7.75 (d, 1H).

Dimethyl sulphate (10.5 ml) was added to a stirred mixture of 4-chloro-2-fluoro-5-hydroxy-1-nitrobenzene (14 g), potassium carbonate (13 g) and DMF (70 ml) and the reaction mixture was stirred at ambient temperature for 16 hours. The mixture was poured into water (500 ml) and the resultant precipitate was isolated and dried under vacuum. The solid so obtained was partitioned between methylene chloride and water. The organic layer was washed with brine, dried over magnesium sulphate and evaporated to give 4-chloro-2-fluoro-5-methoxy-1-nitrobenzene (14.1 g); NMR Spectrum: (CDCl₃) 3.94 (s, 3H), 7.4 (d, 1H), 7.6 (d, 1H).

A mixture of the material so obtained, platinum oxide (0.5 g) and ethanol (250 ml) was stirred under 1.2 atmosphere pressure of hydrogen for 2 hours. The mixture was filtered and the filtrate was evaporated. The residue was purified by column chromatography on silica using methylene chloride as eluent. There was thus obtained 4-chloro-2-fluoro-5-methoxyaniline (8.5 g); NMR Spectrum: (CDCl₃) 3.7 (br s, 2H), 3.81 (s, 3H), 6.38 (d, 1H), 7.02 (d, 1H), 7.28 (s, 1H).

[3] The reaction product was obtained as the dihydrochloride salt; NMR Spectrum: (DMSOd₆ and CF₃CO₂D) 1.85–2.0 (m, 4H), 2.0–2.15 (m, 2H), 2.2–2.3 (m, 2H), 3.15–3.25 (m, 2H), 3.58 (t, 2H), 3.65–3.75 (m, 4H), 3.78 (s, 3H), 3.95 (s, 3H), 4.02 (m, 2H), 4.6 (m, 2H), 5.2 (m, 1H), 6.9 (m, 1H), 7.02 (d, 1H), 7.16 (d, 1H), 7.23 (d, 1H), 8.16 (d, 1H), 8.98 (s, 1H); Mass Spectrum: M+H⁺ 495.

The 4-chloro-7-(2-pyrrolidin-1-ylethoxy)-5-tetrahydropyran-4-yloxyquinazoline used as a starting material is described in Example 19, Note [6].

[4] The reaction product was obtained as the dihydrochloride salt from which the free base was isolated using an analogous procedure to that described in Example 3. The free base gave the following data: NMR Spectrum: (CDCl₃) 2.0–2.15 (m, 2H), 2.15–2.3 (m, 2H), 2.3 (s, 3H), 2.3–2.5 (m, 2H), 2.75 (m, 2H), 3.92 (s, 3H), 4.6 (m, 1H), 6.05 (s, 2H), 6.50 (d, 1H), 6.72 (d, 1H), 6.84 (d, 1H), 6.97 (d, 1H), 8.52 (s, 1H), 9.26 (s, 1H); Mass Spectrum: M+H⁺ 443 and 445.

[5] The reaction product was obtained as the dihydrochloride salt from which the free base was isolated using an analogous procedure to that described in Example 3. The free base gave the following data: NMR Spectrum: (CDCl₃) 1.92–2.1 (m, 2H), 2.2–2.3 (m, 2H), 3.6–3.7 (m, 2H), 4.0–4.1 (m, 2H), 4.8 (m, 1H), 6.1 (s, 2H), 6.7 (m, 1H), 6.75 (d, 1H), 6.98 (d, 1H), 7.15 (m, 1H), 8.6 (s, 1H), 9.32 (s, 1H); Mass Spectrum: M+H⁺ 418 and 420.

The 4-chloro-7-fluoro-5-tetrahydropyran-4-yloxyquinazoline used as a starting material was prepared as follows:

A solution of 3,5-difluoroaniline (10.8 g) in a mixture of 12N aqueous hydrochloric acid solution (7.5 ml) and water (90 ml) was added to a stirred mixture of chloral hydrate (9.2 ml), sodium sulphate decahydrate (240 g) and water (210 ml). A solution of hydroxylamine hydrochloride (18.6 g) in water (90 ml) was then added and the mixture was heated to 120° C. for 45 minutes. The mixture was cooled to ambient temperature and the precipitate was isolated and dried under vacuum. The material so obtained was added to concentrated sulphuric acid (60 ml) and the mixture was stirred and heated to 80–90° C. for 10 minutes. The mixture was cooled to ambient temperature and poured onto a 1:1 mixture of ice and water (600 ml). The precipitate was isolated, washed with water and dried under vacuum at 50° C. to give 4,6-difluoro-2,3-dioxoindoline (14 g); NMR Spectrum: (DMSOd$_6$) 6.61 (m, 1H), 6.9 (m, 1H).

Hydrogen peroxide (35% solution in water, 23 ml) was added dropwise to a stirred solution of 4,6-difluoro-2,3-dioxoindoline (14 g) in a concentrated aqueous sodium hydroxide solution (33%, 115 ml) that was heated to 70° C. The mixture was heated to 70° C. for 15 minutes. The resultant mixture was cooled to 0° C. and the the mixture was acidified to pH4 by the addition of concentrated aqueous hydrochloric acid. The mixture was extracted with ethyl acetate. The organic layer was separated, washed with brine, dried over magnesium sulphate and evaporated to give 2-amino-4,6-difluorobenzoic acid (12 g); NMR Spectrum: (DMSOd$_6$) 6.25 (m, 1H), 6.38 (m, 1H).

Diethyl azodicarboxylate (26.7 ml) was added dropwise to a stirred mixture of 2-amino-4,6-difluorobenzoic acid (26.6 g), triphenylphosphine (45 g), methanol (9 ml) and methylene chloride (350 ml) that had been cooled to 5° C. The mixture was allowed to warm to ambient temperature and was stirred for 2 hours. The reaction mixture was poured onto a chromatography column loaded with silica and eluted with methylene chloride. There was thus obtained methyl 2-amino-4,6-difluorobenzoate (25.2 g); NMR Spectrum: (DMSOd$_6$) 3.8 (s, 3H), 6.3 (m, 1H), 6.4 (m, 1H), 7.0 (br s, 2H); Mass Spectrum: M+H$^+$ 188.

A mixture of methyl 2-amino-4,6-difluorobenzoate (47 g), formamidine acetate (79 g) and 2-methoxyethanol (750 ml) was stirred and heated to reflux for 10 hours. A second portion (26 g) of formamidine acetate was added and the mixture was heated to reflux for a further 2.5 hours. The mixture was cooled to ambient temperature and evaporated. The residue was washed with diethyl ether and with water and dried under vacuum over phosphorus pentoxide. The filtrate was evaporated to dryness and the residue was triturated under diethyl ether. The resultant solid was isolated and dried under vacuum. The two batches of solid were combined and purified by column chromatography on silica using a 19:1 mixture of methylene chloride and methanol as eluent. There was thus obtained 5,7-difluoro-3,4-dihydroquinazolin-4-one (33.7 g); NMR Spectrum: (DMSOd$_6$) 7.3–7.4 (m, 2H), 8.12 (s, 1H); Mass Spectrum: M+H$^+$ 183.

Sodium hydride (60% dispersion in mineral oil; 0.6 g) was added portionwise to a solution of 4-hydroxytetrahydropyran (0.78 g) in DMF (10 ml) that had been cooled to 5° C. The mixture was allowed to warm to ambient temperature and was stirred for 15 minutes. 5,7-Difluoro-3,4-dihydroquinazolin-4-one (0.9 g) was added and the mixture was stirred at ambient temperature for 30 minutes. The mixture was poured into water (100 ml) and, with vigorous stirring, glacial acetic acid was added to acidify the mixture to pH5. The resultant solid was isolated, washed with water and with diethyl ether and dried under vacuum. There was thus obtained 7-fluoro-5-tetrahydropyran-4-yloxy-3,4-dihydroquinazolin-4-one (1.1 g); NMR Spectrum: (DMSOd$_6$) 1.6–1.75 (m, 2H), 1.9–2.0 (m, 2H), 3.5–3.6 (m, 2H), 3.85–3.95 (m, 2H), 4.8 (m, 1H), 6.9 (m, 1H), 7.05 (m, 1H), 8.0 (s, 1H); Mass Spectrum: M+H$^+$ 265.

A mixture of 7-fluoro-5-tetrahydropyran-4-yloxy-3,4-dihydroquinazolin-4-one (1 g), phosphoryl chloride (4 ml), diisopropylethylamine (1.5 ml) and 1,2-dichloroethane (15 ml) was stirred and heated to 80° C. for 3 hours. The mixture was evaporated to give 4-chloro-7-fluoro-5-tetrahydropyran-4-yloxyquinazoline which was used without further purification.

[6] 2,3-Ethylenedioxyaniline (*J. Med. Chem.*, 1995, 38, 4044) was used as a starting material. The reaction product was obtained as the dihydrochloride salt; NMR Spectrum: (DMSOd$_6$ and CF$_3$CO$_2$D) 1.8–2.0 (m, 4H), 2.0–2.1 (m, 2H), 2.15–2.25 (m, 2H), 3.1–3.25 (m, 2H), 3.55 (m, 2H), 3.6–3.75 (m, 4H), 4.0 (m, 2H), 4.32 (m, 2H), 4.42 (m, 2H), 4.58 (t, 2H), 5.2 (m, 1H), 6.85 (d, 1H), 6.95 (m, 1H), 6.99 (d, 1H), 7.2 (d, 1H), 8.0 (d, 1H), 8.94 (s, 1H); Mass Spectrum: M+H$^+$ 493.

[7] The reaction product was obtained as the dihydrochloride salt from which the free base was isolated using an analogous procedure to that described in Example 3. The free base gave the following data: NMR Spectrum: (CDCl$_3$) 1.95–2.1 (m, 2H), 2.15–2.3 (m, 4H), 2.3 (s, 3H), 2.9 (m, 2H), 3.9 (s, 3H), 4.32 (m, 2H), 4.4 (m, 2H), 4.52 (m, 1H), 6.5 (d, 1H), 6.65 (m, 1H), 6.8 (d, 1H), 6.92 (m, 1H), 8.3 (d, 1H), 8.6 (s, 1H), 10.05 (s, 1H); Mass Spectrum: M+H$^+$ 423.

[8] The reactants were 5-(1-tert-butoxycarbonylpiperidin-4-yloxy)-4-chloro-7-methoxyquinazoline and 2,3-ethylenedioxyaniline. The precipitate from the reaction mixture was isolated, washed in turn with isopropanol, ethyl acetate and diethyl ether and dried under vacuum. The material so obtained was dissolved in a 2M solution of hydrogen chloride in diethyl ether and the mixture was stirred at ambient temperature for 2 hours. The resultant solid was isolated, washed with diethyl ether and dried under vacuum. The reaction product so obtained was obtained a dihydrochloride salt; NMR Spectrum: (DMSOd$_6$ and CF$_3$CO$_2$D) 2.0–2.15 (m, 2H), 2.35–2.55 (m, 2H), 3.2 (m, 2H), 3.45 (m, 2H), 4.02 (s, 3H), 4.4 (m, 2H), 4.52 (m, 2H), 5.2 (m, 1H), 6.85 (d, 1H), 6.98 (m, 2H), 7.2 (d, 1H), 8.05 (d, 1H), 8.98 (s, 1H); Mass Spectrum: M+H$^+$ 409.

The 5-(1-tert-butoxycarbonylpiperidin-4-yloxy)-4-chloro-7-methoxyquinazoline used as a starting material is described in Example 33.

EXAMPLE 5

4-(5-chloronaphth-1-ylamino)-7-methoxy-5-(N-methylpiperidin-4-yloxy)quinazoline dihydrochloride A mixture of 4-chloro-7-methoxy-5-(N-methylpiperidin-4-yloxy)quinazoline (0.08 g), 5-chloro-1-naphthylamine (0.055 g), 6.2M hydrogen chloride in isopropanol (0.044 ml) and isopropanol (3 ml) was stirred and heated to reflux for 2 hours. The mixture was cooled to ambient temperature and the precipitate was isolated, washed with diethyl ether and dried under vacuum. There was thus obtained the title compound (0.129 g), a portion of which was treated with a saturated methanolic ammonia solution. The mixture was filtered and the filtrate was evaporated to give the free base; NMR Spectrum: (CDCl$_3$) 1.9–2.1 (m, 4H), 2.22 (s, 3H), 2.25–2.4 (m, 2H), 2.6–2.7 (m, 2H), 3.94 (s, 3H), 4.7 (br s, 1H), 6.6 (s, 1H), 6.9 (s, 1H), 7.4 (m, 1H), 7.62 (d, 1H), 7.7 (m, 1H), 8.0 (m, 2H), 8.25 (d, 1H), 8.46 (s, 1H), 9.9 (br s, 1H); Mass Spectrum: M+H$^+$ 449 and 451.

EXAMPLE 6

4-(3-chlorobenzofuran-7-ylamino)-7-methoxy-5-(N-methylpiperidin-4-yloxy)quinazoline dihydrochloride Using an analogous procedure to that described in Example 5, 4-chloro-7-methoxy-5-(N-methylpiperidin-4-yloxy)quinazoline was reacted with 7-amino-3-chlorobenzofuran to give the title compound, a portion of which was treated with a saturated methanolic ammonia solution. The mixture was filtered and the filtrate was evaporated to give the free base; NMR Spectrum: (CDCl$_3$) 2.0–2.4 (m, 6H), 2.33 (s, 3H), 2.9 (m, 2H), 3.93 (s, 3H), 4.6 (m, 1H), 6.56 (s, 1H), 6.9 (s, 1H), 7.3–7.4 (m, 2H), 7.7 (br s, 1H ), 8.64 (s, 1H), 8.7 (d, 1H), 10.3 (br s, 1H); Mass Spectrum: M+H$^+$ 439 and 441.

The 7-amino-3-chlorobenzofuran used as a starting material was prepared as follows:

For a 30 minute period, chlorine gas was bubbled through a solution of 7-nitrobenzofuran (1.2 g) in glacial acetic acid (12 ml) which had been cooled at 18° C. The resultant mixture was evaporated and the residue was partitioned between diethyl ether and water. The organic layer was washed in turn with a saturated aqueous sodium bicarbonate solution, water and a saturated aqueous sodium chloride solution, dried (MgSO$_4$) and evaporated. The residue was purified by column chromatography on silica to give a mixture of cis and trans 2,3-dichloro-7-nitro-2,3-dihydrobenzofuran. The material so obtained was dissolved in ethanol (2 ml) and a solution of 0.8M potassium hydroxide in ethanol (2.7 ml) was added. The mixture was stirred at ambient temperature for 75 minutes. The mixture was evaporated to remove the ethanol. The residue was diluted with water and the mixture was acidified to pH2 by the addition of concentrated hydrochloric acid. The mixture was extracted with diethyl ether. The organic extract was washed with water and with a saturated aqueous sodium chloride solution, dried (MgSO$_4$) and evaporated. There was thus obtained 3-chloro-7-nitrobenzofuran (0.7 g); NMR Spectrum: (DMSOd$_6$) 7.63 (m, 1H), 8.12 (d, 1H), 8.3 (d, 1H), 8.65 (s, 1H); Mass Spectrum: M+H$^+$ 197 and 199.

A suspension of hydrazine hydrate (0.049 ml) and Raney nickel (0.01 g) in methanol (2 ml) was heated to 60° C. and added dropwise to a mixture of 3-chloro-7-nitrobenzofuran (0.04 g) and methanol (4 ml). The resultant mixture was heated to reflux for 10 minutes, filtered and evaporated. The residue was partitioned between methylene chloride and water. The organic layer was washed with water, dried (MgSO$_4$) and evaporated. The residue was purified by column chromatography on silica using a 1:1 mixture of methylene chloride and petroleum ether as eluent. There was thus obtained 3-chloro-7-aminobenzofuran (0.021 g); NMR Spectrum: (DMSOd$_6$ and CF$_3$COOD) 6.65 (d, 1H), 6.75 (d, 1H), 7.05 (m, 1H), 8.2 (s, 1H); Mass Spectrum: M+H$^+$ 167.

EXAMPLE 7

4-(2,3-methylenedioxyanilino)-7-methoxy-5-(N-methylpiperidin-4-yloxy)quinazoline dihydrochloride Using an analogous procedure to that described in Example 5, 4-chloro-7-methoxy-5-(N-methylpiperidin-4-yloxy)quinazoline was reacted with 2,3-methylenedioxyaniline (*J. Med. Chem.*, 1979, 22, 1354) to give the title compound, a portion of which was treated with a saturated methanolic ammonia solution. The mixture was filtered and the filtrate was evaporated to give the free base; NMR Spectrum: (CDCl$_3$) 2.0–2.1 (m, 2H), 2.15–2.3 (m, 4H), 2.31 (s, 3H), 2.85 (m, 2H), 3.91 (s, 3H), 6.01 (s, 2H), 6.5 (d, 1H), 6.68 (d, 1H), 6.82 (d, 1H), 6.91 (m, 1H), 8.0 (d, 1H), 8.6 (s, 1H), 9.72 (s, 1H); Mass Spectrum: M+H$^+$ 409.

EXAMPLE 8

4-(2-chloro-5-methoxyanilino)-5-(N-methylpiperidin-4-ylmethoxy)quinazoline

A mixture of 5-[N-(tert-butoxycarbonyl)piperidin-4-ylmethoxy]-4-(2-chloro-5-methoxyanilino)quinazoline (0.2 g), a concentrated aqueous formaldehyde solution (37%, 0.4 ml) and formic acid (4 ml) was stirred and heated to 100° C. for 2.5 hours. The mixture was cooled to ambient temperature and evaporated. The residue was triturated under diethyl ether and the resultant solid was isolated and dried under vacuum. There was thus obtained 4-(2-chloro-5-methoxyanilino)-5-(N-methylpiperidin-4-ylmethoxy)quinazoline, as a formic acid salt (0.09 g); NMR Spectrum: (CDCl$_3$) 1.8–2.0 (m, 2H), 2.05–2.15 (m, 2H), 2.35 (m, 1H), 2.6 (t, 2H), 3.55 (d, 2H), 3.93 (s, 3H), 4.21 (d, 2H), 6.68 (m, 1H), 6.95 (d, 1H), 7.31 (d, 1H), 7.54 (d, 1H), 7.7 (m, 1H), 8.35 (br s, 1H), 8.39 (d, 1H), 8.7 (s, 1H); Mass Spectrum: M+H$^+$ 413.

EXAMPLE 9

4-(2-bromo-5-methoxyanilino)-5-(N-methylpiperidin-4-ylmethoxy)quinazoline

Using an analogous procedure to that described in Example 8, 4-(2-bromo-5-methoxyanilino)-5-[N-(tert-butoxycarbonyl)piperidin-4-ylmethoxy]quinazoline (0.22 g) was reacted with concentrated aqueous formaldehyde solution (0.4 ml) to give the title compound, as a formic acid salt (0.183 g); NMR Spectrum: (CDCl$_3$) 1.7–1.9 (m, 2H), 2.06 (d, 2H), 2.2 (m, 1H), 2.58 (t, 2H), 2.68 (s, 3H), 3.51 (d, 2H), 3.8 (s, 3H), 4.24 (d, 2H), 6.64 (m, 1H), 6.94 (d, 1H), 7.48 (d, 1H), 7.54 (d, 1H), 7.69 (m, 1H), 8.2 (d, 1H), 8.3 (br s, 1H), 8.69 (s, 1H), 9.94 (s, 1H); Mass Spectrum: M+H$^+$ 457 and 459.

EXAMPLE 10

4-(2-bromo-5-methoxyanilino)-5-piperidin-4-ylmethoxyquinazoline

A mixture of 4-(2-bromo-5-methoxyanilino)-5-[N-(tert-butoxycarbonyl)piperidin-4-ylmethoxy]quinazoline (0.108 g), trifluoroacetic acid (1 ml) and methylene chloride (1 ml) was stirred at ambient temperature for 1.5 hours. The mixture was evaporated and the residue was triturated under diethyl ether. The resultant solid was isolated and dried under vacuum. The solid was dissolved in methylene chloride and few drops of a saturated methanolic ammonia solution was added. The solution was poured onto a chromatography column filled with silica and eluted with a 97:3 mixture of methylene chloride and a saturated methanolic ammonia solution. There was thus obtained the title compound (0.082 g); NMR Spectrum: (CDCl$_3$) 1.2–1.4 (m, 2H), 1.9 (d, 2H), 2.3 (m, 1H), 2.65 (t, 2H), 3.12 (d, 2H), 3.84 (s, 3H), 4.2 (d, 2H), 6.61 (m, 1H), 6.93 (d, 1H), 7.5 (d, 2H), 7.68 (m, 1H), 8.22 (d, 1H), 8.68 (s, 1H); Mass Spectrum: M+H$^+$ 443 and 445.

EXAMPLE 11

4-(2-chloro-5-methoxyanilino)-7-hydroxy-5-(3-morpholinopropoxy)quinazoline

A mixture of 7-benzyloxy-4-(2-chloro-5-methoxyanilino)-5-(3-morpholinopropoxy)quinazoline (0.185 g), 10% palladium on charcoal catalyst (0.018 g), ethanol (2.5 ml), THF (2.5 ml) and DMF (1 ml) was stirred under an atmosphere pressure of hydrogen for 16 hours. The mixture was filtered and the filtrate was evaporated. The residue was purified by column chromatography on silica using a 9:1 mixture of methylene chloride and a saturated methanolic ammonia solution as eluent. There was thus obtained the title compound (0.045 g); NMR Spectrum: (DMSOd$_6$) 2.05 (m, 2H), 2.35 (br s, 4H), 2.45 (t, 2H), 3.55 (t, 4H), 3.8 (s, 3H), 4.42 (t, 2H), 6.7 (d, 2H), 7.45 (d, 1H), 8.3 (s, 1H), 8.45 (s, 1H), 10.05 (s, 1H); Mass Spectrum: M+H$^+$ 445.

EXAMPLE 12

4-(2-chloro-5-methoxyanilino)-5,7-di-(3-morpholinopropoxy)quinazoline

Di-tert-butyl azodicarboxylate (0.035 g) was added dropwise to a stirred mixture of 4-(2-chloro-5-methoxyanilino)-7-hydroxy-5-(3-morpholinopropoxy)quinazoline (0.045 g), 4-(3-hydroxypropyl)morpholine (0.016 g), triphenylphosphine (0.04 g) and methylene chloride (1 ml). The reaction mixture was stirred at ambient temperature for 10 minutes. The mixture was evaporated and the residue was purified by column chromatography on silica using a 9:10:1 mixture of methylene chloride, ethyl acetate and a saturated methanolic ammonia solution as eluent. The material so obtained was triturated under diethyl ether. The resultant solid was isolated, washed with diethyl ether and dried under vacuum to give the title compound (0.018 g); NMR Spectrum: (DMSOd$_6$ and CF$_3$COOD) 2.2–2.4 (m, 4H), 3.15 (m, 4H), 3.35 (m, 4H), 3.5 (m, 4H), 3.7 (m, 4H), 3.8 (s, 3H), 4.02 (t, 4H), 4.35 (t, 2H), 4.6 (t, 2H), 6.95 (s, 1H), 7.03 (s, 1H), 7.05 (m, 1H), 7.5 (s, 1H), 7.6 (d, 1H), 8.88 (s, 1H); Mass Spectrum: M+H$^+$ 572 and 574.

EXAMPLE 13

4-(2-chloro-5-methoxyanilino)-7-hydroxy-5-(3-pyrrolidin-1-ylpropoxy)quinazoline A mixture of 7-benzyloxy-4-(2-chloro-5-methoxyanilino)-5-(3-pyrrolidin-1-ylpropoxy)quinazoline (0.68 g), 10% palladium on charcoal catalyst (0.16 g), ethanol (13 ml) and THF (13 ml) was stirred under 5 atmospheres pressure of hydrogen for 16 hours. The mixture was filtered and the filtrate was evaporated, The residue was triturated under methanol. The resultant solid was isolated, washed with diethyl ether and dried under vacuum. There was thus obtained the title compound (0.405 g); NMR Spectrum: (DMSOd$_6$) 1.65 (br s, 4H), 2.1 (m, 2H), 2.4 (br s, 4H), 2.55 (t, 2H), 3.8 (s, 3H), 4.4 (t, 2H), 6.7 (m, 2H), 6.75 (m, 1H), 7.48 (d, 1H), 8.3 (d, 1H), 8.4 (s, 1H), 10.05 (s, 1H).

EXAMPLE 14

Using an analogous procedure to that described in Example 12, the appropriate 7-hydroxy-substituted quinazoline was reacted with the appropriate alcohol to give the compounds described in Table III.

TABLE III

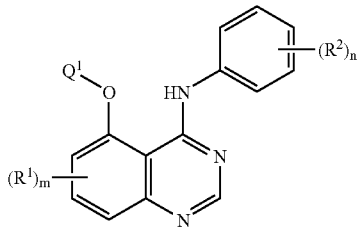

| No. & Note | (R$^1$)$_m$ | Q$^1$ | (R$^2$)$_n$ |
|---|---|---|---|
| [1] | 7-(3-morpholinopropoxy) | 3-pyrrolidin-1-ylpropyl | 2-chloro-5-methoxy |
| [2] | 7-[3-(4-methylpiperiazin-1-yl)propoxy] | 3-pyrrolidin-1-ylpropyl | 2-chloro-5-methoxy |
| [3] | 7-(2-methoxyethoxy) | 3-pyrrolidin-1-ylpropyl | 2-chloro-5-methoxy |
| [4] | 7-[2-(2-methoxyethoxy)ethoxy] | 3-pyrrolidin-1-ylpropyl | 2-chloro-5-methoxy |
| [5] | 7-isopropoxy | 4-piperidinyl | 2-bromo-5-methoxy |
| [6] | 7-(3-methylsulphonyl)propoxy | 4-piperidinyl | 2-bromo-5-methoxy |
| [7] | 7-(2-pyridylmethoxy) | N-(2-pyridylmethyl)-piperidin-4-yl | 2-bromo-5-methoxy |
| [8] | 7-[3-(4-methylpiperazin-1-yl)propoxy] | 4-tetrahydropyranyl | 2-chloro-5-methoxy |
| [9] | 7-(3-morpholinopropoxy) | 4-tetrahydropyranyl | 2-chloro-5-methoxy |
| [10] | 7-(N-methylpiperidin-4-yloxy) | 4-tetrahydropyranyl | 2-bromo-5-methoxy |
| [11] | 7-(2-pyrrolidin-1-ylethoxy) | 4-tetrahydropyranyl | 2-bromo-5-methoxy |
| [12] | 7-(3-pyrrolidin-1-ylpropoxy) | 4-tetrahydropyranyl | 2-bromo-5-methoxy |
| [13] | 7-(2-piperidinoethoxy) | 4-tetrahydropyranyl | 2-bromo-5-methoxy |
| [14] | 7-[2-(4-methylpiperazin-1-yl)ethoxy] | 4-tetrahydropyranyl | 2-bromo-5-methoxy |
| [15] | 7-[3-(4-methylpiperazin-1-yl)propoxy] | 4-tetrahydropyranyl | 2-bromo-5-methoxy |

TABLE III-continued

| No. & Note | (R¹)ₘ | Q¹ | (R²)ₙ |
|---|---|---|---|
| [16] | 7-(2-(2-morpholinomethyl-5-methylimidazol-1-yl)ethoxy] | 4-tetrahydropyranyl | 2-bromo-5-methoxy |
| [17] | 7-{2-[2-(N,N-dimethylcarbamoyl)-pyrrolidin-1-yl]ethoxy} | 4-tetrahydropyranyl | 2-bromo-5-methoxy |
| [18] | 7-{3-[2-(N,N-dimethylcarbamoyl)-pyrrolidin-1-yl]propoxy} | 4-tetrahydropyranyl | 2-bromo-5-methoxy |
| [19] | 7-[2-(2,5-dimethoxymethyl-pyrrolidin-1-yl)ethoxy] | 4-tetrahydropyranyl | 2-bromo-5-methoxy |
| [20] | 7-[2-(4-pyridyloxy)ethoxy] | 4-tetrahydropyranyl | 2-bromo-5-methoxy |
| [21] | 7-(3-morpholinopropoxy) | cyclohexyl | 2-chloro-5-methoxy |
| [22] | 7-(2-pyrrolidin-1-ylethoxy) | cyclopentyl | 2,4-dichloro-5-methoxy |
| [23] | 7-(3-morpholinopropoxy) | isopropyl | 2-chloro-5-methoxy |
| [24] | 7-[3-(4-methylpiperiazin-1-yl)propoxy] | isopropyl | 2-chloro-5-methoxy |
| [25] | 7-(2-pyrrolidin-1-ylethoxy) | 4-tetrahydropyranyl | 2,3-methylenedioxy |
| [26] | 7-(3-pyrrolidin-1-ylpropoxy) | 4-tetrahydropyranyl | 2,3-methylenedioxy |
| [27] | 7-(3-pyridylmethoxy) | 4-piperidinyl | 2-bromo-5-methoxy |
| [28] | 7-(2-pyrrolidin-1-ylethoxy) | 4-tetrahydropyranyl | 2,4-dichloro-5-methoxy |
| [29] | 7-(3-pyrrolidin-1-ylpropoxy) | 4-tetrahydropyranyl | 2,4-dichloro-5-methoxy |
| [30] | 7-(2-piperidinoethoxy) | 4-tetrahydropyranyl | 2,4-dichloro-5-methoxy |
| [31] | 7-[2-(4-methylpiperazin-1-yl)ethoxy] | 4-tetrahydropyranyl | 2,4-dichloro-5-methoxy |
| [32] | 7-(2-morpholinoethoxy) | 4-tetrahydropyranyl | 2,4-dichloro-5-methoxy |
| [33] | 7-{2-[2-(N-methylcarbamoyl)-pyrrolidin-1-yl]ethoxy} | 4-tetrahydropyranyl | 2,4-dichloro-5-methoxy |
| [34] | 7-[2-(2-carbamoylpyrrolidin-1-yl)ethoxy] | 4-tetrahydropyranyl | 2,4-dichloro-5-methoxy |
| [35] | 7-[2-(2-morpholinocarbonyl-pyrrolidin-1-yl)ethoxy] | 4-tetrahydropyranyl | 2,4-dichloro-5-methoxy |
| [36] | 7-{2-[2-(4-methylpiperazin-1-ylcarbonyl)pyrrolidin-1-yl]ethoxy} | 4-tetrahydropyranyl | 2,4-dichloro-5-methoxy |
| [37] | 7-{2-[2-(pyrrolidin-1-ylcarbonyl)-pyrrolidin-1-yl]ethoxy} | 4-tetrahydropyranyl | 2,4-dichloro-5-methoxy |
| [38] | 7-[2-(2-piperidinocarbonyl-pyrrolidin-1-yl)ethoxy] | 4-tetrahydropyranyl | 2,4-dichloro-5-methoxy |
| [39] | 7-[2-(2-methylpyrollidin-1-yl)ethoxy] | 4-tetrahydropyranyl | 2,4-dichloro-5-methoxy |
| [40] | 7-[2-(2-methoxymethylpyrrolidin-1-yl)ethoxy] | 4-tetrahydropyranyl | 2,4-dichloro-5-methoxy |
| [41] | 7-[2-(4-pyridyloxy)ethoxy] | 4-tetrahydropyranyl | 2,4-dichloro-5-methoxy |
| [42] | 7-(3-pyridylmethoxy) | 4-tetrahydropyranyl | 2,4-dichloro-5-methoxy |
| [43] | 7-(4-pyridylmethoxy) | 4-tetrahydrpyranyl | 2,4-dichloro-5-methoxy |
| [44] | 7-(N-methylpiperidin-4-yloxy) | 4-tetrahydropyranyl | 2,4-dichloro-5-methoxy |
| [45] | 7-{2-[2-(N-methylcarbamoyl)-pyrrolidin-1-yl]ethoxy} | 4-tetrahydropyranyl | 2-bromo-5-methoxy |
| [46] | 7-[2-(2-morpholinocarbonyl-pyrrolidin-1-yl)ethoxy] | 4-tetrahydropyranyl | 2-bromo-5-methoxy |
| [47] | 7-{2-[2-(4-mthylpiperazin-1-ylcarbonyl)pyrrolidin-1-yl]ethoxy} | 4-tetrahydropyranyl | 2-bromo-5-methoxy |
| [48] | 7-{2-[2-(pyrrolidin-1-ylcarbonyl)-pyrrolidin-1-yl]ethoxy} | 4-tetrahydropyranyl | 2-bromo-5-methoxy |
| [49] | 7-[2-(2-piperidinocarbonyl-pyrrolidin-1-yl)ethoxy] | 4-tetrahydropyranyl | 2-bromo-5-methoxy |
| [50] | 7-[2-(2-carbamoylpyrrolidin-1-yl)ethoxy] | 4-tetrahydropyranyl | 2-bromo-5-methoxy |

TABLE III-continued

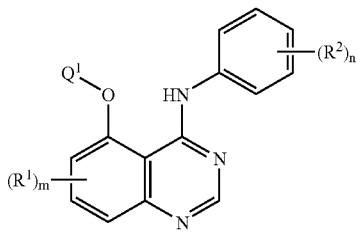

| No. & Note | $(R^1)_m$ | $Q^1$ | $(R^2)_n$ |
|---|---|---|---|
| [51] | 7-[2-(2-methylpyrrolidin-1-yl)ethoxy] | 4-tetrahydropyranyl | 2-bromo-5-methoxy |
| [52] | 7-[2-(2-methoxymethylpyrrolid-1-yl)ethoxy] | 4-tetrahydropyranyl | 2-bromo-5-methoxy |
| [53] | 7-(3-pyridylmethoxy) | 4-tetrahydropyranyl | 2-bromo-5-methoxy |
| [54] | 7-(4-pyridylmethoxy) | 4-tetrahydropyranyl | 2-bromo-5-methoxy |
| [55] | 7-isopropoxy | 4-piperidinyl | 6-chloro-2,3-methylenedioxy |
| [56] | 7-ethoxy | 4-piperidinyl | 6-chloro-2,3-methylenedioxy |
| [57] | 7-isobutoxy | 4-piperidinyl | 6-chloro-2,3-methylenedioxy |
| [58] | 7-(2-fluoroethoxy) | 4-piperidinyl | 6-chloro-2,3-methylenedioxy |
| [59] | 7-[2-(2,5-dimethoxymethyl-pyrrolidin-1-yl)ethoxy] | 4-tetrahydropyranyl | 2,3-methylenedioxy |
| [60] | 7-[2-(4-pyridyloxy)ethoxy] | 4-tetrahydropyranyl | 2,3-methylenedioxy |
| [61] | 7-(3-pyridylmethoxy) | 4-tetrahydropyranyl | 2,3-methylenedioxy |
| [62] | 7-(4-pyridylmethoxy) | 4-tetrahydropyranyl | 2,3-methylenedioxy |
| [63] | 7-{2-[2-(N-methylcarbamoyl)-pyrrolidin-1-yl]ethoxy} | 4-tetrahydropyranyl | 2,3-methylenedioxy |
| [64] | 7-[2-(2-morpholinocarbonyl-pyrrolidin-1-yl)ethoxy] | 4-tetrahydropyranyl | 2,3-methylenedioxy |
| [65] | 7-{2-[2-(4-methylpiperazin-1-ylcarbonyl)pyrrolidin-1-yl]ethoxy} | 4-tetrahydropyranyl | 2,3-methylenedioxy |
| [66] | 7-{2-[2-(pyrrolidin-1-ylcarbonyl)-pyrrolidin-1-yl]ethoxy} | 4-tetrahydropyranyl | 2,3-methylenedioxy |
| [67] | 7-[2-(2-piperidinocarbonyl-pyrrolidin-1-yl)ethoxy] | 4-tetrahydropyranyl | 2,3-methylenedioxy |
| [68] | 7-[2-(2-carbamoylpyrrolidin-1-yl)ethoxy] | 4-tetrahydropyranyl | 2,3-methylenedioxy |
| [69] | 7-[2-(2-methylpyrrolidin-1-yl)ethoxy] | 4-tetrahydropyranyl | 2,3-methylenedioxy |
| [70] | 7-[2-(2-methoxymethylpyrrolidin-1-yl)ethoxy] | 4-tetrahydropyranyl | 2,3-methylenedioxy |
| [71] | 7-(3-piperazin-1-ylpropoxy) | 4-tetrahydropyranyl | 6-chloro-2,3-methylenedioxy |
| [72] | 7-[3-(4-methylpiperazin-1-yl)propoxy] | 4-tetrahydropyranyl | 6-chloro-2,3-methylenedioxy |
| [73] | 7-[2-(4-methylpiperazin-1-yl)ethoxy] | 4-tetrahydropyranyl | 6-chloro-2,3-methylenedioxy |
| [74] | 7-(2-piperidinoethoxy) | 4-tetrahydropyranyl | 6-chloro-2,3-methylenedioxy |
| [75] | 7-(2-piperidin-4-ylethoxy) | 4-tetrahydropyranyl | 6-chloro-2,3-methylenedioxy |
| [76] | 7-[2-(4-pyridyloxy)ethoxy] | 4-tetrahydropyranyl | 6-chloro-2,3-methylenedioxy |
| [77] | 7-[N-(tert-butoxycarbonyl)piperidin-4-ylmethoxy] | 4-tetrahydropyranyl | 6-chloro-2,3-methylenedioxy |
| [78] | 7-(3-pyrrolidin-1-ylpropoxy) | cyclopentyl | 2,3-methylenedioxy |
| [79] | 7-[3-(4-methylpiperazin-1-yl)propoxy] | cyclopentyl | 2,3-methylenedioxy |
| [80] | 7-[2-(4-methylpiperazin-1-yl)ethoxy] | cyclopentyl | 2,3-methylenedioxy |
| [81] | 7-(2-piperidinoethoxy) | cyclopentyl | 2,3-methylenedioxy |
| [82] | 7-{2-[2-(4-methylpiperazin-1-ylcarbonyl)pyrrolidin-1-yl]ethoxy} | cyclopentyl | 2,3-methylenedioxy |
| [83] | 7-piperidin-4-ylmethoxy | cyclopentyl | 2,3-methylenedioxy |
| [84] | 7-(3-piperazin-1-ylpropoxy) | cyclopentyl | 2,3-methylenedioxy |

Notes

[1] The reaction product was treated with a 6M solution of hydrogen chloride in diethyl ether (5 ml) at ambient temperature for 30 minutes. The resultant solid was isolated, washed with isopropanol and with diethyl ether and dried under vacuum to give the product as the trihydrochloride salt; NMR Spectrum: (DMSOd$_6$ and CF$_3$COOD) 1.8–2.1 (m, 4H), 2.35 (m, 4H), 3.05 (m, 2H), 3.15 (t, 2H), 3.35 (m, 4H), 3.55 (m, 4H), 3.8 (s, 3H), 3.85 (t, 2H), 4.05 (d, 2H), 4.4 (t, 2H), 4.7 (t, 2H), 7.0–7.15 (m, 3H), 7.52 (d, 1H), 7.56 (d, 1 H), 8.86 (s, 1H); Mass Spectrum: M+H$^+$ 556 and 558.

[2] The reaction product was treated with a 6M solution of hydrogen chloride in diethyl ether (5 ml) at ambient temperature for 30 minutes. The resultant solid was isolated, washed with isopropanol and with diethyl ether and dried under vacuum to give the product as the trihydrochloride salt; NMR Spectrum: (DMSOd$_6$ and CF$_3$COOD) 1.8–2.05 (m, 4H), 2.4 (m, 4H), 2.95 (s, 3H), 3.02 (m, 2H), 3.2–3.65 (m, 12H), 3.8 (t, 2H), 3.85 (s, 3H), 4.4 (t, 2H), 4.7 (t, 2H), 7.02 (s, 1H), 7.05 (m, 1H), 7.1 (s, 1H), 7.5 (s, 1H), 7.6 (d, 1H), 7.95 (s, 1H).

[3] The reaction product was treated with a 6M solution of hydrogen chloride in diethyl ether (5 ml) at ambient temperature for 30 minutes. The resultant solid was isolated, washed with isopropanol and with diethyl ether and dried under vacuum to give the product as the dihydrochloride salt; NMR Spectrum: (DMSOd$_6$ and CF$_3$COOD) 1.85–2.1 (m, 4H), 2.38 (m, 2H), 3.05 (m, 2H), 3.35 (t, 2H), 3.4 (s, 3H), 3.6 (m, 2H), 3.8 (s, 3H), 3.85 (m, 2H), 4.4 (t, 2H), 4.65 (t, 2H), 7.0 (s, 1H), 7.05 (m, 1H), 7.12 (s, 1H), 7.52 (d, 1H), 7.6 (d, 1H), 8.87 (s, 1H); Mass Spectrum: M+H$^+$ 487 and 489.

[4] The reaction product was treated with a 6M solution of hydrogen chloride in diethyl ether (5 ml) at ambient temperature for 30 minutes. The resultant solid was isolated, washed with isopropanol and with diethyl ether and dried under vacuum to give the product as the dihydrochloride salt; NMR Spectrum: (DMSOd$_6$ and CF$_3$COOD) 1.8–2.05 (m, 4H), 2.35 (m, 2H), 3.0 (m, 2H), 3.25 (s, 3H), 3.35 (t, 2H), 3.5 (t, 2H), 3.55 (m, 2H), 3.65 (t, 2H), 3.8 (s, 3H), 3.85 (m, 2H), 4.35 (m, 2H), 4.65 (t, 2H), 7.0 (s, 1H), 7.05 (m, 1H), 7.12 (s, 1H), 7.45 (s, 1H), 7.57 (d, 1H), 8.85 (s, 1H); Mass Spectrum: M+H$^+$ 531 and 533.

[5] The reaction mixture was stirred at ambient temperature for 2 hours. The reaction product was treated with 6M hydrogen chloride in isopropanol to give 4-(2-bromo-5-methoxyanilino)-7-isopropoxy-5-piperidin-4-yloxyquinazoline dihydrochloride, a portion of which was converted to the free base using an analogous procedure to that described in Example 3. The free base gave the following data: NMR Spectrum: (CDCl$_3$) 1.45 (d, 6H), 1.8–2.0 (m, 2H), 2.25 (d, 2H), 2.75 (m, 2H), 3.2 (m, 2H), 3.82 (s, 3H), 4.65 (m, 1H), 4.75 (m, 1H), 6.52 (d, 1H), 6.65 (m, 1H), 6.85 (d, 1H), 7.5 (d, 1H), 7.92 (d, 1H), 8.52 (s, 1H), 9.72 (s, 1H); Mass Spectrum: M+H$^+$ 487 and 489.

The 4-(2-bromo-5-methoxyanilino)-7-hydroxy-5-piperidin-4-yloxyquinazoline used as a starting material is described in Example 20 hereinafter.

[6] The reaction mixture was stirred at ambient temperature for 1 hour whereafter a second portion of each of di-tert-butyl azodicarboxylate and triphenylphosphine were added and the reaction mixture was stirred at ambient temperature for 30 minutes. The reaction product was dissolved in methanol containing potassium carbonate and heated to reflux for 15 minutes. The mixture was filtered and the filtrate was evaporated to give the required product; NMR Spectrum: (CDCl$_3$) 1.85–2.0 (m, 2H), 2.25 (d, 2H), 2.42 (m, 2H), 2.8 (m, 2H), 3.0 (s, 3H), 3.21 (m, 2H), 3.3 (m, 2H), 3.82 (s, 3H), 4.25 (m, 2H), 4.65 (m, 1H), 6.55 (d, 1H), 6.62 (m, 1H), 6.82 (d, 1H), 7.5 (d, 1H), 7.9 (d, 1H), 8.52 (s, 1H), 9.75 (s, 1H); Mass Spectrum: M+H$^+$ 565 and 567.

[7] The reactants were 4-(2-bromo-5-methoxyanilino)-7-hydroxy-5-piperidin-4-yloxyquinazoline and 2-pyridylmethanol. The reaction mixture was stirred at ambient temperature for 1 hour whereafter a second portion of each of di-tert-butyl azodicarboxylate and triphenylphosphine were added and the reaction mixture was stirred at ambient temperature for 30 minutes. The reaction product was dissolved in methanol containing potassium carbonate and heated to reflux for 15 minutes. The mixture was filtered and the filtrate was evaporated to give the required product; NMR Spectrum: (CDCl$_3$) 2.05–2.2 (m, 2H), 2.2–2.3 (m, 2H), 2.35 (m, 2H), 2.92 (d, 2H), 3.68 (s, 3H), 3.82 (s, 3H), 4.6 (m, 1H), 5.32 (s, 2H), 6.62 (m, 1H), 6.7 (d, 1H), 6.92 (d, 1H), 7.2 (m, 1H), 7.4 (d, 1m), 7.5 (m, 2H), 7.65 (m, 1H), 7.75 (m, 1H), 7.88 (d, 1H), 8.52 (s, 1H), 8.55 (m, 2H), 8.65 (d, 1H), 9.72 (s, 1H); Mass Spectrum: M+H$^+$ 627 and 629.

[8] The reaction mixture was stirred at ambient temperature for 2 hours. The reaction product, obtained as the free base, gave the following data: NMR Spectrum: (CDCl$_3$) 2.0–2.15 (m, 6H), 2.3 (s, 3H), 2.35–2.7 (m, 10H), 3.6 (t, 2H), 3.85 (s, 3H), 4.0–4.2 (m, 4H), 4.75 (m, 1H), 6.6 (s, 1H), 6.7 (m, 1H), 6.9 (s, 1H), 7.32 (d, 1H), 8.2 (s, 1H), 8.58 (s, 1H), 9.85 (s, 1H); Mass Spectrum: M+H$^+$ 542 and 544.

The 4-(2-chloro-5-methoxyanilino)-7-hydroxy-5-tetrahydropyran-4-yloxyquinazoline, used as a starting material, is described in Example 21.

[9] The reaction mixture was stirred at ambient temperature for 2 hours. The reaction product, obtained as the free base, gave the following data: NMR Spectrum: (DMSOd$_6$ and CF$_3$CO$_2$D) 1.85–2.0 (s, 2H), 2.18 (d, 2H), 2.2–2.3 (m, 2H), 3.15 (m, 2H), 3.3–3.4 (m, 2H), 3.5 (d, 2H), 3.7 (t, 2H), 3.8 (s, 3H), 3.95 (m, 2H), 4.05 (d, 2H), 4.3 (t, 2H), 5.15 (m, 1H), 6.9 (s, 1H), 7.02 (m, 1H), 7.1 (s, 1H), 7.6 (m, 2H), 8.9 (s, 1H); Mass Spectrum: M+H$^+$ 529 and 531.

[10] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.8–2.0 (m, 2H), 2.0–2.2 (m, 4H), 2.2–2.3 (m, 4H), 2.33 (s, 3H), 2.78 (m, 2H), 3.6 (m, 2H), 3.84 (s, 3H), 4.08 (m, 2H), 4.45 (m, 1H), 4.75 (m, 1H), 6.55 (s, 1H), 6.65 (m, 1H), 6.85 (d, 1H), 7.5 (d, 1H), 7.92 (d, 1H), 8.52 (s, 1H), 9.7 (s, H); Mass Spectrum: M+H$^+$ 543 and 545.

The 4-(2-bromo-5-methoxyanilino)-7-hydroxy-5-tetrahydropyran-4-yloxyquinazoline, used as a starting material, is described in Example 24.

[11] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.85 (m, 4H), 2.1 (m, 2H), 2.22 (d, 2H), 2.65 (m, 4H), 2.98 (t, 2H), 3.58 (t, 2H), 3.85 (s, 3H), 4.05 (m, 2H), 4.22 (t, 2H), 4.75 (m, 1H), 6.65 (m, 2H), 6.87 (s, 1H), 7.5 (d, 1H), 7.95 (s, 1H), 8.55 (s, 1H), 9.7 (s, 1H); Mass Spectrum: M+H$^+$ 543 and 545.

[12] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.8 (m, 4H), 2.0–2.2 (m, 4H), 2.22 (d, 2H), 2.45–2.6 (m, 4H), 2.68 (m, 2H), 3.6 (m, 2H), 3.85 (s, 3H), 4.05 (m, 2H), 4.15 (m, 2H), 4.78 (m, 1H), 6.55 (d, 1H), 6.65 (m, 1H), 6.85 (d, 1H), 7.5 (d, 1H), 7.95 (d, 1H), 8.55 (s, 1H), 9.7 (s, 1H); Mass Spectrum: M+H$^+$ 557 and 559.

[13] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.63 (br s, 6H), 2.0–2.2 (m, 2H), 2.25 (d, 2H), 2.55 (br s, 4H), 2.85 (t, 2H), 3.6 (m, 2H), 3.84 (s, 3H), 4.05 (m, 2H), 4.25 (m, 2H), 4.75 (m, 1H), 6.62 (m, 2H), 6.85 (d, 1H), 7.5 (d, 1H), 7.95 (d, 1H), 8.55 (s, 1H), 9.7 (s, 1H); Mass Spectrum: M+H$^+$ 557 and 559.

[14] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 2.0–2.18 (m, 2H), 2.25 (d, 2H), 2.31 (s, 3H), 2.5 (br s, 4H), 2.65 (br s, 4H), 2.9 (t, 2H), 3.6 (m, 2H), 3.84 (s, 3H), 4.05 (m, 2H), 4.25 (t, 2H), 4.75 (m, 1H), 6.62 (m, 2H), 6.85 (d, 1H), 7.5 (d, 1H), 7.95 (d, 1H), 8.55 (s, 1H), 9.7 (s, 1H); Mass Spectrum: M+H$^+$ 572 and 574.

[15] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 2.02–2.2 (m, 4H), 2.25 (d, 2H), 2.29 (s, 3H), 2.35–2.7 (m, 10H), 3.6 (m, 2H), 3.84 (s, 3H), 4.1 (m, 2H), 4.15 (t, 2H), 4.75 (m, 1H), 6.55 (s, 1H), 6.65 (m, 1H), 6.85 (d, 1H), 7.5 (d, 1H), 7.95 (d, 1H), 8.55 (s, 1H), 9.7 (s, 1H); Mass Spectrum: M+H$^+$ 586 and 588.

[16] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 2.0–2.2 (m, 2H), 2.22 (d, 2H), 2.3 (s, 3H), 2.45 (br s, 4H), 3.6 (t, 2H), 3.65 (br s, 6H), 3.85 (s, 3H), 4.05 (m, 2H), 4.42 (m, 2H), 4.45 (m, 2H), 4.75 (m, 1H), 6.48 (s, 1H), 6.65 (m, 1H), 6.7 (s, 1H), 6.82 (d, 1H), 7.5 (d, 1H), 7.92 (d, 1H), 8.55 (s, 1H), 9.68 (s, 1H); Mass Spectrum: M+H$^+$ 653 and 655.

The 1-(2-hydroxyethyl)-5-methyl-2-morpholinomethylimidazole used as a starting material was prepared as follows:

A mixture of 4-methyl-1-tritylimidazole (*J. Heterocyclic Chem.*, 1982, 19, 253; 32.5 g), methyl bromoacetate (11.4 ml) and acetone (500 ml) was heated to reflux for 2 hours. The solvent was removed by evaporation and the residue was dissolved in methanol (100 ml) and heated to reflux for 45 minutes. The mixture was evaporated and the residue was triturated under diethyl ether. The resultant precipitate was isolated and stirred at ambient temperature for 1 hour in a mixture of diethyl ether (200 ml) and a saturated methanolic ammonia solution (20 ml). The mixture was filtered and the filtrate was evaporated. The residue was purified by column chromatography on silica using a 49:1 mixture of methylene chloride and methanol as eluent. There was thus obtained methyl 2-(5-methylimidazol-1-yl)acetate (6 g); NMR Spectrum: (CDCl$_3$) 2.16 (s, 3H), 3.78 (s, 3H), 4.61 (s, 3H), 6.8 (s, 1H), 7.42 (s, 1H).

A solution of a portion (1.7 g) of the material so obtained in diethyl ether (20 ml) was added dropwise to a stirred suspension of lithium aluminium hydride (0.76 g) in diethyl ether (70 ml) which was cooled to 0°C. The resultant mixture was stirred at ambient temperature for 1 hour. The mixture was cooled to 0°C. and a 6N aqueous sodium hydroxide solution (0.8 ml) and water (2.4 ml) were added dropwise in turn. The mixture was stirred at ambient temperature for 30 minutes and then evaporated. The residue was dissolved in methylene chloride, dried over magnesium sulphate and evaporated to give 1-(2-hydroxyethyl)-5-methylimidazole (1.1 g); NMR Spectrum: (CDCl$_3$) 2.17 (s, 3H), 3.81 (t, 2H), 3.92 (t, 2H), 6.6 (s, 1H), 7.24 (s, 1H).

Tert-butyldimethylsilyl chloride (9.05 g) was added to a stirred mixture of 1-(2-hydroxyethyl)-5-methylimidazole (6.4 g), imidazole (7.5 g) and methylene chloride (30 ml) which was cooled to 0°C. The reaction mixture was stirred at ambient temperature for 4 hours. The mixture was poured into water. The organic layer was washed with brine, dried over magnesium sulphate and evaporated to give 1-(2-tert-butyldimethylsilyloxyethyl)-5-methylimidazole (11.7 g); NMR Spectrum: (CDCl$_3$) –0.04 (s, 6H), 0.85 (s, 6H), 2.2 (s, 3H), 3.8 (m, 2H), 3.94 (m, 2H), 6.75 (s, 1H), 7.43 (s, 1H).

The material so obtained was dissolved in THF (400 ml) and the solution was cooled at –60° C. n-Butyllithium (2.5M in hexane, 40 ml) was added dropwise and the mixture was stirred at –50° C. for 1 hour. The mixture was cooled to –60° C. and DMF (12.5 ml) was added dropwise. The resultant mixture was allowed to warm to ambient temperature and was stirred for 2 hours. Diethyl ether (500 ml) was added and the reaction mixture was poured into a saturated aqueous ammonium chloride solution. The organic layer was separated, washed with brine, dried over magnesium sulphate and evaporated. The material so obtained was purified by column chromatography on silica using increasingly polar mixtures of methylene chloride and a saturated methanolic ammonia solution as eluent. There was thus obtained 1-(2-tert-butyldimethylsilyloxyethyl)-2-formyl-5-methylimidazole (11 g); NMR Spectrum: (CDCl$_3$) –0.1 (s, 6H), 0.79 (s, 9H), 2.32 (s, 3H), 3.91 (t, 2H), 4.4 (t, 2H), 7.07 (s, 1H), 9.71 (s, 1H).

A portion (0.79 g) of the material so obtained was dissolved in methylene chloride (24 ml) and morpholine (0.263 ml) and acetic acid (0.175 ml) were added. Sodium borohydride triacetate (0.8 g) was added portionwise and the mixture was stirred at ambient temperature for 16 hours. The mixture was evaporated and the residue was purified by column chromatography on silica using a 49:1 mixture of methylene chloride and a saturated methanolic ammonia solution as eluent. There was thus obtained 1-(2-tert-butyldimethylsilyloxyethyl)-5-methyl-2-morpholinomethylimidazole (0.5 g); NMR Spectrum: (CDCl$_3$) 0 (s, 6H), 0.82 (s, 9H), 2.25 (s, 3H), 2.45 (m, 4H), 3.6 (s, 2H), 3.68 (m, 4H), 3.85 (t, 2H), 4.1 (t, 2H), 6.7 (s, 1H).

A mixture of the material so obtained, 12N aqueous hydrochloric acid (0.26 ml) and methanol (10 ml) was stirred at ambient temperature for 5 hours. The mixture was evaporated and the residue was triturated under pentane. The resultant solid was isolated and dried under vacuum. The solid was stirred at ambient temperature for 1 hour in a mixture of methylene chloride and a saturated methanolic ammonia solution. The mixture was filtered and the filtrate was evaporated. The residue was purified by column chromatography on silica using a 19:1 mixture of methylene chloride and a saturated methanolic ammonia solution as eluent. There was thus obtained 1-(2-hydroxyethyl)-5-methyl-2-morpholinomethylimidazole (0.25 g); NMR Spectrum: (CDCl$_3$) 2.2 (s, 3H), 2.6 (br s, 4H), 3.58 (s, 2H), 3.7 (m, 4H), 3.85 (t, 2H), 4.1 (t, 2H), 6.5–6.9 (br s, 1H), 6.65 (s, 1H).

[17] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.75–2.3 (m, 8H), 2.5 (m, 1H), 2.8–2.9 (m, 1H), 2.9 (s, 3H), 3.1 (s, 3H), 3.18 (m, 1H), 3.35 (m, 1H), 3.48 (m, 1H), 3.58 (m, 2H), 3.82 (s, 3H), 4.05 (m, 2H), 4.2 (m, 2H), 4.72 (m, 1H), 6.6 (m, 2H), 6.8 (s, 1H), 7.5 (d, 1H), 7.92 (d, 1H), 8.5 (s, 1H), 9.68 (s, 1H); Mass Spectrum: M+H$^+$ 614 and 616.

The (2S)-1-(2-hydroxyethyl)-N,N-dimethylpyrrolidine-2-carboxamide used as a starting material was prepared as follows:

A mixture of 1-(tert-butoxycarbonyl)-L-proline (10.75 g), 1-(3-dimethylaminopropyl)-3-ethylcarbodiimide hydrochloride (10.6 g), dimethylamine hydrochloride (5.33 g), 4-dimethylaminopyridine (6.1 g) and methylene chloride (200 ml) was stirred at ambient temperature for 4 hours. The mixture was poured into water. The organic layer was separated, washed in turn with a 1N aqueous potassium hydrogen sulphate solution, with a 5% aqueous sodium bicarbonate solution and brine, dried over magnesium sulphate and evaporated to give 1-(tert-butoxycarbonyl)-N,N-dimethyl-L-prolinamide (11.2 g); NMR Spectrum: (CDCl$_3$) 1.4 and 1.5 (2 s, 9H), 1.8–1.9 (m, 2H), 1.95–2.2 (m, 2H), 3.0 and 3.1 (2 d, 6H), 3.35–3.6 (m, 2H), 4.55 and 4.7 (2 m, 1H).

A mixture of a portion (0.24 g) of the material so obtained and trifluoroacetic acid (3 ml) was stirred at ambient temperature for 2 hours. The mixture was evaporated and the residue was triturated under diethyl ether. A slight excess of a 2M solution of hydrogen chloride in diethyl ether was added and the precipitate was isolated and dried under vacuum to give N,N-dimethyl-L-prolinamide hydrochloride salt (0.25 g); NMR Spectrum: (DMSOd$_6$ and CF$_3$CO$_2$D,) 1.7–2.0 (m, 3H), 2.3–2.5 (m, 1H), 2.95 (s, 3H), 3.05 (s, 3H), 3.1–3.4 (m, 2H), 4.6 (m, 1H).

A mixture of N,N-dimethyl-L-prolinamide hydrochloride salt (6.3 g), 2-bromoethanol (3.8 ml), potassium carbonate (14 g) and acetonitrile (70 ml) was stirred and heated to reflux for 16 hours. The mixture was filtered and the filtrate was evaporated. The residue was purified by column chromatography on silica using a 24:1 mixture of methylene chloride and a saturated methanolic ammonia solution as eluent. There was thus obtained (2S)-1-(2-hydroxyethyl)-N,N-dimethylpyrrolidine-2-carboxamide (3.4 g); NMR Spectrum: (CDCl$_3$) 1.6 (m, 1H), 1.6–2.0 (m, 4H), 2.1–2.3 (m, 2H), 2.4 (m, 1H), 2.9 (m, 1H), 3.0 (s, 3H), 3.05 (s, 3H), 3.25–3.4 (m, 2H), 3.75 (m, 1H), 3.9 (m, 1H), 5.1 (br s, 1H); Mass Spectrum: M+H$^+$ 187.

[18] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.7–2.5 (m, 12H), 2.95 (s, 3H), 3.1 (s, 3H), 2.8–3.0 (m, 1H ), 3.2–3.4 (m, 2H), 3.58 (t, 2H), 3.82 (s, 3H), 4.05 (m, 2H), 4.1 (t, 2H), 4.75 (m, 1H), 6.55 (d, 1H), 6.6 (m, 1H), 6.8 (d, 1H), 7.48 (d, 1H), 7.92 (d, 1H), 8.5 (s, 1H), 9.65 (s, 1H); Mass Spectrum: M+H$^+$ 628 and 630.

The (2S)-1-(3-hydroxypropyl)-N,N-dimethylpyrrolidine-2-carboxamide used as a starting material was prepared as follows using an analogous procedure to that described in International Patent Application WO 98/13354 (Example 76 thereof):

Using an analogous procedure to that described in the last paragraph of the portion of Note [17] immediately above that is concerned with the preparation of starting materials, 3-bromopropanol was reacted with N,N-dimethyl-L-prolinamide hydrochloride salt.

[19] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.6–1.8 (m, 2H), 1.9–2.0 (m, 2H), 2.05–2.15 (m, 2H), 2.25 (d, 2H), 3.21 (m, 2H), 3.25–3.5 (m, 6H), 3.33 (s, 3H), 3.34 (s, 3H), 3.58 (m, 2H), 3.84 (s, 3H), 4.05 (m, 2H), 4.25 (m, 2H), 4.75 (m, 1H), 6.6 (d, 1H), 6.65 (m, 1H), 6.9 (d, 1H), 7.5 (d, 1H), 7.95 (d, 1H), 8.55 (s, 1H), 9.7 (s, 1H); Mass Spectrum: M+H$^+$ 631 and 633.

The (2R,5R)-1-(2-hydroxyethyl)-2,5-dimethoxymethylpyrrolidine used as a starting material was prepared as follows:

A mixture of (2R,5R)-2,5-dimethoxymethylpyrrolidine (0.25 g), 2-bromoethanol (1.1 ml), potassium carbonate (2.8 g) and acetonitrile (10 ml) was stirred and heated to reflux for 18 hours. The mixture was filtered and the filtrate was poured on a column of silica and eluted by a 49:1 mixture of methylene chloride and a saturated methanolic ammonia solution. There was thus obtained (2R,5R)-1-(2-hydroxyethyl)-2,5-dimethoxymethylpyrrolidine (0.23 g); Mass Spectrum: M+H$^+$ 204.

[20] 4-(2-Hydroxyethoxy)pyridine (*J. Chem. Soc. Perkin II*, 1987, 1867) was used as a starting material. The product gave the following data: NMR Spectrum: (DMSOd$_6$) 1.65–1.9 (m, 2H), 2.25 (d, 2H), 3.55 (m, 2H), 3.78 (s, 3H), 3.9 (m, 2H), 4.4–4.55 (m, 4H), 5.1 (m, 1H), 6.78 (m, 1H), 6.85 (d, 1H), 7.0 (d, 1H), 7.05 (d, 2H), 7.6 (d, 1H), 7.84 (d, 1H), 8.4 (d, 2H), 8.45 (s, 1H), 9.69 (s, 1H); Mass Spectrum: M+H$^+$ 567 and 569.

[21] The reaction mixture was stirred at ambient temperature for 2 hours. The reaction product, obtained as the free base, gave the following data: NMR Spectrum: (DMSOd$_6$ and CF$_3$CO$_2$D) 1.2–1.35 (m, 1H), 1.4–1.5 (m, 2H), 1.6 (m, 1H), 1.7–1.8 (m, 4H), 2.1–2.15 (m, 2H), 2.2–2.3 (m, 2H), 3.1–3.2 (t, 2H), 3.35 (t, 2H), 3.55 (d, 2H), 3.7 (t, 2H), 3.8 (s, 3H), 4.05 (d, 2H), 4.3 (t, 2H), 4.92 (m, 1H), 6.9 (s, 1H), 7.02 (d, 1H), 7.05 (s, 1H), 7.58 (d, 1H), 7.58 (s, 1H), 7.9 (s, 1H); Mass Spectrum: M+H$^+$ 527 and 529.

The 4-(2-chloro-5-methoxyanilino)-5-cyclohexyloxy-7-hydroxyquinazoline used as a starting material was prepared as follows:

Using an analogous procedure to that described in Example 1, 7-benzyloxy-4-(2-chloro-5-methoxyanilino)-5-hydroxyquinazoline (0.53 g) was reacted with cyclohexanol to give 7-benzyloxy-4-(2-chloro-5-methoxyanilino)-5-cyclohexyloxyquinazoline (0.25 g); NMR Spectrum: (DMSOd$_6$ and CF$_3$CO$_2$D) 1.3–1.4 (m, 1H), 1.4–1.55 (m, 2H), 1.55–1.65 (m, 1H), 1.7–1.85 (m, 4H), 2.15 (m, 2H), 3.82 (s, 3H), 4.95 (m, 1H), 5.4 (s, 2H), 7.0 (d, 1H), 7.05 (m, 1H), 7.2 (s, 1H), 7.4–7.65 (m, 7H), 8.9 (s, 1H); Mass Spectrum: M+H$^+$ 490 and 492.

Using an analogous procedure to that described in Example 20, 7-benzyloxy-4-(2-chloro-5-methoxyanilino)-5-cyclohexyloxyquinazoline was reacted with trifluoroacetic acid to give 4-(2-chloro-5-methoxyanilino)-5-cyclohexyloxy-7-hydroxyquinazoline; NMR Spectrum: (DMSOd$_6$ and CF$_3$CO$_2$D) 1.2–1.35 (m, 1H), 1.4–1.55 (m, 2H), 1.55–1.65 (m, 1H), 1.7–1.85 (m, 4H), 2.15 (m, 2H), 3.82 (s, 3H), 4.85 (m, 1H), 6.8 (s, 1H), 7.0 (s, 1H), 7.05 (m, 1H), 7.55 (d, 1H), 7.6 (d, 1H), 8.82 (s, 1H); Mass Spectrum: M+H$^+$ 400 and 402.

[22] The reaction mixture was stirred at ambient temperature for 2 hours. The reaction product, obtained as the free base, gave the following data: NMR Spectrum: (CDCl$_3$) 1.65–1.75 (m, 2H), 1.75–1.8 (m, 2H), 1.8–1.9 (m, 4H), 2.05–2.18 (m, 4H), 2.65 (m, 4H), 2.98 (m, 2H), 3.95 (s, 3H), 4.22 (m, 2H), 5.02 (m, 1H), 6.62 (d, 1H), 6.85 (d, 1H), 7.4 (s, 1H), 8.38 (s, 1H), 8.55 (s, 1H), 9.8 (s, 1H); Mass Spectrum: M+H$^+$ 517 and 519.

The 5-cyclopentyloxy-4-(2,4-dichloro-5-methoxyanilino)-7-hydroxyquinazoline used as a starting material was prepared as follows:

Di-tert-butyl azodicarboxylate (1.1 g) was added portionwise to a stirred mixture 5-hydroxy-7-methoxy-3,4-dihydroquinazolin-4-one (1 g), cyclopentanol (0.385 ml), triphenylphosphine (1.28 g) and methylene chloride (16 ml) which was maintained at ambient temperature using a water bath. The mixture was stirred at ambient temperature for 1 hour. A 6M solution of hydrogen chloride in diethyl ether (4 ml) was added and the mixture was stirred at ambient temperature for 10 minutes. The resultant precipitate was isolated, washed with methylene chloride and with ethyl acetate and dried under vacuum. The product so obtained was stirred in methanol (16 ml) containing sodium hydroxide (0.28 g) at ambient temperature for 1 hour. The mixture was evaporated and the solid was triturated under water (20 ml) containing acetic acid (1 ml). The resultant precipitate was isolated, washed in turn with water, ethyl acetate and diethyl ether. There was thus obtained 5-cyclopentyloxy-7-methoxy-3,4-dihydroquinazoline-4-one (0.52 g); NMR Spectrum: (CDCl$_3$) 1.55 (br s, 2H), 1.75 (m, 4H), 1.9 (m, 2H), 3.85 (s, 3H), 4.9 (br s, 1H), 6.5 (s, 1H), 6.62 (s, 1H), 7.9 (s, 1H), 11.62 (br s, 1H); Mass Spectrum: M+H$^+$ 261.5.

The material so obtained was mixed with potassium carbonate (0.414 g) and N-methylpyrrolidin-2-one (10 ml) and thiophenol (0.306 ml) was added. The resultant mixture was stirred and heated to 175° C. for 30 minutes. The mixture was evaporated and the residue was poured into water (20 ml) containing acetic acid (1 ml). The resultant precipitate was isolated, washed with ethyl acetate and dried under vacuum to give 5-cyclopentyloxy-7-hydroxy-3,4-dihydroquinazolin-4-one (0.4 g); NMR Spectrum: (DMSOd$_6$) 1.6 (m, 2H), 1.8 (m, 4H), 1.9 (m, 2H), 4.8 (br s, 1H), 6.38 (s, 1H), 6.5 (s, 1H), 7.8 (s, 1H), 10.35 (s, 1H), 11.5 (br s, 1H); Mass Spectrum: M+H$^+$ 247.5.

A mixture of 5-cyclopentyloxy-7-hydroxy-3,4-dihydroquinazolin-4-one (13 g), acetic anhydride (25 ml) and pyridine (21 ml) was stirred and heated to 100° C. for 1 hour. The mixture was evaporated and the residue was dissolved in a mixture of water (70 ml) and methanol (70 ml) and stirred at 15° C. for 30 minutes. The methanol was evaporated and the resultant precipitate was isolated, washed with water and dried under vacuum to give 7-acetoxy-5-cyclopentyloxy-3,4-dihydroquinazolin-4-one (12.2 g); NMR Spectrum: (DMSOd$_6$) 1.6 (br s, 2H), 1.8 (m, 4H), 1.92 (m, 2H), 2.3 (s, 3H), 4.9 (m, 1H), 6.8 (s, 1H), 6.9 (s, 1H), 7.95 (s, 1H), 11.9 (br s, 1H); Mass Spectrum: M+H$^+$ 289.6.

Using an analogous procedure to that described in the last paragraph of Note [9] in Example 15, 7-acetoxy-5-cyclopentyloxy-3,4-dihydroquinazolin-4-one (5 g) was reacted with carbon tetrachloride and triphenylphosphine to give 7-acetoxy-4-chloro-5-cyclopentyloxyquinazoline (5.3 g); NMR Spectrum: (CDCl$_3$) 1.65–1.8 (m, 2H), 1.8–2.05 (m, 4H), 2.1 (m, 2H), 2.4 (s, 3H), 4.95 (m, 1H), 6.78 (d, 1H), 7.35 (d, 1H), 8.9 (s, 1H); Mass Spectrum: M+H$^+$ 307 and 309.

A mixture of a portion (1 g) of the material so obtained, 2,4-dichloro-5-methoxyaniline hydrochloride (0.82 g), triethylamine (0.408 ml) and isopropanol (6 ml) was stirred and heated to 80° C. for 1.5 hours. The precipitate was isolated, washed in turn with isopropanol, ethyl acetate and diethyl ether and dried under vacuum to give 7-acetoxy-5-cyclopentyloxy-4-(2,4-dichloro-5-methoxyanilino)quinazoline (1.2 g); NMR Spectrum: (DMSOd$_6$) 1.6–1.8 (m, 4H), 1.95–2.2 (m, 4H), 2.4 (s, 3H), 3.9 (s, 3H), 5.25 (br s, 1H), 7.3 (s, 2H), 7.82 (s, 1H), 7.9 (s, 1H), 8.82 (s, 1H), 10.32 (s, 1H); Mass Spectrum: M+H$^+$ 462 and 464.

A mixture of the material so obtained and a saturated methanolic ammonia solution (20 ml) was stirred at ambient temperature for 4 hours. The mixture was evaporated and the residue was triturated under water. The resultant solid was isolated and dried under vacuum to give 5-cyclopentyloxy-4-(2,4-dichloro-5-methoxyanilino)-7-hydroxyquinazoline (1 g); NMR Spectrum: (DMSOd$_6$) 1.6–1.8 (m, 4H), 1.95 (m, 2H), 2.0–2.15 (m, 2H), 3.9 (s, 3H), 5.15 (m, 1H), 6.7 (s, 2H), 7.7 (s, 1H), 8.3 (s, 1H), 8.4 (s, 1H), 9.7 (s, 1H), 10.5–10.7 (br s, 1H); Mass Spectrum: M+H$^+$ 420 and 422.

[23] The free base product gave the following data: NM Spectrum: (DMSOd$_6$ and CF$_3$CO$_2$D) 1.5 (d, 6H), 2.2–2.3 (m, 2H), 3.15 (t, 2H), 3.3–3.4 (m, 2H), 3.52 (d, 2H), 3.7 (m, 2H), 3.8 (s, 3H), 4.02 (d, 2H), 4.3 (t, 2H), 5.1–5.2 (m, 1H), 6.9 (s, 1H), 7.0 (m, 2H), 7.55 (d, 1H), 7.65 (s, 1H), 8.9 (s, 1H); Mass Spectrum: M+H$^+$ 487 and 489.

[24] The free base product gave the following data: NM Spectrum: (DMSOd$_6$) 1.5 (d, 6H), 1.95 (m, 2H), 2.18 (s, 3H), 2.2–2.6 (m, 10H), 3.8 (s, 3H), 4.2 (t, 2H), 5.1 (m, 1H), 6.75–6.85 (m, 3H), 7.48 (d, 1H), 8.2 (s, 1H), 8.5 (s, 1H), 10.0 (s, 1H); Mass Spectrum: M+H$^{30}$ 500 and 502.

[25] The reaction mixture was stirred at ambient temperature for 2 hours. The free base product gave the following data: NMR Spectrum: (DMSOd$_6$) 1.7 (br s, 4H), 1.8–1.95 (m, 2H), 2.15 (d, 2H), 2.55 (br s, 4H), 2.85 (m, 2H), 3.55 (m, 2H), 3.95 (m, 2H), 4.22 (m, 2H), 5.05 (m, 1H), 6.15 (s, 2H), 6.75 (d, 1H), 6.85 (d, 1H), 6.9–7.0 (m, 2H), 8.1 (d, 1H), 8.5 (s, 1H), 9.85 (s, 1H); Mass Spectrum: M+H$^+$ 479.

The 4-(2,3-methylenedioxyanilino)-7-hydroxy-5-tetrahydropyran-4-yloxyquinazoline used as a starting material was prepared as follows:

A mixture of 7-acetoxy-5-tetrahydropyran-4-yloxy-3,4-dihydroquinazolin-4-one (3.04 g), diisopropylethylamine (4.34 ml), phosphoryl chloride (1.02 ml) and 1,2-dichloroethane (60 ml) was stirred and heated to 80° C. for 2 hours. The mixture was evaporated to give 7-acetoxy-4-chloro-5-tetrahydropyran-4-yloxyquinazoline which was used without further purification.

A mixture of the material so obtained, 2,3-methylenedioxyaniline (1.5 g) and isopropanol (20ml) was stirred and heated to 80° C. for 1 hour. The mixture was cooled to ambient temperature and the resultant solid was isolated, washed in turn with isopropanol and diethyl ether and dried under vacuum. There was thus obtained 7-acetoxy-4-(2,3-methylenedioxyanilino)-5-tetrahydropyran-4-yloxyquinazoline hydrochloride (3.6 g); NMR Spectrum: (DMSOd$_6$) 1.9–2.05 (m, 2H), 2.1–2.25 (m, 2H), 2.4 (s, 3H), 3.55 (m, 2H), 3.98 (m, 2H), 5.1 (m, 1H), 6.2 (s, 2H), 6.95–7.05 (m, 2H), 7.32 (s, 1H), 7.5 (s, 1H), 7.62 (m, 1H), 9.0 (s, 1H); Mass Spectrum: M+H$^+$424.

Using an analogous procedure to that described in the last paragraph of Note [22] immediately above, 7-acetoxy-4-(2,3-methylenedioxyanilino)-5-tetrahydropyran-4-yloxyquinazoline was reacted with a saturated methanolic ammonia solution to give 4-(2,3-methylenedioxyanilino)-7-hydroxy-5-tetrahydropyran-4-yloxyquinazoline; NMR Spectrum: (DMSOd$_6$) 1.8–1.95 (m, 2H), 2.1–2.2 (m, 2H), 3.52 (m, 2H), 3.8 (s, 3H), 3.9 (m, 2H), 4.95 (m, 1H), 6.7 (s, 1H), 6.75 (d, 1H), 6.85 (s, 1H), 7.6 (d, 1H), 7.88 (s, 1H), 8.4 (s, 1H), 9.65 (s, 1H), 10.6 (br s, 1H); Mass Spectrum: M+H$^+$ 382.

[26] The reaction mixture was stirred at ambient temperature for 2 hours. The free base product gave the following data: NMR Spectrum: (DMSOd$_6$) 1.7 (br s, 4H), 1.75–1.9 (m, 2H), 1.9–2.0 (m, 2H), 2.15 (d, 2H), 2.5 (br s, 4H), 2.6 (m, 2H), 3.55 (m, 2H), 3.9 (m, 2H), 4.18 (m, 2H), 5.0 (m, 1H), 6.1 (s, 2H), 6.72 (d, 1H), 6.8 (s, 1H), 6.9 (m, 2H), 8.08 (d, 1H), 8.5 (s, 1H), 8.82 (s, 1H); Mass Spectrum: M+H$^+$ 493.

[27] The reaction mixture was stirred at ambient temperature for 2 hours. The reaction product was treated with 6M hydrogen chloride in isopropanol to give 4-(2-bromo-5-methoxyanilino)-5-piperidin-4-yloxy-7-(3-pyridylmethoxy)quinazoline dihydrochloride, a portion of which was converted to the free base using an analogous procedure to that described in Example 3. The free base gave the following data: NMR Spectrum: (CDCl$_3$) 1.85–2.0 (m, 2H), 2.25 (d, 2H), 2.78 (m, 2H), 3.2 (m, 2H), 3.85 (s, 3H), 4.65 (m, 1H), 5.2 (s, 2H), 6.62 (s, 1H), 6.65 (m, 1H), 6.92 (d, 1H), 7.38 (m, 1H ), 7.5 (d, 1H), 7.82 (d, 1H), 7.92 (d, 1H), 8.55 (s, 1H), 8.65 (d, 1H), 8.75 (s, 1H), 9.72 (s, 1H); Mass Spectrum: M+H$^+$ 536 and 538.

[28] The reaction mixture was stirred at ambient temperature for 2 hours. The reaction product gave the following data: NMR Spectrum: (CDCl$_3$) 1.8–1.9 (m, 4H), 1.95–2.1 (m, 2H), 2.12 (d, 2H), 2.68 (br s, 4H), 3.0 (t, 2H), 3.58 (t, 2H), 3.98 (s, 3H), 4.08 (m, 2H), 4.25 (t, 2H), 4.72 (m, 1H), 6.8 (d, 1H), 6.9 (d, 1H), 7.42 (s, 1H), 8.4 (s, 1H), 8.6 (s, 1H), 9.9 (s, 1H); Mass Spectrum: M+H$^+$ 533 and 535.

The 4-(2,4-dichloro-5-methoxyanilino)-7-hydroxy-5-tetrahydropyran-4-yloxyquinazoline used as a starting material was prepared as follows:

A mixture of 7-acetoxy-4-chloro-5-tetrahydropyran-4-yloxyquinazoline (prepared from 7-acetoxy-5-tetrahydropyran-4-yloxy-3,4-dihydroquinazolin-4-one (3.04 g) and phosphoryl chloride), 2,4-dichloro-5-methoxyaniline (2.1 g) and isopropanol (20 ml) was stirred and heated to 80° C. for 1 hour. The mixture was cooled to ambient temperature and the resultant solid was isolated, washed in turn with isopropanol and diethyl ether and dried under vacuum. There was thus obtained 7-acetoxy-4-(2,4-dichloro-5-methoxyanilino)-5-tetrahydropyran-4-yloxyquinazoline hydrochloride (3.5 g); NMR Spectrum: (DMSOd$_6$ and CF$_3$CO$_2$D) 1.9–2.1 (m, 2H), 2.15 (d, 2H), 2.4 (s, 3H), 3.52 (t, 2H), 3.9 (s, 3H), 3.95 (m, 2H), 5.1 (m, 1H), 7.4 (d, 1H), 7.55 (d, 1H), 7.78 (s, 1H), 7.95 (s, 1H), 8.95 (s, 1H); Mass Spectrum: M+H$^+$ 478 and 480.

Using an analogous procedure to that described in the last paragraph of Note [22] immediately above, 7-acetoxy-4-(2,4-dichloro-5-methoxyanilino)-5-tetrahydropyran-4-yloxyquinazoline was reacted with a saturated methanolic ammonia solution to give 4-(2,4-dichloro-5-methoxyanilino)-7-hydroxy-5-tetrahydropyran-4-yloxyquinazoline; NMR Spectrum: (DMSOd$_6$) 1.75–1.9 (m, 2H), 2.18 (d, 2H), 3.52 (t, 2H), 3.9 (s, 3H), 3.95 (m, 2H), 4.95 (m, 1H), 6.7 (d, 1H), 6.82 (d, 1H), 7.7 (s, 1H), 8.35 (s, 1H), 8.42 (s, 1H), 9.85 (s, 1H), 10.5–10.7 (br s, 1H); Mass Spectrum: M+H$^+$ 436 and 438.

[29] The reaction mixture was stirred at ambient temperature for 2 hours. The reaction product gave the following data: NMR Spectrum: (CDCl$_3$) 1.85 (br s, 4H), 2.0–2.15 (m, 4H), 2.25 (d, 2H), 2.6 (br s, 4H), 2.68 (t, 2H), 3.6 (t, 2H), 3.96 (s, 3H), 4.08 (m, 2H), 4.18 (t, 2H), 4.75 (m, 1H), 6.6 (d, 1H), 6.88 (d, 1H), 7.45 (s, 1H), 8.4 (s, 1H), 8.6 (s, 1H); Mass Spectrum: M+H$^+$ 547 and 549.

[30] The reaction mixture was stirred at ambient temperature for 2 hours. The reaction product gave the following data: NMR Spectrum: (CDCl$_3$) 1.4–1.5 (m, 2H), 1.5–1.75 (m, 6H), 2.0–2.1 (m, 2H), 2.25 (d, 2H), 2.52 (br s, 4H), 2.85 (t, 2H), 3.58 (m, 2H), 3.96 (s, 3H), 4.08 (m, 2H), 4.25 (t, 2H), 4.75 (m, 1H), 6.65 (d, 1H), 6.68 (d, 1H), 7.25 (s, 1H), 8.4 (s, 1H), 8.58 (s, 1H), 9.85 (s, 1H); Mass Spectrum: M+H$^+$ 547 and 549.

[31] The reaction mixture was stirred at ambient temperature for 2 hours. The reaction product gave the following data: NMR Spectrum: (CDCl$_3$) 1.98–2.12 (m, 4H), 2.22 (d, 2H), 2.32 (s, 3H), 2.5 (br s, 2H), 2.65 (br s, 2H), 2.9 (t, 2H), 3.6 (m, 2H), 3.96 (s, 3H), 4.08 (m, 2H), 4.25 (t, 2H), 4.75 (m, 1H), 6.61 (d, 1H), 6.86 (d, 1H), 7.42 (s, 1H), 8.4 (s, 1H), 8.6 (s, 1H), 9.85 (d, 1H); Mass Spectrum: M+H$^+$ 562 and 564.

[32] The reaction mixture was stirred at ambient temperature for 2 hours. The reaction product gave the following data: NMR Spectrum: (CDCl$_3$) 2.0–2.1 (m, 2H), 2.22 (d, 2H), 2.6 (m, 4H), 2.9 (t, 2H), 3.6 (m, 2H), 3.8 (m, 4H), 3.98 (s, 3H), 4.08 (m, 2H), 4.25 (t, 2H), 4.75 (m, 1H), 6.62 (d,1H), 6.88 (d, 1H), 7.42 (s, 1H), 8.4 (s, 1H), 8.6 (s, 1H), 9.9 (s, 1H); Mass Spectrum: M+H$^+$ 549 and 551.

[33] The reaction mixture was stirred at ambient temperature for 3 hours. The reaction product gave the following data: Mass Spectrum: M+H$^+$ 590 and 592.

The (2S)-1-(2-hydroxyethyl)-N-methylprolinamide used as a starting material was obtained as follows:

A mixture of 1-(tert-butoxycarbonyl)-L-proline (5.4 g), 1-(3-dimethylaminopropyl)-3-ethylcarbodiimide (5.3 g), methylamine hydrochloride (2.2 g), 4-dimethylaminopyridine (3 g) and methylene chloride (50 ml) was stirred at ambient temperature for 16 hours. The resultant mixture was poured in water and the organic layer was separated, washed in turn with a 1M aqueous potassium hydrogen sulphate solution, a saturated aqueous sodium bicarbonate solution and brine, dried over magnesium sulphate and evaporated. There was thus obtained 1-(tert-butoxycarbonyl)-N-methyl-L-prolinamide (5.6 g); Mass Spectrum: M+H$^+$ 229.

A mixture of a portion (4.4 g) of the material so obtained and trifluoroacetic acid (10 ml) was stirred at ambient temperature for 2 hours. The mixture was evaporated and the residue was triturated under diethyl ether. The resultant solid was isolated, washed with diethyl ether and dried under vacuum. There was thus obtained to give N-methyl-L-prolinamide trifluoroacetic acid salt (3.7 g); NMR Spectrum: (DMSOd$_6$ and CF$_3$CO$_2$D) 1.85–2.05 (m, 3H), 2.2–2.3 (m, 1H), 2.73 (s, 3H), 3.2–3.4 (m, 2H), 4.2 (m, 1H).

A mixture of a portion (2.5 g) of the material so obtained, 2-bromoethanol (2.15 ml), potassium carbonate (5.5 g) and acetonitrile (20 ml) was stirred and heated to reflux for 18 hours. The mixture was cooled to ambient temperature, filtered and evaporated and the residue was purified by column chromatography on silica using a 49:1 mixture of methylene chloride and a saturated methanolic ammonia solution as eluent. There was thus obtained (2S)-1-(2-hydroxyethyl)-N-methylprolinamide (0.5 g); NMR Spectrum: (CDCl$_3$) 1.6–2.0 (m, 4H), 2.1–2.3 (m, 1H), 2.3–2.45 (m, 1H), 2.6–2.7 (m, 1H), 2.85 (d, 3H), 2.8–2.9 (m, 1H), 3.1–3.2 (m, 1H), 3.2–3.3 (m, 1H), 3.6–3.8 (m, 2H); Mass Spectrum: M+H$^+$ 173.

[34] The reaction mixture was stirred at ambient temperature for 3 hours. The reaction product gave the following data: Mass Spectrum: M+H$^+$ 576 and 578.

The (2S)-1-(2-hydroxyethyl)prolinamide used as a starting material was prepared by the reaction of L-prolinamide and 2-bromoethanol using an analogous procedure to that described in Note [33] immediately above. There was thus obtained the required starting material; NMR Spectrum: (CDCl$_3$) 1.6–2.0 (m, 4H), 2.1–2.25 (m, 1H), 2.35–2.45 (m, 1H), 2.6–2.7 (m, 1H), 2.8–3.0 (m, 1H), 3.1 (m, 1H), 3.2–3.3 (m, 1H), 3.6–3.8 (m, 2H), 5.6 (br s, 1H), 7.4 (br s, 1H); Mass Spectrum: M+H$^+$ 159.

[35] The reaction mixture was stirred at ambient temperature for 3 hours. The reaction product gave the following data: Mass Spectrum: M+H$^+$ 646 and 648.

The (2S)-1-(2-hydroxyethyl)-2-morpholinocarbonylpyrrolidine used as a starting material was prepared as follows:

Using analogous procedures to those described in Note [33] immediately above, 1-(tert-butoxycarbonyl)-L-proline was reacted with morpholine to give (2S)-1-(tert-butoxycarbonyl)-2-morpholinocarbonylpyrrolidine which was deprotected and reacted with 2-bromoethanol. There was thus obtained the required starting material; NMR Spectrum: (CDCl$_3$) 1.7–2.0 (m, 4H), 2.1–2.2 (m, 1H), 2.4–2.5 (m, 1H), 2.6–2.7 (m, 1H), 2.8–2.9 (m, 1H), 3.3–3.4 (m, 2H), 3.4–3.8 (m, 10H); Mass Spectrum: M+H$^+$ 229.

[36] The reaction mixture was stirred at ambient temperature for 3 hours. The reaction product gave the following data: Mass Spectrum: M+H$^+$ 659 and 661.

The (2S)-1-(2-hydroxyethyl)-2-(4-methylpiperazin-1-ylcarbonyl)pyrrolidine used as a starting material was prepared as follows:

Using analogous procedures to those described in Note [33] immediately above, 1-(tert-butoxycarbonyl)-L-proline was reacted with 1-methylpiperazine to give (2S)-1-(tert-butoxycarbonyl)-2-(4-methylpiperazin-1-ylcarbonyl)pyrrolidine which was deprotected and reacted with 2-bromoethanol. There was thus obtained the required starting material; NMR Spectrum: (CDCl$_3$) 1.7–2.05 (m, 4H), 2.1–2.25 (m, 1H), 2.32 (s, 3H), 2.35–2.5 (m, 4H), 2.6–2.7 (m, 1H), 2.8–2.9 (m, 1H), 3.3–3.7 (m, 8H), 4.15 (br s, 1H); Mass Spectrum: M+H$^+$ 242.

[37] The reaction mixture was stirred at ambient temperature for 3 hours. The reaction product gave the following data: Mass Spectrum: M+H$^+$ 630 and 632.

The (2S)-1-(2-hydroxyethyl)-2-(pyrrolidin-1-ylcarbonyl)pyrrolidine used as a starting material was prepared as follows:

Using analogous procedures to those described in Note [33] immediately above, 1-(tert-butoxycarbonyl)-L-proline was reacted with pyrrolidine to give (2S)-1-(tert-butoxycarbonyl)-2-(pyrrolidin-1-ylcarbonyl)pyrrolidine which was deprotected and reacted with 2-bromoethanol. There was thus obtained the required starting material; NMR Spectrum: (CDCl$_3$) 1.7–2.05 (m, 8H), 2.1–2.3 (m, 1H), 2.4–2.5 (m, 1H), 2.55–2.7 (m, 1H), 2.8–2.9 (m, 1H), 3.2–3.3 (m, 2H), 3.4–3.7 (m, 5H), 4.1 (br s, 1H); Mass Spectrum: M+H$^+$ 213.

[38] The reaction mixture was stirred at ambient temperature for 3 hours. The reaction product gave the following data: Mass Spectrum: M+H$^+$ 644 and 646.

The (2S)-1-(2-hydroxyethyl)-2-piperidinocarbonylpyrrolidine used as a starting material was prepared as follows:

Using analogous procedures to those described in Note [33] immediately above, 1-(tert-butoxycarbonyl)-L-proline was reacted with piperidine to give (2S)-1-(tert-butoxycarbonyl)-2-piperidinocarbonylpyrrolidine which was deprotected and reacted with 2-bromoethanol. There was thus obtained the required starting material; NMR Spectrum: (CDCl$_3$) 1.5–1.9 (m, 10H), 1.9–2.0 (m, 1H), 2.1–2.2 (m, 1H), 2.4–2.5 (m, 1H), 2.55–2.65 (m, 1H), 2.8–2.9 (m, 1H), 3.3–3.7 (m, 6H), 4.3 (br s, 1H); Mass Spectrum: M+H$^+$ 227.

[39] The reaction mixture was stirred at ambient temperature for 3 hours. The reaction product gave the following data: Mass Spectrum: M+H$^+$ 547 and 549.

The (2R)-1-(2-hydroxyethyl)-2-methylpyrrolidine used as a starting material was obtained as follows:

A mixture of (2R)-2-methylpyrrolidine (0.853 g), 2-bromoethanol (1.1 ml), potassium carbonate (2.8 g) and acetonitrile (10 ml) was stirred and heated to reflux for 18 hours. The mixture was filtered and the filtrate was evaporated. The resultant residue was purified by column chromatography on silica using a 49:1 mixture of methylene chloride and a saturated methanolic ammonia solution as eluent. There was thus obtained (2R)-1-(2-hydroxyethyl)-2-methylpyrrolidine (0.35 g); NMR Spectrum: (CDCl$_3$) 1.1 (d, 3H), 1.3–1.5 (m, 1H), 1.6–1.8 (m, 3H), 1.95 (m, 1H), 2.15 (m, 1H), 2.28 (m, 1H), 2.4–2.5 (m, 1H), 2.95–3.05 (m, 1H), 3.2 (m, 1H), 3.5–3.8 (m, 2H); Mass Spectrum: M+H$^+$ 130.

[40] The reaction mixture was stirred at ambient temperature for 3 hours. The reaction product gave the following data: Mass Spectrum: M+H$^+$ 577 and 579.

The (2S)-1-(2-hydroxyethyl)-2-methoxymethylpyrrolidine used as a starting material was obtained as follows:

Using an analogous procedure to those described in Note [39] immediately above, (2S)-2-methoxymethylpyrrolidine was reacted with 2-bromoethanol to give (2S)-1-(2-hydroxyethyl)-2-methoxymethylpyrrolidine; NMR Spectrum: (CDCl$_3$) 1.5–1.65 (m, 1H), 1.65–1.8 (m, 2H), 1.8–2.0 (m, 2H), 2.3 (m, 1H), 2.6 (m, 1H), 2.8 (m, 1H), 2.95–3.05 (m, 1H), 3.17 (m, 1H), 3.3 (t, 1H), 3.35 (t, 1H), 3.37 (s, 3H), 3.5–3.7 (m, 2H).

[41] The reaction mixture was stirred at ambient temperature for 3 hours. The reaction product gave the following data: Mass Spectrum: M+H$^+$ 557 and 559.

[42] The reaction mixture was stirred at ambient temperature for 3 hours. The reaction product gave the following data: Mass Spectrum: M+H$^+$ 527 and 529.

[43] The reaction mixture was stirred at ambient temperature for 3 hours. The reaction product gave the following data: Mass Spectrum: M+H$^+$ 527 and 529.

[44] The reaction mixture was stirred at ambient temperature for 3 hours. The reaction product gave the following data: Mass Spectrum: M+H$^+$ 533 and 535.

[45] (2S)-1-(2-Hydroxyethyl)-N-methylprolinamide was used as a starting material and the reaction mixture was stirred at ambient temperature for 3 hours. The reaction product gave the following data: Mass Spectrum: M+H$^+$ 600 and 602.

[46] (2S)-1-(2-Hydroxyethyl)-2-morpholinocarbonylpyrrolidine was used as a starting material and the reaction mixture was stirred at ambient temperature for 3 hours. The reaction product gave the following data: Mass Spectrum: M+H$^+$ 658 and 660.

[47] (2S)-1-(2-Hydroxyethyl)-2-(4-methylpiperazin-1-yl-carbonyl)pyrrolidine was used as a starting material and the reaction mixture was stirred at ambient temperature for 3 hours. The reaction product gave the following data: Mass Spectrum: M+H⁺ 671 and 673.

[48] (2S)-1-(2-Hydroxyethyl)-2-(pyrrolidin-1-ylcarbonyl)pyrrolidine was used as a starting material and the reaction mixture was stirred at ambient temperature for 3 hours. The reaction product gave the following data: Mass Spectrum: M+H⁺ 642 and 644.

[49] (2S)-1-(2-Hydroxyethyl)-2-piperidinocarbonylpyrrolidine was used as a starting material and the reaction mixture was stirred at ambient temperature for 3 hours. The reaction product gave the following data: Mass Spectrum: M+H⁺ 656 and 658.

[50] (2S)-1-(2-Hydroxyethyl)prolinamide was used as a starting material and the reaction mixture was stirred at ambient temperature for 3 hours. The reaction product gave the following data: Mass Spectrum: M+H⁺ 588 and 590.

[51] (2R)-1-(2-Hydroxyethyl)-2-methylpyrrolidine was used as a starting material and the reaction mixture was stirred at ambient temperature for 3 hours. The reaction product gave the following data: Mass Spectrum: M+H⁺ 557 and 559.

[52] (2S)-1-(2-Hydroxyethyl)-2-methoxymethylpyrrolidine was used as a starting material and the reaction mixture was stirred at ambient temperature for 3 hours. The reaction product gave the following data: Mass Spectrum: M+H⁺ 587 and 589.

[53] The reaction mixture was stirred at ambient temperature for 3 hours. The reaction product gave the following data: Mass Spectrum: M+H⁺ 537 and 539.

[54] The reaction mixture was stirred at ambient temperature for 3 hours. The reaction product gave the following data: Mass Spectrum: M+H⁺ 537 and 539.

[55] The reactants were 5-[N-(tert-butoxycarbonyl)piperidin-4-yloxy]-4-(6-chloro-2,3-methylenedioxyanilino)-7-hydroxyquinazoline and isopropanol. The reaction mixture was stirred at ambient temperature for 1 hour. Thereafter, a 6M solution of hydrogen chloride in diethyl ether was added and the reaction mixture was stirred at ambient temperature for 1 hour. The resultant precipitate was isolated, washed with ethyl acetate and diethyl ether and dried. There was thus obtained the required product, 4-(6-chloro-2,3-methylenedioxyanilino)-7-isopropoxy-5-piperidin-4-yloxyquinazoline; NMR Spectrum: (CDCl₃) 1.4 (d, 6H), 1.8–1.9 (m, 2H), 2.25 (m, 2H), 1.75–1.85 (m, 2H), 3.1–3.2 (m, 2H), 4.7 (m, 1H), 4.72 (m, 1H), 6.05 (s, 2H), 6.5 (d, 1H), 6.7 (d, 1H), 6.82 (d, 1H), 6.98 (d, 1H), 8.5 (s, 1H), 9.32 (s, 1H); Mass Spectrum: M+H⁺ 457 and 459.

The 5-[N-(tert-butoxycarbonyl)piperidin-4-yloxy]4-(6-chloro-2,3-methylenedioxyanilino)-7-hydroxyquinazoline used as a starting material is described in Example 35 hereinafter.

[56] The reactants were 5-[N-(tert-butoxycarbonyl)piperidin-4-yloxy]-4-(6-chloro-2,3-methylenedioxyanilino)-7-hydroxyquinazoline and ethanol. The reaction mixture was stirred at ambient temperature for 1 hour. Thereafter, a 6M solution of hydrogen chloride in diethyl ether was added and the reaction mixture was stirred at ambient temperature for 1 hour. The resultant precipitate was isolated, washed with ethyl acetate and diethyl ether and dried. There was thus obtained the required product, 4(6-chloro-2,3-methylenedioxyanilino)-7-ethoxy-5-piperidin-4-yloxyquinazoline; NMR Spectrum: (CDCl₃) 1.45 (t, 3H), 1.7–1.9 (m, 2H), 2.1–2.25 (m, 2H), 2.7–2.8 (m, 2H), 3.05–3.2 (m, 2H), 4.12 (q, 2H), 4.6 (m, 1H), 6.02 (s, 2H), 6.48 (d, 1H), 6.7 (d, 1H), 6.8 (d, 1H), 6.92 (d, 1H), 8.5 (s, 1H), 9.3 (s, 1H); Mass Spectrum: M+H⁺ 443 and 445.

[57] The reactants were 5-[N-(tert-butoxycarbonyl)piperidin-4-yloxy]-4-(6-chloro-2,3-methylenedioxyanilino)-7-hydroxyquinazoline and isobutanol. The reaction mixture was stirred at ambient temperature for 1 hour. Thereafter, a 6M solution of hydrogen chloride in diethyl ether was added and the reaction mixture was stirred at ambient temperature for 1 hour. The resultant precipitate was isolated, washed with ethyl acetate and diethyl ether and dried. There was thus obtained the required product, 4-(6-chloro-2,3-methylenedioxyanilino)-7-isobutoxy-5-piperidin-4-yloxyquinazoline; NMR Spectrum: (CDCl₃) 1.05 (d, 6H), 1.8–1.9 (m, 2H), 2.12 (m, 1H), 2.2–2.3 (m, 2H, 2.75–2.9 (m, 2H), 3.1–3.2 (m, 2H), 4.85 (d, 2H), 4.65 (m, 1H), 6.05 (s, 2H), 6.5 (d, 1H), 6.7 (d, 1H), 6.8 (d, 1H), 6.95 (d, 1H), 8.5 (s, 1H), 9.32 (s, 1H); Mass Spectrum: M+H⁺ 471 and 473.

[58] The reactants were 5-[N-(tert-butoxycarbonyl)piperidin-4-yloxy]-4-(6-chloro-2,3-methylenedioxyanilino)-7-hydroxyquinazoline and 2-fluoroethanol. The reaction mixture was stirred at ambient temperature for 1 hour. Thereafter, a 6M solution of hydrogen chloride in diethyl ether was added and the reaction mixture was stirred at ambient temperature for 1 hour. The resultant precipitate was isolated, washed with ethyl acetate and diethyl ether and dried. There was thus obtained the required product, 4-(6-chloro-2,3-methylenedioxyanilino)-7-(2-fluoroethoxy)-5-piperidin-4-yloxyquinazoline; NMR Spectrum: (CDCl₃) 1.8–2.0 (m, 2H), 2.2–2.3 (m, 2H), 2.8–2.9 (m, 2H), 3.1–3.3 (m, 2H), 4.3 (m, 1H), 4.4 (m, 1H), 4.7 (m, 1H), 4.8 (m, 1H), 4.9 (m, 1H), 6.08 (s, 2H), 6.6 (d, 1H), 6.75 (d, 1H), 6.82 (d, 1H), 7.0 (d, 1H), 8.55 (s, 1H), 9.35 (s, 1H); Mass Spectrum: M+H⁺ 461 and 463.

[59] (2R,5R)-1-(2-Hydroxyethyl)-2,5-dimethoxymethylpyrrolidine was used as a starting material and the reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl₃) 1.6–1.7 (m, 4H), 1.9–2.1 (m, 2H), 2.22 (m, 2H), 3.15–3.5 (m, 8H), 3.33 (s, 6H), 3.6 (m, 2H), 4.08 (m, 2H), 4.12 (m, 2H), 4.75 (m, 1H), 6.05 (s, 2H), 6.58 (d, 1H), 6.7 (d, 1H), 6.9 (d, 1H), 6.95 (m, 1H), 8.1 (d, 1H), 8.6 (s, 1H), 9.75 (s, 1H); Mass Spectrum: M+H⁺ 567.

[60] The reaction mixture was stirred at ambient temperature for 3 hours. The reaction product was purified by column chromatography on silica using a 24:1 mixture of methylene chloride and a saturated methanolic ammonia solution as eluent. The resultant product gave the following data: Mass Spectrum: M+H⁺ 503.

[61] The reaction mixture was stirred at ambient temperature for 3 hours. The reaction product was purified by column chromatography on silica using increasingly polar mixtures of methylene chloride and a saturated methanolic ammonia solution as eluent. The resultant product gave the following data: Mass Spectrum: M+H⁺ 473.

[62] The reaction mixture was stirred at ambient temperature for 3 hours. The reaction product was purified by column chromatography on silica using increasingly polar mixtures of methylene chloride and a saturated methanolic ammonia solution as eluent. The resultant product gave the following data: Mass Spectrum: M+H⁺ 473.

[63] (2S)-1-(2-Hydroxyethyl)-N-methylprolinamide was used as a starting material and the reaction mixture was stirred at ambient temperature for 3 hours. The reaction product gave the following data: Mass Spectrum: M+H$^+$ 536.

[64] (2S)-1-(2-Hydroxyethyl)-2-morpholinocarbonylpyrrolidine was used as a starting material and the reaction mixture was stirred at ambient temperature for 3 hours. The reaction product gave the following data: Mass Spectrum: M+H$^+$ 592.

[65] (2S)-1-(2-Hydroxyethyl)-2-(4-methylpiperazin-1-ylcarbonyl)pyrrolidine was used as a starting material and the reaction mixture was stirred at ambient temperature for 3 hours. The reaction product gave the following data: Mass Spectrum: M+H$^+$ 605.

[66] (2S)-1-(2-Hydroxyethyl)-2-(pyrrolidin-1-ylcarbonyl)pyrrolidine was used as a starting material and the reaction mixture was stirred at ambient temperature for 3 hours. The reaction product gave the following data: Mass Spectrum: M+H$^+$ 576.

[67] (2S)-1-(2-Hydroxyethyl)-2-piperidinocarbonylpyrrolidine was used as a starting material and the reaction mixture was stirred at ambient temperature for 3 hours. The reaction product gave the following data: Mass Spectrum: M+H$^+$ 590.

[68] (2S)-1-(2-Hydroxyethyl)prolinamide was used as a starting material and the reaction mixture was stirred at ambient temperature for 3 hours. The reaction product gave the following data: Mass Spectrum: M+H$^+$ 522.

[69] (2R)-1-(2-Hydroxyethyl)-2-methylpyrrolidine was used as a starting material and the reaction mixture was stirred at ambient temperature for 3 hours. The reaction product gave the following data: Mass Spectrum: M+H$^+$ 493.

[70] (2S)-1-(2-Hydroxyethyl)-2-methoxymethylpyrrolidine was used as a starting material and the reaction mixture was stirred at ambient temperature for 3 hours. The reaction product gave the following data: Mass Spectrum: M+H$^+$ 523.

[71] The reactants were 4-(6-chloro-2,3-methylenedioxyanilino)-7-hydroxy-5-tetrahydropyran-4-yloxyquinazoline and 1-(tert-butoxycarbonyl)-4-(3-hydroxypropyl)piperazine and the reaction mixture was stirred at ambient temperature for 2 hours. Thereafter, trifluoroacetic acid (1 ml) was added and the mixture was stirred at ambient temperature for 16 hours. The mixture was evaporated and the residue was triturated under a saturated methanolic ammonia solution (1 ml). Methylene chloride was added and the mixture was filtered. The filtrate was evaporated and the residue was purified by column chromatography on silica using a 97:3 mixture of methylene chloride and a saturated methanolic ammonia solution as eluent. The material so obtained was treated with a 6M solution of hydrogen chloride in diethyl ether. The precipitate was isolated, washed with diethyl ether and dried under vacuum to give the dihydrochloride salt (0.11 g) of the required product, a portion of which was converted to the free base using an analogous procedure to that described in Example 3. The free base gave the following data: NMR Spectrum: (CDCl$_3$) 1.9–2.1 (m, 4H), 2.2–2.3 (m, 2H), 2.3–2.5 (m, 4H), 2.55 (m, 2H), 2.91 (m, 4H), 3.65 (m, 2H), 4.05 (m, 2H), 4.15 (m, 2H), 4.8 (m, 1H), 6.06 (s, 2H), 6.5 (d, 1H), 6.72 (d, 1H), 6.84 (d, 1H), 6.97 (d, 1H), 8.5 (s, 1H), 9.26 (s, 1H); Mass Spectrum: M+H$^+$ 542 and 544.

The 4-(6-chloro-2,3-methylenedioxyanilino)-7-hydroxy-5-tetrahydropyran-4-yloxyquinazoline used as a starting material was prepared as follows:

A mixture of 7-benzyloxy-4-(6-chloro-2,3-methylenedioxyanilino)-5-tetrahydropyran-4-yloxyquinazoline (Example 17[34], 0.2 g) and trifluoroacetic acid (2 ml) was stirred and heated to 80° C. for 6 hours. The mixture was evaporated and the residue was triturated under a 6M solution of hydrogen chloride in diethyl ether. The resultant solid was isolated, washed with diethyl ether and dried under vacuum. The solid was treated with a saturated methanolic ammonia solution. The mixture was filtered, the filtrate was evaporated and the residue was triturated under methylene chloride. The solid so obtained was washed with methylene chloride and dried under vacuum. There was thus obtained 4-(6-chloro-2,3-methylenedioxyanilino)-7-hydroxy-5-tetrahydropyran-4-yloxyquinazoline (0.17 g); NMR Spectrum: (DMSOd$_6$) 1.8–1.9 (m, 2H), 2.05–2.2 (m, 2H), 3.5–3.6 (m, 2H), 3.8–3.9 (m, 2H), 4.95 (m, 1H), 6.08 (s, 2H), 6.7 (d, 1H), 6.8 (d, 1H), 6.95 (d, 1H), 7.05 (d, 1H), 8.35 (s, 2H), 9.32 (s, 1H), 10.8 (br s, 1H); Mass Spectrum: M–H$^-$ 414 and 416.

The 1-(tert-butoxycarbonyl)-4-(3-hydroxypropyl)piperazine used as a starting material was prepared using an analogous procedure to that described in European Patent Application No. 0388309:

A mixture of 3-bromopropanol (25 ml), 1-(tert-butoxycarbonyl)piperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation to give the required starting material as an oil.

[72] The reaction mixture was stirred at ambient temperature for 2 hours. The reaction product was treated with 6M hydrogen chloride in diethyl ether to give the dihydrochloride salt of the product, a portion of which was converted to the free base using an analogous procedure to that described in Example 3. The free base gave the following data: NMR Spectrum: (CDCl$_3$) 1.9–2.1 (m, 4H), 2.15–2.3 (m, 2H), 2.28 (s, 3H), 2.4–2.7 (m, 10H), 3.6–3.7 (m, 2H), 4.0–4.1 (m, 2H), 4.15 (m, 2H), 4.75 (m, 1H), 6.05 (s, 2H), 6.5 (d, 1H), 6.72 (d, 1H), 6.83 (d, 1H), 6.97 (d, 1H), 8.52 (s, 1H), 9.26 (s, 1H); Mass Spectrum: M+H$^+$ 556 and 558.

[73] The reaction mixture was stirred at ambient temperature for 2 hours. The reaction product was treated with 6M hydrogen chloride in diethyl ether to give the dihydrochloride salt of the product, a portion of which was converted to the free base using an analogous procedure to that described in Example 3. The free base gave the following data: NMR Spectrum: (CDCl$_3$) 1.9–2.05 (m, 2H), 2.2–2.3(m, 2H), 2.31 (s, 3H), 2.4–2.7(m, 8H), 2.87 (m, 2H), 2.55–2.7 (m, 2H), 3.95–4.05 (m,2H), 4.25 (m, 2H), 4.75 (m, 1H), 6.05 (s, 2H), 6.55 (d, 1H), 6.72 (d, 1H), 6.83 (d, 1H), 6.97 (d, 1H), 8.52 (s, 1 H), 9.26(s, 1H); Mass Spectrum: M+H$^+$ 542 and 544.

[74] The reaction mixture was stirred at ambient temperature for 2 hours. The reaction product was treated with 6M hydrogen chloride in diethyl ether to give the dihydrochloride salt of the product, a portion of which was converted to the free base using an analogous procedure to that described in Example 3. The free base gave the following data: NMR Spectrum: (CDCl$_3$) 1.4–1.5 (m, 2H), 1.6–1.7 (m, 4H), 1.9–2.05 (m, 2H), 2.2–2.3 (m, 2H), 2.5 (br s, 4H), 2.82 (m, 2H), 3.62 (m, 2H), 4.05 (m, 2H), 4.22 (m, 2H), 4.75 (m, 1H), 6.05 (s, 2H), 6.55 (d, 1H), 6.71 (d, 1H), 6.83 (d, 1H), 6.97 (d, 1H), 8.52 (s, 1H), 9.27 (s, 1H); Mass Spectrum: M+H$^+$ 527 and 529.

[75] The reactants were 4-(6-chloro-2,3-methylenedioxyanilino)-7-hydroxy-5-tetrahydropyran-4-yloxyquinazoline and N-(tert-butoxycarbonyl)-4-(2-hydroxyethyl)piperidine (*J. Med. Chem.*, 1994, 37, 2721) and the reaction mixture was stirred at ambient temperature for 2 hours. Thereafter, trifluoroacetic acid (1 ml) was added and the mixture was stirred at ambient temperature for 16 hours. The mixture was evaporated and the residue was triturated under a saturated methanolic ammonia solution (1 ml). Methylene chloride was added and the mixture was filtered. The filtrate was evaporated and the residue was purified by column chromatography on silica using a 97:3 mixture of methylene chloride and a saturated methanolic ammonia solution as eluent. The material so obtained was treated with a 6M solution of hydrogen chloride in diethyl ether. The precipitate was isolated, washed with diethyl ether and dried under vacuum to give the required product; NMR Spectrum: (DMSOd$_6$ and CF$_3$CO$_2$D) 1.35–1.5 (m, 2H), 1.75–1.95(m, 5H), 2.0–2.15 (m, 4H), 2.8–2.95 (m, 2H), 3.3 (d, 2H), 3.55 (m,2H), 3.92 (m, 2H), 4.25 (m, 2H), 5.15 (m, 1H), 6.14 (s, 2H), 6.94(d, 1H), 7.04 (d, 1H), 7.13 (d, 1H), 7.15 (s, 1H), 8.84 (s, 1H); Mass Spectrum: M+H$^+$ 527 and 529.

[76] The reaction mixture was stirred at ambient temperature for 2 hours. The reaction product was treated with 6M hydrogen chloride in diethyl ether to give the dihydrochloride salt of the product, a portion of which was converted to the free base using an analogous procedure to that described in Example 3. The free base gave the following data: NMR Spectrum: (CDCl$_3$) 1.9–2.1 (m, 2H), 2.2–2.3 (m, 2H), 3.6–3.7 (m, 2H), 4.0–4.1 (m, 2H), 4.42 (m, 2H), 4.5(m, 2H), 4.8 (m, 1H), 6.06 (s, 2H), 6.56 (d, 1H), 6.73 (d, 1H), 6.9 (m, 3H), 7.0 (d, 1H), 8.47 (d, 2H), 8.54 (s, 1H), 9.28 (s, 1H); Mass Spectrum: M+H$^+$ 537 and 539.

[77] The reaction mixture was stirred at ambient temperature for 2 hours. The product gave the following data: NMR Spectrum: (CDCl$_3$) 1.25–1.4 (m, 2H), 1.5 (s, 9H), 1.75–1.9 (m, 2H), 1.9–2.1 (m, 3H), 2.2–2.3 (m, 2H), 2.7–2.8 (m, 2H), 3.6–3.7 (m, 2H), 3.95(d, 2H), 4.0–4.1 (m, 2H), 4.1–4.3 (m, 2H), 4.78 (m, 1H), 6.08 (s, 2H), 6.5 (d, 1H), 6.75 (d, 1H), 6.82 (d, 1H), 6.97 (d, 1H), 8.52 (s, 1H), 9.28 (s, 1H); Mass Spectrum: M+H$^+$ 613 and 615.

[78] The reaction mixture was stirred at ambient temperature for 1 hour. The reaction product gave the following data: NMR Spectrum: (CDCl$_3$) 1.6–1.75 (m, 4H), 1.75–1.9 (m, 6H), 2.0–2.2 (m,4H), 2.55(m, 4H), 2.65 (m, 2H), 4.15 (m, 2H), 5.0 (m, 1H), 6.02 (s, 2H), 6.5 (d, 1H), 6.65 (d, 1H), 6.8 (d, 1H), 6.9 (m, 1H), 8.12 (d, 1 H), 8.58 (s, 1H), 8.8 (s, 1H); Mass Spectrum: M+H$^+$ 477.

[79] The reaction mixture was stirred at ambient temperature for 1 hour. The reaction product gave the following data: NMR Spectrum: (CDCl$_3$) 1.65–1.8(m, 4H), 1.9 (m, 2H), 2.0–2.2 (m, 8H), 2.3 (s, 3H), 2.3–2.7 (m, 6H), 4.15 (t, 2H), 5.0 (m, 1H), 6.02 (s, 2H), 6.5 (s, 1H), 6.65 (d, 1H), 6.8 (d, 1H), 6.92 (m,1H), 8.15 (d, 1H), 8.6 (s, 1H), 9.8 (s, 1H); Mass Spectrum: M+H$^+$ 506.

[80] The reaction mixture was stirred at ambient temperature for 1 hour. The reaction product gave the following data: NMR Spectrum: (CDCl$_3$) 1.65–1.8 (m, 2H), 1.8–1.95 (m, 2H), 1.95–2.2(m, 4H), 2.3 (s, 3H), 2.4–2.6 (m, 4H), 2.6–2.8 (m, 4H), 2.9 (m, 2H), 4.2 (m, 2H), 5.0 (m, 1H), 6.0 (s, 2H), 6.52 (d, 1 H), 6.65 (d, 1H), 6.8 (d, 1H), 6.9 (m, 1H), 8.15 (d, 1H), 8.6 (s, 1H), 9.8 (s, 1H); Mass Spectrum: M+H$^+$ 492.

[81] The reaction mixture was stirred at ambient temperature for 1 hour. The reaction product gave the following data: NMR Spectrum: (CDCl$_3$) 1.6–1.7 (m, 6H), 1.7–1.8 (m, 2H), 1.8–1.95 (m, 2H), 2.0–2.2 (m, 4H), 2.55 (br s, 4H), 2.82 (m, 2H), 4.22 (m, 2H), 5.0 (m, 1H), 6.02 (s, 2H), 6.52 (s, 1 H), 6.65 (d, 1H), 6.8 (d, 1H), 6.9 (m, 1H), 8.15 (d, 1H), 8.6 (s, 1H), 9.8 (s, 1H); Mass Spectrum: M+H$^+$ 477.

[82] (2S)-1-(2-Hydroxyethyl)-2-(4-methylpiperazin-1-ylcarbonyl)pyrrolidine was used as a starting material and the reaction mixture was stirred at ambient temperature for 1 hour. The reaction product gave the following data: Mass Spectrum: M+H$^+$ 589.

[83] N-(tert-Butoxycarbonyl)piperidin-4-ylmethanol was used as a reactant. The reaction mixture was stirred at ambient temperature for 1 hour. Thereafter, a 6M solution of hydrogen chloride in diethyl ether (2 ml) was added and the reaction mixture was stirred at ambient temperature for 16 hours. The mixture was diluted with methylene chloride (10 ml) and a saturated methanolic ammonia solution (3 ml) was added. The mixture was filtered and the filtrate was evaporated to dryness. The residue was purified by column chromatography on silica using a 50:47:3 mixture of methylene chloride, ethyl acetate and a saturated methanolic ammonia solution as eluent. The reaction product gave the following data: NMR Spectrum: (CDCl$_3$) 1.25–1.42 (m,2H), 1.6–1.7 (m, 4H), 1.8–2.0 (m, 3H), 2.0–2.2 (m, 4H), 2.7 (m, 2H), 3.15 (d, 2H), 3.95 (d, 2H), 5.05 (m, 1H), 6.02 (s, 2H), 6.5 (d, 1H), 6.65 (d, 1H), 6.8 (d, 1H), 6.9 (m, 1H), 8.15 (d, 1H), 8.6 (s, 1H), 8.8 (s, 1H); Mass Spectrum: M+H$^+$ 463.

[84] 1-(tert-Butoxycarbonyl)-4-(3-hydroxypropyl)piperazine was used as a reactant. The reaction mixture was stirred at ambient temperature for 1 hour. Thereafter, a 6M solution of hydrogen chloride in diethyl ether (2 ml) was added and the reaction mixture was stirred at ambient temperature for 16 hours. The mixture was diluted with methylene chloride (10 ml) and a saturated methanolic ammonia solution (3 ml) was added. The mixture was filtered and the filtrate was evaporated to dryness. The residue was purified by column chromatography on silica using a 50:47:3 mixture of methylene chloride, ethyl acetate and a saturated methanolic ammonia solution as eluent. The reaction product gave the following data: NMR Spectrum: (CDCl$_3$) 1.9–2.1 (m, 2H), 1.8–1.95 (m, 2H), 1.95–2.2 (m, 6H), 1.9 (br s, 4H), 1.95 (m, 2H), 2.9 (m, 4H), 4.15 (m, 2H), 5.0 (m, 1H), 6.02 (s, 2H), 6.5 (d, 1H), 6.65 (d, 1H), 6.8 (d, 1H), 6.9 (m, 1 H), 8.12 (d, 1H), 8.6 (s, 1H), 8.8 (s, 1H); Mass Spectrum: M+H$^+$ 492.

EXAMPLE 15

Using an analogous procedure to that described in Example 5, the appropriate 4-chloroquinazoline was reacted with the appropriate aniline in the presence of hydrogen chloride to give the dihydrochloride salts of the compounds described in Table IV, a portion of each of which was converted to the free base.

TABLE IV

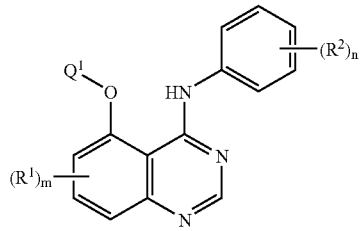

| No. and Note | (R$^1$)$_m$ | Q$^1$ | (R$^2$)$_n$ |
|---|---|---|---|
| [1] | 7-methoxy | piperidin-4-ylmethyl | 2-bromo-5-methoxy |
| [2] | 7-methoxy | piperidin-4-ylmethyl | 2-chloro-5-methoxy |
| [3] | 7-methoxy | piperidin-4-ylmethyl | 2,5-dimethoxy |
| [4] | 7-methoxy | piperidin-4-ylmethyl | 2,5-dichloro |
| [5] | 7-methoxy | piperidin-4-ylmethyl | 2,3-methylenedioxy |
| [6] | 7-methoxy | N-methylpiperidin-4-yl | 2,5-dichloro |
| [7] | 7-methoxy | N-methylpiperidin-4-yl | 2-bromo-5-chloro |
| [8] | 7-benzyloxy | piperidin-4-yl | 2-bromo-5-methoxy |
| [9] | 6-methoxy | N-methylpiperidin-4-yl | 2-chloro-5-methoxy |
| [10] | 7-[3-(4-methylpiperazin-1-yl)propoxy] | 4-tetrahydropyranyl | 2,4-dichloro-5-methoxy |
| [11] | 6-[3-(4-methylpiperazin-1-yl)propoxy] | 4-tetrahydropyranyl | 2-chloro-5-methoxy |
| [12] | 6-[3-(4-methylpiperazin-1-yl)propoxy] | 4-tetrahydropyranyl | 2,5-dichloro |
| [13] | 6-[3-(4-methylpiperazin-1-yl)propoxy] | 4-tetrahydropyranyl | 2-bromo-5-methoxy |
| [14] | 7-[3-(4-methylpiperazin-1-yl)propoxy] | 4-tetrahydropyranyl | 4-chloro-2-fluoro-5-methoxy |
| [15] | 7-[3-(4-methylpiperazin-1-yl)propoxy] | 4-tetrahydropyranyl | 4-bromo-2-fluoro |
| [16] | 7-[3-(4-methylpiperazin-1-yl)propoxy] | 4-tetrahydropyranyl | 2-pyrrolidin-1-yl-5-methoxy |
| [17] | 7-[3-(4-methylpiperazin-1-yl)propoxy] | 4-tetrahydropyranyl | 2,3-methylenedioxy |
| [18] | 7-benzyloxy | N-tert-butoxycarbonyl-piperidin-4-yl | 6-chloro-2,3-methylenedioxy |
| [19] | 7-hydroxy | cyclopentyl | 2,3-methylenedioxy |

Notes

[1] The reactants were 5-[N-(tert-butoxycarbonyl)piperidin-4-ylmethoxy]-4-chloro-7-methoxyquinazoline and 2-bromo-5-methoxyaniline hydrochloride and the reaction mixture was heated to 80° C. for 2 hours. A second portion of 6M hydrogen chloride in isopropanol (0.06 ml) was added and the reaction mixture was heated to 80° C. for a further 4 hours. The reaction product was obtained as the dihydrochloride salt, a portion of which was converted to the free base which gave the following data: NMR Spectrum: (CDCl$_3$) 1.3 (m, 2H), 1.9 (d, 2H), 2.3 (m, 1H), 2.68 (m,2H), 3.12 (d, 2H), 3.85 (s, 3H), 3.95 (s, 3H), 4.15 (d, 2H), 6.52 (d, 1H), 6.62 (m, 1H), 6.88 (s, 1H), 7.5 (d, 1H), 8.22 (d, 1H), 8.6 (s, 1H), 8.9 (s, 1H); Mass Spectrum: M+H$^+$ 473 and 475.

The 5-[N-(tert-butoxycarbonyl)piperidin-4-ylmethoxy]4-chloro-7-methoxyquinazoline used as a starting material was prepared as follows:

Diethyl azodicarboxylate (3.85 ml) was added dropwise to a stirred mixture of 5-hydroxy-7-methoxy-3-pivaloyloxymethyl-3,4-dihydroquinazolin-4-one (5 g), N-(tert-butoxycarbonyl)piperidin-4-ylmethanol (4.2 g), triphenylphosphine (6.4 g) and methylene chloride (50 ml) which had been cooled to 10° C. The mixture was stirred at ambient temperature for 1 hour. The resultant mixture was poured onto a column of silica and eluted with increasingly polar mixtures of methylene chloride and ethyl acetate. The product so obtained was dissolved in a saturated methanolic ammonia solution (250 ml) and solid sodium hydroxide (0.65 g) was added. The resultant mixture was stirred at ambient temperature for 30 minutes. The mixture was evaporated and the residue was purified by column chromatography on silica using increasingly polar mixtures of methylene chloride and ethyl acetate and then methylene chloride, ethyl acetate and methanol as eluent. The product so obtained was triturated under diethyl ether. The resultant solid was isolated, washed with diethyl ether and dried under vacuum. There was thus obtained 5-[N-(tert-butoxycarbonyl)piperidin-4-ylmethoxy]-7-methoxy-3,4-dihydroquinazolin-4-one (3.4 g); NMR Spectrum: (CDCl$_3$) 1.3–1.4 (m, 2H), 1.46 (s, 9H), 1.95 (d, 2H), 2.15 (m, 1H), 2.35 (t, 2H), 3.9 (s, 3H), 3.9 (m, 2H), 4.15 (br s, 2H), 6.45 (d, 1 H), 6.75 (d, 1H), 7.93 (s, 1H), 11.0 (br s, 10H); Mass Spectrum: M+H$^+$ 390.

A mixture of a portion (2.9 g) of the material so obtained, triphenyl phosphine (5.3 g), carbon tetrachloride (3 ml) and 1,2-dichloroethane (50 ml) was stirred and heated to 70° C. for 2.5 hours. The mixture was poured onto silica and eluted with increasingly polar mixtures of methylene chloride and ethyl acetate. The material so obtained was triturated under diethyl ether. The resultant precipitate was isolated, washed with diethyl ether and dried. There was thus obtained 5-[N-(tert-butoxycarbonyl)piperidin-4-ylmethoxyl-4-chloro-7-methoxyquinazoline (1.9 g); NMR Spectrum: (CDCl$_3$) 1.35–1.5 (m, 2H), 1.45 (s, 9H), 1.92 (d, 2H), 2.15 (m, 1H), 2.8 (t, 2H), 3.95 (d, 2H), 3.97 (s, 3H), 4.2 (br s, 2H), 6.6 (d, 1H), 6.98 (d, 1H), 8.82 (s, 1H).

[2] The reactants were 5-N-(tert-butoxycarbonyl)piperidin-4-ylmethoxy]-4-chloro-7-methoxyquinazoline and 2-chloro-5-methoxyaniline and the reaction mixture was heated to 80° C. for 2 hours. A second portion of 6M hydrogen chloride in isopropanol (0.06 ml) was added and the reaction mixture was heated to 80° C. for a further 4 hours. The reaction product was obtained as the dihydrochloride salt, a portion of which was converted to the free base which gave the following data: NMR Spectrum: (CDCl$_3$) 1.3–1.4 (m, 2H), 1.92 (d, 2H), 2.3 (m, 1H), 2.7 (t, 2H), 3.2 (d, 2H), 3.85 (s, 3H), 3.95 (s, 3H), 4.15 (d, 2H), 6.52 (s, 1H), 6.65 (m, 1H), 6.9 (s, 1H), 7.32 (d, 1H), 8.4 (s, 1H), 8.62 (s, 1 H), 10.2 (s, 1H); Mass Spectrum: M+H$^+$ 429 and 431.

[3] The reactants were 5-[N-(tert-butoxycarbonyl)piperidin-4-ylmethoxy]4-chloro-7-methoxyquinazoline and 2,5-dimethoxyaniline and the reaction mixture was heated to 80° C. for 2 hours. The reaction mixture was evaporated and the residue was dissolved in methylene chloride (1 ml). Trifluoroacetic acid (1 ml) was added and the mixture was stirred at ambient temperature for 15 minutes. The resultant mixture was evaporated and the residue was partitioned between ethyl acetate and 1N aqueous sodium hydroxide solution. The organic layer was washed with brine, dried over magnesium sulphate and evaporated. The residue was dissolved in isopropanol (1 ml) and 6M hydrogen chloride in isopropanol (0.1 ml) was added. The resultant precipitate was isolated, washed with isopropanol and with diethyl ether and dried under vacuum. There was thus obtained the required product as the dihydrochloride salt, a portion of which was converted to the free base which gave the following data: NMR Spectrum: (CDCl$_3$) 1.3–1.5 (m, 2H), 1.95 (d, 2H), 2.25 (m, 1H), 2.7 (m,2H), 3.2 (d, 2H), 3.84 (s, 3H), 3.92 (s, 3H), 3.93 (s, 3H), 4.1 (d, 2H), 6.5 (s, 1H), 6.6 (m, 1H), 6.9 (m, 2H), 8.52 (d, 1H), 8.6 (s, 1H), 10.15 (s, 1H); Mass Spectrum: M+H$^+$ 425.

[4] The reactants were 5-[N-(tert-butoxycarbonyl)piperidin-4-ylmethoxy]4-chloro-7-methoxyquinazoline and 2,5-dichloroaniline and the reaction mixture was heated to 80° C. for 2 hours. The reaction mixture was evaporated and the residue was dissolved in methylene chloride (1 ml). Trifluoroacetic acid (1 ml) was added and the mixture was stirred at ambient temperature for 15 minutes. The resultant mixture was evaporated and the residue was partitioned between ethyl acetate and 1N aqueous sodium hydroxide solution. The organic layer was washed with brine, dried over magnesium sulphate and evaporated. The residue was purified by column chromatography on silica using a 9:10:1 mixture of methylene chloride, ethyl acetate and methanol as eluent. The material so obtained was dissolved in isopropanol (1 ml) and 6M hydrogen chloride in isopropanol (0.1 ml) was added. The resultant precipitate was isolated, washed with isopropanol and with diethyl ether and dried under vacuum. There was thus obtained the required product as the dihydrochloride salt, a portion of which was converted to the free base which gave the following data: NMR Spectrum: (CDCl$_3$) 1.25–1.4 (m, 2H), 1.9 (d, 2H), 2.25 (m, 1H), 2.65 (m, 2H), 3.15 (d, 2H), 3.95 (s, 3H), 4.12 (d, 2H), 6.55 (d, 1H), 6.9 (d, 1H), 7.05 (m, 1H), 7.35 (d, 1H), 8.6 (s, 1H), 8.87 (d, 1H), 10.09 (br s, 1 H); Mass Spectrum: M+H$^+$ 433 and 435.

[5] The reactants were 5-[N-(tert-butoxycarbonyl)piperidin-4-ylmethoxy]-4-chloro-7-methoxyquinazoline and 2,3-methylenedioxyaniline and the reaction mixture was heated to 80° C. for 2 hours. The reaction mixture was evaporated and the residue was dissolved in methylene chloride (1 ml). Trifluoroacetic acid (1 ml) was added and the mixture was stirred at ambient temperature for 15 minutes. The resultant mixture was evaporated and the residue was partitioned between ethyl acetate and 1N aqueous sodium hydroxide solution. The organic layer was washed with brine, dried over magnesium sulphate and evaporated. The residue was dissolved in isopropanol (1 ml) and 6M hydrogen chloride in isopropanol (0.1 ml) was added. The resultant precipitate was isolated, washed with isopropanol and with diethyl ether and dried under vacuum. There was thus obtained the required product as the dihydrochloride salt, a portion of which was converted to the free base which gave the following data: NMR Spectrum: (CDCl$_3$) 1.25–1.4 (m, 2H), 1.85 (d, 2H), 2.2 (m, 1H), 2.65 (m, 2H), 3.2 (d, 2H), 3.9 (s, 3H), 4.02 (d, 2H), 6.0 (s, 2H), 6.48 (d, 1H), 6.62 (d, 1H), 6.85 (d, 1H), 6.9 (m, 1H), 8.07 (d, 1H), 8.58 (s, 1H), 9.6 (s, 1H); Mass Spectrum: M+H$^+$ 409.

[6] The free base gave the following data: NMR Spectrum: (CDCl$_3$) 1.95–2.1 (m, 2H), 2.15–2.35 (m, 4H), 2.3 (s, 3H), 2.85 (m,2H), 3.92 (s, 3H), 4.5 (m, 1H), 6.55 (d, 1H), 6.85 (d, 1H), 7.03 (m, 1H), 7.3 (d, 1H), 8.6 (s, 1H), 8.85 (s, 1 H); Mass Spectrum: M+H$^+$ 433 and 435.

[7] The free base gave the following data: NMR Spectrum: (CDCl$_3$) 2.0–2.15 (m, 2H), 2.15–2.3 (m, 4H), 2.28 (s, 3H), 2.85 (m, 2H), 3.92 (s, 3H), 4.5 (m, 1H), 6.5 (s, 1H), 6.85 (s, 1H), 7.0 (m, 1H), 7.5 (d, 1H), 8.35 (s, 1H), 8.55 (s, 1H), 9.7 (s, 1H); Mass Spectrum: M+H$^+$ 477, 479 and 481.

[8] The reactants were 7-benzyloxy-5-[N-(tert-butoxycarbonyl)piperidin-4-yloxy]-4-chloroquinazoline and 2-bromo-5-methoxyaniline hydrochloride and the reaction mixture was heated to 80° C. for 2 hours. A second portion of 6M hydrogen chloride in isopropanol (0.06 ml) was added and the reaction mixture was heated to 80° C. for a further 4 hours. The reaction product was obtained as the dihydrochloride salt, a portion of which was converted to the free base which gave the following data: NMR Spectrum: (CDCl$_3$) 1.95–2.1 (m, 2H), 2.25 (d, 2H), 2.8 (m, 2H), 3.22 (m, 2H), 3.78 (s, 3H), 4.6 (m, 1H), 5.12 (s, 3H), 6.58 (m, 2H), 6.9 (d, 1H), 7.25–7.5 (m, 5H), 7.89 (d, 1H), 8.5 (s, 1H), 9.6 (s, 1H); Mass Spectrum: M+H$^+$ 535 and 537.

The 7-benzyloxy-5-[N-(tert-butoxycarbonyl)piperidin-4-yloxy]-4-chloroquinazoline used as a starting material was prepared as follows:

A mixture of 5,7-dibenzyloxy-3,4-dihydroquinazolin-4-one (2 g), magnesium bromide (1 g) and pyridine (10 ml) was stirred and heated to 120° C. for 20 minutes. The mixture was evaporated and the residue was dissolved in a mixture of water (20 ml) and glacial acetic acid (4 ml) and stirred for 10 minutes. The resultant precipitate was isolated, washed with water and dried under vacuum over phosphorus pentoxide at 50° C. There was thus obtained 7-benzyloxy-5-hydroxy-3,4-dihydroquinazolin-4-one (1.5 g); NMR Spectrum: (DMSOd$_6$) 5.22 (s, 2H), 6.5 (d, 1H), 6.7 (d, 1 H), 7.3–7.5 (m, 5H), 8.05 (s, 1H); Mass Spectrum: M+H$^+$ 269.5.

The material so obtained was added portionwise to a stirred suspension of sodium hydride (60% dispersion in mineral oil, 0.46 g; washed with pentane) in DMF (15 ml) which was cooled to 0° C. The mixture was stirred at ambient temperature for 30 minutes. The resultant mixture was cooled at 0°C., chloromethyl pivalate (1.2 ml) was added and the mixture was stirred at ambient temperature for 1 hour. The mixture was poured into water (70 ml) containing acetic acid (4 ml) and the resultant precipitate was isolated and dried under vacuum. The material so obtained was dissolved in methylene chloride and the organic solution was dried over magnesium sulphate and evaporated. The residue was triturated under pentane and the resultant solid was isolated and dried under vacuum. There was thus obtained 7-benzyloxy-5-hydroxy-3-pivaloyloxymethyl-3,4-dihydroquinazolin-4-one (1.95 g); NMR Spectrum: (CDCl$_3$) 1.2 (s, 9H), 5.12 (s, 2H), 5.88 (s, 2H), 6.58 (d, 1H), 6.72 (d, 1H), 7.3–7.5 (m, 5H), 8.15 (s, 1H), 11.32 (s, 1H); Mass Spectrum: M+H$^+$ 383.

The material so obtained was reacted with N-(tert-butoxycarbonyl)-4-hydroxypiperidine using an analogous procedure to that described in the first paragraph of the portion of Note [1] immediately above that is concerned with the preparation of starting materials. There was thus obtained 7-benzyloxy-5-[N-(tert-butoxycarbonyl)piperidin-4-yloxy]-3,4-dihydroquinazolin-4-one (1.4 g); NMR Spectrum: (CDCl$_3$) 1.5 (s, 9H), 1.82 (m, 4H), 3.52 (m, 2H), 3.7 (m,2H), 4.65 (m, 1H), 5.2 (s, 2H), 6.6 (d, 1H), 6.9 (d, 1H), 7.3–7.5 (m, 5H), 7.92 (s, 1H), 10.56 (br s, 1H); Mass Spectrum: M+H$^+$ 452.6.

A mixture of the material so obtained, triphenylphosphine (1.66 g), carbon tetrachloride (0.92 ml) and 1,2-dichloroethane (40 ml) was stirred and heated to 70° C. for 1.5 hours. The mixture was evaporated and the residue was purified by column chromatography on silica using a 9:1 mixture of methylene chloride and ethyl acetate as eluent. There was thus obtained 7-benzyloxy-5-[N-(tert-butoxycarbonyl)piperidin-4-yloxy]-4-chloroquinazoline (1.1 g); NMR Spectrum: (CDCl$_3$) 1.5 (s, 9H), 1.98 (m, 4H), 3.5–3.7 (m, 4H), 4.75 (m, 1H), 5.2 (s, 2H), 6.7 (d, 1H), 7.08 (d, 1H), 7.32–7.52 (m, 5H), 8.82 (s, 1H); Mass Spectrum: M+H$^+$ 470.

[9] The free base gave the following data: NMR Spectrum: (CDCl$_3$) 1.95–2.15 (m, 6H), 2.25 (s, 3H), 2.85 (br s, 2H), 3.87 (s, 3H), 4.02 (s, 3H), 4.45 (m, 1H), 6.65 (m, 1H), 7.35 (d, 1H), 7.55 (d, 1H), 7.7 (d, 1H), 8.5 (d, 1H), 8.6 (s, 1H), 10.45 (br s, 1H); Mass Spectrum: M+H$^+$ 429 and 431.

The 4-chloro-6-methoxy-5-(N-methylpiperidin-4-yloxy)quinazoline used as a starting material was prepared as follows:

A solution of ferrous sulphate heptahydrate (99 g) in water (410 ml) that had been heated to 70° C. was added to a mixture of 2-benzyloxy-3-methoxy-6-nitrobenzoic acid (*Bull. Soc. Chim. France*, 1965, 1417; 15.5 g) and concentrated aqueous ammonium hydroxide (370 ml) which was heated to 70° C. The resultant mixture was heated to reflux for minutes. The mixture was filtered and the basicity of the filtrate was adjusted to pH8 by the addition of 2N aqueous hydrochloric acid and then the filtrate was acidified to pH4 by the addition of 1M aqueous citric acid solution. The mixture was partitioned between ethyl acetate and water. The organic layer was washed with water and with brine, dried over magnesium sulphate and evaporated to give 6-amino-2-benzyloxy-3-methoxybenzoic acid (12.15 g); NMR Spectrum: (CDCl$_3$) 3.9 (s, 3H), 5.22 (s, 2H), 6.5 (d, 1H), 7.05 (d, 1H), 7.35–7.55 (m, 5H): Mass Spectrum: M+H$^+$ 274.

A mixture of the material so obtained, triazine (3.6 g), piperidine (3 ml) and ethanol (275 ml) was stirred and heated to reflux for 16 hours. The mixture was cooled to ambient temperature. The precipitate was isolated, washed with ethanol and with diethyl ether and dried under vacuum to give 5-benzyloxy-6-methoxy-3,4-dihydroquinazolin-4-one (10.3 g); NMR Spectrum: (CDCl$_3$) 3.9 (s, 3H), 5.15 (s, 2H), 7.2–7.45 (m,4H), 7.5 (d, 1H), 7.62 (d, 2H), 7.8 (s, 1H), 11.1 (br s, 1H); Mass Spectrum: M+H$^+$ 283.

A solution of a portion (5 g) of the material so obtained in trifluoroacetic acid (50 ml) was stirred at ambient temperature for 30 minutes. The mixture was evaporated and the residue was dissolved in water. The solution was basified to pH8.5 by the portionwise addition of sodium bicarbonate. The resultant precipitate was isolated, washed with water and dried under vacuum at 50° C. over phosphorus pentoxide. There was thus obtained 5-hydroxy-6-methoxy-3,4-dihydroquinazolin-4-one (3.4 g); NMR Spectrum: (DMSOd$_6$) 3.85 (s, 3H), 7.12 (d, 1H), 7.52 (d, 1H), 7.98 (s, 1H), 11.89 (s, 1H); Mass Spectrum: M+H$^+$ 193.

The material so obtained was added to a stirred suspension of sodium hydride (1.59 g of a 60% dispersion in mineral oil which was washed with pentane) in DMF (18 ml) which was cooled to 0° C. The mixture was stirred at ambient temperature for 30 minutes. The mixture was cooled to 0° C. and chloromethyl pivalate (4.1 ml) was added dropwise. The mixture was stirred at ambient temperature for 1.5 hours. The resultant precipitate was isolated, washed with water and dried overnight under vacuum. The solid was dissolved in methylene chloride and the solution was dried over magnesium sulphate. The solution was evaporated and the residue was triturated under pentane. The resultant solid was isolated and dried under vacuum. There was thus obtained 5-hydroxy-6-methoxy-3-pivaloyloxymethyl-3,4-dihydroquinazolin-4-one (4.6 g); NMR Spectrum: (CDCl$_3$) 1.25 (s, 9H), 4.0 (s, 3H), 5.9 (s, 2H), 7.2 (d, 1H), 7.38 (d, 1H), 8.08 (s, 1H), 11.5 (s, 1H); Mass Spectrum: M+H$^+$ 307.

A solution of di-tert-butyl azodicarboxylate (1.75 g) in methylene chloride (3 ml) was added to a stirred mixture of 5-hydroxy-6-methoxy-3-pivaloyloxymethyl-3,4-dihydroquinazolin-4-one (1.55 g), triphenylphosphine (1.99 g), 4-hydroxy-1-methylpiperidine (0.75 g) and methylene chloride (12 ml) which had been cooled to 5° C. The mixture was stirred at ambient temperature for 1 hour. The mixture was evaporated and the residue was purified by column chromatography on silica using a 9:10:1 mixture of methylene chloride, ethyl acetate and a saturated methanolic ammonia solution as eluent. The material so obtained was stirred in a saturated methanolic ammonia solution for 48 hours. The mixture was evaporated and the residue was triturated under diethyl ether. The resultant solid was washed with diethyl ether and dried under vacuum to give 6-methoxy-5-(N-methylpiperidin-4-yloxy)-3,4-dihydroquinazolin-4-one (0.92 g); NMR Spectrum: (DMSOd$_6$) 1.7–1.9 (m, 4H), 1.95 (t, 2H), 2.15 (s, 3H), 2.7 (m, 2H), 3.85 (s, 3H), 4.08 (m, 1H), 7.4 (d, 1H), 7.6 (d, 1H), 7.85 (s, 1H), 11.8 (br s, 1H); Mass Spectrum: M+H$^+$ 290.

A mixture of a portion (0.3 g) of the material so obtained, triphenylphosphine (0.54 g), carbon tetrachloride (0.3 ml) and 1,2-dichloroethane (13 ml) was stirred and heated to 70° C. for 2.5 hours. The mixture was evaporated and the residue was purified by column chromatography on silica using a 10:9:1 mixture of ethyl acetate, methylene chloride and a saturated methanolic ammonia solution as eluent. There was thus obtained 4-chloro-6-methoxy-5-(N-methylpiperidin-4-yloxy)quinazoline (0.22 g); NMR Spectrum: (CDCl$_3$) 1.82–2.1 (m, 6H), 2.25 (s, 3H), 2.85 (m, 2H), 4.0 (s, 3H), 4.4 (m, 1H), 7.7 (d, 1H), 7.8 (d, 1H), 8.82 (s, 1H).

[10] The free base gave the following data: NMR Spectrum: (CDCl$_3$) 2.02 (m, 4H), 2.2 (d, 2H), 2.4 (s, 3H), 2.5–2.8 (m, 10H), 3.55 (t, 2H), 3.95 (s, 3H), 4.05 (m, 2H), 4.1 (t, 2H), 4.7 (m, 1H), 6.55 (d, 1H), 6.82 (d, 1H), 7.4 (s, 1H), 8.35 (s, 1H), 8.55 (s, 1H), 9.82 (s, 1H); Mass Spectrum: M+H$^+$ 576 and 578.

The 4-chloro-7-[3-(4-methylpiperazin-1-yl)propoxy]-5-tetrahydropyran-4-yloxyquinazoline used as a starting material was prepared as follows:

5-Hydroxy-7-methoxy-3-pivaloyloxymethyl-3,4-dihydroquinazolin-4-one (0.61 g) was reacted with 4-hydroxytetrahydropyran (0.23 ml) using an analogous procedure to that described in the first paragraph of the portion of Note [1] immediately above that is concerned with the preparation of starting materials. There was thus obtained 7-methoxy-5-tetrahydropyran-4-yloxy-3,4-dihydroquinazolin-4-one (0.3 g); NMR Spectrum: (DMSOd$_6$) 1.6–1.75 (m, 2H), 1.9–2.0 (m, 2H), 3.52 (m, 2H), 3.85 (s, 3H), 3.95 (m, 2H), 4.75 (m, 1H), 6.65 (d, 1H), 6.7 (m,1H), 7.92 (s, 1H).

A mixture of 7-methoxy-5-tetrahydropyran-4-yloxy-3,4-dihydroquinazolin-4-one (4 g), thiophenol (2.2 ml), potassium carbonate (3 g) and N-methylpyrrolidin-2-one (40 ml) was stirred and heated to 200° C. for 25 minutes. The mixture was evaporated and the residue was acidified by the addition of 12N aqueous hydrochloric acid (2 ml). Methylene chloride (5 ml) was added. The resultant precipitate was isolated, washed in turn with water and diethyl ether and dried under vacuum to give 7-hydroxy-5-tetrahydropyran-4-yloxy-3,4-dihydroquinazolin-4-one (3.4 g); NMR Spectrum: (DMSOd$_6$) 1.6–1.75 (m, 2H), 1.9–2.0 (m,2H), 3.45–3.6 (m, 2H), 3.8 (m, 3H), 4.65 (m,1H), 6.5 (d, 1H), 6.65 (m, 1H), 7.92 (s, 1H), 10.4 (s, 1H), 11.5 (s, 1H); Mass Spectrum: M+H$^+$ 263.

A mixture of 7-hydroxy-5-tetrahydropyran-4-yloxy-3,4-dihydroquinazolin-4-one (3.2 g), pyridine (3.2 ml) and acetic anhydride (20 ml) was stirred and heated to 100° C. for 2 hours. The mixture was evaporated. The residue was dissolved in a mixture of methanol and water and stirred at ambient temperature for 2 hours. The mixture was evaporated to remove the methanol and the residual aqueous layer was freeze-dried. The residue was purified by column chromatography on silica using a 19:1 mixture of methylene chloride and methanol as eluent. There was thus obtained 7-acetoxy-5-tetrahydropyran-4-yloxy-3,4-dihydroquinazolin-4-one (3.1 g); NMR Spectrum: (DMSOd$_6$) 1.7 (m, 2H), 1.92 (m, 2H), 2.3 (s, 3H), 3.5 (m, 2H), 3.9 (m, 2H), 4.72 (m, 1H), 6.95 (d, 2H), 7.98 (s, 1H), 10.9 (br s, 1H); Mass Spectrum: M+H$^+$ 305.

A mixture of a portion (1.2 g) of the material so obtained, phosphoryl chloride (0.41 ml), di-isopropylethylamine (1.74 ml) and 1,2-dichloroethane (30 ml) was stirred and heated to 80° C. for 2.5 hours. The mixture was evaporated. The material so obtained was dissolved in a saturated methanolic ammonia solution and stirred for 2.5 hours. The mixture was evaporated and the residue was purified by column chromatography on silica using a 97:3 mixture of methylene chloride and methanol as eluent. There was thus obtained 4-chloro-7-hydroxy-5-tetrahydropyran-4-yloxyquinazoline (0.5 g); NMR Spectrum: (DMSOd$_6$) 1.8 (m, 2H), 2.08 (m, 2H), 3.6 (m, 2H), 3.9 (m, 2H), 4.9 (m, 1H), 6.9 (d, 2H), 8.76 (s, 1H); Mass Spectrum: M+H$^+$ 281 and 283.

Di-tert-butyl azodicarboxylate (0.65 g) was added to a stirred mixture of 4-chloro-7-hydroxy-5-tetrahydropyran-4-yloxyquinazoline (0.5 g), triphenylphosphine (0.75 g), 1-(3-hydroxypropyl)-4-methylpiperazine (0.34 g) and methylene chloride (20 ml) and the mixture was stirred at ambient temperature for 1.5 hours. The mixture was poured onto a column of silica and eluted initially with a 49:1 mixture of methylene chloride and methanol followed by a 97:3 mixture of methylene chloride and a saturated methanolic ammonia solution. There was thus obtained 4-chloro-7-[3-(4-methylpiperazin-4-yl)propoxy]-5-tetrahydropyran-4-yloxyquinazoline (0.54 g); NMR Spectrum: (CDCl$_3$) 1.9–2.2 (m, 6H), 2.25 (s, 3H), 2.32–2.68 (m, 10H), 3.68 (m, 2H), 4.05 (m, 2H), 4.15 (t, 2H), 4.72 (m, 1H), 6.58 (d, 1H), 6.92 (d, 1H), 8.8 (s, 1H); Mass Spectrum: M+H$^+$ 421 and 423.

[11] The free base gave the following data: NMR Spectrum: (CDCl$_3$) 1.95–2.2 (m, 6H), 2.5 (s, 3H), 2.6–2.9 (m, 10H), 3.35 (m, 2H), 3.9 (s, 3H), 4.02 (m, 2H), 4.25 (t, 2H), 4.6 (m,1H), 6.65 (m, 1H), 7.35 (d, 1H), 7.55 (d, 1H), 7.68 (d, 1H), 8.55 (s, 1H), 8.65 (s, 1H), 10.45 (s, 1H); Mass Spectrum: M+H$^+$ 542 and 544.

The 4-chloro-6-[3-(4-methylpiperazin-1-yl)propoxy]-5-tetrahydropyran-4-yloxyquinazoline used as a starting material was prepared as follows:

Di-tert-butyl azodicarboxylate (3.6 g) was added portionwise to a stirred mixture of 5-hydroxy-6-methoxy-3-pivaloyloxymethyl-3,4-dihydroquinazolin-4-one (3 g), triphenylphosphine (4.1 g), 4-hydroxytetrahydropyran (1.2 ml) and methylene chloride (50 ml) and the mixture was stirred at ambient temperature for 30 minutes. The mixture was evaporated and the residue was stirred in a saturated methanolic ammonia solution for 7 hours. The mixture was evaporated and the residue was purified by column chromatography on silica using a 9:10:1 mixture of methylene chloride, ethyl acetate and a saturated methanolic ammonia solution as eluent. There was thus obtained 6-methoxy-5-tetrahydropyran-4-yloxy-3,4-dihydroquinazolin-4-one (2.3 g); NMR Spectrum: (DMSOd$_6$) 1.65–1.8 (m, 2H), 1.8–1.9 (m, 2H), 3.35 (m, 2H), 3.9 (s, 3H), 3.92 (m, 2H), 4.3 (m, 1H), 7.42 (d, 1H), 7.6 (d, 1H), 7.9 (s, 1H), 11.8 (br s, 1H); Mass Spectrum: M+H$^+$ 277.

A mixture of a portion (1.9 g) of the material so obtained, thiophenol (1 ml), potassium carbonate (1.4 g) and N-methylpyrrolid-2-one (20 ml) was stirred and heated to 200° C. for 30 minutes. The mixture was evaporated. The residue was dissolved in a mixture of methylene chloride (25 ml), methanol (1 ml) and acetic acid (2 ml) and the solution was poured onto a column of silica and was eluted with a 9:10:1 mixture of methylene chloride, ethyl acetate and methanol. The material so obtained was triturated under diethyl ether and the resultant solid was washed with diethyl ether and dried under vacuum. There was thus obtained 6-hydroxy-5-tetrahydropyran-4-yloxy-3,4-dihydroquinazolin-4-one (1.65 g); NMR Spectrum: (DMSOd$_6$) 1.7–1.9 (m, 4H), 3.2–3.4 (m, 2H), 3.92 (m, 2H), 4.3 (m, 1H), 7.3 (d, 1H), 7.35 (d, 1H), 7.85 (s, 1H), 9.55 (br s, 1H), 11.75 (br s, 1H); Mass Spectrum: M+H$^+$ 263.

A mixture of a portion (0.7 g) of the material so obtained, piperidine (0.7 ml) and acetic anhydride (10 ml) was heated to reflux for 1 hour. The mixture was evaporated. The residue was dissolved in a 1:1 mixture of methanol and water (18 ml) and stirred at ambient temperature for 1 hour. The resultant precipitate was isolated, washed with water and dried under vacuum to give 6-acetoxy-5-tetrahydropyran-4-yloxy-3,4-dihydroquinazolin-4-one (0.54 g); NMR Spectrum: (CDCl$_3$) 1.8–2.0 (m, 2H), 2.0–2.1 (m, 2H), 2.4 (s, 3H), 3.45 (m, 2H), 4.02 (m, 2H), 4.4 (m, 1H), 7.5–7.6 (m, 2H), 8.0 (s, 1H), 10.5 (br s, 1H); Mass Spectrum: M+H$^+$ 305.

A mixture of the material so obtained, triphenylphosphine (0.93 g), carbon tetrachloride (0.515 ml) and 1,2-dichloroethane (24 ml) was stirred and heated to 70° C. for 2.5 hours. The mixture was evaporated and the residue was dissolved in a saturated methanolic ammonia solution (20 ml) and stirred at ambient temperature for 1 hour. The mixture was filtered and the filtrate was poured onto a column of silica and eluted in turn with methylene chloride, a 1:1 mixture of methylene chloride and ethyl acetate and a 24:25:1 mixture of methylene chloride, ethyl acetate and methanol. There was thus obtained 4-chloro-6-hydroxy-5-tetrahydropyran-4-yloxyquinazoline.

Using an analogous procedure to that described in the last paragraph of the portion of Note [10] immediately above that is concerned with the preparation of starting materials, 4-chloro-6-hydroxy-5-tetrahydropyran-4-yloxyquinazoline (1.12 g) was reacted with 1-(3-hydroxypropyl)-4-methylpiperazine to give 4-chloro-6-[3-(4-methylpiperazin-1-yl)propoxy]-5-tetrahydropyran-4-yloxyquinazoline (0.56 g); NMR Spectrum: (CDCl$_3$) 1.85–2.2 (m, 6H), 2.32 (s, 3H), 2.35–2.7 (m, 10H), 3.42 (m, 2H), 4.05 (m, 2H), 4.25 (m, 2H), 4.65 (m, 1H), 7.75 (d, 1H), 7.85 (d, 1H), 8.9 (s, 1H); Mass Spectrum: M+H$^+$ 421 and 423.

[12] The free base gave the following data: NMR Spectrum: (CDCl$_3$) 1.82–2.18 (m, 6H), 2.35 (s, 3H), 2.4–2.7 (m, 10H), 3.35 (m, 2H), 4.02 (d, 2H), 4.25 (t, 2H), 4.65 (m, 1H), 7.08 (m, 1H), 7.4 (d, 1H), 7.6 (d, 1H), 7.7 (d, 1H), 8.68 (s, 1H), 9.0 (s, 1H), 10.5 (s, 1H); Mass Spectrum: M+H$^+$ 546 and 548.

[13] The free base gave the following data: NMR Spectrum: (CDCl$_3$) 1.9–2.15 (m, 6H), 2.35 (s, 3H), 2.4–2.75 (m, 10H), 3.35 (m, 2H), 3.89 (s, 3H), 4.02 (m, 2H), 4.25 (t, 2H), 4.65 (m, 1H), 6.65 (m, 1H), 7.5 (d, 1H), 7.55 (d, 1H), 7.65 (d, 1H), 8.35 (d, 1H), 8.6 (s, 1H), 10.28 (s, 1H); Mass Spectrum: M+H$^+$ 586 and 588.

[14] 4-Chloro-2-fluoro-5-methoxyaniline is disclosed in International Patent Application WO 86/02642. The free base of the product gave the following data: NMR Spectrum: (CDCl$_3$) 1.9–2.1 (m, 4H), 2.22 (d, 2H), 2.27 (s, 3H), 2.32–2.62 (m, 10H), 3.55 (m, 2H), 3.94 (s, 3H), 4.08 (m, 2H), 4.15 (t, 2H), 4.7 (m, 1H), 6.52 (s, 1H), 6.82 (s, 1H), 7.15 (d, 1H), 8.6 (s, 1H), 8.8 (d, 1H), 10.1 (s, 1H); Mass Spectrum: M+H$^+$ 560 and 562.

[15] The free base gave the following data: NMR Spectrum: (CDCl$_3$) 1.9–2.1 (m, 4H), 2.22 (d, 2H), 2.28 (s, 3H), 2.35–2.7 (m, 10H), 3.6 (m, 2H), 4.08 (m, 2H), 4.12 (t, 2H), 4.7 (m, 1H), 6.5 (d, 1H), 6.82 (d, 1H), 7.25–7.35 (m, 2H), 8.57 (s, 1H), 8.77 (m, 1H), 10.02 (s, 1H); Mass Spectrum: M+H$^+$ 574 and 576.

[16] 2-Pyrrolidin-1-yl-5-methoxyaniline is disclosed in International Patent Application WO 85/01939. The free base of the product gave the following data: NMR Spectrum: (CDCl$_3$) 1.8–2.0 (m, 8H), 2.2 (d, 2H), 2.29 (s, 3H), 2.4–2.7 (m, 12H), 3.1 (t, 2H), 3.6 (m, 2H), 3.82 (s, 3H), 4.02 (m, 2H), 4.15 (t, 2H), 4.7 (m, 1H), 6.5 (d, 1H), 6.65 (m, 1H), 6.85 (d, 1H), 7.05 (d, 1H), 7.9 (d, 1H), 8.55 (s, 1H), 9.82 (s, 1H); Mass Spectrum: M+H$^+$ 577.

[17] The free base gave the following data: NMR Spectrum: (CDCl$_3$) 1.95 (m, 4H), 2.18 (d, 2H), 2.25 (s, 3H), 2.3–2.6 (m, 10H), 3.55 (t, 2H), 4.02 (m, 2H), 4.1 (t, 2H), 4.68 (m, 1H), 5.95 (s, 2H), 6.45 (s, 1H), 6.6 (d, 1H), 6.78 (s, 1H), 6.85 (m, 1H), 8.02 (d, 1H), 8.5 (s, 1H), 9.68 (s, 1H); Mass Spectrum: M+H$^+$ 522.

[18] The reactants were 7-benzyloxy-5-[N-(tert-butoxycarbonyl)piperidin-4-yloxy]-4-chloroquinazoline (1.92 g) and 6-chloro-2,3-methylenedioxyaniline (0.771 g) and the reaction mixture was heated to reflux for 1.5 hours. The reaction mixture was cooled to ambient temperature and the precipitate was isolated, washed in turn with isopropanol, ethyl acetate and diethyl ether and dried under vacuum. The material so obtained was dissolved in a 2M solution of hydrogen chloride in diethyl ether and stirred at ambient temperature for 2 hours. The resultant solid was isolated, washed with diethyl ether and dried under vacuum. There was thus obtained the required compound as a dihydrochloride salt (2.4 g) which gave the following data: NMR Spectrum: (DMSOd$_6$) 1.4 (s, 9H), 1.8–1.95 (m, 2H), 2.0–2.1 (m, 2H), 2.9–3.1 (m, 2H), 3.4 (m, 2H), 5.08 (m, 1H), 5.35 (s, 2H), 6.12 (s, 2H), 7.0–7.05 (m, 2H), 7.12 (d, 1H), 7.22 (d, 1H), 7.3–7.6 (m, 5H), 8.75 (s, 1H), 10.1 (s, 1H); Mass Spectrum: M+H$^+$ 605 and 607.

[19] The reactants were 7-acetoxy-4-chloro-5-cyclopentyloxyquinazoline and 2,3-methylenedioxyaniline. The precipitate from the reaction mixture was isolated, dissolved in a saturated methanolic ammonia solution (20 ml) and stirred at ambient temperature for 2 hours. The mixture was evaporated and the residue was triturated under water. The solid so obtained was washed with water and dried overnight under vacuum. The product gave the following data: NMR Spectrum: (DMSOd$_6$) 1.6–1.7 (m, 2H), 1.7–1.9 (m, 2H), 1.9–2.15 (m, 4H), 5.1 (br s, 1H), 6.12 (s, 2H), 6.63 (s, 1H), 6.65 (s, 1H), 6.72 (d, 1H), 6.9 (m, 1H), 8.15 (d, 1H), 8.42 (s, 1H), 9.8 (s, 1H), 10.58 (s, 1H); Mass Spectrum: M+H$^+$ 366.

EXAMPLE 16

4-(2-iodoanilino)-7-methoxy-5-N-methylpiperidin-4-yloxy)quinazoline dihydrochloride A mixture of 4-chloro-7-methoxy-5-(N-methylpiperidin-4-yloxy)quinazoline (0.08 g), 2-iodoaniline (0.068 g), 6M hydrogen chloride in isopropanol (0.05 ml) and isopropanol (3 ml) was stirred and heated to 80° C. for 2 hours. The mixture was cooled to 0° C. and diethyl ether was added. The resultant precipitate was isolated, washed with diethyl ether and dried under vacuum. The solid so obtained was dissolved in methylene chloride and the solution was washed with a saturated aqueous sodium bicarbonate solution. The organic solution was poured onto a column of silica and eluted with a 9:10:1 mixture of methylene chloride, ethyl acetate and methanol followed by a 9:10:1 mixture of methylene chloride, ethyl acetate and a saturated methanolic ammonia solution. The material so obtained was dissolved in diethyl ether and 6M hydrogen chloride in diethyl ether (0.1 ml) was added. The resultant precipitate was isolated, washed with diethyl ether and dried under vacuum. There was thus obtained the title compound (0.081 g), as the dihydrochloride salt, a portion of which was converted to the free base using an analogous procedure to that described in Example 3. The free base gave the following data: NMR Spectrum: (CDCl$_3$) 2.1–2.4 (m, 6H), 2.3 (s, 3H), 2.8 (m, 2H), 3.92 (s, 3H), 4.6 (m, 1H), 6.55 (s, 1H), 6.85 (s, 1H), 6.95 (t, 1H), 7.42 (t, 1H), 7.9 (d, 2H), 8.5 (s, 1H), 9.5 (s, 1H); Mass Spectrum: M+H$^+$ 491.

EXAMPLE 17

Using an analogous procedure to that described in Example 16, the appropriate 4-chloroquinazoline was reacted with the appropriate aniline in the presence of hydrogen chloride to give the dihydrochloride salt of each of the compounds described in Table V, a portion of each of which was converted to the free base using an analogous procedure to that. described in Example 3.

TABLE V

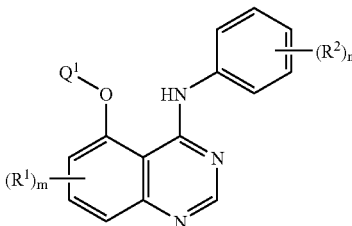

| No. and Note | $(R^1)_m$ | $Q^1$ | $(R^2)_n$ |
|---|---|---|---|
| [1] | 7-methoxy | N-methylpiperidin-4-yl | 2,4-dichloro |
| [2] | 7-methoxy | N-methylpiperidin-4-yl | 4-bromo-2-chloro |
| [3] | 7-methoxy | N-methylpiperidin-4-yl | 2-chloro-4-cyano |
| [4] | 7-methoxy | N-methylpiperidin-4-yl | 2-bromo-4-fluoro |
| [5] | 7-methoxy | N-methylpiperidin-4-yl | 2-bromo-4-chloro |
| [6] | 7-methoxy | N-methylpiperidin-4-yl | 2,4-dibromo |
| [7] | 7-methoxy | N-methylpiperidin-4-yl | 2-bromo |
| [8] | 7-methoxy | N-methylpiperidin-4-yl | 2-bromo-4-methyl |
| [9] | 7-methoxy | N-methylpiperidin-4-yl | 2-fluoro-4-chloro |
| [10] | 7-methoxy | N-methylpiperidin-4-yl | 2-fluoro-4-bromo |
| [11] | 7-methoxy | N-methylpiperidin-4-yl | 2-fluoro-3-chloro |
| [12] | 7-methoxy | N-methylpiperidin-4-yl | 2,4-dimethoxy |
| [13] | 7-methoxy | N-methylpiperidin-4-yl | 2,3-dimethoxy |
| [14] | 7-methoxy | N-methylpiperidin-4-yl | 2-methoxy-5-methyl |
| [15] | 7-methoxy | N-methylpiperidin-4-yl | 2-methoxy-5-chloro |
| [16] | 7-methoxy | N-methylpiperidin-4-yl | 2-methoxy |
| [17] | 7-methoxy | N-methylpiperidin-4-yl | 2-ethoxy |
| [18] | 7-methoxy | N-methylpiperidin-4-yl | 2-methylthio |
| [19] | 7-methoxy | N-methylpiperidin-4-yl | 2-acetyl-4-chloro |
| [20] | 7-methoxy | N-methylpiperidin-4-yl | 2-methyl-5-chloro |
| [21] | 7-methoxy | N-methylpiperidin-4-yl | 2-methyl-3-chloro |
| [22] | 7-methoxy | N-methylpiperidin-4-yl | 2-methyl-4-chloro |
| [23] | 7-methoxy | N-methylpiperidin-4-yl | 2-methyl-5-methoxy |
| [24] | 7-methoxy | N-methylpiperidin-4-yl | 2-isopropenyl |
| [25] | 7-methoxy | N-methylpiperidin-4-yl | 2-(1-pyrrolyl) |
| [26] | 7-methoxy | N-methylpiperidin-4-yl | 2-piperidino |
| [27] | 7-(2-pyrrolidin-1-ylethoxy) | cyclopentyl | 2-bromo-5-methoxy |
| [28] | 7-(2-pyrrolidin-1-ylethoxy) | cyclopentyl | 5-methoxy-2-pyrrolidin-1-yl |
| [29] | 7-(2-pyrrolidin-1-ylethoxy) | cyclopentyl | 5-methoxy-2-morpholinomethyl |
| [30] | 7-(2-pyrrolidin-1-ylethoxy) | cyclopentyl | 6-chloro-2,3-methylenedioxy |
| [31] | 7-methoxy | piperidin-4-ylmethyl | 6-chloro-2,3-methylenedioxy |
| [32] | 7-(2-pyrrolidin-1-ylethoxy) | 4-tetrahydropyranyl | 6-chloro-2,3-methylenedioxy |
| [33] | 7-(3-pyrrolidin-1-ylpropoxy) | 4-tetrahydropyranyl | 6-chloro-2,3-methylenedioxy |
| [34] | 7-benzyloxy | 4-tetrahydropyranyl | 6-chloro-2,3-methylenedioxy |

Notes

[1] The free base gave the following data: NMR Spectrum: (CDCl$_3$) 2.0–2.1 (m, 2H), 2.15–2.4 (m, 4H), 2.3 (s, 3H), 2.75–2.9 (m, 2H), 3.89 (s, 3H), 4.55 (m, 1H), 6.5 (s, 1H), 6.82 (s, 1H), 7.28 (m, 1H), 7.42 (d, 1H), 8.35 (d, 1H), 8.5 (s, 1H), 9.8 (s, 1H); Mass Spectrum: M+H$^+$ 433 and 435.

[2] The free base gave the following data: NMR Spectrum: (CDCl$_3$) 1.95–2.1 (m, 2H), 2.15–2.35 (m, 4H), 2.3 (s, 3H), 2.7–2.9 (m, 2H), 3.9 (s, 3H), 4.42–4.6 (m, 1H), 6.55 (d, 1H), 6.82 (d, 1H), 7.4 (m, 1H), 7.55 (d, 1H), 8.3 (d, 1H), 8.51 (s, 1H), 9.8 (s, 1H); Mass Spectrum: M+H$^+$ 477 and 479.

[3] The free base gave the following data: NMR Spectrum: (CDCl$_3$) 1.95–2.1 (m, 2H), 2.1–2.25 (m, 4H), 2.28 (s, 3H), 2.85 (br d, 2H), 3.9 (s, 3H), 4.5 (m, 1H), 6.55 (d, 1H), 6.85 (d, 1H), 7.58 (m, 1H), 7.7 (s, 1H), 8.6 (s, 1H), 8.82 (d, 1H); Mass Spectrum: M+H$^+$ 424 and 426.

[4] The free base gave the following data: NMR Spectrum: (CDCl$_3$) 2.0–2.1 (m, 2H), 2.15–2.4 (m, 4H), 2.28 (s, 3H), 2.8 (m, 2H), 3.9 (s, 3H), 4.55 (m, 1H), 6.5 (s, 1H), 6.8 (s, 1H), 7.1 (m, 1H), 7.35 (m, 1H), 8.05 (m, 1H), 8.48 (s, 1H), 9.55 (br s, 1H); Mass Spectrum: M+H$^+$ 461 and 463.

[5] The free base gave the following data: NMR Spectrum: (CDCl$_3$) 2.0–2.15 (m, 2H), 2.2–2.4 (m, 4H), 2.3 (s, 3H), 2.8 (m, 2H), 3.9 (s, 3H), 4.5–4.6 (m, 1H), 6.5 (d, 1H), 6.8 (d, 1H), 7.3 (m, 1H), 7.6 (d, 1H), 8.15 (d, 1H), 8.5 (s, 1H), 9.6 (br s, 1H); Mass Spectrum: M+H$^+$ 477 and 479.

[6] The free base gave the following data: NMR Spectrum: (CDCl$_3$) 2.0–2.2 (m, 2H), 2.2–2.35 (m, 4H), 2.25 (s, 3H), 2.7–2.9 (m, 2H), 3.9 (s, 3H), 4.5–4.6 (m, 2H), 6.55 (s, 1H), 6.85 (s, 1H), 7.15 (m, 1H), 7.45 (d, 1H), 8.45 (s, 1H), 8.55 (s, 1H), 9.68 (br s, 1H); Mass Spectrum: M+H$^+$ 521, 523 and 525.

[7] The free base gave the following data: NMR Spectrum: (CDCl₃) 2.0–2.15 (m, 2H), 2.15–2.38 (m, 4H), 2.3 (s, 3H), 2.8 (m, 2H), 3.9 (s, 3H), 4.55 (m, 1H), 6.5 (d, 1H), 6.82 (d, 1H), 7.02 (m, 1H), 7.35 (m, 1H), 7.36 (d, 1H), 8.15 (d, 1H), 8.5 (s, 1H), 9.65 (s, 1H); Mass Spectrum: M+H⁺ 443 and 445.

[8] The free base gave the following data: NM Spectrum: (CDCl₃) 2.0–2.15 (m, 2H), 2.2–2.4 (m, 4H), 2.28 (s, 3H), 2.31 (s, 3H), 2.8 (m, 2H), 3.89 (s, 3H), 4.55 (m, 1H), 6.5 (s, 1H), 6.8 (s, 1H), 7.15 (m, 1H), 7.42 (s, 1H), 7.95 (d, 1H), 8.48 (s, 1H), 9.55 (s, 1H); Mass Spectrum: M+H⁺ 457 and 449.

[9] The free base gave the following data: NMR Spectrum: (CDCl₃) 1.95–2.1 (m, 2H), 2.15–2.3 (m, 4H), 2.3 (s, 3H), 2.85 (d, 1H), 3.9 (s, 3H), 4.5 (m, 1H), 6.5 (d, 1H), 6.82 (d, 1H), 7.1–7.2 (m, 2H), 8.58 (s, 1H), 8.75 (m, 1H); Mass Spectrum: M+H⁺ 417 and 419.

[10] The free base gave the following data: NMR Spectrum: (CDCl₃) 1.95–2.1 (m, 2H), 2.15–2.35 (m, 4H), 2.32 (s, 3H), 2.9 (m, 2H), 3.89 (s, 3H), 4.55 (m, 1H), 6.5 (d, 1H), 6.85 (d, 1H), 7.25–7.35 (m, 2H), 8.58 (s, 1H), 8.75 (m, 1H); Mass Spectrum: M+H⁺ 461 and 463.

[11] The free base gave the following data: NMR Spectrum: (CDCl₃) 1.95–2.1 (m, 2H), 2.12–2.28 (m, 4H), 2.28 (s, 3H), 2.85 (m, 2H), 3.86 (s, 3H), 4.5 (m, 1H), 6.5 (s, 1H), 6.8 (s, 1H), 7.0–7.1 (m, 2H), 8.55 (s, 1H), 8.68 (m, 1H); Mass Spectrum: M+H⁺ 417 and 419.

[12] The free base gave the following data: NMR Spectrum: (CDCl₃) 1.95–2.1 (m, 2H), 2.1–2.22 (m, 4H), 2.25 (s, 3H), 2.82 (m, 2H), 3.77 (s, 3H), 3.83 (s, 3H), 3.85 (s, 3H), 4.48 (m, 1H), 6.45 (d, 1H), 6.52 (m, 1H), 6.8 (m, 2H), 8.45 (d, 1H), 8.52 (s, 1H); Mass Spectrum: M+H⁺ 425.

[13] The free base gave the following data: NMR Spectrum: (CDCl₃) 1.9–2.1 (m, 2H), 2.1–2.25 (m, 4H), 2.28 (s, 3H), 2.7–2.9 (m, 2H), 3.8 (s, 3H), 3.85 (s, 3H), 3.9 (s, 3H), 4.5 (m, 1H), 6.45 (d, 1H), 6.5–6.6 (m, 2H), 6.8 (m, 1H), 8.4 (d, 1H), 8.5 (s, 1H), 9.85 (s, 1H); Mass Spectrum: M+H⁺ 425.

[14] The free base gave the following data: NMR Spectrum: (CDCl₃) 1.95–2.1 (m, 2H), 2.15–2.3 (m, 4H), 2.27 (s, 3H), 2.3 (s, 3H), 2.85 (m, 2H), 3.87 (s, 3H), 3.89 (s, 3H), 4.5 (m, 1H), 6.5 (s, 1H), 6.8–6.9 (m, 3H), 8.45 (s, 1H), 8.55 (s, 1H); Mass Spectrum: M+H⁺ 409.

[15] The free base gave the following data: NMR Spectrum: (CDCl₃) 1.95–2.1 (m, 2H), 2.15–2.3 (m, 4H), 2.3 (s, 3H), 2.85 (d, 2H), 3.89 (s, 3H), 3.9 (s, 3H), 4.5 (m, 1H), 6.5 (d, 1H), 6.8 (m, 2H), 7.0 (m, 1H), 8.6 (s, 1H), 8.85 (d, 1H); Mass Spectrum: M+H⁺ 429 and 431.

[16] The free base gave the following data: NMR Spectrum: (CDCl₃) 2.0–2.1 (m, 2H), 2.15–2.3 (m, 4H), 2.29 (s, 3H), 2.85 (m, 2H), 3.88 (s, 3H), 3.9 (s, 3H), 4.52 (m, 1H), 6.5 (s, 1H), 6.8 (s, 1H), 6.95 (m, 1H), 7.02 (m, 2H), 8.55 (s, 1H), 8.65 (m, 1H); Mass Spectrum: M+H⁺ 395.

[17] The free base gave the following data: NMR Spectrum: (CDCl₃) 1.4 (t, 3H), 1.9–2.1 (m, 2H), 2.1–2.3 (m, 4H), 2.24 (s, 3H), 2.7–2.9 (m, 2H), 3.9 (s, 3H), 4.2 (q, 2H), 4.4–4.55 (m, 1H), 6.5 (d, 1H), 6.8 (d, 1H), 6.9 (m, 1H), 6.95–7.1 (m, 2H), 8.38 (m, 1H), 8.5 (s, 1H), 9.85 (br s, 1H); Mass Spectrum: M+H⁺ 409.

[18] The free base gave the following data: NMR Spectrum: (CDCl₃) 2.05–2.35 (m, 6H), 2.27 (s, 3H), 2.38 (s, 3H), 2.7–2.9 (m, 2H), 3.9 (s, 3H), 4.5–4.6 (m, 1H), 6.5 (d, 1H), 6.8 (d, 1H), 7.15 (m, 1H), 7.26 (m, 1H), 7.38 (m, 1H), 7.98 (d, 1H), 8.5 (s, 1H), 9.7 (br s, 1H); Mass Spectrum: M+H⁺ 411.

[19] The free base gave the following data: NMR Spectrum: (CDCl₃) 2.15–2.35 (m, 6H), 2.27 (s, 3H), 2.57 (s, 3H), 2.82 (m, 2H), 3.89 (s, 3H), 4.55 (m, 1H), 6.52 (s, 1H), 6.8 (s, 1H), 7.48 (m, 1H), 7.75 (d, 1H), 8.3 (d, 1H), 8.5 (s, 1H); Mass Spectrum: M+H⁺ 441 and 443.

[20] The free base gave the following data: NMR Spectrum: (CDCl₃) 1.9–2.0 (m, 2H), 2.15–2.4 (m, 4H), 2.26 (s, 3H), 2.28 (s, 3H), 2.75 (br s, 2H), 3.9 (s, 3H), 4.55 (br s, 1H), 6.5 (d, 1H), 6.82 (s, 1H), 7.1 (m, 1H), 7.18 (d, 1H), 7.8 (s, 1H), 8.48 (s, 1H), 9.1 (s, 1H); Mass Spectrum: M+H⁺ 413 and 415.

[21] The free base gave the following data: NMR Spectrum: (CDCl₃) 1.9–2.0 (m, 2H), 2.15–2.25 (m, 2H), 2.28 (s, 3H), 2.25–2.38 (m, 2H), 2.35 (s, 3H), 2.7 (br s, 2H), 3.9 (s, 3H), 4.6 (m, 1H), 6.5 (d, 1H), 6.8 (d, 1H), 7.18 (m, 1H), 7.28 (m, 1H), 7.5 (d, 1H), 8.45 (s, 1H), 9.35 (s, 1H); Mass Spectrum: M+H⁺ 413 and 415.

[22] The free base gave the following data: NMR Spectrum: (CDCl₃) 1.9–2.0 (m, 2H), 2.2–2.4 (m, 4H), 2.27 (s, 3H), 2.65–2.8 (m, 2H), 3.89 (s, 3H), 4.55 (m, 1H), 6.5 (d, 1H), 6.8 (d, 1H), 7.15–7.25 (m, 2H), 7.6 (d, 1H), 8.45 (s, 1H), 9.25 (s, 1H); Mass Spectrum: M+H⁺ 413 and 415.

[23] The free base gave the following data: NMR Spectrum: (CDCl₃) 1.9–2.0 (m, 2H), 2.15–2.22 (m, 4H), 2.17 (s, 3H), 2.22 (s, 3H), 2.72 (m, 2H), 3.78 (s, 3H), 3.89 (s, 3H), 4.55 (m, 1H), 6.5 (d, 1H), 6.7 (m, 1H), 6.8 (d, 1H), 7.15 (d, 1H), 7.3 (d, 1H), 8.45 (s, 1H), 9.3 (s, 1H); Mass Spectrum: M+H⁺ 409.

[24] The free base gave the following data: NMR Spectrum: (CDCl₃) 1.85–2.0 (m, 2H), 2.05 (s, 3H), 2.1–2.3 (m, 4H), 2.28 (s, 3H), 2.72 (m, 2H), 3.92 (s, 3H), 4.5 (m, 1H), 5.1 (s, 1H), 5.25 (s, 1H), 6.5 (s, 1H), 6.82 (s, 1H), 7.2 (t, 1H), 7.3 (d, 1H), 7.35 (t, 1H), 7.85 (d, 1H), 8.5 (s, 1H), 9.35 (s, 1H).

[25] The free base gave the following data: NMR Spectrum: (CDCl₃) 1.45–1.6 (m, 2H), 1.8–1.95 (m, 2H), 2.05–2.2 (m, 2H), 2.2 (s, 3H), 2.4–2.55 (br s, 2H), 3.95 (s, 3H), 4.25–4.35 (m, 2H), 6.25 (d, 2H), 6.4 (s, 1H), 6.8 (s, 1H), 6.85 (d, 2H), 7.2 (m, 1H), 7.3 (m, 1H), 7.35 (m, 1H), 8.05 (d, 1H), 8.5 (s, 1H), 9.25 (br s, 1H); Mass Spectrum: M+H⁺ 430.

[26] The free base gave the following data: NMR Spectrum: (CDCl₃) 1.6 (m, 2H), 1.7 (m, 4H), 2.1 (m, 2H), 2.2 (s, 3H), 2.2 (m, 2H), 2.3 (m, 2H), 2.7 (m, 2H), 2.9 (m, 4H), 3.95 (s, 3H), 4.6 (m, 1H), 6.1 (d, 1H), 6.9 (d, 1H), 7.1–7.2 (m, 3H), 8.02 (m, 1H), 8.52 (s, 1H), 9.72 (s, 1H); Mass Spectrum: M+H⁺ 448.

[27] The free base gave the following data: NMR Spectrum: (CDCl₃) 1.6–1.78,(m, 4H), 1.85 (m, 4H), 2.1 (m, 4H), 2.65 (m, 4H), 2.98 (m, 2H), 3.82 (s, 3H), 4.25 (m, 2H), 5.02 (m, 1H), 6.4 (d, 1H), 6.45 (m, 1H), 6.82 (d, 1H), 7.5 (d, 1H), 7.85 (d, 1H), 8.52 (s, 1H), 9.62 (s, 1H); Mass Spectrum: M+H⁺ 527 and 529.

The 4-chloro-5-cyclopentyloxy-7-(2-pyrrolidin-1-ylethoxy)quinazoline used as a starting material was prepared as follows:

A mixture of 7-acetoxy4-chloro-5-cyclopentyloxyquinazoline (1 g), a saturated methanolic ammonia solution (10 ml) and methanol (10 ml) was stirred at ambient temperature for 30 minutes. The mixture was evaporated and the residue was triturated under water. The resultant solid was isolated, washed with water and dried under vacuum to give 4-chloro-5-cyclopentyloxy-7-hydroxyquinazoline (0.67 g); NMR Spectrum: (DMSOd₆) 1.6–1.75 (m, 2H), 1.75–1.85 (m, 2H), 1.85–2.05 (m, 4H), 5.0 (m, 1H), 6.72 (d, 1H), 6.8 (d, 1H), 8.7 (s, 1H); Mass Spectrum: M+H⁺ 265.

Using an analogous procedure to that described in Example 1, 4-chloro-5-cyclopentyloxy-7-hydroxyquinazoline (0.84 g) was reacted with 2-pyrrolidin-1-ylethanol (0.448 ml). There was thus obtained 4-chloro-5-cyclopentyloxy-7-

(2-pyrrolidin-1-ylethoxy)quinazoline (0.82 g); NMR Spectrum: (CDCl$_3$) 1.65–2.12 (m, 12H), 2.65 (m, 4H), 2.97 (m, 2H), 4.25 (m, 2H), 4.9 (m, 1H), 6.65 (d, 1H), 6.92 (d, 1H), 8.8 (s, 1H); Mass Spectrum: M+H$^+$ 362 and 364.

[28] The reaction product was purified by column chromatography on reversed phase silica using decreasingly polar mixtures of water, acetonitrile and a saturated methanolic ammonia solution as eluent. The free base gave the following data: NMR Spectrum: (CDCl$_3$) 1.6–1.75 (m, 2H), 1.8 (m, 2H), 1.8–1.95 (m, 8H), 2.05 (m, 4H), 2.65 (br s, 1H), 2.95 (m, 2H), 3.05 (br s, 4H), 3.8 (s, 3H), 4.25 (m, 2H), 4.95 (m, 1H), 6.55 (s, 1H), 6.65 (m, 1H), 6.8 (s, 1H), 7.1 (d, 1H), 7.75 (d, 1H), 8.5 (s, 1H), 9.7 (s, 1H); Mass Spectrum: M+H$^+$ 518.

[29] The free base gave the following data: NMR Spectrum: (CDCl$_3$) 1.65–1.9 (m, 8g), 1.9–2.15 (m, 4H), 2.35 (m, 4H), 2.65 (m, 4H), 2.98 (m, 2H), 3.42 (s, 2H), 3.55 (m, 4H), 3.82 (s, 3H), 4.25 (m, 2H), 5.0 (m, 1H), 6.6 (s, 1H), 6.8 (m, 2H), 7.1 (s, 1H), 7.38 (d, 1H), 8.42 (s, 1H), 9.3 (s, 1H); Mass Spectrum: M+H$^+$ 548.

The 2-morpholinomethyl-5-methoxyaniline used as a starting material was prepared as follows:

A mixture of 4-methoxy-2-nitrotoluene (20 g), N-bromosuccinimide (23 g), a catalytic amount of benzoyl peroxide and carbon tetrachloride (100 ml) was heated to reflux for 8 hours. The mixture was diluted with methylene chloride (200 ml) and washed in turn with a 2N aqueous sodium hydroxide solution and brine. The organic layer was dried over magnesium sulphate and evaporated. There was thus obtained 4-methoxy-2-nitrobenzyl bromide (29 g) which was used without further purification.

Morpholine (2.8 ml) was added to a stirred solution of 4-methoxy-2-nitrobenzyl bromide (4 g) in diethyl ether (150 ml) which was cooled to 0° C. The resultant mixture was stirred at ambient temperature for 16 hours. The mixture was filtered and the filtrate was evaporated. There was thus obtained 2-morpholinomethyl-5-methoxy-1-nitrobenzene (4 g); NMR Spectrum: (CDCl$_3$) 2.4 (m, 4H), 3.68 (m, 4H), 3.7 (s, 2H), 3.88 (s, 3H), 7.1 (m, 1H), 7.35 (d, 1H), 7.45 (d, 1H).

A mixture of the material so obtained, 10% palladium on charcoal catalyst (0.2 g) and methanol (100 ml) was stirred under an atmosphere pressure of hydrogen for 1 hour. The mixture was filtered and the filtrate was evaporated. The residue was purified by column chromatography on silica using a 49:1 mixture of methylene chloride and methanol as eluent. There was thus obtained 2-morpholinomethyl-5-methoxyaniline (1.9 g); NMR Spectrum: (CDCl$_3$) 2.4 (br s, 4H), 3.48 (s, 2H), 3.7 (m, 4H), 3.78 (s, 3H), 4.75 (br s, 2H), 6.2 (s, 1H), 6.25 (d, 1H), 6.9 (d, 1H).

[30] The free base gave the following data: NMR Spectrum: (CDCl$_3$) 1.7–1.8 (m, 2H), 1.9 (br s, 4H), 2.1 (m, 2H), 2.65 (br s, 4H), 3.0 (br s, 2H), 4.25 (m, 2H), 5.0 (m, 1H), 6.05 (s, 1H), 6.55 (d, 1H), 6.7 (d, 1H), 6.8 (d, 1H), 6.98 (d, 1H), 8.5 (s, 1H), 9.3 (s, 1H); Mass Spectrum: M+H$^+$ 497 and 499.

The 6-chloro-2,3-methylenedioxyaniline used as a starting material was prepared as follows:

Sulphuryl chloride (72.5 ml) was added dropwise during 1.7 hours to a stirred mixture of benzodioxole (100 g), aluminium trichloride (0.43 g) and diphenyl sulphide (0.55 ml). Once the reaction started with the evolution of sulphur dioxide, the reaction mixture was cooled in a water bath to a temperature of approximately 22° C. After completion of the addition, the reaction mixture was stirred at ambient temperature for 45 minutes. The reaction mixture was degassed under vacuum and filtered and the filtrate was distilled at atmospheric pressure using a Vigreux distillation column. There was thus obtained 5-chloro-1,3-benzodioxole; b.p. 185–187° C.; NMR Spectrum: (CDCl$_3$) 6.0 (s, 2H); 6.7 (d, 1H); 6.75–6.9 (m, 2H).

A mixture of diisopropylamine (4.92 ml) and THF (100 ml) was cooled to −78° C. and n-butyllithium (2.5 M in hexane, 14 ml) was added dropwise. The mixture was stirred at −78° C. for 15 minutes. 5-Chloro-1,3-benzodioxole (3.73 ml) was added dropwise and the reaction mixture was stirred at −78° C. for 30 minutes. Dry carbon dioxide gas was bubbled into the reaction mixture for 30 minutes. The resultant reaction mixture was allowed to warm to/ambient temperature and was stirred for a further hour. Water was added and the organic solvent was evaporated. The residue was acidified to pH2 by the addition of 2N aqueous hydrochloric acid solution. The resultant solid was isolated and washed in turn with water and diethyl ether. There was thus obtained 5-chloro-1,3-benzodioxole-4-carboxylic acid (5.4 g); NMR Spectrum: (DMSOd$_6$) 6.15 (s, 2H), 7.0 (m, 2H), 13.7 (br s, 1H).

A portion (1 g) of the material so obtained was dissolved in 1,4-dioxane (15 ml) and anhydrous tert-butanol (4 ml), diphenylphosphoryl azide (1.12 ml) and triethylamine (0.73 ml) were added in turn. The resultant mixture was stirred and heated to 100° C. for 4 hours. The mixture was evaporated and the residue was partitioned between ethyl acetate and a 5% aqueous citric acid solution. The organic phase was washed in turn with water, a saturated aqueous sodium bicarbonate solution and brine, dried over magnesium sulphate and evaporated. The residue was purified by column chromatography on silica using a 9:1 mixture of petroleum ether (b.p. 40–60° C.) and ethyl acetate as eluent. There was thus obtained tert-butyl 5-chloro-1,3-benzodioxol-4-ylcarbamate (1.1 g); NMR Spectrum: (DMSOd$_6$) 1.45 (s, 9H), 6.1 (s, 2H), 6.85 (d, 1H), 6.95 (d, 1H), 8.75 (s, 1H).

A mixture of the material so obtained (1.1 g), trifluoroacetic acid (6 ml) and methylene chloride (20 ml) was stirred at ambient temperature for 3 hours. The solvent was evaporated and the residue was partitioned between ethyl acetate and a saturated aqueous sodium bicarbonate solution. The organic phase was washed with brine, dried over magnesium sulphate and evaporated. There was thus obtained 6-chloro-2,3-methylenedioxyaniline (0.642 g); NMR Spectrum: (DMSOd$_6$) 5.15 (s, 2H), 6.0 (s, 2H), 6.25 (d, 1H), 6.75 (d, 1H).

[31] The reactants were 5-[N-(tert-butoxycarbonyl)piperidin-1-ylmethoxy]-4-chloro-7-methoxyquinazoline (0.4 g) and 6-chloro-(2,3-methylenedioxy)aniline (0.089 g). After basification and purification by column chromatography, the reaction product was suspended in a 2M solution of hydrogen chloride in diethyl ether (15 ml) and stirred at ambient temperature for 3 hours. The resultant solid was isolated, washed with diethyl ether and dried under vacuum. The dihydrochloride salt so obtained gave the following data: NMR Spectrum: (DMSOd$_6$) 1.4–1.6 (m, 2H), 1.95 (d, 2H), 2.3–2.4 (m, 1H), 2.8–2.9 (m, 2H), 3.3 (m, 2H), 3.97 (s, 3H), 4.4 (d, 2H), 6.12 (s, 2H), 6.95 (d, 1H), 7.03 (d, 1H), 7.07 (d, 1H), 7.11 (d, 1H), 8.74 (s, 1H), 8.8–9.0 (m, 2H), 10.25 (br s, 1H); Mass Spectrum: M+H$^+$ 443 and 445.

[32] The free base gave the following data: NMR Spectrum: (CDCl$_3$) 1.8–1.9 (m, 4H), 1.9–2.05 (m, 2H), 2.2–2.3 (m, 2H), 2.6–2.7 (m, 4H), 2.95 (m, 2H), 3.6–3.7 (m, 2H), 4.05 (m, 2H), 4.25 (m, 2H), 4.75 (m, 1H), 6.05 (s, 2H), 6.6 (d, 1H), 6.71 (d, 1H), 6.84 (d, 1H), 6.97 (d, 1H), 8.5 (s, 1H), 9.3 (s, 1H); Mass Spectrum: M+H$^+$ 513 and 515.

The 4-chloro-7-(2-pyrrolidin-1-ylethoxy)-5-tetrahydropyran-4-yloxyquinazoline used as a starting material is described in Note [6] in Example 19.

[33] The free base gave the following data: NMR Spectrum: (CDCl$_3$) 1.75–1.9 (m, 4H), 1.9–2.15 (m, 4H), 2.2–2.3 (m, 2H), 2.55 (br s, 4H), 2.65 (m, 2H), 3.65 (m, 2H), 4.02 (m, 2H), 4.15 (m, 2H), 4.8 (m, 1H), 6.05 (s, 2H), 6.52 (d, 1H), 6.72 (d, 1H), 6.82 (d, 1H), 6.97 (d, 1H), 8.5 (s, 1H), 9.26 (s, 1H); Mass Spectrum: M+H$^+$ 527 and 529.

The 4-chloro-7-(3-pyrrolidin-1-ylpropoxy)-5-tetrahydropyran-4-yloxyquinazoline used as a starting material was prepared as follows:

Using an analogous procedure to that described in Note [6] below Example 19, 4-chloro-7-hydroxy-5-tetrahydropyran-4-yloxyquinazoline (0.112 g) was reacted with 1-(3-hydroxypropyl)pyrrolidine (0.062 g) to give 4-chloro-7-(3-pyrrolidin-1-ylpropoxy)-5-tetrahydropyran-4-yloxyquinazoline (0.125 g); NMR Spectrum: (CDCl$_3$) 1.7–1.9 (m, 4H), 1.95–2.2 (m, 6H), 2.55 (br s, 4H), 2.65 (m, 2H), 3.65–3.75 (m, 2H), 4.0–4.1 (m, 2H), 4.2 (m, 2H), 4.75 (m, 1H), 6.6 (d, 1H), 6.95 (d, 1H), 8.8 (s, 1H); Mass Spectrum: M+H$^+$ 392 and 394.

[34] The free base gave the following data: NMR Spectrum: (CDCl$_3$) 2.1–2.2 (m, 2H), 2.15–2.3 (m, 2H), 3.52–3.65 (m, 2H), 3.95–4.08 (m, 2H), 4.75 (m, 1H), 5.18 (s, 2H), 6.05 (s, 2H), 6.6 (d, 1H), 6.75 (d, 1H), 6.9–7.0 (m, 2H), 7.3–7.5 (m, 5H), 8.55 (s, 1H), 9.34 (s, 1H); Mass Spectrum: M+H$^+$ 506 and 508.

The 7-benzyloxy-4-chloro-5-tetrahydropyran-4-yloxyquinazoline used as a starting material was prepared as follows:

Di-tert-butyl azodicarboxylate (16.3 g) was added portionwise to a stirred mixture of 7-benzyloxy-5-hydroxy-3-pivaloyloxymethyl-3,4-dihydroquinazolin-4-one (17 g), 4-hydroxytetrahydropyran (5.4 g) and methylene chloride (200 ml) that had been cooled to 5° C. The mixture was allowed to warm to ambient temperature and was stirred for 2 hours. The mixture was evaporated and the residue was dissolved in a saturated methanolic ammonia solution. The resultant mixture was stirred at ambient temperature for 16 hours. The mixture was evaporated and the residue was triturated under diethyl ether. The solid so obtained was dried under vaccuum to give 7-benzyloxy-5-tetrahydropyran-4-yloxy-3,4-dihydroquinazolin-4-one (12.5 g); NMR Spectrum: (DMSOd$_6$) 1.6–1.7 (m, 2H), 1.85–1.95 (m, 2H), 3.5 (m, 2H), 3.9 (m, 2H), 4.75 (m, 1H), 5.22 (s, 2H), 6.7 (d, 1H), 6.8 (d, 1H), 7.3–7.5 (m, 5H), 7.9 (s, 1H); Mass Spectrum: M+H$^+$ 353.

A mixture of 7-benzyloxy-5-tetrahydropyran-4-yloxy-3,4-dihydroquinazolin-4-one (9 g), phosphoryl chloride (2.8 ml), di-isopropylethylamine (11.4 ml) and 1,2-dichloroethane (130 ml) was stirred and heated to 80° C. for 3 hours. The mixture was evaporated to give 7-benzyloxy-4-chloro-5-tetrahydropyran-4-yloxyquinazoline which was used without further purification.

EXAMPLE 18

4-(2,6-dichloroanilino)-7-methoxy-5-(N-methylpiperidin-4-yloxy)quinazoline dihydrochloride Sodium hexamethyldisilazane (1M solution in THF; 0.65 ml) was added to a solution of 2,6-dichloroaniline (0.105 g) in DMF (3 ml) and the mixture was stirred at ambient temperature for 5 minutes. A solution of 4-chloro-7-methoxy-5-(N-methylpiperidin-4-yloxy)quinazoline (0.1 g) in DMF (8 ml) was added and the mixture was stirred at ambient temperature for 1 hour. A saturated aqueous ammonium chloride solution was added and the mixture was extracted with ethyl acetate. The organic layer was evaporated and the residue was purified by column chromatography on silica using as eluent a 9:10:1 mixture of methylene chloride, ethyl acetate and methanol followed by a 9:10:1 mixture of methylene chloride, ethyl acetate and a saturated methanolic ammonia solution. The material so obtained was triturated under diethyl ether. The solid was isolated and dried under vacuum. The material so obtained was dissolved in a mixture of isopropanol (2 ml) and diethyl ether (2 ml) and 6M hydrogen chloride in isopropanol (0.11 ml) was added. The mixture was evaporated and the residual solid was dried under vacuum. There was thus obtained the title compound as a dihydrochloride salt (0.06 g), a portion of which was converted into the free base using an analogous procedure to that described in Example 3. The free base gave the following characterising data: NMR Spectrum: (CDCl$_3$) 2.0–2.1 (m, 2H), 2.15–2.25 (m, 2H), 2.3 (s, 3H), 2.4 (m, 2H), 2.68 (m, 2H), 3.95 (s, 3H), 4.65 (m, 1H), 6.55 (d, 1H), 6.85 (d, 1H), 7.22 (m, 1H), 7.45 (d, 2H), 8.5 (s, 1H), 9.3 (s, 1H); Mass Spectrum: M+H$^+$ 433 and 435.

EXAMPLE 19

Using an analogous procedure to that described in Example 18, the appropriate 4-chloroquinazoline was reacted with the appropriate aniline in the presence of sodium hexamethyldisilazane to give the compounds described in Table VI. Each product was purified by way of its dihydrochloride salt and, unless otherwise stated, a portion of each compound was converted to the free base using an analogous procedure to that described in Example 3.

TABLE VI

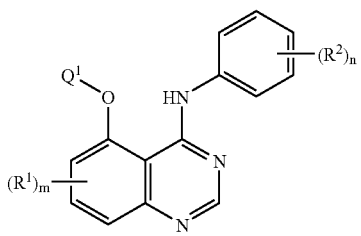

| No. & Note | $(R^1)_m$ | $Q^1$ | $(R^2)_n$ |
|---|---|---|---|
| [1] | 7-methoxy | N-methylpiperidin-4-yl | 2-bromo-4-chloro-6-fluoro |

TABLE VI-continued

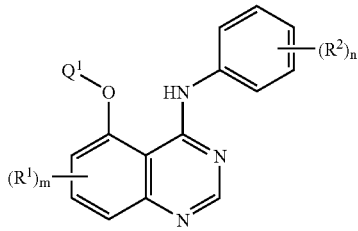

| No. & Note | $(R^1)_m$ | $Q^1$ | $(R^2)_n$ |
|---|---|---|---|
| [2] | 7-methoxy | N-methylpiperidin-4-yl | 4-chloro-2-trifluoromethyl |
| [3] | 7-methoxy | N-methylpiperidin-4-yl | 4-cyano-2-trifluoromethyl |
| [4] | 7-(2-pyrroldin-1-ylethoxy) | cyclopentyl | 2-bromo-4-chloro-6-fluoro |
| [5] | 7-(2-pyrrolidin-1-ylethoxy) | cyclopentyl | 4-chloro-2-trifluoromethyl |
| [6] | 7-(2-pyrrolidin-1-ylethoxy) | 4-tetrahydropyranyl | 4-chloro-2-trifluoromethyl |
| [7] | 7-(2-pyrrolidin-1-ylethoxy) | 4-tetrahydropyranyl | 2-bromo-4-chloro-6-fluoro |

Notes

[1] The free base gave the following data: NMR Spectrum: (CDCl$_3$) 1.98–2.1 (m, 2H), 2.22 (m, 2H), 2.31 (s, 3H), 2.4 (m, 2H), 2.7 (br s, 2H), 3.95 (s, 3H), 4.65 (m, 1H), 6.55 (d, 1H), 6.85 (d, 1H), 7.25 (m, 1H), 7.52 (d, 1H), 8.48 (s, 1H), 9.15 (s, 1H); Mass Spectrum: M+H$^+$ 495, 497 and 499.

[2] The free base gave the following data: NMR Spectrum: (CDCl$_3$) 1.82–2.05 (m, 2H), 2.1–2.3 (m, 4H), 2.25 (s, 3H), 2.75 (m, 2H), 3.9 (s, 3H), 4.5 (m, 1H), 6.5 (d, 1H), 6.8 (d, 1H), 7.55 (m, 1H), 7.65 (d, 1H), 7.82 (d, 1H), 8.4 (s, 1H), 9.5 (s, 1H); Mass Spectrum: M+H$^+$ 467 and 469.

[3] The free base gave the following data: N Spectrum: (CDCl$_3$) 1.9–2.0 (m, 2H), 15 2.15–2.25 (m, 4H), 2.3 (s, 3H), 2.85 (br s, 2H), 3.85 (s, 3H), 4.55 (m, 1H), 6.6 (d, 1H), 6.9 (d, 1H), 7.88 (m, 1H), 8.0 (s, 1H), 8.3 (d, 1H), 8.52 (s, 1H), 9.78 (s, 1H); Mass Spectrum: M+H$^+$ 458.

[4] The free base gave the following data: N Spectrum: (CDCl$_3$) 1.7–1.95 (m, 8H), 2.05 (br s, 4H), 2.65 (br s, 4H), 2.95 (m, 2H), 4.25 (m, 2H), 5.02 (m, 1H), 6.6 (s, 1H), 6.85 (s, 1H), 7.2 (m, 1H), 7.5 (s, 1H), 8.45 (s, 1H), 9.1 (s, 1H); Mass Spectrum: M+H$^+$ 549 and 551.

[5] The free base gave the following data: NMR Spectrum: (CDCl$_3$) 1.5–1.75 (m, 2H), 1.75–1.9 (m, 6H), 1.9–2.05 (m, 2H), 2.05–2.15 (m, 2H), 2.62 (br s, 4H), 2.98 (m, 2H), 4.25 (m, 2H), 4.98 (m, 1H), 6.6 (s, 1H), 6.85 (s, 1H), 7.55 (m, 1H), 7.65 (d, 1H), 7.85 (d, 1H), 8.45 (s, 1H), 9.45 (s, 1H); Mass Spectrum: M+H$^+$ 521 and 523.

[6] The dihydrochloride salt gave the following data: NMR Spectrum: (DMSOd$_6$ and CF$_3$CO$_2$D) 1.8–2.2 (m, 8H), 3.1–3.3 (m, 2H), 3.5 (t, 2H), 3.6–3.75 (m, 4H), 3.95 (d, 2H), 4.6 (t, 2H), 5.1 (m, 1H), 7.0 (d, 1H), 7.2 (d, 1H), 7.75 (d, 1H), 7.95 (m, 1H), 8.0 (d, 1H), 8.8 (s, 1H); Mass Spectrum: M+H$^+$ 537 and 539.

The 4-chloro-7-(2-pyrrolidin-1-ylethoxy)-5-tetrahydropyran-4-yloxyquinazoline used as a starting material was prepared as follows:

Di-tert-butyl azodicarboxylate (0.99 g) was added to a stirred mixture of 4-chloro-7-hydroxy-5-tetrahydropyran-4-yloxyquinazoline (0.75 g), triphenylphosphine (1.14 g), 1-(2-hydroxyethyl)pyrrolidine (0.372 g) and methylene chloride (20 ml) and the mixture was stirred at ambient temperature for 0.5 hours. The mixture was poured onto a column of silica and eluted initially with a 49:1 mixture of methylene chloride and methanol followed by a 97:3 mixture of methylene chloride and a saturated methanolic ammonia solution. There was thus obtained 4-chloro-7-(2-pyrrolidin-1-ylethoxy)-5-tetrahydropyran-4-yloxyquinazoline (0.9 g); NMR Spectrum: (CDCl$_3$) 1.8–1.9 (m, 4H), 1.9–2.05 (m, 2H), 2.1–2.2 (m, 2H), 2.6–2.7 (m, 4H), 2.97 (m, 2H), 3.65–3.75 (m, 2H), 4.0–4.1 (m, 2H), 4.25 (m, 2H), 4.75 (m, 1H), 6.7 (d, 1H), 6.96 (d, 1H), 9.81 (s, 1H); Mass Spectrum: M+H$^+$ 378 and 380.

[7] The dihydrochloride salt gave the following data: NMR Spectrum: (DMSOd$_6$ and CF$_3$CO$_2$D) 1.85–2.2 (m, 8H), 3.15–3.25 (m, 2H), 3.5–3.65 (m, 2H), 3.65–3.75 (m, 4H), 4.0 (m, 2H), 4.6 (t, 2H), 5.15 (m, 1H), 7.0 (d, 1H), 7.22 (d, 1H), 7.73 (m, 1H), 7.87 (d, 1H), 8.88 (s, 1H); Mass Spectrum: M+H$^+$ 565 and 567.

EXAMPLE 20

4-(2-bromo-5-methoxyanilino)-7-hydroxy-5-piperidin-4-yloxyquinazoline

A mixture of 7-benzyloxy4-(2-bromo-5-methoxyanilino)-5-piperidin-4-yloxyquinazoline (0.35 g) and trifluoroacetic acid (6 ml) was stirred and heated to 80° C. for 5 hours. The mixture was evaporated and the residue was dissolved in water (12 ml). The solution was basified to pH8 by the addition of sodium bicarbonate. The resultant precipitate was isolated, washed with water and with ethyl acetate and dried under vacuum. There was thus obtained the title compound (0.26 g); NMR Spectrum: (DMSOd$_6$) 1.95–2.15 (m, 2H), 2.32 (d, 2H), 3.05 (t, 2H), 3.3–3.4 (m, 2H), 3.8 (s, 3H), 5.0 (m, 1H), 6.75 (m, 2H), 6.85 (s, 1H), 7.6 (d, 1H), 7.98 (s, 1H), 8.4 (s, 1H), 9.58 (s, 1H); Mass Spectrum: M+H$^+$ 445 and 447.

EXAMPLE 21

4-(2-chloro-5-methoxyanilino)-7-hydroxy-5-tetrahydropyran-4-yloxyquinazoline

Using an analogous procedure to that described in Example 20, 7-benzyloxy-4-(2-chloro-5-methoxyanilino)-5-tetrahydropyran-4-yloxyquinazoline (0.78 g) was reacted with trifluoroacetic acid (5 ml). The reaction mixture was evaporated and the residue was triturated under diethyl ether. The precipitate was isolated and the solid was dissolved in a mixture of methylene chloride and a saturated methanolic ammonia solution. The mixture was evaporated and the residue was purified by column chromatography on silica using a 97:3 mixture of methylene chloride and methanol as eluent. There was thus obtained the title compound (0.47 g); NMR Spectrum: (DMSOd$_6$) 1.8–1.9 (m, 2H), 2.2 (d, 2H), 3.52 (t, 2H), 3.8 (s, 3H), 3.92 (m, 2H), 4.95 (m, 1H), 6.7 (s, 1H), 6.75–6.85 (m, 2H), 7.5 (d, 1H), 8.12 (d, 1H), 8.4 (s, 1H), 9.85 (s, 1H); Mass Spectrum: M+H$^+$ 402 and 404.

EXAMPLE 22

4-(2-chloro-5-methoxyanilino)-7-[(2R)-2-hydroxy-3-morpholinopropoxy]-5-tetrahydropyran-4-yloxyquinazoline A mixture of 4-(2-chloro-5-methoxyanilino)-7-[(2R)-2,3-epoxypropoxy]-5-tetrahydropyran-4-yloxyquinazoline (0.08 g), morpholine (0.044 ml), ethanol (1 ml) and chloroform (1 ml) was stirred and heated to 45° C. for 16 hours. The mixture was cooled to ambient temperature and evaporated. The residue was triturated under pentane. The resultant solid was isolated, washed with diethyl ether and dried under vacuum to give the title compound (0.08 g); NMR Spectrum: (DMSOd$_6$ and CF$_3$CO$_2$D) 1.9–2.05 (m, 2H), 2.15 (d, 2H), 3.1–3.45 (m, 5H), 3.45–3.6 (m, 3H), 3.7–3.9 (m, 2H), 3.8 (s, 3H), 3.9–4.1 (m, 2H), 4.22 (m, 1H), 4.45 (m, 1H), 5.15 (m, 1H), 6.95 (s, 1H), 7.02 (m, 1H), 7.15 (s, 1H), 7.5–7.6 (m, 2H), 8.9 (s, 1H); Mass Spectrum: M+H$^+$ 545 and 547.

The 4-(2-chloro-5-methoxyanilino)-7-[(2R)-2,3-epoxypropoxy]-5-tetrahydropyran-4-yloxyquinazoline used as a starting material was prepared as follows:

Caesium fluoride (0.213 g) and (2R)-(–)-glycidyl tosylate (0.119 g) were added in turn to a solution of 4-(2-chloro-5-methoxyanilino)-7-hydroxy-5-tetrahydropyran-4-yloxyquinazoline (0.19 g) in DMA (2 ml) and the reaction mixture was stirred and heated to 50° C. for 4.5 hours. The mixture was evaporated and the residue was partitioned between ethyl acetate and a saturated aqueous sodium bicarbonate solution. The organic layer was washed with water and with brine, dried over magnesium sulphate and evaporated. The residue was purified by column chromatography on silica using a 49:1 mixture of methylene chloride and methanol as eluent. There was thus obtained 4-(2-chloro-5-methoxyanilino)-7-[(2R)-2,3-epoxypropoxy]-5-tetrahydropyran-4-yloxyquinazoline (0.155 g); NMR Spectrum: (CDCl$_3$) 2.0–2.1 (m, 2H), 2.25 (d, 2H), 2.8 (m, 1H), 2.98 (m, 1H), 3.45 (br s, 1H), 3.6 (t, 2H), 3.85 (s, 3H), 3.95–4.1 (m, 3H), 4.45 (m, 1H), 4.75 (m, 1H), 6.6–6.7 (m, 2H), 6.85 (s, 1H), 7.32 (d, 1H), 8.2 (d, 1H), 8.6 (s, 1H), 9.85 (s, 1H); Mass Spectrum: M+H$^+$ 458 and 460.

EXAMPLE 23

4-(2-chloro-5-methoxyanilino)-7-[(2R)-2-hydroxy-3-(4-methylpiperazin-1-yl)propoxy]-5-tetrahydropyran-4-yloxyquinazoline Using an analogous procedure to that described in Example 22, 4-(2-chloro-5-methoxyanilino)-7-[(2R)-2,3-epoxypropoxy]-5-tetrahydropyran-4-yloxyquinazoline (0.07 g) was reacted with 1-methylpiperazine (0.05 ml) to give the title compound (0.04 g); NMR Spectrum: (DMSOd$_6$) 1.8–1.9 (m, 2H), 2.2 (s, 3H), 2.2 (d, 2H), 2.25–2.6 (m, 10H), 3.55 (t, 2H), 3.8 (s, 3H), 3.92 (m, 2H), 4.05 (m, 2H), 4.2 (m, 1H), 4.9 (d, 1H), 5.1 (m, 1H), 6.8 (m, 1H), 6.85 (d, 1H), 6.95 (d, 1H), 7.5 (d, 1H), 8.12 (d, 1H), 8.5 (s, 1H), 9.9 (s, 1H); Mass Spectrum: M+H$^+$ 558 and 560.

EXAMPLE 24

4-(2-bromo-5-methoxyanilino)-7-hydroxy-5-tetrahydropyran-4-yloxyquinazoline

A mixture of 7-acetoxy-4-chloro-5-tetrahydropyran-4-yloxyquinazoline (1.7 g), 2-bromo-5-methoxy aniline (1.1 g) and isopropanol (10 ml) was stirred and heated to 80° C. for 1 hour. The resultant precipitate was isolated, washed with isopropanol and dried under vacuum to give 7-acetoxy-4-(2-bromo-5-methoxyanilino)-5-tetrahydropyran- 4-yloxyquinazoline hydrochloride (2 g); NMR Spectrum: (DMSOd$_6$ and CF$_3$CO$_2$D) 1.9–2.1 (m, 2H), 2.17 (d, 2H), 2.38 (s, 3H), 3.5 (t, 2H), 3.8 (s, 3H), 3.95 (m, 2H), 5.1 (m, 1H), 7.0 (m, 1H), 7.32 (s, 1H), 7.42 (d, 1H), 7.5 (s, 1H), 7.7 (d, 1H), 8.9 (s, 1H); Mass Spectrum: M+H$^+$ 488 and 490.

A mixture of a portion (0.15 g) of the material so obtained and a saturated methanolic ammonia solution (5 ml) was stirred at ambient temperature for 16 hours. The mixture was evaporated and the residue was triturated under water. The resultant solid was isolated and dried under vacuum to give the title compound (0.091 g); NMR Spectrum: (DMSOd$_6$) 1.8–2.0 (m, 2H), 2.15 (d, 2H), 3.52 (t, 2H), 3.8 (s, 3H), 3.9 (m, 2H), 4.95 (m, 1H), 6.7 (s, 1H), 6.75 (m, 1H), 6.8 (d, 1H), 7.6 (d, 1H), 7.85 (d, 1H), 8.35 (s, 1H), 9.65 (s, 1H), 10.58 (s, 1H); Mass Spectrum: M+H$^+$ 446 and 448.

The 7-acetoxy-4-chloro-5-tetrahydropyran-4-yloxyquinazoline used as a starting material was prepared as follows:

A solution of 7-acetoxy-5-tetrahydropyran-4-yloxy-3,4-dihydroquinazolin-4-one (1.52 g) in 1,2-dichloroethane (30 ml) containing phosphorus oxychloride (0.51 ml) and di-isopropylethylamine (2.17 ml) was stirred and heated to 80° C. for 2 hours. The mixture was evaporated to give the required material which was used without further purification.

EXAMPLE 25

4-(2-chloro-5-methoxyanilino)-7-hydroxy-5-tetrahydrofuran-3-yloxyquinazoline

Using an analogous procedure to that described in Example 20, 7-benzyloxy-4-(2-chloro-5-methoxyanilino)-5-tetrahydrofuran-3-yloxyquinazoline (0.39 g) was reacted with trifluoroacetic acid (2.5 ml). The reaction mixture was evaporated and the residue was triturated under diethyl ether. The precipitate was isolated and the solid was dissolved in a mixture of methylene chloride and a saturated methanolic ammonia solution. The mixture was evaporated and the residue was purified by column chromatography on silica using a 97:3 mixture of methylene chloride and methanol as eluent. There was thus obtained the title compound (0.47 g); NMR Spectrum: (DMSOd$_6$ and CF$_3$CO$_2$D) 2.2–2.3 (m, 1H), 2.3–2.5 (m, 1H), 3.8 (s, 3H), 3.75–3.9 (m, 1H), 3.9–4.0 (m, 2H), 4.2 (d, 1H), 5.5 (m, 1H), 6.8 (s, 1H), 6.92 (s, 1H), 7.02 (m, 1H), 7.55 (d, 1H), 7.6 (d, 1H), 8.85 (s, 1H); Mass Spectrum: M+H$^+$ 388 and 390.

EXAMPLE 26

4-(2-chloro-5-methoxyanilino)-7-hydroxy-5-isopropoxyquinazoline

Using an analogous procedure to that described in Example 20, 7-benzyloxy-4-(2-chloro-5-methoxyanilino)-5-isopropoxyquinazoline (0.33 g) was reacted with trifluoroacetic acid. There was thus obtained the title compound (0.17 g); NMR Spectrum: (DMSOd$_6$ and CF$_3$CO$_2$D) 1.55 (d, 6H), 3.85 (s, 3H), 5.1 (m, 1H), 6.8 (s, 1H), 6.92 (s, 1H), 7.0 (m, 1H), 7.58 (d, 1H), 7.65 (d, 1H), 8.85 (s, 1H); Mass Spectrum: M+H$^+$ 360 and 362.

EXAMPLE 27

4-(benzofuran-7-ylamino)-7-methoxy-5-(N-methylpiperidin-4-yloxy)quinazoline dihydrochloride Using an analogous procedure to that described in Example 5, 4-chloro-7-methoxy-5-(N-methylpiperidin-4-yloxy)quinazoline was reacted with 7-aminobenzofuran to give the title compound, a portion of which was treated with a saturated methanolic ammonia solution. The mixture was filtered and the filtrate was evaporated to give the free base; NMR Spectrum: (CDCl$_3$) 2.15–2.35 (m, 6H), 2.32 (s, 3H), 2.92 (m, 2H), 3.9 (s, 3H), 4.6 (m, 1H), 6.5 (d, 1H), 6.8 (d, 1H), 6.85 (d, 1H), 7.25–7.4 (m, 2H), 7.68 (d, 1H), 8.58 (d, 1H), 8.6 (s, 1H), 10.25 (br s, 1H); Mass Spectrum: M+H$^+$ 405.

The 7-aminobenzofuran used as a starting material was prepared as follows

Hydrazine hydrate (0.45 ml) was added dropwise to a stirred mixture of 7-nitrobenzofuran (*J. Med. Chem.*, 1988, 31, 1934; 0.5 g), Raney nickel (0.02 g) and methanol (9 ml) that had been warmed to 55° C. The resultant mixture was heated to reflux for 30 minutes. The catalyst was removed by filtration and the filtrate was evaporated. The residue was partitioned between methylene chloride and water. The organic phase was dried over magnesium sulphate and evaporated to give 7-aminobenzofuran (0.4 g) as an oil; NMR Spectrum: (DMSOd$_6$) 5.25 (br s, 2H), 6.55 (d, 1H), 6.8 (m, 2H), 6.9 (t, 1H), 7.85 (d, 1H).

EXAMPLE 28

4-(3-chlorobenzofuran-7-ylamino)-7-[3-(4-methylpiperazin-1-yl)propoxy]-5-tetrahydropyran-4-yloxyquinazoline dihydrochloride Using an analogous procedure to that described in Example 5, 4-chloro-7-[3-(4-methylpiperazin-1-yl)propoxy]-5-tetrahydropyran-4-yloxyquinazoline was reacted with 7-amino-3-chlorobenzofuran to give the title compound, a portion of which was treated with a saturated methanolic ammonia solution. The mixture was filtered and the filtrate was evaporated to give the free base; NMR Spectrum: (CDCl$_3$) 2.07 (m, 2H), 2.1 (m, 2H), 2.25 (m, 2H), 2.27 (s, 3H), 2.35–2.68 (m, 10H), 3.6 (t, 2H), 4.0–4.2 (m, 4H), 4.75 (m, 1H), 6.52 (s, 1H), 6.85 (s, 1H), 7.35 (m, 2H), 7.65 (s, 1H), 8.6 (s, 1H), 8.7 (d, 1H), 10.3 (s, 1H); Mass Spectrum: M+H$^+$ 522 and 524.

EXAMPLE 29

4-(2,4-dichloro-5-methoxyanilino)-7-(3-piperazin-1-ylpropoxy)-5-tetrahydropyran-4-yloxyquinazoline dihydrochloride A mixture of 4-(2,4-dichloro-5-methoxyanilino)-7-[3-(4-tert-butoxycarbonylpiperazin-1-yl)propoxy]-5-tetrahydropyran-4-yloxyquinazoline (0.12 g) and trifluoroacetic acid (2 ml) was stirred at ambient temperature for 2 hours. The mixture was evaporated and the residue was triturated under diethyl ether. The resultant solid was isolated and dried under vacuum. The solid was dissolved in diethyl ether and 6M hydrogen chloride gas in diethyl ether (0.5 ml) was added. The resultant solid was isolated, washed with diethyl ether and dried under vacuum. There was thus obtained the title compound (0.112 g); NMR Spectrum: (DMSOd$_6$ and CF$_3$CO$_2$H) 1.9–2.1 (m, 2H), 2.15 (d, 2H), 2.28–2.4 (m, 2H), 3.4 (m, 2H), 3.4–3.9 (m, 10H), 3.92 (s, 3H), 3.95 (m, 2H), 4.39 (t, 2H), 5.2 (m, 1H), 7.0 (d, 1H), 7.2 (d, 1H), 7.78 (s, 1H), 7.82 (s, 1H), 8.9 (s, 1H); Mass Spectrum: M+H$^+$ 562 and 564.

The 4-(2,4-dichloro-5-methoxyanilino)-7-[3-(4-tert-butoxycarbonylpiperazin-1-yl)propoxy]-5-tetrahydropyran-4-yloxyquinazoline used as a starting material was prepared as follows:

Using an analogous procedure to that described in Example 12, 4-(2,4-dichloro-5-methoxyanilino)-7-hydroxy-5-tetrahydropyran-4-yloxyquinazoline (0.109 g) was reacted with 1-tert-butoxycarbonyl-4-(3-hydroxypropyl)piperazine (0.074 g) to give 4-(2,4-dichloro-5-methoxyanilino)-7-[3-(4-tert-butoxycarbonylpiperazin-1-yl)propoxy]-5-tetrahydropyran-4-yloxyquinazoline (0.12 g).

Example 30

4-(2,4-dichloro-5-methoxyanilino)-7-piperidin-4-ylmethoxy-5-tetrahydropyran-4-yloxyquinazoline A mixture of 4-(2,4-dichloro-5-methoxyanilino)-7-(1-tert-butoxycarbonylpiperidin-4-ylmethoxy)-5-tetrahydropyran-4-yloxyquinazoline (0.11 g) and trifluoroacetic acid (2 ml) was stirred at ambient temperature for 2 hours. The mixture was evaporated and the residue was triturated under diethyl ether. The resultant solid was isolated and dried under vacuum. The solid was dissolved in diethyl ether and 6M hydrogen chloride gas in diethyl ether (0.5 ml) was added. The resultant solid was isolated, washed with diethyl ether and dried under vacuum. There was thus obtained the dihydrochloride salt of the title compound. The solid was dissolved in methylene chloride and few drops of a saturated methanolic ammonia solution was added. The solution was poured onto a chromatography column filled with silica and eluted with a 24:1 mixture of methylene chloride and a saturated methanolic ammonia solution. There was thus obtained the title compound (0.08 g); NMR Spectrum: (CDCl$_3$) 1.9–2.1 (m, 2H), 1.95 (d, 2H), 1.9–2.15 (m, 3H), 2.52 (d, 2H), 2.7 (m, 2H), 3.2 (d, 2H), 3.6 (m, 2H), 3.9–4.0 (m, 2H), 4.05 (s, 3H), 4.1 (td, 2H), 4.75 (m, 1H), 6.6 (d, 1H), 6.85 (m, 1H), 7.45 (s, 1H), 8.4 (s, 1H), 8.6 (s, 1H); Mass Spectrum: M+H$^+$ 533 and 535.

The 4-(2,4-dichloro-5-methoxyanilino)-7-(1-tert-butoxycarbonylpiperidin-4-ylmethoxy)-5-tetrahydropyran-4-yloxyquinazoline used as a starting material was prepared as follows:

Using an analogous procedure to that described in Example 12, 4-(2,4-dichloro-5-methoxyanilino)-7-hydroxy- 5-tetrahydropyran-4-yloxyquinazoline (0.109 g) was reacted with 1-tert-butoxycarbonylpiperidin-4-ylmethanol (0.065 g) to give 4-(2,4-dichloro-5-methoxyanilino)-7-(1-tert-butoxycarbonylpiperidin-4-ylmethoxy)-5-tetrahydropyran-4-yloxyquinazoline (0.11 g).

EXAMPLE 31

4-(6-chloro-2,3-methylenedioxyanilino)-7-fluoro-5-piperidin-4-yloxyquinazoline dihydrochloride A mixture of 5-(1-tert-butoxycarbonylpiperidin-4-yloxy)-4-(6-chloro-2,3-methylenedioxyanilino)-7-fluoroquinazoline dihydrochloride (0.12 g) and a 2M solution of hydrogen chloride in diethyl ether (5 ml) was stirred at ambient temperature for 1 hour. The resultant precipitate was isolated, washed with diethyl ether and dried under vacuum. There was thus obtained the title compound (0.086 g); NMR Spectrum: (DMSOd$_6$) 2.1–2.3 (m, 4H), 3.0–3.15 (m, 2H), 3.3 (m, 2H), 5.1 (m, 1H), 6.12 (s, 2H), 7.01 (d, 1H), 7.1 (d, 1H), 7.3 (d, 1H), 7.53 (d, 1H), 8.75 (s, 1H), 9.05 (br s, 1H), 9.3 (br s, 1H), 9.95 (br s, 1H); Mass Spectrum: M+H$^+$ 417 and 419.

The 5-(1-tert-butoxycarbonylpiperidin-4-yloxy)-4-(6-chloro-2,3-methylenedioxyanilino)-7-fluoroquinazoline dihydrochloride used as a starting material was prepared as follows:

Sodium hydride (60% dispersion in mineral oil; 0.55 g) was added portionwise to a solution of tert-butyl 4-hydroxypiperidine-1-carboxylate (1.65 g) in DMF (10 ml) and the resultant mixture was stirred at ambient temperature for 15 minutes. 5,7-Difluoro-3,4-dihydroquinazolin-4-one (1 g) was added and the mixture was stirred at ambient temperature for 30 minutes. The mixture was poured into water (100 ml) and, with vigorous stirring, glacial acetic acid was added to acidify the mixture to pH5. The resultant solid was isolated, washed with water and with diethyl ether and dried under vacuum. There was thus obtained 5-(1-tert-butoxycarbonylpiperidin-4-yloxy)-7-fluoro-3,4-dihydroquinazolin-4-one (1.4 g); NMR Spectrum: (CDCl$_3$) 1.47 (s, 9H), 1.94 (m, 4H), 3.5–3.8 (m, 4H), 4.7 (m, 1H), 6.68 (m, 1H), 7.0 (m, 1H), 7.9 (s, 1H), 10.55 (br s, 1H); Mass Spectrum: M+H$^+$ 364.

A mixture of 5-(1-tert-butoxycarbonylpiperidin-4-yloxy)-7-fluoro-3,4-dihydroquinazolin-4-one (0.15 g), triphenylphosphine (0.216 g), carbon tetrachloride (0.12 ml) and 1,2-dichloroethane (5 ml) was stirred and heated to 70° C. for 1 hour. The mixture was evaporated and the residue was purified by column chromatography on silica using a 9:1 mixture of methylene chloride and ethyl acetate as eluent. There was thus obtained 5-(1-tert-butoxycarbonylpiperidin-4-yloxy)-4-chloro-7-fluoroquinazoline (0.1 g); NMR Spectrum: (CDCl$_3$) 1.48 (s, 9H), 2.0 (m, 4H), 3.5–3.7 (m, 4H), 4.8 (m, 1H), 6.8 (m, 1H), 7.3 (m, 1H), 8.9 (s, 1H); Mass Spectrum: M+H$^+$ 382 and 384.

A mixture of the material so obtained, 6-chloro-2,3-methylenedioxyaniline (0.049 g), 5M hydrogen chloride in isopropanol (1 drop) and isopropanol (1 ml) was stirred and heated to 50° C. for 15 minutes and then to 80° C. for 45 minutes. The precipitate was isolated, washed in turn with isopropanol, ethyl acetate and diethyl ether and dried under vacuum. There was thus obtained 5-(1-tert-butoxycarbonylpiperidin-4-yloxy)-4-(6-chloro-2,3-methylenedioxyanilino)-7-fluoroquinazoline dihydrochloride (0.065 g); NMR Spectrum: (DMSOd$_6$) 1.4 (s, 9H), 1.8–2.0 (m, 2H), 2.0–2.15 (m, 2H), 3.05 (br s, 2H), 3.9 (d, 2H), 5.05 (m, 1H), 6.11 (s, 2H), 7.1 (d, 1H), 7.16 (d, 1H), 7.2 (m, 1H), 7.52 (d, 1H), 8.7 (s, 1H), 9.92 (br s, 1H); Mass Spectrum: M+H$^+$ 517 and 519.

EXAMPLE 32

4-(6-chloro-2,3-methylenedioxyanilino)-5-piperidin-4-yloxyquinazoline dihydrochloride Using an analogous procedure to that described in Example 31, 5-(1-tert-butoxycarbonylpiperidin-4-yloxy)-4-(6-chloro-2.3-methylenedioxyanilino)quinazoline dihydrochloride (0.14 g) was reacted with hydrogen chloride to give the title compound (0.113 g); NMR Spectrum: (DMSOd$_6$) 2.15–2.34 (m, 4H), 3.15 (m, 2H), 3.3 (m, 2H), 5.17 (m, 1H), 6.17 (s, 2H), 7.07 (d, 1H), 7.16 (d, 1H), 7.58 (m, 1H), 8.06 (m, 1H), 8.88 (s, 1H), 9.14 (br s, 1H), 9.32 (br s, 1H), 10.28 (s, 1H); Mass Spectrum: M+H$^+$ 399 and 401.

The 5-(1-tert-butoxycarbonylpiperidin-4-yloxy)-4-(6-chloro-2,3-methylenedioxyanilino)quinazoline dihydrochloride used as a starting material was prepared as follows using analogous procedures to those described in the portion of example 31 that is concerned with the preparation of starting materials:

Thus, tert-butyl 4-hydroxypiperidine-1-carboxylate (0.33 g) was reacted with 5-fluoro-3,4-dihydroquinazolin-4-one (0.18 g) to give 5-(1-tert-butoxycarbonylpiperidin-4-yloxy)-3,4-dihydroquinazolin-4-one (0.39 g); NM Spectrum: (CDCl$_3$) 1.5 (s, 9H), 1.9–2.0 (m, 4H), 3.52 (m, 2H), 3.7 (m, 2H), 4.72 (m, 1H), 6.95 (d, 1H), 7.32 (d, 1H), 7.65 (m, 1H), 7.95 (s, 1H), 10.22 (br s, 1H); Mass Spectrum: M+H$^+$ 346;

5-(1-tert-butoxycarbonylpiperidin-4-yloxy)-3,4-dihydroquinazolin-4-one (0.31 g) was reacted with triphenylphosphine and carbon tetrachloride to give 5-(1-tert-butoxycarbonylpiperidin-4-yloxy)-4-chloroquinazoline (0.156 g); NM Spectrum: (CDCl$_3$) 1.5 (s, 9H), 1.9–2.1 (m, 4H), 3.5–3.8 (m, 4H), 4.8 (m, 1H), 7.05 (d, 1H), 7.65 (d, 1H), 7.82 (m, 1H), 8.95 (s, 1H); Mass Spectrum: M+H$^+$ 364 and 366; and a portion (0.124 g) of the material so obtained and 6-chloro-2,3-methylenedioxyaniline (0.064 g) were reacted to give 5-(1-tert-butoxycarbonylpiperidin-4-yloxy)-4-(6-chloro-2,3-methylenedioxyanilino)quinazoline dihydrochloride (0.14 g); NMR Spectrum: (DMSOd$_6$) 1.4 (s, 9H), 1.85–2.0 (m, 2H), 2.1 (m, 2H), 2.95–3.2 (m, 2H), 3.92 (d, 2H), 5.1 (m, 1H), 6.15 (s, 2H), 7.08 (d, 1H), 7.15 (d, 1H), 7.55 (d, 1H), 7.6 (d, 1H), 8.05 (m, 1H), 8.86 (s, 1H), 10.35 (s, 1H); Mass Spectrum: M+H$^+$ 499 and 501.

EXAMPLE 33

4-(6-chloro-2,3-methylenedioxyanilino)-7-methoxy-5-piperidin-4-yloxyquinazoline

A mixture of 5-(1-tert-butoxycarbonylpiperidin-4-yloxy)-4-(6-chloro-2,3-methylenedioxyanilino)-7-methoxyquinazoline dihydrochloride (2.39 g), trifluoroacetic acid (10 ml) and methylene chloride (35 ml) was stirred at ambient temperature for 1.5 hours. The mixture was evaporated and the residue was partitioned between ethyl acetate and a 1N aqueous sodium hydroxide solution. The organic layer was washed with water and brine, dried over magnesium sulphate and evaporated. The residue was purified by column chromatography on silica using a 19:1 mixture of methylene chloride and methanol as eluent. There was thus obtained the title compound (1.44 g); NMR Spectrum: (CDCl$_3$) 1.8–2.0 (m, 2H), 2.15–2.3 (m, 2H), 2.75–2.9 (m, 2H), 3.1–3.2 (m, 2H), 3.9 (s, 3H), 4.65 (m, 1H), 6.0 (s, 2H), 6.46 (d, 1H), 6.72 (d, 1H), 6.8 (d, 1H), 6.91 (d, 1H), 8.5 (s, 1H), 9.21 (s, 1H); Mass Spectrum: M+H$^+$ 429 and 431.

The 5-(1-tert-butoxycarbonylpiperidin-4-yloxy)-4-(6-chloro-2,3-methylenedioxyanilino)-7-methoxyquinazoline dihydrochloride used as a starting material was prepared as follows:

Di-tert-butyl azodicarboxylate (1.13 g) was added portionwise to a stirred mixture of 5-hydroxy-7-methoxy-3-pivaloyloxymethyl-3,4-dihydroquinazolin-4-one (1 g), tert-butyl 4-hydroxypiperidine-1-carboxylate (0.788 g), triphenylphosphine (1.28 g) and methylene chloride (15 ml) which had been cooled to 10° C. The mixture was allowed to warm to ambient temperature and was stirred for 1 hour. The mixture was evaporated and the residue was dissolved in methanol (25 ml). Sodium hydroxide (0.2 g) was added and the mixture was stirred at ambient temperature for 1 hour. The resultant mixture was evaporated and the residue was purified by column chromatography on silica using a 47:50:3 mixture of methylene chloride, ethyl acetate and methanol as eluent. There was thus obtained 5-(1-tert-butoxycarbonylpiperidin-4-yloxy)-7-methoxy-3,4-dihydroquinazolin-4-one (1.09 g); NMR Spectrum: (CDCl$_3$) 1.5 (s, 9H), 1.87–2.0 (m, 4H), 3.48–3.6 (m, 2H), 3.6–3.75 (m, 2H), 3.9 (s, 3H), 4.65 (m, 1H), 6.5 (d, 1H), 6.77 (d, 1H), 7.91 (s, 1H), 10.7 (br s, 1H); Mass Spectrum: M+H$^+$ 376.

Using an analogous procedure to that described in the portion of Example 31 that is concerned with the preparation of starting materials, 5-(1-tert-butoxycarbonylpiperidin-4-yloxy)-7-methoxy-3,4-dihydroquinazolin-4-one (1 g) was reacted with triphenylphosphine and carbon tetrachloride to give 5-(1-tert-butoxycarbonylpiperidin-4-yloxy)-4-chloro-7-methoxyquinazoline (0.8 g); NMR Spectrum: (CDCl$_3$) 1.5 (s, 9H), 1.9–2.1 (m, 4H), 3.5–3.7 (m, 4H), 3.96 (s, 3H), 4.72 (m, 2H), 6.6 (d, 1H), 6.98 (d, 1H), 8.82 (s, 1H); Mass Spectrum: M+H$^+$ 394 and 396.

Using an analogous procedure to that also described in the portion of Example 31 that is concerned with the preparation of starting materials, 5-(1-tert-butoxycarbonylpiperidin-4-yloxy)-4-chloro-7-methoxyquinazoline (0.14 g) and 6-chloro-2,3-methylenedioxyaniline (0.064 g) were reacted to give 5-(1-tert-butoxycarbonylpiperidin-4-yloxy)-4-(6-chloro-2,3-methylenedioxyanilino)-7-methoxyquinazoline dihydrochloride (0.17 g); NMR Spectrum: (DMSOd$_6$) 1.42 (s, 9H), 1.8–2.0 (m, 2H), 2.0–2.15 (m, 2H), 3.0–3.2 (m, 2H), 3.85–3.95 (m, 2H), 3.99 (s, 3H), 5.1 (m, 1H), 6.96 (d, 1H), 7.05 (d, 1H), 7.12 (s, 1H), 7.15 (d, 1H), 8.78 (s, 1H), 10.1 (s, 1H); Mass Spectrum: M+H$^+$ 529 and 531.

EXAMPLE 34

4-(6-chloro-2,3-methylenedioxyanilino)-7-hydroxy-5-piperidin-4-yloxyquinazoline

A mixture of 7-benzyloxy-5-[N-(tert-butoxycarbonyl)piperidin-4-yloxy]-4-(6-chloro-2,3-methylenedioxyanilino) quinazoline dihydrochloride (2.3 g) and trifluoroacetic acid 28 ml) was stirred and heated to 80° C. for 6 hours. The mixture was evaporated and the residue was dissolved in water and the solution was basified to pH10 by the addition of 1N aqueous sodium hydroxide solution. The mixture was stirred at ambient temperature for 1 hour. The solid was isolated, washed with water and dried under vacuum. There was thus obtained the title compound (1.1 g); NMR Spectrum: (DMSOd$_6$) 1.6–1.8 (m, 2H), 2.0–2.15 (m, 2H), 2.65–2.75 (m, 2H), 2.9–3.05 (m, 2H), 4.8 (m, 1H), 6.1 (s, 2H), 6.62 (s, 1H), 6.7 (s, 1H), 6.92 (d, 1H), 7.05 (d, 1H), 8.25 (s, 1H), 9.2 (s, 1H); Mass Spectrum: M+H$^+$ 415 and 417.

EXAMPLE 35

5-[N-(tert-butoxycarbonyl)piperidin-4-yloxy]-4-(6-chloro-2,3-methylenedioxyanilino)-7-hydroxyquinazoline A mixture of 4-(6-chloro-2,3-methylenedioxyanilino)-7-hydroxy-5-piperidin-4-yloxyquinazoline (1.4 g), di-tert-butyl dicarbonate (0.737 g) and DMF (14 ml) was stirred at ambient temperature for 2 hours. The mixture was evaporated and the residue was partitioned between ethyl acetate and water. The organic phase was washed with brine, dried over magnesium sulphate and evaporated. The residue was purified by column chromatography on silica using a 24:1 mixture of methylene chloride and methanol as eluent. There was thus obtained the title compound (1.2 g); NMR Spectrum: (CDCl$_3$) 1.5 (s, 9H), 1.7–1.9 (m, 2H), 2.0–2.15 (m, 2H), 3.0–3.15 (m, 2H), 3.8–3.95 (m, 2H), 4.6 (m, 1H), 6.02 (s, 2H), 6.55 (s, 1H), 6,72 (d, 1H), 6.98 (m, 2H), 8.4 (s, 1H), 9.4 (s, 1H); Mass Spectrum: M+H$^+$ 515 and 517.

EXAMPLE 36

4-(6-chloro-2,3-methylenedioxyanilino)-5-piperidin-4-yloxy-7-(2,2,2-trifluoroethoxy)quinazoline A mixture of 5-[N-(tert-butoxycarbonyl)piperidin-4-yloxy]-4-(6-chloro-2,3-methylenedioxyanilino)-7-hydroxyquinazoline (0.15 g), 2,2,2-trifluoroethyl 4-toluenesulphonate (0.089 g), potassium carbonate (0.1 g) and DMF (3 ml) was stirred and heated to 95° C. for 24 hours. The mixture was cooled to ambient temperature and partitioned between ethyl acetate and water. The organic solution was washed with 1N aqueous sodium hydroxide solution and with brine and dried over magnesium sulphate. The organic solution was filtered and a 6N solution of hydrogen chloride in diethyl ether (2 ml) was added. The mixture was stirred at ambient temperature for 16 hours. The mixture was evaporated. The residue was dissolved in methylene chloride (3 ml) and a saturated methanolic ammonia solution (1 ml) was added. The mixture was filtered and the filtrate was evaporated. The residue was purified by column chromatography on silica using a 19:1 mixture of methylene chloride and a saturated methanolic ammonia solution as eluent. There was thus obtained the title compound (0.061 g); NMR Spectrum: (CDCl$_3$) 1.85–2.0 (m, 2H), 2.3 (m, 2H), 2.8–2.95 (m, 2H), 3.1–3.3 (m, 2H), 4.5 (m, 2H), 4.72 (m, 1H), 6.08 (s, 2H), 6.6 (d, 1H), 6.75 (d, 1H), 6.82 (d, 1H), 7.0 (d, 1H), 8.58 (s, 1H), 9.32 (s, 1H); Mass Spectrum: M+H$^+$ 497 and 499.

EXAMPLE 37

4-(6-chloro-2,3-methylenedioxyanlino)-5-(N-methylpiperidin-4-yloxy)quinazoline

4-Hydroxy-1-methylpiperidine (0.049 g) was added to a stirred suspension of sodium hydride (60% dispersion in mineral oil, 0.043 g) in DMF (2 ml) and the mixture was stirred at ambient temperature for 5 minutes. The dihydrochloride salt of 4-(6-chloro-2,3-methylenedioxyanilino)-5-fluoroquinazoline was treated with a saturated methanolic ammonia solution to give the free base (0.1 g) which was added to the above-mentioned solution of the sodium salt of 4-hydroxy-1-methylpiperidine. The resultant mixture was stirred and heated to 50° C. for 30 minutes. The mixture was cooled to ambient temperature and partitioned between ethyl acetate and water. The organic layer was washed with water and with brine, dried over magnesium sulphate and evaporated. The residue was purified by column chromatography on silica using a 25:24:1 mixture of ethyl acetate, methylene chloride and a saturated methanolic ammonia solution as eluent. There was thus obtained 4-(6-chloro-2,3-methylenedioxyanilino)-5-(N-methylpiperidin-4-yloxy)quinazoline (0.054 g); NMR Spectrum: (CDCl$_3$) 1.95–2.1 (m, 2H), 2.1–2.25 (m, 2H), 2.3 (s, 3H), 2.3–2.4 (m, 2H), 2.7 (br s, 2H), 4.65 (m, 1H), 6.01 (s, 2H), 6.7 (d, 1H), 6.8 (d, 1H), 6.85 (d, 1H), 7.45 (d, 1H), 7.6 (m, 1H), 8.56 (s, 1H), 9.5 (br s, 1H); Mass Spectrum: M+H$^+$ 413 and 415.

The 4-(6-chloro-2,3-methylenedioxyanilino)-5-fluoroquinazoline dihydrochloride used as a starting material was prepared was prepared as follows using analogous procedures to those described in the portion of Example 31 that is concerned with the preparation of starting materials:

Thus, 5-fluoro-3,4-dihydroquinazolin-4-one (2 g) was reacted with triphenylphosphine and carbon tetrachloride to give 5-fluoro-4-chloroquinazoline (1.34 g); NMR Spectrum: (CDCl$_3$) 7.4–7.5 (m, 1H), 7.9–8.0 (m, 2H), 9.1 (s, 1H); and a portion (0.4 g) of the material so obtained and 6-chloro-2,3-methylenedioxyaniline (0.413 g) were reacted to give 4-(6-chloro-2,3-methylenedioxyanilino)-5-fluoroquinazoline dihydrochloride (0.73 g); NMR Spectrum: (DMSOd$_6$) 6.18 (s, 2H), 7.05 (d, 1H), 7.12 (d, 1H), 7.7 (m, 1H), 7.85 (d, 1H), 8.12 (m, 1H), 8.87 (s, 1H); Mass Spectrum: M+H$^+$ 318 and 320.

EXAMPLE 38

4-(6-chloro-2,3-methylenedioxyanilino)-7-isopropoxy-5-(N-methylpiperidin-4-yloxy)quinazoline Sodium triacetoxyborohydride (0.087 g) was added portionwise to a stirred mixture of 4-(6-chloro-2,3-methylenedioxyanilino)-7-isopropoxy-5-piperidin-4-yloxyquinazoline (0.125 g), aqueous formaldehyde (13N, 0.042 ml), acetic acid (0.019 ml), methylene chloride (5 ml) and methanol (2 ml) and the resultant mixture was heated to reflux for 3 minutes. The mixture was evaporated and the residue was partitioned between ethyl acetate and 1N aqueous sodium hydroxide solution. The organic layer was washed with brine, dried over magnesium sulphate and evaporated to give the title compound (0.11 g); NMR Spectrum: (CDCl$_3$) 1.42 (d, 6H), 1.95–2.1 (m, 2H), 2.15–2.25 (m, 2H), 2.3 (s, 3H), 2.3–2.4 (m, 2H), 2.7–2.8 (m, 2H), 4.6 (m, 1H), 4.72 (m, 1H), 6.05 (s, 2H), 6.5 (d, 1H), 6.75 (d, 1H), 6.82 (d, 1H), 6.99 (d, 1H), 8.52 (s, 1H), 9.3 (s, 1H); Mass Spectrum: M+H$^+$ 471 and 473.

EXAMPLE 39

4-(6-chloro-2,3-methylenedioxyanilino)-5-piperidin-4-ylmethoxyquinazoline dihydrochloride Using an analogous procedure to that described in Example 37, N-(tert-butoxycarbonyl)piperidin-4-ylmethanol was reacted with 4-(6-chloro-2,3-methylenedioxyanilino)-5-fluoroquinazoline (0.1 g). The product so obtained was dissolved in a 2M solution of hydrogen chloride in diethyl ether (20 ml) and stirred at ambient temperature for 3 hours. The mixture was evaporated and the residue was triturated under diethyl ether. The solid so obtained was washed with diethyl ether and dried under vacuum. There was thus obtained the tilte compound (0.121 g); NMR Spectrum: (DMSOd$_6$) 1.5–1.6 (m, 2H), 1.9–2.0 (m, 2H), 2.3–2.4 (m, 1H), 2.8–2.9 (m, 2H), 3.3 (d, 2H), 4.42 (d, 2H), 6.15 (s, 2H), 7.07 (d, 1H), 7.15 (d, 1H), 7.53 (m, 2H), 8.06 (m, 1H), 8.87 (s, 1H), 10.57 (br s, 1H); Mass Spectrum: M+H$^+$ 413 and 415.

EXAMPLE 40

4-(6-chloro-2,3-methylenedioxyanilino)-5-(N-methylpiperidin-4-ylmethoxy)quinazoline dihydrochloride Using an analogous procedure to that described in Example 38, 4-(6-chloro-2,3-methylenedioxyanilino)-5-piperidin-4-ylmethoxyquinazoline (obtained from the dihydrochloride salt by trituration under a saturated methanolic ammonia solution) was reacted with aqueous formaldehyde and sodium triacetoxyborohydride. The reaction product, obtained as the free base, was triturated under a 2M solution of hydrogen chloride in diethyl ether. The resultant precipitate was isolated, washed with diethyl ether and dried under vacuum. There was thus obtained the title compound, a portion of which was converted to the free base by trituration under a saturated methanolic ammonia solution. The free base gave the following data: NMR Spectrum: (CDCl$_3$) 1.35–1.55 (m, 2H), 1.9–2.1 (m, 5H), 2.3 (s, 3H), 2.9 (d, 2H), 4.12 (d, 2H), 6.04 (s, 2H), 6.75 (d, 1H), 6.9 (d, 1H), 6.98 (d, 1H), 7.48 (d, 1H), 7.64 (m, 1H), 8.62 (s, 1H), 9.38 (s, 1H); Mass Spectrum: M+H$^+$ 427 and 429.

EXAMPLE 41

4-(6-chloro-2,3-methylenedioxyanilino)-7-(3-piperidinopropoxy)-5-tetrahydropyran-4-yloxyquinazoline A mixture of 7-(3-bromopropoxy)-4-(6-chloro-2,3-methylenedioxyanilino)-5-tetrahydropyran-4-yloxyquinazoline (0.536 g), piperidine (0.12 ml), potassium carbonate (0.4 g) and DMF (2 ml) was stirred at ambient temperature for 16 hours. The mixture was evaporated and the residue was triturated under methylene chloride. The mixture was filtered and the filtrate was purified by column chromatography on silica using initially a 1:1 mixture of ethyl acetate and methylene chloride and then a 10:9:1 mixture of ethyl acetate, methylene chloride and a saturated methanolic ammonia solution as eluent. There was thus obtained the title compound (0.53 g); NMR Spectrum: (CDCl$_3$) 1.4–1.5 (m, 2H), 1.55–1.7 (m, 4H), 1.9–2.1 (m, 4H), 2.2–2.3 (m, 2H), 2.4 (m, 4H), 2.5 (m, 2H), 3.6–3.7 (m, 2H), 4.0–4.1 (m, 2H), 4.15 (m, 2H), 4.8 (m, 1H), 6.08 (s, 2H), 6.52 (d, 1H), 6.75 (d, 1H), 6.85 (d, 1H), 7.0 (d, 1H), 8.55 (s, 1H), 9.35 (s, 1H); Mass Spectrum: M+H$^+$ 541 and 543.

The 7-(3-bromopropoxy)-4-(6-chloro-2,3-methylenedioxyanilino)-5-tetrahydropyran-4-yloxyquinazoline used as a starting material was prepared as follows:

Di-tert-butyl azodicarboxylate (1.66 g) was added to a stirred mixture of 4-(6-chloro-2,3-methylenedioxyanilino)-7-hydroxy-5-tetrahydropyran-4-yloxyquinazoline (1.5 g), 3-bromopropan-1-ol (0.49 ml), triphenylphosphine (1.9 g) and methylene chloride (20 ml) and the mixture was stirred at ambient temperature for 1 hour. A second portion (1.66 g) of di-tert-butyl azodicarboxylate was added and the mixture was stirred at ambient temperature for 16 hours. The mixture was filtered and the filtrate was purified by column chromatography on silica using initially a 1:1 mixture of ethyl acetate and methylene chloride and then a 25:24:1 mixture of ethyl acetate, methylene chloride and methanol as eluent. The material so obtained was triturated under diethyl ether. The resultant solid was isolated, washed with diethyl ether and dried under vacuum to give the required starting material (0.536 g).

EXAMPLE 42

Using an analogous procedure to that described in Example 41, the appropriate haloalkoxy substituted quinazoline was reacted with the appropriate amine to give the compound described in Table VII.

TABLE VII

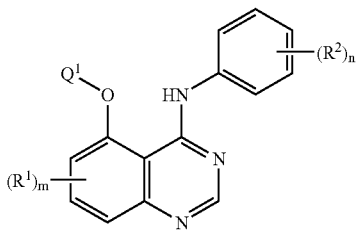

| No. & Note | $(R^1)_m$ | $Q^1$ | $(R^2)_n$ |
|---|---|---|---|
| [1] | 7-[3-(4-hydroxypiperidin-1-yl)propoxy] | 4-tetrahydropyranyl | 6-chloro-2,3-methylenedioxy |

Note

[1] 4-Hydroxypiperidine was used as the amine. The product gave the following data: NMR Spectrum: (CDCl$_3$) 1.5–1.7 (m, 2H), 1.85–2.05 (m, 6H), 2.05–2.25 (m, 4H), 2.5 (m, 2H), 2.8 (m, 2H), 3.55–3.65 (m, 2H), 3.6 (m, 1H), 3.95–4.05 (m, 2H), 4.12 (m, 2H), 4.75 (m, 1H), 6.05 (s, 2H), 6.5 (s, 1H), 6.7 (d, 1H), 6.8 (d, 1H), 6.95 (d, 1H), 8.5 (s, 1H), 9.25 (s, 1H); Mass Spectrum: M+H$^+$ 557 and 559.

EXAMPLE 43

4-(6-chloro-2,3-methylenedioxyanilino)-7-piperidin-4-ylmethoxy-5-tetrahydropyran-4-yloxyquinazoline A mixture of 7-[N-(tert-butoxycarbonyl)piperidin-4-ylmethoxy]-4-(6-chloro-2,3-methylenedioxyanilino)-5-tetrahydropyran-4-yloxyquinazoline (0.25 g), trifluoroacetic acid (1 ml) and methylene chloride (1 ml) was stirred at ambient temperature for 1.5 hours. The mixture was evaporated and the residue was purified by column chromatography on silica using a 93:7 mixture of methylene chloride and a saturated methanolic ammonia solution as eluent. The material so obtained was partitioned between ethyl acetate and an aqueous ammonium hydroxide solution. The organic layer was dried over magnesium sulphate and evaporated. There was obtained the title compound (0.07 g); NMR Spectrum: (CDCl$_3$ and D$_2$O) 1.5–1.7 (m, 2H), 1.9–2.1 (m, 4H), 2.2–2.3 (m, 2H), 2.8 (m, 2H), 3.32 (d, 2H), 3.65 (m, 2H), 3.9–4.1 (m, 3H), 4.8 (m, 1H), 6.08 (s, 2H), 6.52 (br s, 1H), 6.72 (d, 1H), 6.8 (s, 1H), 6.98 (d, 1H), 8.5 (s, 1H); Mass Spectrum: M+H$^+$ 513 and 515.

EXAMPLE 44

4-(6-chloro-2,3-methylenedioxyanilino)-7-(N-methylpiperidin-4-ylmethoxy)-5-tetrahydropyran-4-yloxyquinazoline A mixture of 7-[N-(tert-butoxycarbonyl)piperidin-4-ylmethoxy]-4-(6-chloro-2,3-methylenedioxyanilino)-5-tetrahydropyran-4-yloxyquinazoline (0.25 g), a concentrated aqueous formaldehyde solution (37%, 0.5 ml) and formic acid (5 al) was stirred and heated to 100° C. for 2 hours. The mixture was cooled to ambient temperature and evaporated. The residue was purified by column chromatography on silica using a 24:1 mixture of methylene chloride and a saturated methanolic ammonia solution as eluent. The material so obtained was partitioned between methylene chloride and an aqueous ammonium hydroxide solution. The organic layer was dried over magnesium sulphate and evaporated. There was thus obtained the title compound (0.1 g); NMR Spectrum: (CDCl$_3$) 1.4–1.6 (m, 2H), 1.75–1.9 (m, 3H), 1.9–2.1 (m, 4H), 2.2–2.3 (m, 2H), 2.29 (s, 3H), 2.9 (d, 2H), 3.6–3.7 (m, 2H), 3.95 (d, 2H), 4.0–4.1 (m, 2H), 4.75 (m, 1H), 6.05 (s, 2H), 6.5 (d, 1H), 6.72 (d, 1H ), 6.81 (d, 1H), 6.97 (d, 1H), 8.5 (s, 1H), 9.26 (s, 1H); Mass Spectrum: M+H$^+$ 527 and 529.

EXAMPLE 45

4-(6-chloro-2,3-methylenedioxyanilino)-7-[(2R)-2,3-epoxypropoxy]-5-tetrahydropyran-4-yloxyquinazoline Caesium fluoride (0.46 g) and (2R)-(−)-glycidyl tosylate (0.275 g) were added in turn to a solution of 4-(6-chloro-2,3-methylenedioxyanilino)-7-fluoro-5-tetrahydropyran-4-yloxyquinazoline (0.416 g) in DMF (5 ml) and the reaction mixture was stirred and heated to 60° C. for 2 hours and to 70° C. for a further 1.5 hours. The mixture was evaporated and the residue was partitioned between ethyl acetate and a saturated aqueous sodium bicarbonate solution. The organic layer was washed with water and with brine, dried over magnesium sulphate and evaporated. The residue was purified by column chromatography on silica using a 49:1 mixture of methylene chloride and methanol as eluent. There was thus obtained the title compound (0.36 g); NMR Spectrum: (CDCl$_3$) 1.9–2.1 (m, 2H), 2.2–2.3 (m, 2H), 2.8 (m, 1H), 2.98 (m, 1H), 3.42 (m, 1H), 3.6–3.7 (m, 2H), 3.95–4.1 (m, 3H), 4.45 (m, 1H), 4.8 (m, 1H), 6.02 (s, 2H), 6.59 (m, 12H), 6.72 (d, 1H), 6.81 (d, 1H), 6.97 (d, 1H), 8.5 (s, 1H), 9.27 (s, 1H); Mass Spectrum: M+H$^+$ 472 and 474.

EXAMPLE 46

4-(6-chloro-2,3-methylenedioxyanilino)-7-[3-(4-cyanomethylpiperazin-1-yl)propoxy]-5-tetrahydropyran-4-yloxyquinazoline A mixture of 4-(6-chloro-2,3-methylenedioxyanilino)-7-(3-piperazin-1-ylpropoxy)-5-tetrahydropyran-4-yloxyquinazoline (1.3 g), 2-chloroacetonitrile (0.167 ml), sodium iodide (0.036 g), potassium carbonate (0.331 g) and DMF (15 ml) was stirred at ambient temperature for 5 hours. The mixture was evaporated and the residue was partitioned between ethyl acetate and water. The organic phase was washed with brine, dried over magnesium sulphate and evaporated. The residue was purified by column chromatography on silica using a 10:9:1 mixture of ethyl acetate, methylene chloride and methanol as eluent. There was thus obtained the title compound (0.69 g); NMR Spectrum: (CDCl$_3$) 1.85–2.0 (m, 4H), 2.1 (m, 2H), 2.4–2.5 (m, 6H), 2.5–2.6 (m, 4H), 3.42 (s, 2H), 3.5–3.6 (m, 2H), 3.9–4.0 (m, 2H), 4.0–4.1 (m, 2H), 4.7 (m, 1H), 6.0 (s, 2H), 6.42 (s, 1H), 6.65 (d, 1H), 6.78 (d, 1H), 6.9 (d, 1H), 8.42 (s, 1H), 9.2 (s, 1H ); Mass Spectrum: M+H$^+$ 581 and 583.

EXAMPLE 47

4-(6-chlorobenzofuran-7-ylamino)-7-(2-pyrrolidin-1-ylethoxy)-5-cyclopentyloxyquinazoline dihydrochloride Sodium hexamethyldisilazane (1M solution in THF; 0.55 ml) was added to a solution of 7-amino-6-chlorobenzofuran (0.093 g) in DMF (3 ml) which was cooled to 10° C. and the mixture was stirred at 10° C. for 5 minutes. A solution of 4-chloro-5-cyclopentyloxy-7-(2-pyrrolidin-1-ylethoxy)quinazoline (0.1 g) in DMF (8 ml) was added and the mixture was stirred at ambient temperature for 1 hour. The mixture was partitioned between ethyl acetate and water. The organic layer was evaporated and the residue was purified by column chromatography on silica using a 49:1 mixture of methylene chloride and methanol as eluent. The material so obtained was dissolved in diethyl ether and 6M hydrogen chloride in isopropanol (0.1 ml) was added. The mixture was stirred for 5 minutes and then evaporated. There was thus obtained the title compound as a dihydrochloride salt (0.095 g), a portion of which was converted into the free base using an analogous procedure to that described in Example 3. The free base gave the following characterising data: NMR Spectrum: (CDCl$_3$) 1.55–1.75 (m, 4H), 1.75–1.95 (m, 4H), 2.08 (m, 2H), 2.6–2.75 (m, 4H), 3.0 (m, 2H), 4.25 (m, 2H), 5.05 (m, 1H), 6.6 (d, 1H), 6.8 (d, 1H), 6.85 (d, 1H), 7.38 (d, 1H), 7.45 (d, 1H), 7.6 (d, 1H), 8.42 (s, 1H), 9.5 (s, 1H); Mass Spectrum: M+H$^+$ 493 and 495.

The 7-amino-6-chlorobenzofuran used as a starting material was prepared as follows:

Sodium hydride (60% dispersion in mineral oil; 4.6 g) was added to a stirred solution of 6-chloroanthranilic acid (18 g) in DMF (100 ml) and the mixture was stirred at ambient temperature for 30 minutes. Ethyl iodide (10 ml) was added and the reaction mixture was stirred at ambient temperature for 2 days. The solvent was evaporated and the residue was partitioned between ethyl acetate and water. The organic phase was washed in turn with water and brine, dried over magnesium sulphate and evaporated. The residue was purified by column chromatography on silica using a 4:1 mixture of petroleum ether (b.p. 60–80° C.) and ethyl acetate as eluent. There was thus obtained ethyl 6-chloroanthranilate (15.8 g) as an oil; NMR Spectrum: (DMSOd$_6$) 1.3 (t, 3H), 4.3 (q, 2H), 5.7 (br s, 2H), 6.6 (d, 1H), 6.7 (d, 1H), 7.1 (t, 1H).

A solution of sodium nitrite (4.5 g) in water (100 ml) was added dropwise during 5 minutes to a stirred suspension of ethyl 6-chloroanthranilate (12.7 g) in a mixture of concentrated sulphuric acid (27.9 ml), water (38 ml) and ice (76 g). The reaction mixture was stirred at 0°C. for an additional 20 minutes and then heated to 120° C. for 1 hour. The resultant mixture was poured into a mixture of ice and water and the product was extracted with diethyl ether. The organic phase was washed in turn with water and brine, dried over magnesium sulphate and evaporated. The residue was purified by column chromatography on silica using a 4:1 mixture of petroleum ether (b.p. 60–80° C.) and methylene chloride as eluent. There was thus obtained ethyl 6-chloro-2-hydroxybenzoate (9.8 g); NMR Spectrum: (DMSOd$_6$) 1.3 (t, 3H), 4.3 (q, 2H), 6.9 (d, 1H), 6.95 (d, 1H), 7.25 (d, 1H), 10.45 (br s, 1H).

Allyl bromide (5.5 ml) was added to a stirred mixture of ethyl 6-chloro-2-hydroxybenzoate (9.8 g), 1,5,7-triazabicyclo[4,4,0]dec-5-ene (10.4 g) and acetonitrile (250 ml) and the reaction mixture was stirred at ambient temperature for 20 hours. The mixture was evaporated and the residue was purified by column chromatography on silica using a 17:3 mixture of petroleum ether (b.p. 60–80° C.) and diethyl ether as eluent. There was thus obtained ethyl 2-allyloxy-6-chlorobenzoate (10.3 g); NMR Spectrum: (DMSOd$_6$) 1.3 (t, 3H), 4.35 (q, 2H), 4.65 (d, 2H), 5.25 (d, 1H), 5.4 (d, 1H), 6.0 (m, 1H), 7.15 (m, 2H), 7.45 (t, 1H).

The material so obtained was heated to 230° C. for 1 hour. The reaction product was cooled to ambient temperature and purified by column chromatography on silica using a 4:1 mixture of petroleum ether (b.p. 60–80° C.) and methylene chloride as eluent. There was thus obtained ethyl 3-allyl-6-chloro-2-hydroxybenzoate (7.3 g); NMR Spectrum: (DMSOd$_6$) 1.3 (t, 3H), 3.3 (m, 2H), 4.35 (q, 2H), 5.05 (m, 2H), 5.95 (m, 1H), 6.95 (d, 1H), 7.15 (d, 1H), 9.7 (br s, 1H).

The material so obtained was dissolved in methanol and cooled to −78° C. Ozone was bubbled through the solution for 30 min. Dimethyl sulfide (5.4 ml) was added and the reaction mixture was allowed to warm to ambient temperature. The mixture was evaporated and the residue was partitioned between diethyl ether and water. The organic phase was washed in turn with water and brine, dried over magnesium sulphate and evaporated. The residue was purified by column chromatography on silica using a 1:1 mixture of petroleum ether (b.p. 60–80° C.) and methylene chloride and then a 9:1 mixture of methylene chloride and diethyl ether as eluent. There was thus obtained 2-(4-chloro-3-ethoxycarbonyl-2-hydroxyphenyl)acetaldehyde which was immediately suspended in 85% phosphoric acid (18 ml) and the mixture was heated to 100° C. for 1 hour. The mixture was cooled to ambient temperature and partitioned between diethyl ether and water. The organic phase was washed in turn with water and brine, dried over magnesium sulphate and evaporated. The residue was purified by column chromatography on silica using a 1:1 mixture of petroleum ether (b.p. 60–80° C.) and methylene chloride as eluent. There was thus obtained ethyl 6-chlorobenzofuran-7-carboxylate (5.9 g); NMR Spectrum: (DMSOd$_6$) 1.35 (t, 3H), 4.45 (q, 2H), 7.10 (d, 1H), 7.45 (d, 1H), 7.85 (d, 1H), 8.15 (d, 1H).

A mixture of the material so obtained, 35% aqueous potassium hydroxide solution (12.7 ml) and methanol (20 ml) was stirred and heated to reflux for 1 hour. The methanol was evaporated and the residue was diluted with water and acidified to pH1 by the addition of 6N aqueous hydrochloric acid. The resultant precipitate was isolated, washed with water and dried under vacuum over phosphorus pentoxide to give 6-chlorobenzofuran-7-carboxylic acid (4.6 g); NMR Spectrum: (DMSOd$_6$) 7.05 (d, 1H), 7.4 (d, 1H), 7.75 (d, 1H), 8.1 (d, 1H).

A mixture of a portion (1 g) of the material so obtained, diphenylphosphoryl azide 2.2 ml), triethylamine (1.4 ml) and tert-butanol (2.7 ml) was stirred and heated to reflux for 18 hours. The mixture was allowed to cool to ambient temperature, poured into water and extracted with ethyl acetate. The organic phase was washed in turn with water and brine, dried over magnesium sulphate and evaporated. The residue was purified by column chromatography on alumina using increasingly polar solvent mixtures starting with mixtures of petroleum ether and methylene chloride and ending with a 4:1 mixture of methylene chloride and ethyl acetate. There was thus obtained a mixture of 7-amino-6-chlorobenzofuran and tert-butyl 6-chlorobenzofuran-7-carbamate. A solution of the mixture so obtained in methylene chloride (15 ml) was cooled to 0°C. and trifluoroacetic acid (1.2 ml) was added. The resultant mixture was stirred for 1 hour. The mixture was evaporated and the residue was partitioned between ethyl acetate and a saturated aqueous sodium bicarbonate solution. The organic phase was dried over magnesium sulphate and evaporated. The residue was purified by column chromatography on silica using a 3:1 mixture of petroleum ether (b.p. 60–80° C.) and methylene chloride as eluent. There was thus obtained 7-amino-6-chlorobenzofuran (0.376 g); NMR Spectrum: (DMSOd$_6$) 5.5 (br s, 2H), 6.85 (m, 2H), 7.1 (d, 1H), 7.95 (d, 1H); Mass Spectrum: M+H$^+$ 167.

EXAMPLE 48

4-(3-chlorobenzofuran-7-ylamino)-7-(2-pyrrolidin-1-ylethoxy)-5-cyclopentyloxyquinazoline dihydrochloride Using an analogous procedure to that described in Example 47, 4-chloro-5-cyclopentyloxy-7-(2-pyrrolidin-1-ylethoxy)quinazoline (0.1 g) was reacted with 7-amino-3-chlorobenzofuran (0.051 g) to give the title compound, as a dihydrochloride salt (0.074 g), a portion of which was converted into the free base using an analogous procedure to that described in Example 3. The free base gave the following characterising data: NMR Spectrum: (CDCl$_3$) 1.7–1.8 (m, 2H), 1.8–2.0 (m, 6H), 2.1–2.3 (m, 4H), 2.7 (br s, 4H), 3.02 (m, 2H), 4.3 (t, 2H), 5.08 (m, 1H), 6.61 (d, 1H), 6.84 (d, 1H), 7.3–7.45 (m, 2H), 7.65 (s, 1H), 8.64 (s, 1H), 8.76 (d, 1H), 10.3 (s, 1H); Mass Spectrum: M+H$^+$ 493 and 495.

EXAMPLE 49

4-(2-chloro-5-methoxyanilino)-5-(4-methylpiperazin-1-yl)-7-(2-pyrrolidin-1-ylethoxy)quinazoline trihydrochloride Using an analogous procedure to that described in Example 5, 4-chloro-5-(4-methylpiperazin-1-yl)-7-(2-pyrrolidin-1-ylethoxy)quinazoline (0.11 g) was reacted with 2-chloro-5-methoxyaniline hydrochloride (0.064 g) in the presence of a 6M solution of hydrogen chloride in isopropanol (0.05 ml) to give the title compound, as a trihydrochloride salt (0.092 g), a portion of which was converted into the free base using an analogous procedure to that described in Example 3. The free base gave the following characterising data: NMR Spectrum: (CDCl$_3$) 1.8–1.9 (m, 4H), 2.32 (s, 3H), 2.48 (m, 2H), 2.65 (br s, 4H), 2.82 (d, 2H), 2.98 (m, 4H), 3.2 (d, 2H), 3.82 (s, 3H), 4.25 (m, 2H), 6.65 (m, 1H), 6.95 (m, 1H), 7.3 (d, 1H), 8.02 (d, 1H), 8.52 (s, 1H); Mass Spectrum: M+H$^+$ 497 and 499.

The 4-chloro-5-(4-methylpiperazin-1-yl)-7-(2-pyrrolidin-1-ylethoxy)quinazoline used as a starting material was prepared as follows:

A mixture of 5,7-difluoro-3,4-dihydroquinazolin-4-one (0.091 g), 1-methylpiperazine (0.1 g) and DMF (2 ml) was stirred and heated to 100° C. for 1 hour. The mixture was evaporated and the residue was purified by column chromatography using a 97:3 mixture of methylene chloride and a saturated methanolic ammonia solution as eluent. There was thus obtained 7-fluoro-5-(4-methylpiperazin-1-yl)-3,4-dihydroquinazolin-4-one (0.09 g); NMR Spectrum: (CDCl$_3$) 2.42 (s, 3H), 2.72 (br s, 4H), 3.2 (br s, 4H), 6.72 (m, 1H), 7.0 (m, 1H), 8.0 (s, 1H); Mass Spectrum: M+H$^+$ 263.

Sodium hydride (60% dispersion in mineral oil; 0.96 g) was added to a stirred solution of 1-(2-hydroxyethyl)pyrrolidine (1.4 ml) in DMF (20 ml) and the mixture was stirred at ambient temperature for 10 minutes. 7-Fluoro-5-(4-methylpiperazin-1-yl)-3,4-dihydroquinazolin-4-one (0.09 g) was added and the mixture was stirred and heated to 100° C. for 3 hours. The resultant mixture was evaporated and acetic acid (1.4 ml) and methylene chloride were added in turn to the residue. The mixture was filtered and the filtrate was poured onto a column of silica and eluted with a 19:1 mixture of methylene chloride and a saturated methanolic ammonia solution. The material so obtained as triturated under pentane, isolated, washed with pentane and dried under vacuum. There was thus obtained 5-(4-methylpiperazin-1-yl)-7-(2-pyrrolidin-1-ylethoxy)-3,4-dihydroquinazolin-4-one (0.74 g); NMR Spectrum: (CDCl$_3$) 1.7–1.9 (m, 4H), 2.4 (s, 3H), 2.6–2.8 (m, 8H), 2.92 (t, 2H), 3.15 (br s, 4H), 4.2 (t, 2H), 6.6 (d, 1H), 6.8 (d, 1H), 7.92 (s, 1H); Mass Spectrum: M+H$^+$ 358.

A mixture of a portion (0.65 g) of the material so obtained, phosphoryl chloride (0.252 ml), diisopropylethylamine (0.94 ml) and 1,2-dichloroethane (30 ml) was stirred and heated to 80° C. for 2 hours. The mixture was evaporated and the residue was purified by column chromatography on silica using a 24:1 mixture of methylene chloride and a saturated methanolic ammonia solution as eluent. There was thus obtained 4-chloro- 5-(4-methylpiperazin-1-yl)-7-(2-pyrrolidin-1-ylethoxy)quinazoline (0.23 g); NMR Spectrum: (CDCl$_3$) 1.9–2.1 (br s, 4H), 2.5 (s, 3H), 2.65 (m, 2H), 2.85–3.1 (m, 10H), 3.32 (d, 2H), 4.4 (br s, 2H), 6.85 (d, 1H), 7.05 (d, 1H), 8.8 (s, 1H); Mass Spectrum: M+H$^+$ 376.

EXAMPLE 50

4-(6-chloro-2,3-methylenedioxyanilino)-5-(N-methylpiperidin-4-yloxy)-7-(2,2,2-trifluoroethoxy)quinazoline A mixture of 4-(6-chloro-2,3-methylenedioxyanilino)-7-hydroxy-5-(N-methylpiperidin-4-yloxy)quinazoline (0.1 g), 2,2,2-trifluoroethyl 4-toluenesulphonate (0.071 g), potassium carbonate (0.08 g) and DMF (2 ml) was stirred and heated to 95° C. for 24 hours. The mixture was cooled to ambient temperature and partitioned between ethyl acetate and water. The organic solution was washed with water and with brine, dried over magnesium sulphate and evaporated. The residue was purified by column chromatography on silica using a 45:46:4 mixture of methylene chloride, ethyl acetate and methanol as eluent. There was thus obtained the title compound (0.058 g); NM: Spectrum: (CDCl$_3$) 1.95–2.1 (m, is 2H), 2.1–2.3 (m, 2H), 2.32 (s, 3H), 2.3–2.45 (m, 2H), 2.75 (m, 2H), 4.48 (m, 2H), 4.64 (m, 1H), 6.05 (s, 2H), 6.6 (d, 1H), 6.74 (d, 1H), 6.78 (d, 1H), 6.97 (d, 1H), 8.5 (s, 1H), 9.28 (s, 1H); Mass Spectrum: M+H$^+$ 511 and 513.

The 4-(6-chloro-2,3-methylenedioxyanilino)-7-hydroxy-5-(N-methylpiperidin-4-yloxy)quinazoline used as a starting material was prepared as follows:

A solution of di-tert-butyl azodicarboxylate (5.44 g) in methylene chloride (20 ml) was added dropwise to a stirred mixture of 7-benzyloxy-5-hydroxy-3-pivaloyloxymethyl-3,4-dihydroquinazolin-4-one (6 g) 4-hydroxy-N-methylpiperidine (2.17 g), triphenylphosphine (6.17 g) and methylene chloride (100 ml) that had been cooled to 0° C. The resultant mixture was stirred at ambient temperature for 1 hour. The mixture was evaporated and the residue was purified by column chromatography on silica using a 10:9:1 mixture of methylene chloride, ethyl acetate and a saturated methanolic ammonia solution as eluent. The material so obtained was dissolved in a saturated methanolic ammonia solution (240 ml) and stirred at ambient temperature for 16 hours. The mixture was evaporated and the residue was triturated under diethyl ether. The resultant solid was isolated, washed with diethyl ether and dried under vacuum. There was thus obtained 7-benzyloxy-5-(N-methylpiperidin-4-yloxy)-3,4-dihydroquinazolin-4-one (3.68 g); NMR Spectrum: (CDCl$_3$) 2.0 (m, 4H), 2.3 (s, 3H), 2.35 (m, 2H), 2.75 (m, 2H), 4.5 (m, 1H), 5.15 (s, 2H), 6.6 (d, 1H), 6.82 (d, 1H), 7.3–7.5 (m, 5H), 7.92 (s, 1H); Mass Spectrum: M+H$^+$ 366.

A mixture of the material so obtained, triphenylphosphine (8.65 g), carbon tetrachloride (10 ml) and 1,2-dichloroethane (100 ml) was stirred and heated to 70° C. for 2 hours. The mixture was evaporated and the 7-benzyloxy-4-chloro-5-(N-methylpiperidin-4-yloxy)quinazoline so obtained was dissolved in isopropanol (2 ml) and 6-chloro-2,3-methylenedioxyaniline (1.9 g) and a 5M hydrogen chloride solution in isopropanol (2.1 ml) were added in turn. The resultant mixture was stirred at 50° C. for 20 minutes and at 80° C. for 30 minutes. The mixture was evaporated and the residue was suspended in ethyl acetate and stirred for 1 hour at ambient temperature. The resultant solid was isolated, washed with ethyl acetate and with diethyl ether. The solid was dissolved in a 19:1 mixture of methylene chloride and a saturated methanolic ammonia solution and stirred at ambient temperature for 15 minutes. The mixture was filtered, the filtrate was evaporated and the residue was purified by column chromatography on silica using a 50:47:3 mixture of ethyl acetate, methylene chloride and methanol as eluent. There was thus obtained 7-benzyloxy-4-(6-chloro-2,3-methylenedioxyanilino)-5-(N-methylpiperidin-4-yloxy)quinazoline (4.2 g); NMR Spectrum:(CDCl$_3$) 2.0–12.1 (m, 2H), 2.2 (m, 2H), 2.3 (s, 3H), 2.25–2.35 (m, 2H), 2.75 (m, 2H), 4.6 (m, 1H), 5.2 (s, 2H), 6.1 (s, 2H), 6.6 (s, 1H), 6.75 (d, 1H), 6.95 (s, 1H), 7.0 (d, 1H), 7.32–7.52 (m, 5H), 8.52 (s, 1H), 9.3 (s, 1H) ; Mass Spectrum: M+H$^+$ 519 and 521.

A mixture of a portion (1.5 g) of the material so obtained and trifluoroacetic acid (15 ml) was stirred and heated to reflux for 6 hours. The mixture was evaporated and the residue was dissolved in water and basified to pH9 by the addition of solid sodium bicarbonate. The mixture was extracted with ethyl acetate and the organic layer was washed with brine, dried over magnesium sulphate and evaporated. The residue was purified by column chromatography on silica using a 10:9:2 mixture of ethyl acetate, methylene chloride and methanol as eluent. There was thus obtained 4-(6-chloro-2,3-methylenedioxyanilino)-7-hydroxy-5-(n-methylpiperidin-4-yloxy)quinazoline (0.8 g); NMR Spectrum: (CDCl$_3$) 1.9–2.05 (m, 2H), 2.05–2.15 (m, 2H), 2.2–2.3 (m, 2H), 2.28 (s, 3H), 2.7 (m, 2H), 4.5 (br s, 1H), 6.05 (s, 2H), 6.5 (d, 1H), 6.7 (d, 1H), 6.85 (d, 1H), 6.95 (d, 1H), 8.4 (s, 1H), 9.35 (s, 1H); Mass Spectrum M+H$^+$ 429 and 431.

EXAMPLE 51

4-(6-chloro-2,3-methylenedioxyanilino)-7-ethoxy-5-(N-methylpiperidin-4-yloxy)quinazoline A solution of di-tert-butyl azodicarboxylate (0.26 g) in methylene chloride (1 ml) was added dropwise to a stirred mixture of 4-(6-chloro-2,3-methylenedioxyanilino)-7-hydroxy- 5-(N-methylpiperidin-4-yloxy)quinazoline (0.12 g), ethanol (0.019 g), triphenylphosphine (0.15 g) and methylene chloride (2 ml) and the resultant mixture was stirred at ambient temperature for 1 hour. A 2M solution of hydrogen chloride in diethyl ether (3 ml) was added and the mixture was stirred at ambient temperature for 1.5 hours. Diethyl ether (1 ml) was added and the precipitate was isolated and dried under vacuum. The solid so obtained was dissolved in a 9:1 mixture of methylene chloride and a saturated methanolic ammonia solution. The mixture was filtered and the filtrate was evaporated. The residue was triturated under pentane and the resultant solid was isolated and dried under vacuum. There was thus obtained the title compound (0.092 g); NMR Spectrum: (CDCl$_3$) 1.5 (t, 3H), 1.95–2.1 (m, 2H), 2.15–2.5 (m, 2H), 2.3 (s, 3H), 2.3–2.4 (m, 2H), 2.7 (br s, 2H), 4.15 (m, 2H), 4.6 (m, 1H), 6.05 (s, 2H), 6.5 (d, 1H), 6.7 (d, 1H), 6.8 (d, 1H), 6.95 (d, 1H), 8.5 (s, 1H), 9.25 (br s, 1H); Mass Spectrum: M+H$^+$ 457 and 459.

EXAMPLE 52

4-(6-chloro-2,3-methylenedioxyanilino)-7-(2-fluoroethoxy)-5-(N-methylpiperidin-4-yloxy)quinazoline Using an analogous procedure to that described in Example 51, 4-(6-chloro-2,3-methylenedioxyanilino)-7-hydroxy-5-(N-methylpiperidin-4-yloxy)quinazoline was reacted with 2-fluoroethanol to give the title compound; NMR Spectrum: (CDCl$_3$) 2.0–2.1 (m, 2H), 2.15–2.3 (m, 2H), 2.35 (s, 3H), 2.3–2.4 (m, 2H), 2.8 (br s, 2H), 4.32 (m, 1H), 4.4 (m, 1H), 4.65 (m, 1H), 4.8 (m, 1H), 4.9 (m, 1H), 6.05 (s, 2H), 6.6 (s, 1H), 6.75 (d, 1H), 6.85 (s, 1H), 7.0 (d, 1H), 8.55 (s, 1H), 9.3 (s, 1H); Mass Spectrum: M+H$^+$ 475 and 477.

EXAMPLE 53

4-(6-chloro-2,3-methylenedioxyanilino)-7-isobutoxy-5-(N-methylpiperidin-4-yloxy)quinazoline Using an analogous procedure to that described in Example 51, 4-(6-chloro-2,3-methylenedioxyanilino)-7-hydroxy-5-(N-methylpiperidin-4-yloxy)quinazoline was reacted with isobutanol to give the title compound; NMR Spectrum: (CDCl$_3$) 1.05 (d, 6H), 1.95–2.05 (m, 2H), 2.08–2.28 (m, 3H), 2.3 (s, 3H), 2.3–2.4 (m, 2H), 2.7 (br s, 2H), 3.82 (d, 2H), 4.6 (m, 1H), 6.03 (s, 2H), 6.5 (s, 1H), 6.7

(d, 1H), 6.8 (s, 1H), 6.95 (d, 1H), 8.5 (s, 1H), 9.25 (s, 1H); Mass Spectrum: M+H$^+$ 485 and 487.

EXAMPLE 54

4-(2,3-methylenedioxyanilino)-5-(4-methylpiperazin-1-yl)-7-(2-pyrrolidin-1-ylethoxy)quinazoline trihydrochloride Using an analogous procedure to that described in Example 5, 4-chloro-5-(4-methylpiperazin-1-yl)-7-(2-pyrrolidin-1-ylethoxy)quinazoline (0.11 g) was reacted with 2,3-methylenedioxyaniline (0.045 g) in the presence of a 6M solution of hydrogen chloride in isopropanol to give the title compound, as a trihydrochloride salt (0.105 g), a portion of which was converted into the free base using an analogous procedure to that described in Example 3. The free base gave the following characterising data: NMR Spectrum: (CDCl$_3$) 1.78 (br s, 4H), 2.3 (s, 3H), 2.5 (m, 2H), 2.6 (br s, 4H), 2.8 (d, 2H), 2.95 (m, 4H), 3.08 (d, 2H), 4.18 (m, 2H), 5.98 (s, 2H), 6.6 (d, 1H), 6.86 (m, 1H), 6.94 (s, 1H), 8.06 (d, 1H), 8.5 (s, 1H), 11.8 (s, 1H); Mass Spectrum: M+H$^+$ 477.

EXAMPLE 55

4-(6-chloro-2,3-methylenedioxyanilino)-5-morpholino-7-(2-pyrrolidin-1-ylethoxy)quinazoline A mixture of 4-chloro-5-morpholino-7-(2-pyrrolidin-1-ylethoxy)quinazoline (0.27 g), 6-chloro-2,3-methylenedioxyaniline (0.14 g) and isopropanol (4 ml) was stirred and heated to 80° C. for 1 hour. The mixture was evaporated and the residue was dissolved in a 49:1 mixture of methylene chloride and a saturated methanolic ammonia solution. The mixture was filtered and the filtrate was poured onto a column of silica and eluted with a 97:3 mixture of methylene chloride and a saturated methanolic ammonia solution. The material so obtained was triturated under diethyl ether. The resultant solid was isolated, washed with diethyl ether and dried under vacuum. There was thus obtained the title compound (0.035 g); NMR Spectrum: (CDCl$_3$) 1.85 (br s, 4H), 2.65 (br s, 4H), 3.0 (m, 2H), 3.08 (m, 2H), 3.18 (d, 2H), 3.82 (m, 2H), 4.05 (m, 2H), 4.25 (m, 2H), 6.05 (s, 2H), 6.75 (d, 1H), 6.95–7.1 (m, 3H), 8.52 (s, 1H); Mass Spectrum: M+H$^+$ 498 and 500.

The 4-chloro-5-morpholino-7-(2-pyrrolidin-1-ylethoxy)quinazoline used as a starting material was prepared as follows:

A mixture of 5,7-difluoro-3,4-dihydroquinazolin-4-one (0.91 g), morpholine (0.9 ml) and DMF (20 ml) was stirred and heated to 100° C. for 1 hour. The mixture was evaporated. A saturated methanolic ammonia solution (1 ml) was added to the residue and the mixture was stirred at ambient temperature for 5 minutes. The mixture was evaporated and the residue was triturated under water. The resultant solid was isolated, washed with water and with diethyl ether and dried under vacuum. There was thus obtained 7-fluoro-5-morpholino- 3,4-dihydroquinazolin-4-one (0.85 g); NMR Spectrum: (DMSOd$_6$) 3.05 (br s, 4H), 3.8 (t, 4H), 6.8 (m, 1H), 6.92 (m, 1H), 8.02 (s, 1H); Mass Spectrum: M+H$^+$ 250.

Sodium hydride (60% dispersion in mineral oil, 0.5 g) was added to a stirred solution of 1-(2-hydroxyethyl)pyrrolidine (0.7 ml) in DMF (15 ml) which had been cooled to 5° C. The mixture was stirred for 10 minutes. 7-Fluoro-5-morpholino-3,4-dihydroquinazolin-4-one (0.75 g) was added and the mixture was heated to 80° C. for 1 hour and then to 90° C. for 3 hours. The mixture was evaporated and the residue was dissolved in acetic acid (0.9 ml) and diluted with a mixture of methylene chloride and methanol. The resultant solution was poured onto a column of silica and eluted with a 47:3 mixture of methylene chloride and methanol as eluent. The material so obtained was triturated under diethyl ether and the resultant solid was isolated, washed with diethyl ether and dried under vacuum. There was thus obtained 5-morpholino-7-(2-pyrrolidin-1-ylethoxy)-3,4-dihydroquinazolin-4-one (0.5 g); NMR Spectrum: (DMSOd$_6$) 1.7 (br s, 4H), 2.8 (m, 2H), 3.02 (br s, 4H), 3.8 (m, 4H), 4.2 (m, 2H), 6.45 (d, 1H), 6.7 (d, 1H), 7.92 (s, 1H), 11.7 (br s, 1H); Mass Spectrum: M+H$^+$ 345.

A mixture of a portion (0.26 g) of the material so obtained, phosphoryl chloride (0.084 ml), diisopropylethylamine (0.34 ml) and 1,2-dichloroethane (5 ml) was stirred and heated to 80° C. for 3 hours. The mixture was evaporated to give 4-chloro-5-morpholino-7-(2-pyrrolidin-1-ylethoxy)quinazoline which was used without further purification.

EXAMPLE 56

4-(6-chloro-2,3-methylenedioxyanilino)-5-phenoxyquinazoline monohydrochloride

A mixture of 4-(6-chloro-2,3-methylenedioxyanilino)-5-fluoroquinazoline (0.213 g), phenol (0.45 g), potassium carbonate (0.828 g) and DMF (3 ml) was stirred and heated to 90° C. for 30 hours. The mixture was evaporated and the residue was partitioned between ethyl acetate and a 2N aqueous sodium hydroxide solution. The organic layer was washed with brine, dried over magnesium sulphate and evaporated. The residue was purified by column chromatography on silica using a 99:1 mixture of methylene chloride and methanol as eluent. The material so obtained was dissolved in diethyl ether and a 6M solution of hydrogen chloride in diethyl ether (1 equivalent) was added. The resultant solid was isolated, washed with diethyl ether and dried under vacuum. There was thus obtained the title compound (0.05 g); NMR Spectrum: (DMSOd$_6$ and CF$_3$CO$_2$D) 6.18 (s, 2H), 6.95 (d, 1H), 7.05 (d, 1H), 7.1 (d, 1H), 7.35 (d, 1H), 7.42 (m, 1H), 7.52–7.62 (m, 3H), 8.0 (m, 1H), 9.0 (s, 1H); Mass Spectrum: M+H$^+$ 392 and 394.

EXAMPLE 57

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

-continued

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

The invention claimed is:

1. A quinazoline derivative of the Formula I $$\text{(Formula I)}$$

wherein m is 0, 1, 2 or 3;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^3-X^1-$ wherein $X^1$ is a direct bond or is selected from O, S, SO, $SO_2$, $N(R^4)$, CO, $CH(OR^4)$, $CON(R^4)$, $N(R^4)$CO, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, CON(R⁵), N(R⁵)CO, SO₂N(R⁵), N(R⁵)SO₂, CH=CH and C≡C wherein R⁵ is hydrogen or (1–6C)alkyl, and wherein any CH₂=CH— or HC≡C— group within a R¹ substituent optionally bears at the terminal CH₂= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q⁴-X²— wherein X² a direct bond or is selected from CO and N(R⁶)CO, wherein R⁶ is hydrogen or (1–6C)alkyl, and Q⁴ is aryl, aryl-(1–6C)alkyl, heteroaryl, heteroaryl-(1–6C)alkyl, heterocyclyl or heterocyclyl-(1–6C)alkyl, and wherein any CH₂ or CH₃ group within a R¹ substituent optionally bears on each said CH₂ or CH₃ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X³-Q⁵ wherein X³ is a direct bond or is selected from O, S, SO, SO₂, N(R⁷), CO, CH(OR⁷), CON(R⁷), N(R⁷)CO, SO₂N(R⁷), N(R⁷)SO₂, C(R⁷)₂O, C(R⁷)₂S and N(R⁷)C(R⁷)₂, wherein R⁷ is hydrogen or (1–6C)alkyl, and Q⁵ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on R¹ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X⁴—R⁸ wherein X⁴ is a direct bond or is selected from O and N(R⁹), wherein R⁹ is hydrogen or (1–6C)alkyl, and R⁸ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—X⁵-Q⁶ wherein X⁵ is a direct bond or is selected from O, CO and N(R¹⁰), wherein R¹⁰ is hydrogen or (1–6C)alkyl, and Q⁶ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on R¹ optionally bears 1 or 2 oxo or thioxo substituents;

R² is hydrogen or (1–6C)alkyl;

R³ is hydrogen or (1–6C)alkyl;

Z is a direct bond or is selected from O, S, SO, SO₂, N(R¹¹), CO, CH(OR¹¹), CON(R¹¹), N(R¹¹)CO, SO₂N(R¹¹), N(R¹¹)SO₂, OC(R¹¹)₂, SC(R¹¹)₂ and N(R¹¹)C(R¹¹)₂, wherein R¹¹ is hydrogen or (1–6C)alkyl;

Q¹ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or, when Z is a direct bond or O, Q¹ may be halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (1–6C)alkylthio-(1–6C)alkyl, (1–6C)alkylsulphinyl-(1–6C)alkyl or (1–6C)alkylsulphonyl-(1–6C)alkyl, and wherein adjacent carbon atoms in any (2–6C)alkylene chain within the Q¹-Z- group are optionally separated by the insertion into the chain of a group selected from O, S, SO, SO₂, N(R¹²), CO, CH(OR¹²), CON(R¹²), N(R¹²)CO, SO₂N(R¹²), N(R¹²)SO₂, CH=CH and C≡C wherein R¹² is hydrogen or (1–6C)alkyl, and wherein any CH₂=CH— or HC≡C— group within the Q¹-Z- group optionally bears at the terminal CH₂= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q⁷-X⁶— wherein X⁶ is a direct bond or is selected from CO and N(R¹³)CO, wherein R¹³ is hydrogen or (1–6C)alkyl, and Q⁷ is aryl, aryl-(1–6C)alkyl, heteroaryl, heteroaryl-(1–6C)alkyl, heterocyclyl or heterocyclyl-(1–6C)alkyl, and wherein any CH₂ or CH₃ group within the Q¹-Z- group optionally bears on each said CH₂ or CH₃ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)

alkyl]sulphamoyl, (1–6C)alkanesulphonylamino and N-(1–6C)alkyl-(1–6C)alkanesulphonylamino, or from a group of the formula:

—X⁷-Q⁸ wherein $X^7$ is a direct bond or is selected from O, S, SO, SO₂, N(R¹⁴), CO, CH(OR¹⁴), CON(R¹⁴), N(R¹⁴)CO, SO₂N(R¹⁴), N(R¹⁴)SO₂, C(R¹⁴)₂O, C(R¹⁴)₂S and N(R¹⁴)C¹⁴)₂, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C) alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C) alkenyloxy, (2–6C)alkynyloxy, (1–6C)alkylthio, (1–6C)alkylsulphinyl, (1–6C)alkylsulphonyl, (1–6C) alkylamino, di-[(1–6C)alkyl]amino, (1–6C)alkoxycarbonyl, N-(1–6C)alkylcarbamoyl, N,N-di-[(1–6C)alkyl] carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C) alkyl]sulphamoyl, (1–6C)alkanesulphonylamino and N-(1–6C)alkyl-(1–6C)alkanesulphonylamino, or from a group of the formula:

—X⁸—R¹⁵ wherein $X^8$ is a direct bond or is selected from O and N(R¹⁶), wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X⁹-Q⁹ wherein $X^9$ is a direct bond or is selected from O, CO and N(R¹⁷), wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents; and $Q^2$ is an aryl group of formula Ia

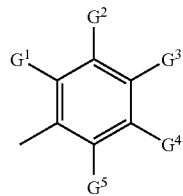

Ia wherein $G^1$ is selected from halogeno, trifluoromethyl, cyano, nitro, hydroxy, amino, carboxy, carbamoyl, (1–6C)alkyl, (2–8C)alkenyl, (2–8C)alkynyl, (1–6C) alkoxy, (2–6C)alkenyloxy, (2–6C)alkynyloxy, (1–6C)alkylthio, (1–6C)alkylsulphinyl, (1–6C) alkylsulphonyl, (1–6C)alkylamino, di-[(1–6C)alkyl] amino, (1–6C)alkoxycarbonyl, N-(1–6C)alkylcarbamoyl, N,N-di-[(1–6C)alkyl]carbamoyl, (2–6C) alkanoyl, (2–6C)alkanoyloxy, (2–6C) alkanoylamino, N-(1–6C)alkyl-(2–6C) alkanoylamino, (3–6C)alkenoylamino, N-(1–6C) alkyl-(3–6C)alkenoylamino, (3–6C)alkynoylamino, N-(1–6C)alkyl-(3–6C)alkynoylamino, N-(1–6C) alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X¹⁰—R¹⁸ wherein $X^{10}$ is a direct bond or is selected from O and N(R¹⁹), wherein $R^{19}$ is hydrogen or (1–6C) alkyl, and $R^{18}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C) alkylamino-(1–6C)alkyl or di-[(1–6C)alkyl] amino-(1–6C)alkyl, or from a group of the formula:

—X¹¹-Q¹⁰ wherein $X^{11}$ is a direct bond or is selected from O, S, SO, SO₂, N(R²⁰), CO, CH(OR²⁰), CON(R²⁰), N(R²⁰)CO, SO₂N(R²⁰), N(R²⁰)SO₂, C(R²⁰)₂O, C(R²⁰)₂S and N(R²⁰)C(R²⁰)₂, wherein $R^{20}$ is hydrogen or (1–6C)alkyl, and $Q^{10}$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and any heterocyclyl group within $Q^{10}$ optionally bears 1 or 2 oxo or thioxo substituents, and each of $G^2$, $G^3$, $G^4$ and $G^5$, which may be the same or different, is selected from hydrogen, halogeno, trifluoromethyl, cyano, nitro, hydroxy, amino, (1–6C)alkyl, (2–8C)alkenyl, (2–8C)alkynyl, (1–6C) alkoxy, (1–6C)alkylamino and di-[(1–6C)alkyl] amino, or $G^1$ and $G^2$ together form a group of formula:
—CH=CH—CH=CH—, —N=CH—CH=CH—, —CH=N—CH=CH—, —CH=CH—N=CH—, —CH=CH—CH=N—, —N=CH—N=CH—, —CH=N—CH=N—, —N=CH—CH=N—, —N=N—CH=CH—, —CH=CH—N=N—, —CH=CH—O—, —O—CH=CH—, —CH=CH—S—, —S—CH=CH—, —CH₂—CH₂—O—, —O—CH₂—CH₂—, —CH₂—CH₂—S—, —S—CH₂—CH₂—, —O—CH₂—O—, —O—CH₂—CH₂—O—, —S—CH₂—S—, —S—CH₂—CH₂—S—, —CH=CH—NH—, —NH—CH=CH—, —CH₂—CH₂—NH—, —NH—CH₂—CH₂—, —N=CH—NH—, —NH—CH=N—, —NH—CH₂—NH—, —O—CH=N—, —N=CH—O—, —S—CH=N—, —N=CH—S—, —O—CH₂—NH—, —NH—CH₂—O—, —S—CH₂—NH—, —NH—CH₂—S—, —O—N=CH—, —CH=N—O—, —S—N=CH—, —CH=N—S—, —O—NH—CH₂—, —CH₂—NH—O—, —S—NH—CH₂—, —CH₂—NH—S—, —NH—N=CH—, —CH=N—NH—, —NH—NH—CH$_2$—, —CH$_2$—NH—NH—, —N=N—NH— or —NH—N=N—, or G$^1$ has any of the meanings defined hereinbefore and G$^2$ and G$^3$ together or G$^3$ and G$^4$ together form a group of formula: —CH=CH—CH=CH—, —N=CH—CH=CH—, —CH=N—CH=CH—, —CH=CH—N=CH—, —CH=CH—CH=N—, —N=CH—N=CH—, —CH=N—CH=N—, —N=CH—CH=N—, —N=N—CH=CH—, —CH=CH—N=N—, —CH=CH—O—, —O—CH=CH—, —CH=CH—S—, —S—CH=CH—, —CH$_2$—CH$_2$—O—, —O—CH$_2$—CH$_2$—, —CH$_2$—CH$_2$—S—, —S—CH$_2$—CH$_2$—, —O—CH$_2$—O—, —O—CH$_2$—CH$_2$—O—, —S—CH$_2$—S—, —S—CH$_2$—CH$_2$—S—, —CH=CH—NH—, —NH—CH=CH—, —CH$_2$—CH$_2$—NH—, —NH—CH$_2$—CH$_2$—, —N=CH—NH—, —NH—CH=N—, —NH—CH$_2$—NH—, —O—CH=N—, —N=CH—O—, —S—CH=N—, —N=CH—S—, —O—CH$_2$—NH—, —NH—CH$_2$—O—, —S—CH$_2$—NH—, —NH—CH$_2$—S—, —O—N=CH—, —CH=N—O—, —S—N=CH—, —CH=N—S—, —O—NH—CH$_2$—, —CH$_2$—NH—O—, —S—NH—CH$_2$—, —CH$_2$—NH—S—, —NH—N=CH—, —CH=N—NH—, —NH—NH—CH$_2$—, —CH$_2$—NH—NH—, —N=N—NH— or —NH—N=N—, and the 9- or 10-membered bicyclic heteroaryl or heterocyclic ring formed when G$^1$ and G$^2$ together, G$^2$ and G$^3$ together or G$^3$ and G$^4$ together are linked optionally bears on the heteroaryl or heterocyclic portion of the bicyclic ring 1, 2 or 3 substituents, which may be the same or different, selected from halogeno, trifluoromethyl, cyano, nitro, hydroxy, amino, (1–6C)alkyl, (2–8C)alkenyl, (2–8C)alkynyl, (1–6C)alkoxy, (1–6C)alkylamino and di-[(1–6C)alkyl]amino, and any bicyclic heterocyclic ring so formed optionally bears 1 or 2 oxo or thioxo groups;

or a pharmaceutically-acceptable salt thereof.

2. A quinazoline derivative of the Formula I according to claim 1, or a pharmaceutically-acceptable salt thereof, wherein each of m, R$^1$, R$^2$, R$^3$ and Q$^2$ has any of the meanings defined in claim 1 and Z is a direct bond or is selected from O, S, SO, SO$_2$, N(R$^{11}$), CO, CH(OR$^{11}$), CON(R$^{11}$), N(R$^{11}$)CO, SO$_2$N(R$^{11}$), N(R$^{11}$)SO$_2$, OC(R$^{11}$)$_2$, SC(R$^{11}$)$_2$ and N(R$^{11}$)C(R$^{11}$)$_2$, wherein R$^{11}$ is hydrogen or (1–6C)alkyl; and Q$^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the Q$^1$-Z- group are optionally separated by the insertion into the chain of a group selected from O, S, SO, SO$_2$, N(R$^{12}$), CO, CH(OR$^{12}$), CON(R$^{12}$), N(R$^{12}$)CO, SO$_2$N(R$^{12}$), N(R$^{12}$)SO$_2$, CH=CH and C≡C wherein R$^{12}$ is hydrogen or (1–6C)alkyl, and wherein any CH$_2$ or CH$_3$ group within the Q$^1$-Z- group optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^7$-Q$^8$ wherein X$^7$ is a direct bond or is selected from O, S, SO, SO$_2$, N(R$^{14}$), CO, CH(OR$^{14}$), CON(R$^{14}$), N(R$^{14}$)CO, SO$_2$N(R$^{14}$), N(R$^{14}$)SO$_2$, C(R$^{14}$)$_2$O, C(R$^{14}$)$_2$S and N(R$^{14}$)C(R$^{14}$)$_2$, wherein R$^{14}$ is hydrogen or (1–6C)alkyl, and Q$^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the Q$^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^8$—R$^{15}$ wherein X$^8$ is a direct bond or is selected from O and N(R$^{16}$), wherein R$^{16}$ is hydrogen or (1–6C)alkyl, and R$^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X$^9$-Q$^9$ wherein X$^9$ is a direct bond or is selected from O, CO and N(R$^{17}$), wherein R$^{17}$ is hydrogen or (1–6C)alkyl, and Q$^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q$^1$-Z- group optionally bears 1 or 2 oxo or thioxo substituents.

3. A quinazoline derivative of the Formula I according to claim 1, or a pharmaceutically-acceptable salt thereof, wherein each of m, R$^1$, R$^2$, R$^3$ and Q$^2$ has any of the meanings defined in claim 1 and Z is selected from O, S, SO, SO$_2$, N(R$^{11}$), CO, CH(OR$^{11}$), CON(R$^{11}$), N(R$^{11}$)CO, SO$_2$N(R$^{11}$), N(R$^{11}$)SO$_2$, OC(R$^{11}$)$_2$, SC(R$^{11}$)$_2$ and N(R$^{11}$)C(R$^{11}$)$_2$, wherein R$^{11}$ is hydrogen or (1–6C)alkyl; and Q$^1$ is (3–7C)cycloalkyl, (3–7C)cycloalkyl-(1–6C)alkyl, (3–7C)cycloalkenyl, (3–7C)cycloalkenyl-(1–6C)alkyl, heterocyclyl or heterocyclyl-(1–6C)alkyl, and wherein adjacent carbon atoms in any (2–6C)alkylene chain within the Q$^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, CH=CH and C≡C wherein $R^{12}$ is hydrogen or (1–6C)alkyl, and wherein any $CH_2$ or $CH_3$ group within the $Q^1$-Z-group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any heterocyclyl group within the $Q^1$-Z-group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z-group optionally bears 1 or 2 oxo or thioxo substituents.

4. A quinazoline derivative of the Formula I according to claim 1, or a pharmaceutically-acceptable salt thereof, wherein each of m, $R^1$, $R^2$, $R^3$, Z and $Q^1$ has any of the meanings defined in claim 1 and $Q^2$ is an aryl group of formula Ia

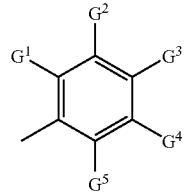

Ia wherein $G^1$ is halogeno or trifluoromethyl,
each of $G^2$ and $G^5$ is hydrogen,
$G^3$ is selected from hydrogen, halogeno, trifluoromethyl, cyano, hydroxy, (1–6C)alkyl, (2–8C)alkenyl, (2–8C)alkynyl and (1–6C)alkoxy, and
$G^4$ is halogeno or (1–6C)alkoxy.

5. A quinazoline derivative of the Formula I according to claim 1, or a pharmaceutically-acceptable salt thereof, wherein each of m, $R^1$, $R^2$, $R^3$, Z and $Q^1$ has any of the meanings defined in claim 1 and $Q^2$ is an aryl group of formula Ia wherein
$G^1$ and $G^2$ together form a group of formula: —O—$CH_2$—O—,
each of $G^3$ and $G^4$, which may be the same or different, is selected from hydrogen, halogeno, trifluoromethyl, cyano, hydroxy, (1–6C)alkyl and (1–6C)alkoxy, and
$G^5$ is halogeno.

6. A quinazoline derivative of the Formula I according to claim 1 wherein:

m is 0 or m is 1 and
the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1)-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy, and wherein adjacent carbon atoms in any (2–6C) alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

the $Q^1$-Z- group is selected from 2-hydroxyethoxy, 3-hydroxypropoxy, 2-methoxyethoxy, 3-methoxypropoxy, cyclopentyloxy, cyclohexyloxy, phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

each of $R^2$ and $R^3$ is hydrogen; and $Q^2$ is an aryl group of formula Ia

Ia

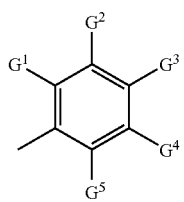

wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, or $G^1$ and $G^2$ together form a group of formula: —CH═CH—CH═CH—, —O—CH═CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoromethyl, cyano, hydroxy, methyl, ethyl, methoxy and ethoxy;

or a pharmaceutically-acceptable acid-addition salt thereof.

7. A quinazoline derivative of the Formula I according to claim 1 wherein:

m is 0 or m is 1 and the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy, and wherein adjacent carbon atoms in any (2–6C) alkylene chain within a $R^1$ substituent are optionally separated by the insertion into the chain of a group selected from O, NH, CH═CH and C≡C.

and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

the $Q^1$-Z- group is selected from phenoxy, benzyloxy, tetrahydrofuran-3-yloxy, tetrahydropyran-3-yloxy, tetrahydropyran-4-yloxy, 2-imidazol-1-ylethoxy, 2-(1,2,4triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

each of $R^2$ and $R^3$ is hydrogen; and $Q^2$ is an aryl group of formula Ia

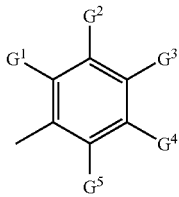

Ia wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, or $G^1$ and $G^2$ together form a group of formula: —CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$ which may be the same or different, is selected from hydrogen, fluoro, chloro, bromo, trifluoromethyl, cyano, hydroxy, methyl, ethyl, methoxy and ethoxy;

or a pharmaceutically-acceptable acid-addition salt thereof.

8. A quinazoline derivative of the Formula I according to claim 1 wherein:

m is 1 and the $R^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)-propoxy, 2-[(2S)-2-N-methylcarbamoyl)pyrrolidin-1-yl]ethoxy, 2-[(2S)-2-(N,N-dimethylcarbamoyl)pyrrolidin-1-yl]ethoxy, 2-hydroxyethoxy, 3-hydroxypropoxy, 2-methoxyethoxy, 3-methoxypropoxy, 2-methylsulphonylethoxy, 3-methylsulphonylpropoxy, 2-(2-methoxyethoxy)ethoxy, 2-(4-pyridyloxy)ethoxy, 2-pyridylmethoxy, 3-pyridylmethoxy and 4-pyridylmethoxy;

and wherein any CH$_2$ group within a $R^1$ substituent that is attached to two carbon atoms optionally bears a hydroxy group on said CH$_2$ group;

the $Q^1$-Z- group is selected from tetrahydrofuran-3-yloxy, tetrahydropyran-4-yloxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 3-piperidinyloxy, N-methylpiperidin-3-yloxy, 4-piperidinyloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy, 3-(4-methylpiperazin-1-yl)propoxy, cyclobutyloxy, cyclopentyloxy and cyclohexyloxy, and wherein any CH$_2$ group within the $Q^1$-Z- group that is attached to two carbon atoms optionally bears a hydroxy group on said CH$_2$ group;

and wherein any heterocyclyl group within the $Q^1$-Z- group optionally bears 1 or 2 oxo substituents;

each of $R^2$ and $R^3$ is hydrogen; and $Q^2$ is an aryl group of formula Ia

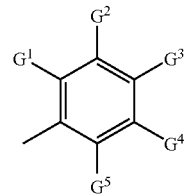

Ia wherein $G^1$ is selected from fluoro, chloro, bromo, iodo, trifluoromethyl, cyano, methyl, ethyl, vinyl, isopropenyl, ethynyl and methoxy, $G^2$ is hydrogen, each of $G^3$ and $G^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and $G^5$ is hydrogen or methoxy, or $G^1$ and $G^2$ together form a group of formula: —CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of $G^3$, $G^4$ and $G^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

9. A quinazoline derivative of the Formula I according to claim 1 wherein:

m is 1 and the $R^1$ group is located at the 7-position and is selected from methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-piperidinoethoxy, 3-piperidinopropoxy, 2-piperidin-4-ylethoxy, 2-(N-methylpiperidin-4-yl)ethoxy, 2-morpholinoethoxy, 3-morpholinopropoxy, 2-(1,1-dioxotetrahydro-4H-1,4-thiazin-4-yl)ethoxy, 3-(1,1- dioxotetrahydro-4H-1,4-thiazin-4-yl)propoxy, 2-homopiperidin-1-ylethoxy, 3-homopiperidin-1-ylpropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, piperidin-4-ylmethoxy, N-methylpiperidin-4-ylmethoxy, 2-(4-pyridyloxy)ethoxy, 2-pyridylmethoxy, 3-pyridylmethoxy, 4-pyridylmethoxy and 2-cyanopyrid-4-ylmethoxy, and wherein any CH$_2$ group within a R$^1$ substituent that is attached to two carbon atoms optionally bears a hydroxy group on said CH$_2$ group;

the Q$^1$-Z- group is selected from tetrahydropyran-4-yloxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, 4-piperidinyloxy, N-methylpiperidin-4-yloxy, piperidin-4-ylmethoxy, N-methylpiperidin-4-ylmethoxy, 3-(4-methylpiperazin-1-yl)propoxy, cyclopentyloxy and cyclohexyloxy;

each of R$^2$ and R$^3$ is hydrogen; and

Q$^2$ is an aryl group of formula Ia

Ia wherein G$^1$ is selected from chloro, bromo, trifluoromethyl, methyl and methoxy, G$^2$ is hydrogen, G$^3$ is selected from hydrogen and chloro, G$^4$ is methoxy, and G$^5$ is hydrogen, or G$^1$ and G$^2$ together form a group of formula: —O—CH=CH—, —O—CH=C(Cl)— or —O—CH$_2$—O—, each of G$^3$ and G$^4$ is hydrogen, and G$^5$ is hydrogen or chloro;

or a pharmaceutically-acceptable acid-addition salt thereof.

10. A quinazoline derivative of the Formula I according to claim 1 wherein:

m is 1 and the R$^1$ group is located at the 7-position and is selected from methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-piperidinoethoxy, 3-piperidinopropoxy, 3-(4-hydroxypiperidin-1-yl)propoxy, 2-piperidin-4-ylethoxy, 2-(N-methylpiperidin-4-yl)ethoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, piperidin-4-ylmethoxy, N-methylpiperidin-4-ylmethoxy 2-(4-pyridyloxy)ethoxy, 2-pyridylmethoxy, 3-pyridylmethoxy and 4-pyridylmethoxy;

the Q$^1$-Z- group is selected from tetrahydropyran-4-yloxy, 4-piperidinyloxy, N-methylpiperidin-4-yloxy, piperidin-4-ylmethoxy, N-methylpiperidin-4-ylmethoxy, cyclopentyloxy and cyclohexyloxy;

each of R$^2$ and R$^3$ is hydrogen; and

Q$^2$ is an aryl group of formula Ia

Ia wherein G$^1$ and G$^2$ together form a group of formula: —O—CH$_2$—O—, each of G$^3$ and G$^4$ is hydrogen, and G$^5$ is chloro;

or a pharmaceutically-acceptable acid-addition salt thereof.

11. A quinazoline derivative of the Formula I according to claim 1 selected from:

4-(2-chloro-5-methoxyanilino)-5,7-di-(3-morpholinopropoxy)quinazoline, 4-(2-bromo-5-methoxyanilino)-7-methoxy-5-(N-methylpiperidin-4-yloxy)quinazoline, 4-(2-chloro-5-methoxyanilino)-7-methoxy-5-(N-methylpiperidin-4-yloxy)quinazoline, 4-(2-chloro-5-methoxyanilino)-7-[3-(4-methylpiperazin-1-yl)propoxy]-5-tetrahydropyran-4-yloxyquinazoline, 4-(2-chloro-5-methoxyanilino)-7-(3-morpholinopropoxy)-5-tetrahydropyran-4-yloxyquinazoline, 4-(2-chloro-5-methoxyanilino)-7-[2-hydroxy-3-(4-methylpiperazin-1-yl)propoxy]-5-tetrahydropyran-4-yloxyquinazoline, 4-(2-chloro-5-methoxyanilino)-7-(2-hydroxy-3-morpholinopropoxy)-5-tetrahydropyran-4-yloxyquinazoline, 4-(2-chloro-5-methoxyanilino)-7-[3-(4-methylpiperazin-1-yl)propoxy]-5-tetrahydrofuran-3-yloxyquinazoline, 4-(2-chloro-5-methoxyanilino)-7-(3-morpholinopropoxy)-5-tetrahydrofuran-3-yloxyquinazoline, 4-(5-chloronaphth-1-ylamino)-7-methoxy-5-(N-methylpiperidin-4-yloxy)quinazoline, 4-(3-chlorobenzofuran-7-ylamino)-7-methoxy-5-(N-methylpiperidin-4-yloxy)quinazoline, 7-benzyloxy-4-(2-bromo-5-methoxyanilino)-5-piperidin-4-yloxyquinazoline, 4-(2-bromo-5-methoxyanilino)-7-(3-methylsulphonylpropoxy)-5-piperidin-4-yloxyquinazoline, 4-(2-bromo-5-methoxyanilino)-7-methoxy-5-piperidin-4-ylmethoxyquinazoline, 4-(2,4-dichloro-5-methoxyanilino)-7-methoxy-5-(N-methylpiperidin-4-yloxy)quinazoline, 4-(2,5-dimethoxyaniline)-7-methoxy-5-(N-methylpiperidin-4-yloxy)quinazoline, 4-(2,4-dichloro-5-methoxyanilino)-7-(2-pyrrolidin-1-ylethoxy)-5-tetrahydropyran-4-yloxyquinazoline, 4-(2,4-dichloro-5-methoxyanilino)-7-(2-piperidinoethoxy)-5-tetrahydropyran-4-yloxyquinazoline, 4-(2,4-dichloro-5-methoxyanilino)-7-(2-morpholinoethoxy)-5-tetrahydropyran-4-yloxyquinazoline, 4-(2,4-dichloro-5-methoxyanilino)-7-[2-(4-methylpiperazin-1-yl)ethoxy]-5-tetrahydropyran-4-yloxyquinazoline, 4-(2-bromo-5-methoxyanilino)-7-(2-pyrrolidin-1-ylethoxy)-5-tetrahydropyran-4-yloxyquinazoline, 4-(2-bromo-5-methoxyanilino)-7-(2-piperidinoethoxy)-5-tetrahydropyran-4-yloxyquinazoline,
4-(2-bromo-5-methoxyanilino)-7-[2-(4-methylpiperazin-1-yl)ethoxy]-5-tetrahydropyran-4-yloxyquinazoline,
4-(2-bromo-5-methoxyanilino)-7-(4-pyridyloxyethoxy)-5-tetrahydropyran-4-yloxyquinazoline,
4-(2-bromo-5-methoxyanilino)-7-{2-[(2S)-2-(N,N-dimethylcarbamoyl)pyrrolidin-1-yl]ethoxy}-5-tetrahydropyran-4-yloxyquinazoline,
4-(2-bromo-5-methoxyanilino)-7-{2-[(2S)-2-(N-methylcarbamoyl)pyrrolidin-1-yl]ethoxy}-5-tetrahydropyran-4-yloxyquinazoline,
4-(2-bromo-5-methoxyanilino)-7-(4-pyridylmethoxy)-5-tetrahydropyran-4-yloxyquinazoline,
4-(5-methoxy-2-pyrrolidin-1-ylanilino)-7-[3-(4-methylpiperazin-1-yl)propoxy]-5-tetrahydropyran-4-yloxyquinazoline and
4-(2-bromo-5-methoxyanilino)-5-cyclopentyloxy-7-(2-pyrrolidin-1-ylethoxy)quinazoline;
or a pharmaceutically-acceptable acid-addition salt thereof.

12. A quinazoline derivative of the Formula I according to claim 1 selected from:
4-(6-chloro-2,3-methylenedioxyanilino)-5-cyclopentyloxy-7-(2-pyrrolidin-1-ylethoxy)quinazoline,
4-(6-chloro-2,3-methylenedioxyanilino)-5-piperidin-4-yloxyquinazoline,
4-(6-chloro-2,3-methylenedioxyanilino)-7-methoxy-5-piperidin-4-yloxyquinazoline,
4-(6-chloro-2,3-methylenedioxyanilino)-7-methoxy-5-(N-methylpiperidin-4-yloxy)quinazoline,
4-(6-chloro-2,3-methylenedioxyanilino)-7-methoxy-5-piperidin-4-ylmethoxyquinazoline,
4-(6-chloro-2,3-methylenedioxyanilino)-7-(2-pyrrolidin-1-ylethoxy)-5-tetrahydropyran-4-yloxyquinazoline,
4-(6-chloro-2,3-methylenedioxyanilino)-7-(3-pyrrolidin-1-ylpropoxy)-5-tetrahydropyran-4-yloxyquinazoline,
4-(6-chloro-2,3-methylenedioxyanilino)-7-[3-(4-methylpiperazin-1-yl)propoxy]-5-tetrahydropyran-4-yloxyquinazoline,
4-(6-chloro-2,3-methylenedioxyanilino)-7-[2-(4-methylpiperazin-1-yl)ethoxy]-5-tetrahydropyran-4-yloxyquinazoline,
4-(6-chloro-2,3-methylenedioxyanilino)-7-(2-piperidinoethoxy)-5-tetrahydropyran-4-yloxyquinazoline,
4-(6-chloro-2,3-methylenedioxyanilino)-7-[2-(4-pyridyloxy)ethoxy]-5-tetrahydropyran-4-yloxyquinazoline,
4-(6-chloro-2,3-methylenedioxyanilino)-7-piperidin-4-ylmethoxy-5-tetrahydropyran-4-yloxyquinazoline and
4-(6-chloro-2,3-methylenedioxyanilino)-7-(N-methylpiperidin-4-ylmethoxy)-5-tetrahydropyran-4-yloxyquinazoline;
or a pharmaceutically-acceptable acid-addition salt thereof.

13. A process for the preparation of a quinazoline derivative of the Formula I, or a pharmaceutically-acceptable salt thereof, according to claim 1 which comprises:
(a) the reaction of a quinazoline of the Formula II

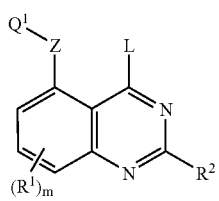

II wherein L is a displaceable group and $Q^1$, Z, m, $R^1$ and $R^2$ have any of the meanings defined in claim 1 except that any functional group is protected if necessary, with an aniline of the Formula $Q^2NHR^3$ wherein $Q^2$ and $R^3$ have any of the meanings defined in claim 1 except that any functional group is protected if necessary, whereafter any protecting group that is present is removed by conventional means;

(b) for the production of those compounds of the Formula I wherein Z is an oxygen atom, the coupling of an alcohol of the Formula $Q^1$-OH wherein $Q^1$ has any of the meanings defined in claim 1 except that any functional group is protected if necessary with a quinazoline of the Formula IV

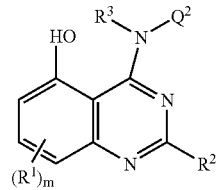

IV wherein m, $R^1$, $R^2$, $R^3$ and $Q^2$ have any of the meanings defined in claim 1 except that any functional group is protected if necessary, whereafter any protecting group that is present is removed by conventional means;

(c) for the production of those compounds of the Formula I wherein m is 1 and $R^1$ is a group of the formula $Q^3$-$X^1$— wherein $Q^3$ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)alkyl group and $X^1$ is an oxygen atom, the coupling of a quinazoline of the Formula VI

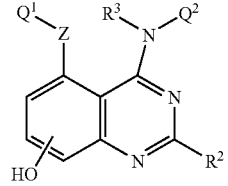

VI wherein $Q^1$, Z, $R^2$, $R^3$ and $Q^2$ have any of the meanings defined in claim 1 except that any functional group is protected if necessary, with an appropriate alcohol wherein any functional group is protected if necessary, whereafter any protecting group that is present is removed by conventional means;

(d) for the production of those compounds of the Formula I wherein $R^1$ is a hydroxy group, the cleavage of a quinazoline derivative of the Formula I wherein $R^1$ is a (1–6C)alkoxy or arylmethoxy group;

(e) for the production of those compounds of the Formula I wherein $Q^1$, $R^1$ or $Q^2$ contains a primary or secondary amino group, the cleavage of the corresponding compound of Formula I wherein $Q^1$, $R^1$ or $Q^2$ contains a protected primary or secondary amino group;

(f) for the production of those compounds of the Formula I wherein $Q^1$, $R^1$ or $Q^2$ contains a (1–6C)alkoxy or substituted (1–6C)alkoxy group or a (1–6C)alkylamino or substituted (1–6C)alkylamino group, the alkylation of a quinazoline derivative of the formula I wherein $Q^1$, $R^1$ or $Q^2$ contains a hydroxy group or a primary or secondary amino group as appropriate;

(g) for the production of those compounds of the Formula I wherein $Q^1$, $R^1$ or $Q^2$ contains an amino-hydroxy-disubstituted (1–6C)alkoxy group, the reaction of a compound of the Formula I wherein $Q^1$, $R^1$ or $Q^2$ contains an epoxy-substituted (1–6C)alkoxy group with a heterocyclyl compound or an appropriate amine;

(h) the reaction of a quinazoline of the Formula VII

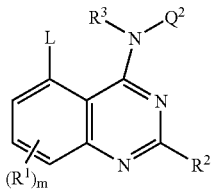

wherein L is a displaceable group and m, $R^1$, $R^2$, $R^3$ and $Q^2$ have any of the meanings defined in claim 1 except that any functional group is protected if necessary, with a compound of the Formula $Q^1ZH$ wherein $Q^1$ and Z have any of the meanings defined in claim 1 except that any functional group is protected if necessary, whereafter any protecting group that is present is removed by conventional means; or (i) for the production of those compounds of the Formula I wherein $Q^1$, $R^1$ or $Q^2$ contains an amino-substituted (1–6C)alkoxy group, the reaction of a compound of the Formula I wherein $Q^1$, $R^1$ or $Q^2$ contains a halogeno-substituted (1–6C)alkoxy group with a heterocyclyl compound or an appropriate amine;

and optionally forming a pharmaceutically-acceptable salt of a quinazoline derivative of the Formula I.

14. A pharmaceutical composition which comprises a quinazoline derivative of the Formula I, or a pharmaceutically-acceptable thereof, as defined in claim 1 in association with a pharmaceutically-acceptable diluent or carrier.

15. The quinazoline derivative of the Formula I according to claim 1 being:
  4-(6-chloro-2,3-methylenedioxyanilino)-7-fluoro-5-tetrahydropyran-4-yloxyquinazoline;
or a pharmaceutically-acceptable salt thereof.

16. The quinazoline derivative of the Formula I according to claim 1 being:
  4-(6-chloro-2,3-methylenedioxyanilino)-7-(2-pyrrolidin-1-ylethoxy)-5-tetrahydropyran-4-yloxyquinazoline;
or a pharmaceutically-acceptable acid-addition salt thereof.

17. The quinazoline derivative of the Formula I according to claim 1 being:
  4-(6-chloro-2,3-methylenedioxyanilino)-7-(3-pyrrolidin-1-ylpropoxy)-5-tetrahydropyran-4-yloxyquinazoline;
or a pharmaceutically-acceptable acid-addition salt thereof.

18. The quinazoline derivative of the Formula I according to claim 1 being:
  4-(6-chloro-2,3-methylenedioxyanilino)-7-[3-(4-methylpiperazin-1-yl)propoxy]-5-tetrahydropyran-4-yloxyquinazoline;
or a pharmaceutically-acceptable acid-addition salt thereof.

19. The quinazoline derivative of the Formula I according to claim 1 being:
  4-(6-chloro-2,3-methylenedioxyanilino)-7-[2-(4-methylpiperazin-1-yl)ethoxy]-5-tetrahydropyran-4-yloxyquinazoline;
or a pharmaceutically-acceptable acid-addition salt thereof.

20. The quinazoline derivative of the Formula I according to claim 1 being:
  4-(6-chloro-2,3-methylenedioxyanilino)-7-(N-methylpiperidin-4-ylmethoxy)-5-tetrahydropyran-4-yloxyquinazoline;
or a pharmaceutically-acceptable acid-addition salt thereof.

21. A quinazoline derivative of the Formula I

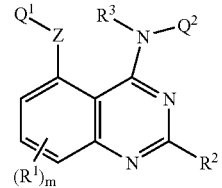

wherein
  m is 0, 1, 2 or 3;
  each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^3-X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C) alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl, and wherein any —CH$_2$=CH— or HC≡C— group within a R$^1$ substituent optionally bears at the terminal CH$_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q$^4$-X$^2$— wherein X$^2$ is a direct bond or is selected from CO and N(R$^6$)CO, wherein R$^6$ is hydrogen or (1–6C)alkyl, and Q$^4$ is aryl, aryl-(1–6C)alkyl, heteroaryl, heteroaryl-(1–6C)alkyl, heterocyclyl or heterocyclyl-(1–6C)alkyl, and wherein any CH$_2$ or CH$_3$ group within a R$^1$ substituent optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^3$-Q$^5$ wherein X$^3$ is a direct bond or is selected from O, S, SO, SO$_2$, N(R$^7$), CO, CH(OR$^7$), CON(R$^7$), N(R$^7$)CO, SO$_2$N(R$^7$), N(R$^7$)SO$_2$, C(R$^7$)$_2$O, C(R$^7$)$_2$S and N(R$^7$)C(R$^7$)$_2$, wherein R$^7$ is hydrogen or (1–6C)alkyl, and Q$^5$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on R$^1$ optionally bears 1, 2 or 3 substituents, which may be the same or different, selected from halogen, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^4$—R$^8$ wherein X$^4$ is a direct bond or is selected from O and N(R$^9$), wherein R$^9$ is hydrogen or (1–6C)alkyl, and R$^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—X$^5$-Q$^6$ wherein X$^5$ is a direct bond or is selected from O, CO and N(R$^{10}$), wherein R$^{10}$ is hydrogen or (1–6C)alkyl, and Q$^6$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on R$^1$ optionally bears 1 or 2 oxo or thioxo substituents;

R$^2$ is hydrogen or (1–6C)alkyl;

R$^3$ is hydrogen or (1–6C)alkyl;

Z is a direct bond or is selected from O, S, SO, SO$_2$, N(R$^{11}$), CO, CH(OR$^{11}$), CON(R$^{11}$), N(R$^{11}$)CO, SO$_2$N(R$^{11}$), N(R$^{11}$)SO$_2$, OC(R$^{11}$)$_2$, SC(R$^{11}$)$_2$ and N(R$^{11}$)C(R$^{11}$)$_2$, wherein R$^{11}$ is hydrogen or (1–6C)alkyl;

Q$^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or, when Z is a direct bond or O, Q$^1$ may be (1–6C)alkyl, (2–8C)alkenyl, (2–8C)alkynyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (1–6C)alkylthio-(1–6C)alkyl, (1–6C)alkylsulphinyl-(1–6C)alkyl or (1–6C)alkylsulphonyl-(1–6C)alkyl, and wherein adjacent carbon atoms in any (2–6C)alkylene chain within the Q$^1$-Z- group are optionally separated by the insertion into the chain of a group selected from O, S, SO, SO$_2$, N(R$^{12}$), CO, CH(OR$^{12}$), CON(R$^{12}$), N(R$^{12}$)CO, SO$_2$N(R$^{12}$), N(R$^{12}$)SO$_2$, CH=CH and C≡C wherein R$^{12}$ is hydrogen or (1–6C)alkyl, and wherein any CH$_2$=CH— or HC≡C— group within the Q$^1$-Z- group optionally bears at the terminal CH$_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q$^7$-X$^6$— wherein X$^6$ a direct bond or is selected from CO and N(R$^{13}$)CO, wherein R$^{13}$ is hydrogen or (1–6C)alkyl, and Q$^7$ is aryl, aryl-(1–6C)alkyl, heteroaryl, heteroaryl-(1–6C)alkyl, heterocyclyl or heterocyclyl-(1–6C)alkyl, and wherein any CH$_2$ or CH$_3$ group within the Q$^1$-Z- group optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X⁷-Q⁸ wherein X⁷ is a direct bond or is selected from O, S, SO, SO₂, N(R¹⁴), CO, CH(OR¹⁴), CON(R¹⁴), N(R¹⁴)CO, SO₂N(R¹⁴), N(R¹⁴)SO₂, C(R¹⁴)₂O, C(R¹⁴)₂S and N(R¹⁴)C(R¹⁴)₂, wherein R¹⁴ is hydrogen or (1–6C)alkyl, and Q⁸ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the Q¹-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X⁸—R¹⁵ wherein X⁸ is a direct bond or is selected from O and N(R¹⁶), wherein R¹⁶ is hydrogen or (1–6C)alkyl, and R¹⁵ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X⁹-Q⁹ wherein X⁹ a direct bond or is selected from O, CO and N(R¹⁷), wherein R¹⁷ is hydrogen or (1–6C)alkyl, and Q⁹ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q¹-Z- group optionally bears 1 or 2 oxo or thioxo substituents; and Q² is an aryl group of formula Ia

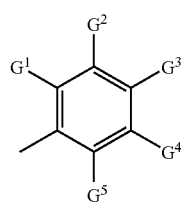

Ia wherein each of G3, G4 and G5, which may be the same or different, is selected from hydrogen, halogeno, trifluoromethyl, cyano, nitro, amino, (1–6C)alkyl, (2–8C)alkenyl, (2–8C)alkynyl, (1–6C)alkoxy, (1–6C)alkylamino and di-[(1–6C)alkyl]amino, and G¹ and G² together form a group of formula —CH=CH—CH=CH—, —N=CH—CH=CH—, —CH=N—CH=CH—, —CH=CH—N=CH—, —CH=CH—CH=N—, —N=CH—N=CH—, —CH=N—CH=N—, —N=CH—CH=N—, —N=N—CH=CH—, —CH=CH—N=N—, —CH=CH—O—, —O—CH=CH—, —CH=CH—S—, —S—CH=CH—, —CH₂—CH₂—O—, —O—CH₂—CH₂—, —CH₂—CH₂—S—, —S—CH₂—CH₂—, —O—CH₂—O—, —O—CH₂—CH₂—O—, —S—CH₂—S—, —S—CH₂—CH₂—S—, —CH=CH—NH—, —NH—CH=CH—, —CH₂—CH₂—NH—, —NH—CH₂—CH₂—, —N=CH—NH—, —NH—CH=N—, —NH—CH₂—NH—, —O—CH=N—, —N=CH—O—, —S—CH=N—, —N=CH—S—, —O—CH₂—NH—, —NH—CH₂—O—, —S—CH₂—NH—, —NH—CH₂—S—, —O—N=CH —, —CH=N—O—, —S—N=CH—, —CH=N—S—, —O—NH—CH₂—, —CH₂—NH—O—, —S—NH—CH₂—, —CH₂—NH—S—, —NH—N=CH—, —CH=N—NH—, —NH—NH—CH₂—, —CH₂—NH—NH—, —N=N—NH— or —NH—N=N—, and the 9- or 10-membered bicyclic heteroaryl or heterocyclic ring formed when G¹ and G² together are linked optionally bears on the heteroaryl or heterocyclic portion of the bicyclic ring 1, 2 or 3 substituents, which may be the same or different, selected from halogeno, trifluoromethyl, cyano, nitro, amino, (1–6C)alkyl, (2–8C)alkenyl, (2–8C)alkynyl, (1–6C)alkoxy, (1–6C)alkylamino and di-[(1–6C)alkyl]amino, and any bicyclic heterocyclic ring so formed optionally bears 1 or 2 oxo or thioxo groups;

or a pharmaceutically-acceptable salt thereof.

22. A quinazoline derivative of the Formula I according to claim 21, or a pharmaceutically-acceptable salt thereof, wherein each of m, R¹, R², R³ and Q² has any of the meanings defined in claim 1 and Z is a direct bond or is selected from O, S, SO, SO₂, N(R¹¹), CO, CH(OR¹¹), CON(R¹¹), N(R¹¹)CO, SO₂N(R¹¹), N(R¹¹)SO₂, OC(R¹¹)₂, SC(R¹¹)₂ and N(R¹¹)C(R¹¹)₂, wherein R¹¹ is hydrogen or (1–6C)alkyl; and Q¹ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the Q¹-Z- group are optionally separated by the insertion into the chain of a group selected from O, S, SO, SO₂, N(R¹²), CO, CH(OR¹²), CON(R¹²), N(R¹²)CO, SO₂N(R¹²), N(R¹²)SO₂, CH=CH and C≡C wherein R¹² is hydrogen or (1–6C)alkyl, and wherein any CH₂ or CH₃ group within the Q¹-Z- group optionally bears on each said CH₂ or CH₃ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)

alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N N-di-[(l –6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

23. A quinazoline derivative of the Formula I according to claim 21, or a pharmaceutically-acceptable salt thereof, wherein each of m, $R^1$, $R^2$, $R^3$ and $Q^2$ has any of the meanings defined in claim 21 and Z is selected from O, S, SO, $SO_2$, $N(R^{11})$, CO, $CH(OR^{11})$, $CON(R^{11})$, $N(R^{11})CO$, $SO_2N(R^{11})$, $N(R^{11})SO_2$, $OC(R^{11})_2$, $SC(R^{11})_2$ and $N(R^{11})C(R^{11})_2$, wherein $R^{11}$ is hydrogen or (1–6C)alkyl; and $Q^1$ is (3–7C)cycloalkyl, (3–7C)cycloalkyl-(1–6C)alkyl, (3–7C)cycloalkenyl, (3–7C)cycloalkenyl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})$ CO, $SO_2N(R^{12})$, $N(R^{12})SO_2$, CH=CH and C≡C wherein $R^{12}$ is hydrogen or (1–6C)alkyl, and wherein any $CH_2$ or $CH_3$ group within the $Q^1$-Z-group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

24. A quinazoline derivative of the Formula I according to claim 21, or a pharmaceutically-acceptable salt thereof, wherein each of m, $R^1$, $R^2$, $R^3$, Z and $Q^1$ has any of the meanings defined in claim 23 and Q² is an aryl group of formula Ia wherein
G¹ and G² together form a group of formula:
—O—CH₂—O—,
each of G³ and G⁴, which may be the same or different, is selected from hydrogen, halogeno, trifluoromethyl, cyano, (1–6C)alkyl and (1–6C)alkoxy, and
G⁵ is halogeno.

25. A quinazoline derivative of the Formula I according to claim 21 wherein:
m is 0 or m is 1 and
the R¹ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy,
and wherein adjacent carbon atoms in any (2–6C) alkylene chain within a R¹ substituent are optionally separated by the insertion into the chain of a group selected from O, NH, CH=CH and C≡C,
and wherein any CH₂ or CH₃ group within a R¹ substituent optionally bears on each said CH₂ or CH₃ group a substituent selected from hydroxy, amino, methoxy, methylsulphonyl, methylamino and dimethylamino,
and wherein any phenyl or heterocyclyl group within a substituent on R¹ optionally bears 1 or 2 substituents, which may be the same or different, selected from fluoro, chloro, trifluoromethyl, hydroxy, amino, methyl, ethyl and methoxy,
and wherein any heterocyclyl group within a substituent on R¹ optionally bears 1 or 2 oxo substituents;
the Q¹-Z- group is selected from propoxy, isopropoxy, 2-hydroxyethoxy, 3-hydroxypropoxy, 2-methoxyethoxy, 3-methoxypropoxy, cyclopentyloxy, cyclohexyloxy, phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy,
and wherein any CH₂ or CH₃ group within the Q¹-Z- group optionally bears on each said CH₂ or CH₃ group a substituent selected from hydroxy, amino, methoxy, methylsulphonyl, methylamino and dimethylamino,
and wherein any phenyl or heterocyclyl group within the Q¹-Z- group optionally bears 1 or 2 substituents, which may be the same or different, selected from fluoro, chloro, trifluoromethyl, hydroxy, amino, methyl, ethyl and methoxy,
and wherein any heterocyclyl group within the Q¹-Z- group optionally bears 1 or 2 oxo substituents;
each of R² and R³ is hydrogen; and
Q² is an aryl group of formula Ia

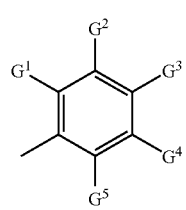

Ia wherein G¹ and G² together form a group of formula:—CH=CH—CH=CH—, —O—CH=CH— or —O—CH₂—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of G³, G⁴ and G⁵, which may be the same or different, is selected from hydrogen, fluoro, chloro, bromo, trifluoromethyl, cyano, methyl, ethyl, methoxy and ethoxy;
or a pharmaceutically-acceptable acid-addition salt thereof.

26. A quinazoline derivative of the Formula I according to claim 21 wherein:
m is 0 or m is 1 and
the R¹ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy,
and wherein adjacent carbon atoms in any (2–6C) alkylene chain within a R¹ substituent are optionally separated by the insertion into the chain of a group selected from O, NH, CH=CH and C≡C, and wherein any CH$_2$ or CH$_3$ group within a R$^1$ substituent optionally bears on each said CH$_2$ or CH$_3$ group a substituent selected from hydroxy, amino, methoxy, methylsulphonyl, methylamino and dimethylamino, and wherein any phenyl or heterocyclyl group within a substituent on R$^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on R$^1$ optionally bears 1 or 2 oxo substituents;

the Q$^1$-Z- group is selected from phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any CH$_2$ or CH$_3$ group within the Q$^1$-Z- group optionally bears on each said CH$_2$ or CH$_3$ group a substituent selected from hydroxy, amino, methoxy, methylsulphonyl, methylamino and dimethylamino, and wherein any phenyl or heterocyclyl group within the Q$^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the Q$^1$-Z- group optionally bears 1 or 2 oxo substituents;

each of R$^2$ and R$^3$ is hydrogen; and

Q$^2$ is an aryl group of formula Ia

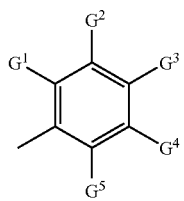

Ia wherein G$^1$ and G$^2$ together form a group of formula:—CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of G$^3$, G$^4$ and G$^5$, which may be the same or different, is selected from hydrogen, fluoro, chloro, bromo, trifluoromethyl, cyano, hydroxy, methyl, ethyl, methoxy and ethoxy;

or a pharmaceutically-acceptable acid-addition salt thereof.

27. A quinazoline derivative of the Formula I according to claim 21 wherein:

m is 1 and the R$^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)-propoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 2-hydroxyethoxy, 3-hydroxypropoxy, 2-methoxyethoxy, 3-methoxypropoxy, 2-methylsulphonylethoxy, 3-methylsulphonylpropoxy, 2-(2-methoxyethoxy)ethoxy, 2-(4-pyridyloxy)ethoxy, 2-pyridylmethoxy, 3-pyridylmethoxy and 4-pyridylmethoxy;

and wherein any CH$_2$ group within a R$^1$ substituent that is attached to two carbon atoms optionally bears a hydroxy group on said CH$_2$ group;

the Q$^1$-Z- group is selected from tetrahydrofuran-3-yloxy, tetrahydropyran-4-yloxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 3-piperidinyloxy, N-methylpiperidin-3-yloxy, 4-piperidinyloxy, N-methylpiperidin-4-yloxy, piperidin-3-ylmethoxy, N-methylpiperidin-3-ylmethoxy, piperidin-4-ylmethoxy N-methylpiperidin-4-ylmethoxy, 2-(4-methylpiperazin-1-yl)-ethoxy, 3-(4-methylpiperazin-1-yl)propoxy, cyclobutyloxy, cyclopentyloxy and cyclohexyloxy, and wherein any CH$_2$ group within the Q$^1$-Z- group that is attached to two carbon atoms optionally bears a hydroxy group on said CH$_2$ group;

and wherein any heterocyclyl group within the Q$^1$-Z- group optionally bears 1 or 2 oxo substituents;

each of R$^2$ and R$^3$ is hydrogen; and

Q$^2$ is an aryl group of formula Ia

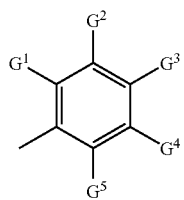

Ia wherein G$^1$ and G$^2$ together form a group of formula:—CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of G³, G⁴ and G⁵, which may be the same or different, is selected from hydrogen, fluoro, chloro, bromo, trifluoromethyl, cyano, hydroxy, methyl and methoxy;

or a pharmaceutically-acceptable acid-addition salt thereof.

28. A quinazoline derivative of the Formula I according to claim 21 wherein m is 1 and the R¹ group is located at the 7-position and is selected from methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-piperidinoethoxy, 3-piperidinopropoxy, 2-piperidin-4-ylethoxy, 2-(N-methylpiperidin-4-yl)ethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-homopiperidin-1-ylethoxy, 3-homopiperidin-1-ylpropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, piperidin-4-ylmethoxy, N-methylpiperidin-4-ylmethoxy, 2-(4-pyridyloxy)ethoxy, 2-pyridylmethoxy, 3-pyridylmethoxy, 4-pyridylmethoxy and 2-cyanopyrid-4-ylmethoxy, and wherein any CH₂ group within a R¹ substituent that is attached to two carbon atoms optionally bears a hydroxy group on said CH₂ group;

the Q¹-Z- group is selected from tetrahydropyran-4-yloxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, 4-piperidinyloxy, N-methylpiperidin-4-yloxy, piperidin-4-ylmethoxy, N-methylpiperidin-4-ylmethoxy, 3-(4-methylpiperazin-1-yl)propoxy, cyclopentyloxy and cyclohexyloxy;

each of R² and R³ is hydrogen; and

Q² is an aryl group of formula Ia

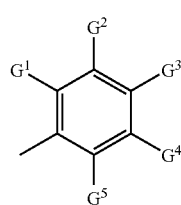

wherein G¹ and G² together form a group of formula: —O—CH=CH—, —O—CH=C(Cl)— or —O—CH₂—O—, each of G³ and G⁴ is hydrogen, and G⁵ is hydrogen or chloro;

or a pharmaceutically-acceptable acid-addition salt thereof.

29. A quinazoline derivative of the Formula I

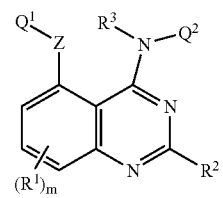

wherein m is 0, 1, 2 or 3;

each R¹ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

Q³-X¹— wherein X¹ is a direct bond or is selected from O, S, SO, SO₂, N(R⁴), CO, CH(OR⁴), CON(R⁴), N(R⁴)CO, SO₂N(R⁴), N(R⁴)SO₂, OC(R⁴)₂, SC(R⁴)₂ and N(R⁴)C(R⁴)₂, wherein R⁴ is hydrogen or (1–6C) alkyl, and Q³ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or (R¹)ₘ is (1–3C)alkylenedioxy, and wherein adjacent carbon atoms in any (2–6C) alkylene chain within a R¹ substituent are optionally separated by the insertion into the chain of a group selected from O,S SO, SO₂, N(R⁵), CO, CH(OR⁵), CON(R⁵), N(R⁵)CO, SO₂N(R⁵), N(R⁵)SO₂, CH=CH and C≡C wherein R⁵ is hydrogen or (1–6C)alkyl, and wherein any CH₂=CH— or HC≡C— group within a R¹ substituent optionally bears at the terminal CH₂= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q⁴-X²— wherein X² is a direct bond or is selected from CO and N(R⁶)CO, wherein R⁶ is hydrogen or (1–6C) alkyl, and Q⁴ is aryl, aryl-(1–6C)alkyl, heteroaryl, heteroaryl-(1–6C)alkyl, heterocyclyl or heterocyclyl-(1–6C)alkyl, and wherein any CH₂ or CH₃ group within a R¹ substituent optionally bears on each said CH₂ or CH₃ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^3$-$Q^5$ wherein $X^3$ is a direct bond or is selected from O, S, SO, $SO_2$, N($R^7$), CO, CH(O$R^7$), CON($R^7$), N($R^7$)CO, $SO_2$N($R^7$), N($R^7$)$SO_2$, C($R^7$)$_2$O, C($R^7$)$_2$S and N($R^7$)C($R^7$)$_2$, wherein $R^7$ is hydrogen or (1–6C)alkyl, and $Q^5$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^4$—$R^8$ wherein $X^4$ is a direct bond or is selected from O and N($R^9$), wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—$X^5$-$Q^6$ wherein $X^5$ is a direct bond or is selected from O, CO and N($R^{10}$), wherein $R^{10}$ is hydrogen or (1–6C)alkyl, and $Q^6$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo or thioxo substituents;

$R^2$ is hydrogen or (1–6C)alkyl;
$R^3$ is hydrogen or (1–6C)alkyl;

Z is a direct bond or is selected from O, S, SO, $SO_2$, N($R^{11}$), CO, CH(O$R^{11}$), CON($R^{11}$), N($R^{11}$)CO, $SO_2$N($R^{11}$), N($R^{11}$)$SO_2$, OC($R^{11}$)$_2$, SC($R^{11}$)$_2$ and N($R^{11}$)C($R^{11}$)$_2$, wherein $R^{11}$ is hydrogen or (1–6C)alkyl;

$Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or, when Z is a direct bond or O, $Q^1$ may be halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (1–6C)alkylthio-(1–6C)alkyl, (1–6C)alkylsulphinyl-(1–6C)alkyl or (1–6C)alkylsulphonyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, N($R^{12}$), CO, CH(O$R^{12}$), CON($R^{12}$), N($R^{12}$)CO, $SO_2$N($R^{12}$), N($R^{12}$)$SO_2$, CH=CH an C≡C wherein $R^{12}$ is hydrogen or (1–6C)alkyl, and wherein any $CH_2$=CH— or HC≡C— group within the $Q^1$-Z- group optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^7$-$X^6$— wherein $X^6$ is a direct bond or is selected from CO and N($R^{13}$)CO, wherein $R^{13}$ is hydrogen or (1–6C)alkyl, and $Q^7$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, N($R^{14}$), CO, CH(O$R^{14}$), CON($R^{14}$), N($R^{14}$)CO, $SO_2$N($R^{14}$), N($R^{14}$)$SO_2$, C($R^{14}$)$_2$O, C($R^{14}$)$_2$S and N($R^{14}$)C($R^{14}$)$_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)

alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X⁸—R¹⁵ wherein X⁸ is a direct bond or is selected from O and N(R¹⁶), wherein R¹⁶ is hydrogen or (1–6C)alkyl, and R¹⁵ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X⁹-Q⁹ wherein X⁹ is a direct bond or is selected from O, CO and N(R¹⁷), wherein R¹⁷ is hydrogen or (1–6C)alkyl, and Q⁹ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q¹-Z-group optionally bears 1 or 2 oxo or thioxo substituents; and Q² is an aryl group of formula Ia

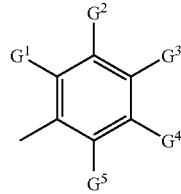

Ia wherein G¹ is selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X¹⁰—R¹⁸ wherein X¹⁰ is a direct bond or is selected from O and N(R¹⁹), wherein R¹⁹ hydrogen or (1–6C)alkyl, and R¹⁸ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X¹¹-Q¹⁰ wherein X¹¹ is a direct bond or is selected from O, S, SO, SO₂, N(R²⁰), CO, CH(OR²⁰), CON(R²⁰), N(R²⁰)CO, SO₂N(R²⁰), N(R²⁰)SO₂, C(R²⁰)₂O, C(R²⁰)₂S and N(R²⁰)C(R²⁰)₂, wherein R²⁰ is hydrogen or (1–6C)alkyl, and Q¹⁰ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and any heterocyclyl group within Q¹⁰ optionally bears 1 or 2 oxo or thioxo substituents, and each of G², G³, G⁴ and G⁵, which may be the same or different, is selected from hydrogen, halogeno, trifluoromethyl, cyano, nitro, hydroxy, amino, (1–6C)alkyl, (2–8C)alkenyl, (2–8C)alkynyl, (1–6C)alkoxy, (1–6C)alkylamino and di-[(1–6C)alkyl]amino, or G¹ and G² together form a group of formula: —CH=CH—CH=CH—, —N=CH—CH=CH—, —CH=N—CH=CH—, —CH=CH—N=CH—, —CH=CH—CH=N—, —CH=CH—O—, —O—CH=CH—, —CH=CH—S—, —S—CH=CH—, —O—CH₂—O— or —O—CH₂—CH₂—O—, and the 9- or 10-membered bicyclic heteroaryl or heterocyclic ring formed when G and G² together are linked optionally bears on the heteroaryl or heterocyclic portion of the bicyclic ring 1, 2 or 3 substituents, which may be the same or different, selected from halogeno, trifluoromethyl, cyano, hydroxy, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of G³, G⁴ and G⁵, which may be the same or different, is selected from hydrogen, halogeno, trifluoromethyl, cyano, hydroxy, (1–6C)alkyl, (2–8C)alkenyl, (2–8C)alkynyl and (1–6C)alkoxy;

or a pharmaceutically-acceptable salt thereof.

30. A quinazoline derivative of the Formula I

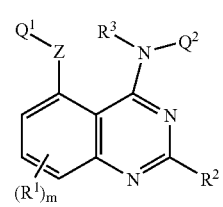

I wherein
m is 0, 1, 2 or 3;
each R¹ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C) alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C) alkyl]sulphamoyl, (1–6C)alkanesulphonylamino and N-(1–6C)alkyl-(1–6C)alkanesulphonylamino, or from a group of the formula:

$Q^3$-$X^1$— wherein $X^1$ is a direct bond or is selected from O, S, SO, $SO_2$, $N(R^4)$, CO, $CH(OR^4)$, $CON(R^4)$, $N(R^4)$ CO, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C) alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C) alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl] carbamoyl, amino-(1–6C)alkyl, (1–6C)alkylamino-(1–6C)alkyl and di-[(1–6C)alkyl]amino-(1–6C)alkyl or from a group of the formula:

$Q^4$-$X^2$— wherein $X^2$ is a direct bond or is selected from CO and $N(R^6)CO$, wherein $R^6$ is hydrogen or (1–6C) alkyl, and $Q^4$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C) alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C) alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^3$-$Q^5$ wherein $X^3$ is a direct bond or is selected from O, S, SO, $SO_2$, $N(R^7)$, CO, $CH(OR^7)$, $CON(R^7)$, $N(R^7)$ CO, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C) alkyl, and $Q^5$ is aryl, aryl-(1–6C)alkyl, (3–7C) cycloalkyl, (3–7C)cycloalkyl-(1–6C)alkyl, (3–7C)cycloalkenyl, (3–7C)cycloalkenyl-(1–6C) alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C) alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C) alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^4$—$R^8$ wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C) alkyl, (1–6C)alkoxy-(1–6C)alkyl, cyano-(1–6C) alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C) alkoxycarbonylamino-(1–6C)alkyl, or from a group of the formula:

—$X^5$-$Q^6$ wherein $X^5$ is a direct bond or is selected from O, CO and $N(R^{10})$, wherein $R^{10}$ is hydrogen or (1–6C) alkyl, and $Q^6$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C) alkoxy, and wherein any heterocyclyl group within a substituent on $R^1$ optionally bears 1 or 2 oxo or thioxo substituents;

$R^2$ is hydrogen or (1–6C)alkyl;

$R^3$ is hydrogen or (1–6C)alkyl;

Z is a direct bond or is selected from O, S, SO, $SO_2$, $N(R^{11})$, CO, $CH(OR^{11})$, $CON(R^{11})$, $N(R^{11})CO$, $SO_2N(R^{11})$, $N(R^{11})SO_2$, $OC(R^{11})_2$, $SC(R^{11})_2$ and $N(R^{11})C(R^{11})_2$, wherein $R^{11}$ is hydrogen or (1–6C)alkyl;

$Q^1$ is aryl, aryl-(1–6C)alkyl, (3–7C)cycloalkyl, (3–7C) cycloalkyl-(1–6C)alkyl, (3–7C)cycloalkenyl, (3–7C) cycloalkenyl-(1–6C)alkyl, heteroaryl, heteroaryl-(1–6C)alkyl, heterocyclyl or heterocyclyl-(1–6C)alkyl, or, when Z is a direct bond or O, $Q^1$ may be (1–6C) alkyl, (2–8C)alkenyl, (2–8C)alkynyl, halogeno-(1–6C) alkyl, hydroxy-(1–6C)alkyl, (1–6C)alkoxy-(1–6C) alkyl, cyano-(1–6C)alkyl, amino-(1–6C)alkyl, (1–6C) alkylamino-(1–6C)alkyl, di-[(1–6C)alkyl]amino-(1–6C)alkyl, (1–6C)alkylthio-(1–6C)alkyl, (1–6C) alkylsulphinyl-(1–6C)alkyl or (1–6C)alkylsulphonyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, CH=CH an C≡C wherein $R^{12}$ is hydrogen or (1–6C)alkyl, and wherein any CH$_2$=CH— or HC≡C— group within the Q$^1$-Z- group optionally bears at the terminal CH$_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q$^7$-X$^6$— wherein X$^6$ is a direct bond or is selected from CO and N(R$^{13}$)CO, wherein R$^{13}$ is hydrogen or (1–6C)alkyl, and Q$^7$ is aryl, aryl-(1–6C)alkyl, heteroaryl, heteroaryl-(1–6C)alkyl, heterocyclyl or heterocyclyl-(1–6C)alkyl, and wherein any CH$_2$ or CH$_3$ group within the Q$^1$-Z- group optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^7$-Q$^8$ wherein X$^7$ is a direct bond or is selected from O, S, SO, SO$_2$, N(R$^{14}$), CO, CH(OR$^{14}$), CON(R$^{14}$), N(R$^{14}$)CO, SO$_2$N(R$^{14}$), N(R$^{14}$)SO$_2$, C(R$^{14}$)$_2$O, C(R$^{14}$)$_2$S and N(R$^{14}$)C(R$^{14}$)$_2$, wherein R$^{14}$ is hydrogen or (1–6C)alkyl, and Q$^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the Q$^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^8$—R$^{15}$ wherein X$^8$ is a direct bond or is selected from O and N(R$^{16}$), wherein R$^{16}$ is hydrogen or (1–6C)alkyl, and R$^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X$^9$-Q$^9$ wherein X$^9$ is a direct bond or is selected from O, CO and N(R$^{17}$), wherein R$^{17}$ is hydrogen or (1–6C)alkyl, and Q$^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q$^1$-Z- group optionally bears 1 or 2 oxo or thioxo substituents; and Q$^2$ is an aryl group of formula Ia

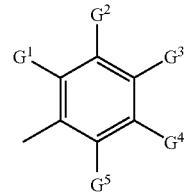

Ia wherein G$^1$ and G$^2$ together form a group of formula:
—CH=CH—CH=CH—, —N=CH—CH=CH—, —CH=N—CH=CH—, —CH=CH—N=CH—, —CH=CH—CH=N—, —CH=CH—O—, —O—CH=CH—, —CH=CH—S—, —S—CH=CH—, —O—CH$_2$—O— or —O—CH$_2$—CH$_2$—O—, and the 9- or 10-membered bicyclic heteroaryl or heterocyclic ring formed when G$^1$ and G$^2$ together are linked optionally bears on the heteroaryl or heterocyclic portion of the bicyclic ring 1, 2 or 3 substituents, which may be the same or different, selected from halogeno, trifluoromethyl, cyano, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of G$^3$, G$^4$ and G$^5$, which may be the same or different, is selected from hydrogen, halogeno, trifluoromethyl, cyano, (1–6C)alkyl, (2–8C)alkenyl, (2–8C)alkynyl and (1–6C)alkoxy;

or a pharmaceutically-acceptable salt thereof.

31. A quinazoline derivative of the Formula I

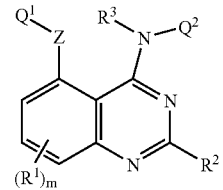

I wherein
m is 0, 1, 2 or 3;
each R$^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C) alkyl]sulphamoyl, (1–6C)alkanesulphonylamino and N-(1–6C)alkyl-(1–6C)alkanesulphonylamino, or from a group of the formula:

$Q^3\text{-}X^1\text{---}$ wherein $X^1$ is a direct bond or is selected from O, S, SO, $SO_2$, $N(R^4)$, CO, $CH(OR^4)$, $CON(R^4)$, $N(R^4)$CO, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)$CO, $SO_2N(R^5)$, $N(R^5)SO_2$, CH=CH and C≡C wherein $R^5$ is hydrogen or (1–6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4\text{-}X^2\text{---}$ wherein $X^2$ is a direct bond or is selected from CO and $N(R^6)CO$, wherein $R^6$ hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^3\text{-}Q^5$ wherein $X^3$ is a direct bond or is selected from O, S, SO, $SO_2$, $N(R^7)$, CO, $CH(OR^7)$, $CON(R^7)$, $N(R^7)$CO, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^5$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^4\text{—}R^8$ wherein $X^4$ is a direct bond or is selected from O and $N(R^9)$, wherein $R^9$ hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—$X^5\text{-}Q^6$ wherein $X^5$ is a direct bond or is selected from O, CO and $N(R^{10})$, wherein $R^{10}$ is hydrogen or (1–6C)alkyl, and $Q^6$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo or thioxo substituents;

$R^2$ is hydrogen or (1–6C)alkyl;

$R^3$ is hydrogen or (1–6C)alkyl;

Z is a direct bond or is selected from O, S, SO, $SO_2$, $N(R^{11})$ and CO, wherein $R^{11}$ is hydrogen or (1–6C)alkyl;

$Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or, when Z is a direct bond or O, $Q^1$ may be halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (1–6C)alkylthio-(1–6C)alkyl, (1–6C)alkylsulphinyl-(1–6C)alkyl or (1–6C)alkylsulphonyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, CH=CH an C≡C wherein $R^{12}$ is hydrogen or (1–6C)alkyl, and wherein any $CH_2$=CH— or HC≡C— group within the $Q^1$-Z- group optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^7$-$X^6$— wherein $X^6$ is a direct bond or is selected from CO and N($R^{13}$)CO, wherein $R^{13}$ is hydrogen or (1–6C)alkyl, and $Q^7$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, N($R^{14}$), CO, CH(O$R^{14}$), CON($R^{14}$), N($R^{14}$)CO, $SO_2$N($R^{14}$), N($R^{14}$)$SO_2$, C($R^{14}$)$_2$O, C($R^{14}$)$_2$S and N($R^{14}$)C($R^{14}$)$_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and N($R^{16}$), wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and N($R^{17}$), wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z-group optionally bears 1 or 2 oxo or thioxo substituents; and $Q^2$ is an aryl group of formula Ia

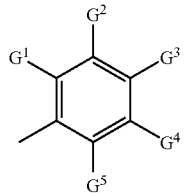

Ia wherein $G^1$ is selected from halogeno, trifluoromethyl, cyano, (1–6C)alkyl, (2–8C)alkenyl, (2–8C)alkynyl and (1–6C)alkoxy, and each of $G^2$, $G^3$, $G^4$ and $G^5$, which may be the same or different, is selected from hydrogen, halogeno, trifluoromethyl, cyano, (1–6C)alkyl, (2–8C)alkenyl, (2–8C)alkynyl and (1–6C)alkoxy, or $G^1$ and $G^2$ together form a group of formula —CH═CH—CH═CH—, —N═CH—CH═CH—, —CH═N—CH═CH—, —CH═CH—N═CH—, —CH═CH—CH═N—, —CH═CH—O—, —O—CH═CH—, —CH═CH—S—, —S—CH═CH—, —O—$CH_2$—O— or —O—$CH_2$—$CH_2$—O—, and the 9- or 10-membered bicyclic heteroaryl or heterocyclic ring formed when $G^1$ and $G^2$ together are linked optionally bears on the heteroaryl or heterocyclic portion of the bicyclic ring 1, 2 or 3 substituents, which may be the same or different, selected from halogeno, trifluoromethyl, cyano, hydroxy, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of $G^3$, $G^4$ and $G^5$, which may be the same or different, is selected from hydrogen, halogeno, trifluoromethyl, cyano, hydroxy, (1–6C)alkyl, (2–8C)alkenyl, (2–8C)alkynyl and (1–6C)alkoxy;

or a pharmaceutically-acceptable salt thereof.

32. A quinazoline derivative of the Formula I according to claim 31, or a pharmaceutically-acceptable salt thereof, wherein each of m, $R^1$, $R^2$, $R^3$ and $Q^2$ has any of the meanings defined in claim 33 and Z is a direct bond or is selected from O, S, SO, $SO_2$, N($R^{11}$) and CO, wherein $R^{11}$ is hydrogen or (1–6C)alkyl; and $Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, N($R^{12}$), CO, CH(O$R^{12}$), CON($R^{12}$), N($R^{12}$)CO, $SO_2$N($R^{12}$), N($R^{12}$)$SO_2$, CH═CH and C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2O$, $C(R^{14})_2$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

33. A quinazoline derivative of the Formula I according to claim 31, or a pharmaceutically-acceptable salt thereof, wherein each of m, $R^1$, $R^2$, $R^3$ and $Q^2$ has any of the meanings defined in claim 33 and Z is selected from O, S, SO, $SO_2$, $N(R^{11})$ and CO, wherein $R^{11}$ is hydrogen or (1–6C)alkyl; and $Q^1$ is (3–7C)cycloalkyl, (3–7C)cycloalkyl-(1–6C)alkyl, (3–7C)cycloalkenyl, (3–7C)cycloalkenyl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, CH═CH and C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$-$R^{15}$ wherein $X^8$ is a direct bond or is selected from O and $N(R^{16})$, wherein $R^{16}$ is hydrogen or (1–6C)alkyl, and $R^{115}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

34. A quinazoline derivative of the Formula I according to claim 31, or a pharmaceutically-acceptable salt thereof, wherein each of m, $R^1$, $R^2$, $R^3$, Z and $Q^1$ has any of the meanings defined in claim 33 and $Q^2$ is an aryl group of formula Ia

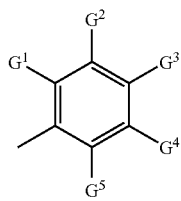

Ia wherein $G^1$ is halogeno or trifluoromethyl,
each of $G^2$ and $G^5$ is hydrogen,
$G^3$ is selected from hydrogen, halogeno, trifluoromethyl, cyano, (1–6C)alkyl, (2–8C)alkenyl, (2–8C)alkynyl and (1–6C)alkoxy, and
$G^4$ is halogeno or (1–6C)alkoxy.

35. A quinazoline derivative of the Formula I according to claim 31 wherein:
m is 0 or m is 1 and
the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy,
and wherein adjacent carbon atoms in any (2–6C) alkylene chain within a $R^1$ substituent are optionally separated by the insertion into the chain of a group selected from O, NH, CH=CH and C≡C,
and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino,
and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy,
and wherein any heterocyclyl group within a substituent on $R^1$ optionally bears 1 or 2 oxo substituents;
the $Q^1$-Z- group is selected from 2-hydroxyethoxy, 3-hydroxypropoxy, 2-methoxyethoxy, 3-methoxypropoxy, cyclopentyloxy, cyclohexyloxy, phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy,
and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino,
and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy,
and wherein any heterocyclyl group within the $Q^1$-Z- group optionally bears 1 or 2 oxo substituents;
each of $R^2$ and $R^3$ is hydrogen; and
$Q^2$ is an aryl group of formula Ia

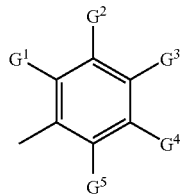

Ia wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, methyl, ethyl, vinyl, allyl, isopropenyl, ethynyl, methoxy and ethoxy,
or $G^1$ and $G^2$ together form a group of formula —CH=CH—CH=CH—, —O—CH=CH— or —O—$CH_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoromethyl, cyano, hydroxy, methyl, ethyl, methoxy and ethoxy;
or a pharmaceutically-acceptable acid-addition salt thereof.

36. A quinazoline derivative of the Formula I

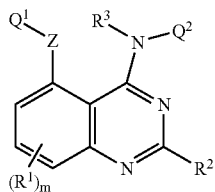

wherein
m is 0, 1, 2 or 3;
each R¹ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

Q³-X¹— wherein X¹ is a direct bond or is selected from O, S, SO, SO₂, N(R⁴), CO, CH(OR⁴), CON(R⁴), N(R⁴)CO, SO₂N(R⁴), N(R⁴)SO₂, OC(R⁴)₂, SC(R⁴)₂ and N(R⁴)C(R⁴)₂, wherein R⁴ is hydrogen or (1–6C)alkyl, and Q³ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or (R¹)ₘ is (1–3C)alkylenedioxy,
and wherein adjacent carbon atoms in any (2–6C)alkylene chain within a R¹ substituent are optionally separated by the insertion into the chain of a group selected from O, S, SO, SO₂, N(R⁵), CO, CH(OR⁵), CON(R⁵), N(R⁵)CO, SO₂N(R⁵), N(R⁵)SO₂, CH=CH and C≡C wherein R⁵ is hydrogen or (1–6C)alkyl,
and wherein any CH₂=CH— or HC≡C— group within a R¹ substituent optionally bears at the terminal CH₂= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q⁴-X²— wherein X² is a direct bond or is selected from CO and N(R⁶)CO, wherein R⁶ is hydrogen or (1–6C)alkyl, and Q⁴ is aryl, aryl-(1–6C)alkyl, heteroaryl, heteroaryl-(1–6C)alkyl, heterocyclyl or heterocyclyl-(1–6C)alkyl,
and wherein any CH₂ or CH₃ group within a R¹ substituent optionally bears on each said CH₂ or CH₃ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X³-Q⁵ wherein X³ is a direct bond or is selected from O, S, SO, SO₂, N(R⁷), CO, CH(OR⁷), CON(R⁷), N(R⁷)CO, SO₂N(R⁷), N(R⁷)SO₂, C(R⁷)₂O, C(R⁷)₂S and N(R⁷)C(R⁷)₂, wherein R⁷ is hydrogen or (1–6C)alkyl, and Q⁵ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-1–6C)alkyl, and wherein any aryl, heteroaryl or heterocyclyl group within a substituent on R¹ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X⁴—R⁸ wherein X⁴ is a direct bond or is selected from O and N(R⁹), wherein R⁹ hydrogen or (1–6C)alkyl, and R⁸ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—X⁵-Q⁶ wherein X⁵ is a direct bond or is selected from O, CO and N(R¹⁰), wherein R¹⁰ is hydrogen or (1–6C)alkyl, and Q⁶ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on R¹ optionally bears 1 or 2 oxo or thioxo substituents;

R² is hydrogen or (1–6C)alkyl;
R³ is hydrogen or (1–6C)alkyl;

Z is a direct bond or is selected from O, S, SO, SO$_2$, N(R$^{11}$) and CO, wherein R$^{11}$ is hydrogen or (1–6C)alkyl;

Q$^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or, when Z is a direct bond or O, Q$^1$ may be (1–6C)alkyl, (2–8C)alkenyl, (2–8C)alkynyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkyl (1–6C)alkyl, di-[(1–6C)alkyl]amino-(1–6C)alkyl, (1–6C)alkylthio-(1–6C)alkyl, (1–6C)alkylsulphinyl-(1–6C)alkyl or (1–6C)alkylsulphonyl-(1–6C)alkyl, and wherein adjacent carbon atoms in any (2–6C)alkylene chain within the Q$^1$-Z- group are optionally separated by the insertion into the chain of a group selected from O, S, SO, SO$_2$, N(R$^{12}$), CO, CH(OR$^{12}$), CON(R$^{12}$), N(R$^{12}$)CO, SO$_2$N(R$^{12}$), N(R$^{12}$)SO$_2$, CH=CH an C≡C wherein R$^{12}$ is hydrogen or (1–6C)alkyl, and wherein any CH$_2$=CH— or HC≡C— group within the Q$^1$-Z- group optionally bears at the terminal CH$_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q$^7$-X$^6$— wherein X$^6$ is a direct bond or is selected from CO and N(R$^{13}$)CO, wherein R$^{13}$ is hydrogen or (1–6C)alkyl, and Q$^7$ is aryl, aryl-(1–6C)alkyl, heteroaryl, heteroaryl-(1–6C)alkyl, heterocyclyl or heterocyclyl-(1–6C)alkyl, and wherein any CH$_2$ or CH$_3$ group within the Q$^1$-Z- group optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^7$-Q$^8$ wherein X$^7$ is a direct bond or is selected from O, S, SO, SO$_2$, N(R$^{14}$), CO, CH(OR$^{14}$), CON(R$^{14}$), N(R$^{14}$)CO, SO$_2$N(R$^{14}$), N(R$^{14}$)SO$_2$, C(R$^{14}$)$_2$O, C(R$^{14}$)$_2$S and N(R$^{14}$)C(R$^{14}$)$_2$, wherein R$^{14}$ is hydrogen or (1–6C)alkyl, and Q$^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the Q$^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^8$—R$^{15}$ wherein X$^8$ is a direct bond or is selected from O and N(R$^{16}$), wherein R$^{16}$ is hydrogen or (1–6C)alkyl, and R$^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X$^9$-Q$^9$ wherein X$^9$ is a direct bond or is selected from O, CO and N(R$^{17}$), wherein R$^{17}$ is hydrogen or (1–6C)alkyl, and Q$^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q$^1$-Z- group optionally bears 1 or 2 oxo or thioxo substituents; and Q$^2$ is an aryl group of formula Ia

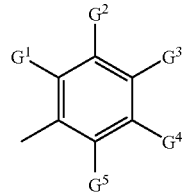

Ia wherein G$^1$ and G$^2$ together form a group of formula —CH=CH—CH=CH—, —N=CH—CH=CH—, —CH=N—CH=CH—, —CH=CH—N=CH—, —CH=CH—CH=N—, —CH=CH—O—, —O—CH=CH—, —CH=CH—S—, —S—CH=CH—, —O—CH$_2$—O— or —O—CH$_2$—CH$_2$—O—, and the 9- or 10-membered bicyclic heteroaryl or heterocyclic ring formed when G$^1$ and G$^2$ together are linked optionally bears on the heteroaryl or heterocyclic portion of the bicyclic ring 1, 2 or 3 substituents, which may be the same or different, selected from halogeno, trifluoromethyl, cyano, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of G$^3$, G$^4$ and G$^5$, which may be the same or different, is selected from hydrogen, halogeno, trifluoromethyl, cyano; (1–6C)alkyl, (2–8C)alkenyl, (2–8C)alkynyl and (1–6C)alkoxy;

or a pharmaceutically-acceptable salt thereof.

37. A quinazoline derivative of the Formula I according to claim 36, or a pharmaceutically-acceptable salt thereof, wherein each of m, $R^1$, $R^2$, $R^3$ and $Q^2$ has any of the meanings defined in claim 36 and Z is a direct bond or is selected from O, S, SO, $SO_2$, $N(R^{11})$ and CO, wherein $R^{11}$ is hydrogen or (1–6C)alkyl; and $Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, CH=CH and C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

38. A quinazoline derivative of the Formula I according to claim 36, or a pharmaceutically-acceptable salt thereof, wherein each of m, $R^1$, $R^2$, $R^3$ and $Q^2$ has any of the meanings defined in claim 36 and Z is selected from O, S, SO, $SO_2$, $N(R^{11})$ and CO, wherein $R^{11}$ is hydrogen or (1–6C)alkyl; and $Q^1$ is (3–7C)cycloalkyl, (3–7C)cycloalkyl-(1–6C)alkyl, (3–7C)cycloalkenyl, (3–7C)cycloalkenyl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, CH=CH an C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl,
or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

39. A quinazoline derivative of the Formula I

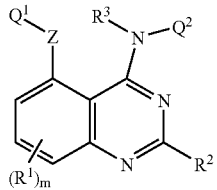

wherein
m is 0,1 or 2;
each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino, or from a group of the formula:

$Q^3$-$X^1$— wherein $X^1$ is a direct bond or is selected from O, $N(R^4)$, $CON(R^4)$, $N(R^4)CO$ and $OC(R^4)_2$, wherein $R^4$ is hydrogen or (1–6C)alkyl, and $Q^3$ is aryl, aryl-(1–6C)alkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, $N(R^5)$, $CON(R^5)$, $N(R^5)CO$, CH=CH and C≡C wherein $R^5$ hydrogen or (1–6C)alkyl, and wherein any $CH_2$=CH— or HC≡C— group within a $R^1$ substituent optionally bears at the terminal $CH_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4$-$X^2$— wherein $X^2$ is a direct bond or is selected from CO and $N(R^6)CO$, wherein $R^6$ is hydrogen or (1–6C)

alkyl, and $Q^4$ is heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

—$X^3$-$Q^5$ wherein $X^3$ is a direct bond or is selected from O, $N(R^7)$, $CON(R^7)$, $N(R^7)CO$ and $C(R^7)_2O$, wherein $R^7$ is hydrogen or (1–6C)alkyl, and $Q^5$ is heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or from a group of the formula:

—$X^4$—$R^8$ wherein $X^4$ is a direct bond or is selected from O and $N(R^9)$, wherein $R^9$ is hydrogen or (1–6C)alkyl, and $R^8$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl,
or from a group of the formula:

—$X^5$-$Q^6$ wherein $X^5$ a direct bond or is selected from O, CO and $N(R^{10})$, wherein $R^{10}$ hydrogen or (1–6C)alkyl, and $Q^6$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo substituents;

$R^2$ is hydrogen;
$R^3$ hydrogen;
the $Q^1$-Z- group is selected from halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, halogeno-(1–6C)alkoxy, hydroxy-(1–6C)alkoxy, (1–6C)alkoxy-(1–6C)alkoxy, cyano-(1–6C)alkoxy, amino-(1–6C)alkoxy, (1–6C)alkylamino-(1–6C)alkoxy and di-[(1–6C)alkyl]amino-(1–6C)alkoxy, or Z is a direct bond or is selected from O, S, SO, $SO_2$, $N(R^{11})$ and CO, wherein $R^{11}$is hydrogen or (1–6C)alkyl, and $Q^1$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, $N(R^{12})$, $CON(R^{12})$, $N(R^{12})CO$, CH=CH and C≡C wherein $R^{12}$ is hydrogen or (1–6C)alkyl, and wherein any $CH_2$=CH— or HC≡C— group within the $Q^1$-Z- group optionally bears at the terminal $CH_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^7\text{-}X^6—$ wherein $X^6$ is a direct bond or is selected from CO and $N(R^{13})CO$, wherein $R^{13}$ is hydrogen or (1–6C)alkyl, and $Q^7$ is heteroaryl, heteroaryl-(1–6C)alkyl, heterocyclyl or heterocyclyl-(1–6C)alkyl, and wherein any $CH_2$ or $CH_3$ group within the $Q^1\text{-}Z\text{-}$ group optionally bears on each said $CH_2$ or $CH_3$ group a substituent selected from hydroxy, amino, (1–6C)alkoxy, (1–6C)alkylthio, (1–6C)alkylsulphinyl, (1–6C)alkylsulphonyl, (1–6C)alkylamino and di-[(1–6C)alkyl]amino, or from a group of the formula:

$—X^7\text{-}Q^8$ wherein $X^7$ is a direct bond or is selected from O, $N(R^{14})$, $CON(R^{14})$, $N(R^{14})CO$ and $C(R^{14})_2O$, wherein $R^{14}$ is hydrogen or (1–6C)alkyl, and $Q^8$ is heteroaryl, heteroaryl-(1–6C)alkyl, heterocyclyl or heterocyclyl-(1–6C)alkyl, and wherein any aryl, heteroaryl or heterocyclyl group within the $Q^1\text{-}Z\text{-}$ group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or from a group of the formula:

$—X^8—R^{15}$ wherein $X^8$ is a direct bond or is selected from O and $N(R^{16})$, wherein $R^{16}$ is hydrogen or (1–6C)alkyl, and $R^{15}$ is hydroxy-(1–6C)alkyl, (1–6C)alkoxy-(1–6C)alkyl, amino-(1–6C)alkyl, (1–6C)alkylamino-(1–6C)alkyl or di-[(1–6C)alkyl]amino-(1–6C)alkyl, or from a group of the formula:

$—X^9\text{-}Q^9$ wherein $X^9$ is a direct bond or is selected from O, CO and $N(R^{17})$, wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1\text{-}Z\text{-}$ group optionally bears 1 or 2 oxo substituents; and $Q^2$ is an aryl group of formula Ia

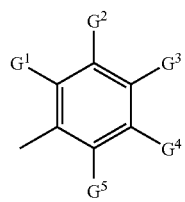

Ia wherein $G^1$ is selected from halogeno, trifluoromethyl, cyano, (1–6C)alkyl, (2–8C)alkenyl, (2–8C)alkynyl and (1–6C)alkoxy, and each of $G^2$, $G^3$, $G^4$ and $G^5$, which may be the same or different, is selected from hydrogen, halogeno, trifluoromethyl, cyano, (1–6C)alkyl, (2–8C)alkenyl, (2–8C)alkynyl and (1–6C)alkoxy, or $G^1$ and $G^2$ together form a group of formula —CH═CH—CH═CH—, —N═CH—CH═CH—, —CH═N—CH═CH—, —CH═CH—N═CH—, —CH═CH—CH═N—, —CH═CH—O—, —O—CH═CH—, —CH═CH—S—, —S—CH═CH—, —O—$CH_2$—O— or —O—$CH_2$—$CH_2$—O—, and the 9- or 10-membered bicyclic heteroaryl or heterocyclic ring formed when $G^1$ and $G^2$ together are linked optionally bears on the heteroaryl or heterocyclic portion of the bicyclic ring 1, 2 or 3 substituents, which may be the same or different, selected from halogeno, trifluoromethyl, cyano, hydroxy, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of $G^3$, $G^4$ and $G^5$, which may be the same or different, is selected from hydrogen, halogeno, trifluoromethyl, cyano, hydroxy, (1–6C)alkyl, (2–8C)alkenyl, (2–8C)alkynyl and (1–6C)alkoxy;

or a pharmaceutically-acceptable salt thereof.

40. A quinazoline derivative of the Formula I according to claim 39, or a pharmaceutically-acceptable salt thereof, wherein each of m, $R^1$, $R^2$, $R^3$ and $Q^2$ has any of the meanings defined in claim 39 and Z is a direct bond or is selected from O, S, SO, $SO_2$, $N(R^{11}{}_1)$ and CO, wherein $R^{11}$ is hydrogen or (1–6C)alkyl; and $Q^1$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1\text{-}Z\text{-}$ group are optionally separated by the insertion into the chain of a group selected from O, $N(R^{12})$, $CON(R^{12})$, $N(R^{12})CO$, CH═CH and C≡C wherein $R^{12}$ is hydrogen or (1–6C)alkyl, and wherein any $CH_2$ or $CH_3$ group within the $Q^1\text{-}Z\text{-}$ group optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

$—X^7\text{-}Q^8$ wherein $X^7$ is a direct bond or is selected from O, $N(R^{14})$, $CON(R^{14})$, $N(R^{14})CO$ and $C(R^{14})_2O$, wherein $R^{14}$ is hydrogen or (1–6C)alkyl, and $Q^8$ is heteroaryl, heteroaryl-(1–6C)alkyl, heterocyclyl or heterocyclyl-(1–6C)alkyl, and wherein any aryl, heteroaryl or heterocyclyl group within the $Q^1\text{-}Z\text{-}$ group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or from a group of the formula:

$—X^8—R^{15}$ wherein $X^8$ is a direct bond or is selected from O and $N(R^{16})$, wherein $R^{16}$ is hydrogen or (1–6C)alkyl, and $R^{15}$ is hydroxy-(1–6C)alkyl, (1–6C)alkoxy-(1–6C)alkyl, amino-(1–6C)alkyl, (1–6C)alkylamino-(1–6C)alkyl or di-[(1–6C)alkyl]amino-(1–6C)alkyl, or from a group of the formula:

$—X^9\text{-}Q^9$ wherein $X^9$ is a direct bond or is selected from O, CO and $N(R^{17})$, wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo substituents.

41. A quinazoline derivative of the Formula I according to claim 39, or a pharmaceutically-acceptable salt thereof, wherein each of m, $R^1$, $R^2$, $R^3$ and $Q^2$ has any of the meanings defined in claim 39 and Z is selected from O, S, SO, $SO_2$, $N(R^{11})$ and CO, wherein $R^{11}$ is hydrogen or (1–6C)alkyl; and $Q^1$ is (3–7C)cycloalkyl, (3–7C)cycloalkyl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, $N(R^{12})$, $CON(R^{12})$, $N(R^{12})CO$, CH=CH and C≡C wherein $R^{12}$ is hydrogen or (1–6C)alkyl, and wherein any $CH_2$ or $CH_3$ group within the $Q^1$-Z-group optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

—$X^7$-$Q^8$ wherein $X^7$ is a direct bond or is selected from O, $N(R^{14})$, $CON(R^{14})$, $N(R^{14})CO$ and $C(R^{14})_2O$, wherein $R^{14}$ is hydrogen or (1–6C)alkyl, and $Q^8$ is heteroaryl, heteroaryl-(1–6C)alkyl, heterocyclyl or heterocyclyl-(1–6C)alkyl, and wherein any heterocyclyl group within the $Q^1$-Z-group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is hydroxy-(1–6C)alkyl, (1–6C)alkoxy-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z-group optionally bears 1 or 2 oxo substituents.

42. A quinazoline derivative of the Formula I

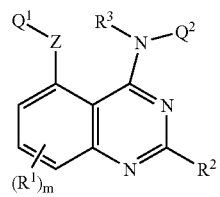

I wherein m is 0,1 or 2;

each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino, or from a group of the formula:

$Q^3$-$X^1$— wherein $X^1$ is a direct bond or is selected from O, $N(R^4)$, $CON(R^4)$, $N(R^4)CO$ and $OC(R^4)_2$, wherein $R^4$ is hydrogen or (1–6C)alkyl, and $Q^3$ is aryl, aryl-(1–6C)alkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, $N(R^5)$, $CON(R^5)$, $N(R^5)CO$, CH=CH and C≡C wherein $R^5$ hydrogen or (1–6C)alkyl, and wherein any $CH_2$=CH— or HC≡C— group within a $R^1$ substituent optionally bears at the terminal $CH_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4$-$X^2$— wherein $X^2$ a direct bond or is selected from CO and $N(R^6)CO$, wherein $R^6$ is hydrogen or (1–6C)alkyl, and $Q^4$ is heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

—$X^3$-$Q^5$ wherein $X^3$ is a direct bond or is selected from O, $N(R^7)$, $CON(R^7)$, $N(R^7)CO$ and $C(R^7)_2O$, wherein $R^7$ is hydrogen or (1–6C)alkyl, and $Q^5$ is heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or from a group of the formula:

—$X^4$—$R^8$ wherein $X^4$ is a direct bond or is selected from O and $N(R^9)$, wherein $R^9$ is hydrogen or (1–6C)alkyl, and $R^8$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino- (1–6C)alkyl, (2–6C)alkanoylamino-(1–6C)alkyl or (1–6C)alkoxycarbonylamino-(1–6C)alkyl, or from a group of the formula:

—X⁵-Q⁶ wherein X⁵ is a direct bond or is selected from O, CO and N(R¹⁰), wherein R¹⁰ hydrogen or (1–6C)alkyl, and Q⁶ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on R¹¹ optionally bears 1 or 2 oxo substituents;

R² is hydrogen;

R³ is hydrogen;

the Q¹-Z- group is selected from (1–6C)alkyl, (2–8C)alkenyl, (2–8C)alkynyl, (1–6C)alkoxy, (2–8C)alkenyloxy, (2–8C)alkynyloxy, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, halogeno-(1–6C)alkoxy, hydroxy-(1–6C)alkoxy, (1–6C)alkoxy-(1–6C)alkoxy, cyano-(1–6C)alkoxy, amino-(1–6C)alkoxy, (1–6C)alkylamino-(1–6C)alkoxy and di-[(1–6C)alkyl]amino-(1–6C)alkoxy, or Z is a direct bond or is selected from O, S, SO, SO₂, N(R¹¹) and CO, wherein R¹¹ is hydrogen or (1–6C)alkyl, and Q¹ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the Q¹-Z- group are optionally separated by the insertion into the chain of a group selected from O, N(R¹²), CON(R¹²), N(R¹²)CO, CH=CH and C≡C wherein R¹² is hydrogen or (1–6C)alkyl, and wherein any CH₂=CH— or HC≡C— group within the Q¹-Z- group optionally bears at the terminal CH₂= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q⁷-X⁶— wherein X⁶ is a direct bond or is selected from CO and N(R¹³)CO, wherein R¹³ is hydrogen or (1–6C)alkyl, and Q⁷ is heteroaryl, heteroaryl-(1–6C)alkyl, heterocyclyl or heterocyclyl-(1–6C)alkyl, and wherein any CH₂ or CH₃ group within the Q¹-Z- group optionally bears on each said CH₂ or CH₃ group a substituent selected from hydroxy, amino, (1–6C)alkoxy, (1–6C)alkylthio, (1–6C)alkylsulphinyl, (1–6C)alkylsulphonyl, (1–6C)alkylamino and di-[(1–6C)alkyl]amino, or from a group of the formula:

—X⁷-Q⁸ wherein X⁷ is a direct bond or is selected from O, N(R¹⁴), CON(R¹⁴), N(R¹⁴)CO and C(R¹⁴)₂O, wherein R¹⁴ is hydrogen or (1–6C)alkyl, and Q⁸ is heteroaryl, heteroaryl-(1–6C)alkyl, heterocyclyl or heterocyclyl-(1–6C)alkyl, and wherein any aryl, heteroaryl or heterocyclyl group within the Q¹-Z- group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or from a group of the formula:

—X⁸—R¹⁵ wherein X⁸ is a direct bond or is selected from O and N(R¹⁶), wherein R¹⁶ is hydrogen or (1–6C)alkyl, and R¹⁵ is hydroxy-(1–6C)alkyl, (1–6C)alkoxy-(1–6C)alkyl, amino-(1–6C)alkyl, (1–6C)alkylamino-(1–6C)alkyl or di-[(1–6C)alkyl]amino-(1–6C)alkyl, or from a group of the formula:

—X⁹-Q⁹ wherein X⁹ is a direct bond or is selected from O, CO and N(R¹⁷), wherein R¹⁷ is hydrogen or (1–6C)alkyl, and Q⁹ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q¹-Z- group optionally bears 1 or 2 oxo substituents; and Q² is an aryl group of formula Ia

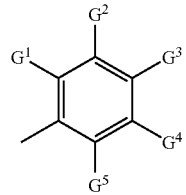

Ia wherein G¹ and G² together form a group of formula —CH=CH—CH=CH—, —N=CH—CH=CH—, —CH=N—CH=CH—, —CH=CH—N=CH—, —CH=CH—CH=N—, —CH=CH—O—, —O—CH=CH—, —CH=CH—S—, —S—CH=CH—, —O—CH₂—O— or —O—CH₂—CH₂—O—, and the 9- or 10-membered bicyclic heteroaryl or heterocyclic ring formed when G¹ and G² together are linked optionally bears on the heteroaryl or heterocyclic portion of the bicyclic ring 1, 2 or 3 substituents, which may be the same or different, selected from halogeno, trifluoromethyl, cyano, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of G³, G⁴ and G⁵, which may be the same or different, is selected from hydrogen, halogeno, trifluoromethyl, cyano, (1–6C)alkyl, (2–8C)alkenyl, (2–8C)alkynyl and (1–6C)alkoxy;

or a pharmaceutically-acceptable salt thereof.

43. A quinazoline derivative of the Formula I

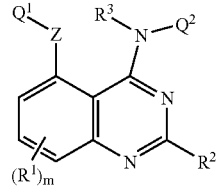

I wherein m is 0, 1, 2 or 3;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^3$-$X^1$— wherein $X^1$ is a direct bond or is selected from O, S, SO, $SO_2$, $N(R^4)$, CO, $CH(OR^4)$, $CON(R^4)$, $N(R^4)$CO, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein adjacent carbon atoms in any (2–6C) alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)$CO, $SO_2N(R^5)$, $N(R^5)SO_2$, CH=CH and C≡C wherein $R^5$ is hydrogen or (1–6C)alkyl, and wherein any $CH_2$=CH— or HC≡C— group within a $R^1$ substituent optionally bears at the terminal $CH_2$= or HC≡C— position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl and wherein any $CH_2$ or $CH_3$ group within a $R^1$ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkcanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^4$—$R^8$ wherein $X^4$ is a direct bond or is selected from O and $N(R^9)$, wherein $R^9$ hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—$X^5$-$Q^6$ wherein $X^5$ is a direct bond or is selected from O, CO and $N(R^{10})$, wherein $R^{10}$ hydrogen or (1–6C)alkyl, and $Q^6$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^{11}$ optionally bears 1 or 2 oxo or thioxo substituents;

$R^2$ is hydrogen or (1–6C)alkyl;

$R^3$ is hydrogen or (1–6C)alkyl;

Z is a direct bond or is selected from O, S, SO, $SO_2$, $N(R^{11})$ and CO, wherein $R^{11}$ is hydrogen or (1–6C)alkyl;

$Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or, when Z is a direct bond or O, $Q^1$ may be (1–6C)alkyl, (2–8C)alkenyl, (2–8C)alkynyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (1–6C)alkylthio-(1–6C)alkyl, (1–6C)alkylsulphinyl-(1–6C)alkyl or (1–6C)alkylsulphonyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})$CO, $SO_2N(R^{12})$, $N(R^{12})SO_2$, CH=CH and C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl] carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)

alkyl]sulphamoyl, (1–6C)alkanesulphonylamino and N-(1–6C)alkyl-(1–6C)alkanesulphonylamino, and wherein any aryl, heteroaryl or heterocyclyl group within the Q$^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^8$—R$^{15}$ wherein X$^8$ is a direct bond or is selected from O and N(R$^{16}$) wherein R$^{16}$ is hydrogen or (1–6C)alkyl, and R$^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X$^9$-Q$^9$ wherein X$^9$ is a direct bond or is selected from O, CO and N(R$^{17}$), wherein R$^{17}$ is hydrogen or (1–6C)alkyl, and Q$^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q$^1$-Z- group optionally bears 1 or 2 oxo or thioxo substituents; and Q$^2$ is an aryl group of formula Ia

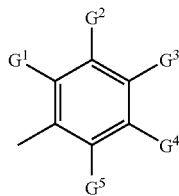

Ia wherein each of G$^3$, G$^4$ and G$^5$, which may be the same or different, is selected from hydrogen, halogeno, trifluoromethyl, cyano, (1–6C)alkyl, (2–8C)alkenyl, (2–8C)alkynyl and (1–6C)alkoxy, and G$^1$ and G$^2$ together form a group of formula:
—CH═CH—CH═CH—, —N═CH—CH═CH—, —CH═N—CH═CH—, —CH═CH—N═CH—, —CH═CH—CH═N—, —CH═CH—O—, —O—CH═CH—, —CH═CH—S—, —O—CH$_2$—O— or —O—CH$_2$—CH$_2$—O—, and the 9- or 10-membered bicyclic heteroaryl or heterocyclic ring formed when G$^1$ and G$^2$ together are linked optionally bears on the heteroaryl or heterocyclic portion of the bicyclic ring 1, 2 or 3 substituents, which may be the same or different, selected from halogeno, trifluoromethyl, cyano, (1–6C)alkyl, (2–8C)alkenyl, (2–8C)alkynyl and (1–6C)alkoxy, and any bicyclic heterocyclic ring so formed optionally bears 1 or 2 oxo or thioxo groups;

and wherein any one of the 'Q' groups (Q$^1$, Q$^3$, Q$^6$ and Q$^9$) when it is aryl or for the aryl group within a 'Q' group is phenyl or naphthyl, any one of the 'Q' groups (Q$^1$, Q$^3$, Q$^6$ and Q$^9$) when it is heteroaryl or for the heteroaryl group within a 'Q' group is an aromatic 5- or 6-membered monocyclic ring or a 9- or 10-membered bicyclic ring with up to five ring heteroatoms selected from oxygen, nitrogen and sulphur, and any one of the 'Q' groups (Q$^1$, Q$^3$, Q$^6$ and Q$^9$) when it is heterocyclyl or for the heterocyclyl group within a 'Q' group is a non-aromatic saturated or partially saturated 3 to 10 membered monocyclic or bicyclic ring with up to five heteroatoms selected from oxygen, nitrogen and sulphur;

or a pharmaceutically-acceptable salt thereof.

44. A quinazoline derivative of the Formula I according to claim 43, or a pharmaceutically-acceptable salt thereof, wherein each of m, R$^1$, R$^2$, R$^3$ and Q$^2$ has any of the meanings defined in claim 43 and Z is a direct bond or is selected from O, S, SO, SO$_2$, N(R$^{11}$) and CO, wherein R$^{11}$ is hydrogen or (1–6C)alkyl; and Q$^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the Q$^1$-Z- group are optionally separated by the insertion into the chain of a group selected from O, S, SO, SO$_2$, N(R$^{12}$), CO, CH(OR$^{12}$), CON(R$^{12}$), N(R$^{12}$)CO, SO$_2$N(R$^{12}$), N(R$^{12}$)SO$_2$, CH═CH and C≡C wherein R$^{12}$ is hydrogen or (1–6C)alkyl, and wherein any CH$_2$ or CH$_3$ group within the Q$^1$-Z- group optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, and wherein any aryl, heteroaryl or heterocyclyl group within the Q$^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and N($R^{16}$), wherein $R^{16}$ is hydrogen or (1–6C)alkyl, and $R^{115}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and N($R^{17}$), wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

45. A quinazoline derivative of the Formula I according to claim 43, or a pharmaceutically-acceptable salt thereof, wherein each of m, $R^1$, $R^2$, $R^3$ and $Q^2$ has any of the meanings defined in claim 43 and Z is selected from O, S, SO, $SO_2$, N($R^{11}$) and CO, wherein $R^{11}$ is hydrogen or (1–6C)alkyl; and $Q^1$ is (3–7C)cycloalkyl, (3–7C)cycloalkyl-(1–6C)alkyl, (3–7C)cycloalkenyl, (3–7C)cycloalkenyl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, N($R^{12}$), CO, CH(O$R^{12}$), CON($R^{12}$), N($R^{12}$)CO, $SO_2$N($R^{12}$), N($R^{12}$)$SO_2$, CH=CH and C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, and wherein any heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^9$ is a direct bond or is selected from O, and N($R^{16}$), wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

$X^9$-$Q^9$ wherein $X^9$ is a direct bond or is selected from O, CO and N($R^{17}$), wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

46. A method for treating a solid tumour sensitive to inhibition of one or more non-receptor tyrosine kinases in a warm-blooded animal in need thereof comprising administering to said animal an effective tyrosine kinase inhibiting amoun of a quinazoline derivative of the Formula I, or a pharmaceutically-acceptable salt thereof, as defined in any one of claim 1, claim 21, claim 29, claim 30, claim 31, claim 36, claim 39, claim 42, or claim 43.

* * * * *